(12) United States Patent
Lewis et al.

(10) Patent No.: US 7,199,105 B2
(45) Date of Patent: *Apr. 3, 2007

(54) LINCOMYCIN DERIVATIVES POSSESSING ANTIBACTERIAL ACTIVITY

(75) Inventors: Jason G. Lewis, Hayward, CA (US); Dinesh V. Patel, Fremont, CA (US); Sampath Kumar Anandan, Fremont, CA (US); Mikhail F. Gordeev, South San Francisco, CA (US)

(73) Assignee: Vicuron Pharmaceuticals, Inc., King of Prussia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/777,455

(22) Filed: Feb. 11, 2004

(65) Prior Publication Data

US 2004/0230046 A1 Nov. 18, 2004

Related U.S. Application Data

(63) Continuation-in-part of application No. 10/642,807, filed on Aug. 15, 2003.

(60) Provisional application No. 60/479,502, filed on Jun. 17, 2003, provisional application No. 60/403,770, filed on Aug. 15, 2002.

(51) Int. Cl.
*A61K 31/70* (2006.01)
*C07H 15/00* (2006.01)

(52) U.S. Cl. .................. 514/24; 536/16.2; 536/16.3

(58) Field of Classification Search ............ 536/16.2, 536/16.3, 16.5; 514/24
See application file for complete search history.

(56) References Cited

U.S. PATENT DOCUMENTS

| | | | |
|---|---|---|---|
| 2,851,463 A | 9/1958 | Hinman et al. |
| 2,928,844 A | 3/1960 | De Boer et al. |
| 3,086,912 A | 4/1963 | Bergy et al. |
| 3,255,174 A | 6/1966 | Bannister et al. |
| 3,268,556 A | 8/1966 | Hoeksema |
| 3,282,917 A | 11/1966 | Magerlein |
| 3,361,739 A | 1/1968 | Argoudelis et al. |
| 3,364,197 A | 1/1968 | Hoeksema |
| 3,380,992 A | 4/1968 | Argoudelis et al. |
| 3,435,025 A | 3/1969 | Birkenmeyer |
| 3,475,407 A | 10/1969 | Birkenmeyer |
| 3,496,163 A | 2/1970 | Birkenmeyer et al. |
| 3,502,648 A | 3/1970 | Birkenmeyer et al. |
| 3,509,127 A | 4/1970 | Kagan et al. |
| 3,539,689 A | 11/1970 | Birkenmeyer et al. |
| 3,544,551 A | 12/1970 | Kagan et al. |
| 3,549,615 A | 12/1970 | Birkenmeyer |
| 3,555,007 A | 1/1971 | Magerlein |
| 3,671,647 A | 6/1972 | Argoudelis et al. |
| 3,674,647 A | 7/1972 | Visser |
| 3,692,767 A | 9/1972 | Magerlein |
| 3,702,322 A | 11/1972 | Bannister |
| 3,714,141 A | 1/1973 | Shephard |
| 3,715,346 A | 2/1973 | Magerlein |
| 3,764,672 A | 10/1973 | Argoudelis et al. |
| 3,787,390 A | 1/1974 | Birkenmeyer |
| 3,817,979 A | 6/1974 | Argoudelis et al. |
| 3,833,475 A | 9/1974 | Reusser et al. |
| 3,849,396 A | 11/1974 | Birkenmeyer et al. |
| 3,853,843 A | 12/1974 | Morozwich |
| 3,856,943 A | 12/1974 | Birkenmeyer |
| 3,870,699 A | 3/1975 | Bannister |
| 3,892,729 A | 7/1975 | Birkenmeyer |
| 3,892,730 A | 7/1975 | Birkenmeyer |
| 3,915,954 A | 10/1975 | Bannister |
| 4,031,304 A | 6/1977 | Bannister |
| RE29,558 E | 2/1978 | Bannister |
| 4,271,266 A | 6/1981 | Bergy et al. |
| 4,278,789 A | 7/1981 | Birkenmeyer |
| 4,293,547 A | 10/1981 | Lewis et al. |
| 4,309,533 A | 1/1982 | Birkenmeyer |
| 4,310,660 A | 1/1982 | Birkenmeyer |
| 4,317,903 A | 3/1982 | Hofstetter |
| 4,383,109 A | 5/1983 | Argoudelis et al. |
| 4,430,495 A | 2/1984 | Patt et al. |
| 4,464,466 A | 8/1984 | Argoudelis et al. |
| 4,568,741 A | 2/1986 | Livingston |
| 4,710,565 A | 12/1987 | Livingston et al. |
| 2004/0116690 A1 | 6/2004 | Lewis et al. |

FOREIGN PATENT DOCUMENTS

EP 0161 794 11/1985

(Continued)

OTHER PUBLICATIONS

Bannister, B. et al. (1989). "The S-Alkylation of Sulphides by an Activated Carbohydrate Epimine Under Acidic Catalysis: The Formation of α-Acetamido-Sulphides. Part 5. The Introduction of Functionality into the Sulphide Substituent," *J. Chem. Res.* 4:701-794.

Corrected version of an International Search Report mailed on Jul. 26, 2004, for PCT Patent Application PCT/US03/25820 filed on Aug. 15, 2003, 2 pages.

Spizek, J. et al. (2004). "Lincomycin, Cultivation of Producing Strains and Biosynthesis," *Appl. Microbiol. Biotechnol.* 63:510-519.

(Continued)

*Primary Examiner*—Elli Peselev
(74) *Attorney, Agent, or Firm*—Gregg C. Benson; Frank W. Forman

(57) ABSTRACT

Novel lincomycin derivatives are disclosed. These lincomycin derivatives exhibit antibacterial activity. As the compounds of the subject invention exhibit potent activities against bacteria, including gram positive organisms, they are useful antimicrobial agents. Methods of synthesis and of use of the compounds are also disclosed.

29 Claims, No Drawings

FOREIGN PATENT DOCUMENTS

| | | |
|---|---|---|
| GB | 1 298 295 | 11/1972 |
| GB | 1 347 598 | 2/1974 |
| WO | WO 89/04672 | 6/1989 |
| WO | WO 99/63937 | 12/1999 |
| WO | WO 2004/016632 | 2/2004 |
| WO | WO 2005/007665 | 1/2005 |
| WO | WO 2005/012320 | 2/2005 |

OTHER PUBLICATIONS

Sztaricskai, F. et al. (Nov. 1999). "Structural Modification of the Lincomycin Antibiotic," *The Journal of Antibiotics* 52(11):1050-1055.

Sztaricskai, F. et al. (Oct. 1997). "Chemical Synthesis and Structural Study of Lincomycin Sulfoxides and a Sulfone," *The Journal of Antibiotics* 50(10):866-873.

Sztaricskai, F. et al. (Sep. 1996). "Semisynthetic Modification of Antibiotic Lincomycin," *The Journal of Antibiotics* 49(9):941-943.

Anonymous (2001). "The Merck Index: Clindamycin," *Merck & Co.* Monograph No. 2377, XP-002271008, one page.

Anonymous (2001). "The Merck Index: Lincomycin," *Merck & Co.* Monograph No. 5522, XP-002271009, one page.

International Search Report mailed on May 18, 2004, for PCT Patent Application PCT/US03/25820 filed on Aug. 15, 2003, six pages.

Alexander, J. et al. (1988). "(Acyloxy)alkyl Carbamates as Novel Bioreversible Prodrugs for Amines: Increased Permeation through Biological Membranes," *Journal of Medicinal Chemistry* 31(2):318-322.

Alexander, J. et al. (1996). "Investigation of (Oxodioxolenyl)methyl Carbanates as Nonchiral Bioreversible Prodrug Moietes for Chiral Amines," *J. Med. Chem.* 39(2):480-486.

Baldwin, J. E. et. al. (1990). "Stereoppecific Synthesis of Dealanylalahopcin," *Tetrahedron* 46(13/14):4733-4748.

Baldwin, J. E. et al. (1989). "Amino Acid Synthesis Using (L)-Pyroglutamic Acid As A Chiral Starting Material," *Tetrahedron* 45(23):7459-7468.

Birkenmeyer, R. D. et al. (1984). "Synthesis and Antimicrobial Activity of Clindamycin Analogues: A Potent Antibacterial Agent," *Journal of Medicinal Chemistry* 27(2):216-223.

Bousquet, Y. et al. (1997). "Preparation of Enantiopure 4-Oxygenated Pipeolic Acid Derivatives," *Tetrahedron* 53(46):15671-15680.

Bundgaard, H. et al. (1980). "Prodrugs as Drug Delivery Systems IV: N-Mannich bases as Potential Novel Prodrugs for Amides, Ureide, Amines, and Other NH-Acidic Compounds," *Journal of Pharmaceutical Sciences* 69(1):44-46.

Demange, L. et al. (1998). "Practical Synthesis of the Boc and Fmoc Protected 4-Fluoro and 4-Difluoroprolines from *Trans*-4-Hydroxyproline," *Tetrahedron Letters* 39:1169-1172.

Del Valle, J. R. et al. (2003), "Asymmetric Hydrogenations for the Synthesis of Boc-Protected 4-Alkylprolinols and Prolines," *Journal of Organic Chemistry* 68(10):3923-3931.

Flaherty, P. et al. (1996). "Synthesis and Selective Monoamine Oxidase B-Inhibiting Properties of 1-Methyl-2,3,6-Tetrahydropyrid-4yl Carbomate Derivatives: Potential Prodrugs of (R)- and (S)- Nordeprenyl," *Journal of Medicinal Chemistry* 39(24):4756-4761.

Goldstein, B. P. et al. (1995). "Antimicrobial Activity of MDL 63,246, a New Semisynthetic Glycopeptide Antibiotic,"*Antimicrob. Agents & Chemother.* 39(7):1580-1588.

Jensen, N.P. et al. (1980). "Use of Aceylacetone to Prepare A Prodrug of Cycloserine," *Journal of Medicinal Chemistry* 23(1):6-8.

Magerlein, B. J. (1972). "Lincomycin. 14. An Improved Synthesis and Resolution of the Antimalarial Agent, 1'-Demethyl-4'-Depropyle-4'(R)-(S)-Pentyclindamycin Hydrochloride (U-24, 729A)," *Journal of Medicinal Chemistry* 15(12):1255-1259.

Osuch, C. et al. (1956). "The Use of Organolithium Compounds to Effect the Alkylation of 2- and 4- Picoline," *Journal of American Chemical Society* 78:1723-1725.

Sakamoto, F. et al. (1984). "Studies on Prodrugs. II. Preparation and Characterization of (5-Substited 2-Oxo-1,3-Dioxolen-4-yl)methyl Esters of Ampicillin," *Chem, Pharm. Bull.* 36(6):2241-2448.

Schroeder, W. et al. (1967). "Lincomycin. III. The Structure and Steroechemistry of the Carbohydrate Moiety," *Journal of the American Chemical Society* 89(10):2448-2453.

Shek, E. et al. (1976). "Improved Delivery through Biological Membranes. 2. Distribution, Excretion , and Metabolism of N-Methyl-1,6-dihyropyrident-2-Carbaldoxime Hydrochloride, A Pro-Drug of N-Methylpyridinium-2Carbalkdoxime Chloride," *Journal of Medicinal Chemistry* 19(1):108-112.

Shuman, R. T. et al. (1990). "An Improved Synthesis of Homoproline and Derivatives," *Journal of Organic Chemistry* 55:738-741.

Weiss, W. J. et al. (1999). "In Vivo Activities of Peptidic Prodrugs of Novel Aminomethyl Tetrahydrofuranyl-1β-Methylcarbapenems," *Antimicrobial Agents and Chemotherapy* 43(3):460-464.

Yong, K. et al. (2001). "Studies on the Alkylation of 3-Methyl-3-buten-1-ol Dianion: An Efficient Synthesis of 3-Methylene-lalkanols Including A San Jose Scale Sex Pheromone," *Journal of Organic Chemistry* 66(24):8248-8251.

Zhang, R. et al. (1998). "Pseudo -A(1,3) Strain as a Key Conformational Control Element in the Design of Poly-L-Proline Type II Peptide Mimics," *J. Am. Chem. Soc.* 120(16):3894-3902.

International Search Report mailed on May 6, 2005, for PCT Patent Application PCT/US2004/019497 filed on Jun. 17, 2004, 7 pages.

International Search Report mailed on Aug. 8, 2005, for PCT Application PCT/US2004/019689 filed on Jun. 17, 2004, 21 pages.

Bannister, B. et al. (1980) "The S-Alkylation of Sulphides by an Activated Carbohydrate Epimine Under Acidic Catalysis: the Formation of a-Acetamido-sulphides. Part 4. Reactions with Dithioacetals and Monothioacetals" Journal of the Chemical Society, Perkins Transactions 1 2:540-552.

Bannister, B. et al. (1989) "The S-Alkylation of Sulphides by an Activated Carbohydrate Epimine Under Acidic Catalysis: the formation of a-Acetamido-sulphides. Part 5. The Introduction of Functionality into the Sulphide Substituent" Journal of Chemical Research 4:90-91.

Deiters, A. et al. (2004) "Synthesis of Oxygen-and Nitrogen-Containing Heterocycles by Ring-Closing Metathesis" Chem. Rev. 104: 2199-2238.

Dondoni, A. et al. (1997) "Stereoselective Addition of 2-Furyl-lithium and 2-Thiazolyllithium to Sugar Nitrones. Synthesis of Carbon-Linked Glycoglycines." Journal of Organic Chemistry 62(16): 5484-96.

Dondini, A. (1994) "Synthesis of N-Benzyl Nitrones" Synthetic Communications 24(18):2537-50.

Fukuyama, T. et al. (1995) "2-and 4-Nitrobenzenesulfonamides: Exceptionally Versatile Means for Preparation of Secondary Amines and Protection of Amines." Tetrahedron Letters 36(36): 6373-74.

Griffith, W.P. et al. (1990) "TPAP: Tetra-n-propylammonium Perruthenate, A Mild and Convenient Oxidant for Alcohols." Aldrichimica Acta 23(1): 13-19.

Ibatullin, F.M. et al. (2002) "Reaction of 1,2-trans-glycosyl acetates with phosphorus pentachloride: new efficient approach to 1,2-trans-glycosyl chlorides" Tetrahedron Letters 43: 9577-9580.

Magerlein, B.J. et al. (1969) "Lincomycin. VIII. 4'-Alkyl-1'-demethyl-4'-depropylclindamycins, Potent Antibacterial and Antimalarial Agents" Journal of Medicinal Chemistry 12: 780-84.

Magerlein, B.J. (1967) "Lincomycin, VIII. 4'-depropyl-4'-ethoxylincomycins" Journal of Medicinal Chemistry 10(6): 1161-63.

Misiek, M. et al. (1973) "Microbiological Properties of a New Cephalosporin, BL-S 339: 7-(Phenylacetimidoyl-aminoacetamido)-3-(2-Methyl-1,3,4-Thiadiazol-5-Ylthiomethyl)Ceph-3-em-4-Carboxylic Acid" Antimicrobial Agents and Chemotherapy. 3(1):40-48.

Myers, A.G. et al. (1999) "Greatly Simplified Procedures for the Synthesis of a-Amino Acids by the Direct Alkylation of Alkylation of Pseudoephedrine Glycinamide Hydrate" J. Org. Chem. 64: 3322-27.

Watanabe, T. et al. (1982) "Synthesis of a-Amino-cycloheptatriene-1-acetic Acids and Their 7-Acylaminocephalosporin Derivatives" Chemical Pharmaceutical Bulletin 30(7): 2579-82.

Anonymous (2001). "The Merck Index: Clindamycin," *Merck & Co.* Monograph No. 2377, XP-002271008, one page.

Anonymous (2001). "The Merck Index: Lincomycin," *Merck & Co.* Monograph No. 5522, XP-002271009, one page.

International Search Report mailed on May 18, 2004, for PCT Patent Application PCT/US03/25820 filed on Aug. 15, 2003, six pages.

Invitation to Pay Additional Fees mailed Dec. 30, 2004 issued for PCT Patent Application No. PCT/US2004/019689, five pages.

LINCOMYCIN DERIVATIVES POSSESSING ANTIBACTERIAL ACTIVITY

CROSS-REFERENCE TO RELATED APPLICATIONS

This application is a continuation-in-part of U.S. patent application Ser. No. 10/642,807, filed Aug. 15, 2003, which claims the benefit under 35 U.S.C. §119(e) of U.S. Provisional Application No. 60/403,770 filed on Aug. 15, 2002. This application also claims the benefit under 35 U.S.C. §119(e) of U.S. Provisional Application No. 60/479,502, filed on Jun. 17, 2003. The disclosures of all of the priority documents are hereby incorporated by reference in their entireties.

BACKGROUND OF THE INVENTION

1. Field of the Invention

This invention relates to lincomycin derivatives that exhibit antibacterial activity.

2. State of the Art

Lincomycin is a biosynthetic product that adversely affects growth of various microorganisms, in particular gram positive bacteria. The characteristics and preparation of lincomycin are disclosed in U.S. Pat. No. 3,086,912. A variety of derivatives of lincomycin, which also have antimicrobial activity, have been prepared. These derivatives include, for example, clindamycin, which is described in U.S. Pat. No. 3,496,163.

Lincomycin derivatives remain attractive targets for antibacterial drug discovery. Accordingly, lincomycin derivatives that possess antimicrobial activity are desired as potential antibacterial agents.

SUMMARY OF THE INVENTION

The present invention provides lincomycin derivatives that possess antibacterial activity.

In one of its composition aspects, this invention is directed to a compound of formula (I):

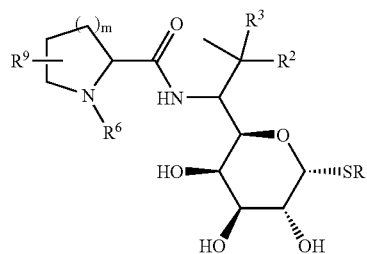

(I)

wherein:

$R^1$ is alkyl;

$R^2$ and $R^3$ are independently H, alkyl, hydroxy, fluoro, or cyanoalkyl or one of $R^2$ and $R^3$ is =$NOR^7$ and the other is absent, or one of $R^2$ and $R^3$ is $CH_2$ and the other is absent, with the provisos that both $R^2$ and $R^3$ are not H; when one of $R^2$ and $R^3$ is fluoro, the other is not hydrogen or hydroxy; and when one of $R^2$ and $R^3$ is hydroxy, the other is not fluoro, hydrogen, or hydroxy;

$R^6$ is selected from the group consisting of H, alkyl, hydroxyalkyl, —C(O)O-alkylene-cycloalkyl, —C(O)O-alkylene-substituted cycloalkyl, —C(O)O-alkyl, —C(O)O-substituted alkyl, —C(O)O-aryl, —C(O)O-substituted aryl, —C(O)O-heteroaryl, —C(O)O-substituted heteroaryl, —[C(O)O]$_p$-alkylene-heterocycle, —[C(O)O]$_p$-alkylene-substituted heterocycle, wherein p is 0 or 1;

$R^7$ is H or alkyl;

$R^9$, which can be singly or multiply substituted in the ring on the same or different carbons, is independently selected from the group consisting of alkyl, substituted alkyl, alkoxy, substituted alkoxy, alkoxyalkoxy, cycloalkyl, substituted cycloalkyl, substituted oxygen, substituted nitrogen, halogen, phenyl, substituted phenyl, —(CH$_2$)$_n$—OH, —(CH$_2$)$_n$—NR$^4$R$^5$, -alkylene-$R^a$ where $R^a$ is selected from monofluorophenyl and monochlorophenyl, and branched chain isomers thereof wherein n is an integer of from 1 to 8 inclusive and $R^4$ and $R^5$ are H or alkyl; and m is 0, 1, 2 or 3; and prodrugs, tautomers or pharmaceutically acceptable salts thereof;

with the proviso that the compound of formula I has a minimum inhibition concentration of 32 µg/mL or less against at least one of the organisms selected from the group consisting of *Streptococcus pneumoniae*, *Staphylococcus aureus*, *Staphylococcus epidermidis*, *Enterococcus faecalis*, *Enterococcus faecium*, *Haemophilus influenzae*, *Moraxella catarrhalis*, *Escherichia coli*, *Bacteroides fragilis*, *Bacteroides thetaiotaomicron*, and *Clostridium difficile*.

In one embodiment, m is 0. In another embodiment, m is 1. In another embodiment, m is 2. In another embodiment, m is 3.

In a preferred embodiment, $R^1$ is methyl.

In one embodiment, one of $R^2$ and $R^3$ is H, and the other is alkyl. In one embodiment, one of $R^2$ and $R^3$ is H, and the other is methyl. In one embodiment, one of $R^2$ and $R^3$ is H, and the other is cyanoalkyl. In one embodiment, both of $R^2$ and $R^3$ are F. In one embodiment, one of $R^2$ and $R^3$ is hydroxy, and the other is alkyl. In one embodiment, $R^2$ and $R^3$ together are hydroxyimino or alkoxyimino. In one embodiment, $R^2$ and $R^3$ together are methylene (=CH$_2$).

In a preferred embodiment, $R^6$ is H, alkyl, or hydroxyalkyl. In a preferred embodiment, $R^6$ is selected from the group consisting of H, methyl, ethyl, 2-hydroxyethyl, 2-methyl-2-hydroxyethyl, and 3-hydroxypropyl. In another embodiment, $R^6$ is not one of the following:

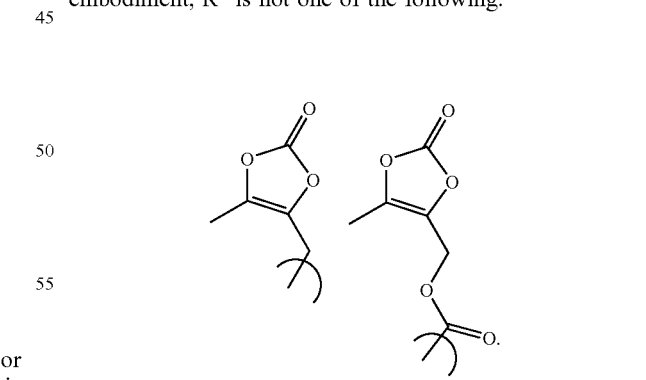

In one embodiment, each $R^9$ is independently selected from the group consisting of alkyl, substituted alkyl, alkoxyalkoxy, cycloalkyl, cycloalkylalkyl, substituted cycloalkyl, substituted oxygen, substituted nitrogen, halogen, phenyl, substituted phenyl, —(CH$_2$)$_n$—OH, —(CH$_2$)$_n$—NR$^4$R$^5$, -alkylene-, $R^a$ where $R^a$ is selected from monofluorophenyl and monochlorophenyl, and branched chain isomers thereof wherein n is an integer of from 1 to 8 inclusive and $R^4$ and $R^5$ are H or alkyl.

In one embodiment, $R^9$ is a substituted alkyl, and wherein the one or more substituents on the alkyl group are selected from the group consisting of halogen, oxygen, hydroxy, amine (primary), amine (secondary-amine substituted by alkyl above), amine (tertiary-amine substituted by alkyl as above), sulfur, —SH, and phenyl.

In a preferred embodiment, each $R^9$ is independently selected from the group consisting of halogen, alkyl, substituted alkyl, alkoxy, alkoxyalkoxy, substituted alkoxy, and cycloalkyl. In another preferred embodiment, each $R^9$ is independently selected from the group consisting of alkyl, and substituted alkyl.

In one embodiment, $R^9$ is selected from the group consisting of 1-ethylpropyl; 2-(4-fluorophenyl)ethyl; 2,2-difluoroethoxymethyl/fluoro; 2,2-difluoropentyl; 2-cyclobutyl-ethyl; 2-cyclopropyl-ethyl; 2-fluoroethoxy; 2-methoxyethoxy; 2-propoxy-ethyl; 3-(2-fluoro-ethoxy)propyl; 3-(3-fluoro-propoxy)-propyl; 3-(4-chlorophenyl)propyl; 3-(cyclopropyl-methoxy)propyl; 3,3,3-trifluoropropoxy; 3,3-difluorobutyl; 3,3-difluoropentyl; 3,3-difluoropropyl; 3,3-difluoropropyl/fluoro; 3-cyclobutyl-propyl; 3-cyclopentyl-propyl; 3-cyclopropyl-propyl; 3-ethoxy-propyl; 3-fluoropropoxy; 3-fluoro-propoxy-methyl; 3-fluoropropyl; 3-fluoropropyl/fluoro; 3-hydroxy-3-ethylpentyl; 3-methoxy-propyl; 3-propoxy-propyl; 4,4-difluorobutyl; 4,4-difluoropentyl; 4-fluorobutoxy; 4-fluorobutyl; 4-methoxy-butyl; 5,5-difluoropentyl; 5-fluoropentyl; butoxy; butyl; cyclobutyl-methyl; cyclohexyl; cyclohexyl-methyl; cyclopropyl-methoxy; cyclopropyl-methyl; ethyl; ethyl/fluoro; fluoro/butyl; fluoro/propyl; isobutyl; isopentyl; iso-propyl; methoxy; n-butyl; n-pentyl; pentoxy; pentyl; propoxy-methyl; and propyl. In another embodiment, $R^9$ is propyl.

In one embodiment, $R^9$ is selected from the group consisting of 1-ethylpropyl; 2-(4-fluorophenyl)ethyl; 2,2-difluoropentyl; 2-cyclobutyl-ethyl; 2-cyclopropyl-ethyl; 2-methoxyethoxy; 3-(2-fluoro-ethoxy)-propyl; 3-(4-chlorophenyl)propyl; 3,3-difluorobutyl; 3,3-difluoropentyl; 3,3-difluoropropyl; 3-cyclobutyl-propyl; 3-cyclopentyl-propyl; 3-cyclopropyl-propyl; 3-ethoxy-propyl; 3-fluoropropyl; 3-hydroxy-3-ethylpentyl; 3-methoxy-propyl; 3-propoxy-propyl; 4,4-difluorobutyl; 4-fluorobutyl; 5,5-difluoropentyl; 5-fluoropentyl; butoxy; butyl; cyclobutyl-methyl; cyclohexyl; cyclohexyl-methyl; cyclopropyl-methoxy; cyclopropyl-methyl; ethyl; isobutyl; isopentyl; iso-propyl; methoxy; n-butyl; n-pentyl; pentoxy; pentyl; propoxy-methyl; and propyl.

In one embodiment, $R^9$ not 2,2-difluoroethoxymethyl/fluoro; 2-fluoroethoxy; 2-propoxy-ethyl; 3-(3-fluoro-propoxy)-propyl; 3-(cyclopropyl-methoxy)-propyl; 3,3,3-trifluoropropoxy; 3,3-difluoropropyl/fluoro; 3-fluoropropoxy; 3-fluoro-propoxy-methyl; 3-fluoropropyl/fluoro; 4,4-difluoropentyl; 4-fluorobutoxy; 4-methoxy-butyl; ethyl/fluoro; fluoro/butyl; or fluoro/propyl.

In one of its composition aspects, this invention is directed to a prodrug compound of the formula (IV):

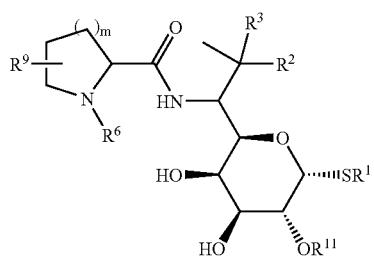

wherein $R^1$, $R^2$, $R^3$, and $R^9$ are as defined for formula I; wherein $R^6$ is as defined for formula I or is a suitable prodrug group which is cleavable in vivo; and wherein $R^{11}$ is H or a suitable prodrug group which is cleavable in vivo.

In one embodiment, the compound is a prodrug wherein $R^6$ is selected from the group consisting of hydrogen; 1-(acetyloxy)-ethyl-oxycarbonyl; 1-amino-2-methyl-butyl-carbonyl; 1-amino-2-methyl-butyl-carbonyl-oxy-methyl-oxycarbonyl; 1-amino-2-methyl-propyl-carbonyl; 1-amino-2-phenyl-ethyl-carbonyl; 1-amino-ethyl-carbonyl; 1-methyl-1,2,3,6 tetrahydro-pyridin-4-yl-oxycarbonyl; 1-methyl-1,4 dihydro-pyridin-3-yl-carbonyl; 1-methyl-3-oxo-but-1-enyl; 5-methyl-[1,3]dioxol-2-one-4-yl-methoxy-carbonyl; 5-methyl-[1,3]dioxol-2-one-4-yl-methyl; ethoxy-carbonyl; ethyl-carbonylamino-methyl; fluorenyl-methylene-oxy-carbonyl; phenoxy-carbonyl; piperidin-4-yl-carbonyl-oxy-methyl-oxycarbonyl; and pyridine-3-yl-carbonylamino-methyl.

In another embodiment, the compound is a prodrug wherein $R^6$ is selected from the group consisting of hydrogen; 1-(acetyloxy)-ethyl-oxycarbonyl; 1-amino-2-methyl-butyl-carbonyl; 1-amino-2-methyl-butyl-carbonyl-oxy-methyl-oxycarbonyl; 1-amino-2-methyl-propyl-carbonyl; 1-amino-2-phenyl-ethyl-carbonyl; 1-amino-ethyl-carbonyl; 1-methyl-1,2,3,6 tetrahydro-pyridin-4-yl-oxycarbonyl; 1-methyl-1,4 dihydro-pyridin-3-yl-carbonyl; 1-methyl-3-oxo-but-1-enyl; ethyl-carbonylamino-methyl; piperidin-4-yl-carbonyl-oxy-methyl-oxycarbonyl; and pyridine-3-yl-carbonylamino-methyl.

In another embodiment, the compound is a prodrug wherein $R^6$ is not 5-methyl-[1,3]dioxol-2-one-4-yl-methoxy-carbonyl; 5-methyl-[1,3]dioxol-2-one-4-yl-methyl; ethoxy-carbonyl; fluorenyl-methylene-oxy-carbonyl; or phenoxy-carbonyl.

In another embodiment, the compound is a prodrug wherein $R^6$ is not 5-methyl-[1,3]dioxol-2-one-4-yl-methoxy-carbonyl; or 5-methyl-[1,3]dioxol-2-one-4-yl-methyl.

In a preferred embodiment, the compound is a prodrug wherein $R^{11}$ is selected from the group consisting of hydrogen; 2-(N-(2-morpholin-4-yl-ethyl)-amino-carbonyl)-ethyl-carbonyl; —C(O)CH$_2$CH$_2$COOH; N,N-dimethyl-amino-methyl-carbonyl; pentadecyl-carbonyloxy; and —PO$_3$H$_2$.

In a preferred embodiment, this invention provides compounds of formula (II)

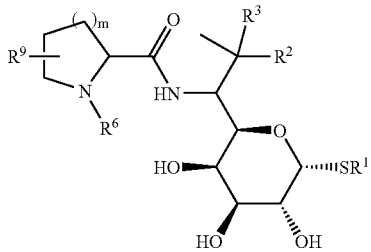

(II)

wherein
R[1] is alkyl;
R[2] and R[3] are independently H, alkyl, or cyanoalkyl, with the proviso that both R[2] and R[3] are not H;
R[6] is H, alkyl, or hydroxyalkyl;
R[9], which can be singly or multiply substituted in the ring on the same or different carbons, is independently selected from the group consisting of alkyl, substituted alkyl, alkoxyalkoxy, cycloalkyl, substituted cycloalkyl, substituted oxygen, substituted nitrogen, halogen, phenyl, substituted phenyl, —(CH$_2$)$_n$—OH, —(CH$_2$)$_n$—NR$^4$R$^5$, -alkylene-R$^a$ where R$^a$ is selected from monofluorophenyl and monochlorophenyl, and branched chain isomers thereof wherein n is an integer of from 1 to 8 inclusive and R[4] and R[5] are H or alkyl; and
m is 1 or 2; and
prodrugs and pharmaceutically acceptable salts thereof;
with the proviso that the compound of formula II has a minimum inhibition concentration of 32 μg/mL or less against at least one of the organisms selected from the group consisting of *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron,* and *Clostridium difficile.*

In a particularly preferred embodiment, this invention provides compounds of formula (III):

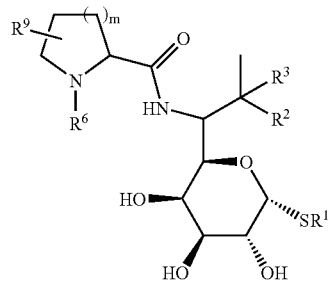

(III)

wherein
R[1] is alkyl;
R[2] and R[3] are fluoro;
R[6] is H, alkyl, or hydroxyalkyl;
R[9], which can be singly or multiply substituted in the ring on the same or different carbons, is independently selected from the group consisting of alkyl, substituted alkyl, alkoxyalkoxy, cycloalkyl, substituted cycloalkyl, substituted oxygen, substituted nitrogen, halogen, phenyl, substituted phenyl, —(CH$_2$)$_n$—OH, —(CH$_2$)$_n$—NR$^4$R$^5$, —alkylene—R$^a$ where R$^a$ is selected from monofluorophenyl and monochlorophenyl, and branched chain isomers thereof wherein n is an integer of from 1 to 8 inclusive and R[4] and R[5] are H or alkyl; and
m is 1 or 2; and
prodrugs and pharmaceutically acceptable salts thereof, with the proviso that the compound of formula III has a minimum inhibition concentration of 32 μg/mL or less against at least one of the organisms selected from the group consisting of *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron,* and *Clostridium difficile.*

In another preferred embodiment, this invention is directed to a compound of formula (V):

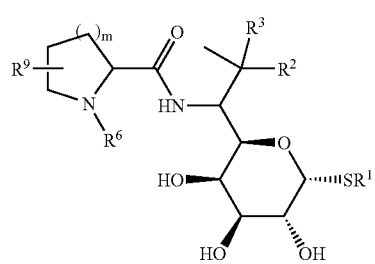

(V)

wherein:
R[1] is alkyl;
R[2] and R[3] are independently H, or alkyl, hydroxy, fluoro, or cyanoalkyl or one of R[2] and R[3] is =NOR[7] and the other is absent, or one of R[2] and R[3] is =CH$_2$ and the other is absent, with the provisos that both R[2] and R[3] are not H; when one of R[2] and R[3] is fluoro, the other is not hydrogen or hydroxy; and when one of R[2] and R[3] is hydroxy, the other is not fluoro, hydrogen, or hydroxy;
R[6] is selected from the group consisting of —C(O)O-alkylene-cycloalkyl, —C(O)O-alkylene-substituted cycloalkyl, —C(O)O-alkyl, —C(O)O-substituted alkyl, —C(O)O-aryl, —C(O)O-substituted aryl, —C(O)O-heteroaryl, —C(O)O-substituted heteroaryl, —[C(O)O]$_p$-alkylene-heterocycle, —[C(O)O]$_p$-alkylene-substituted heterocycle, wherein p is 0 or 1 with the proviso that —C(O)O-substituted alkyl does not include the following:

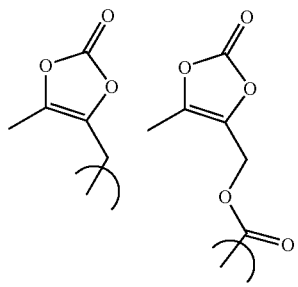

R[7] is H or alkyl;
R[9], which can be singly or multiply substituted in the ring on the same or different carbons, is independently selected from the group consisting of alkyl, substituted alkyl, alkoxyalkoxy, cycloalkyl, substituted cycloalkyl, substituted oxygen, substituted nitrogen, halogen, phenyl, substituted phenyl, $-(CH_2)_n-OH$, $-(CH_2)_n-NR^4R^5$, -alkylene-$R^a$ where $R^a$ is selected from monofluorophenyl and monochlorophenyl, and branched chain isomers thereof wherein n is an integer of from 1 to 8 inclusive and $R^4$ and $R^5$ are H or alkyl; and m is 1 or 2; and prodrugs, tautomers or pharmaceutically acceptable salts thereof;

with the proviso that the compound of formula V has a minimum inhibition concentration of 32 μg/mL or less against at least one of the organisms selected from the group consisting of *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron,* and *Clostridium difficile.*

Lincomycin derivatives within the scope of this invention include those set forth in Tables I and II as follows:

TABLE I

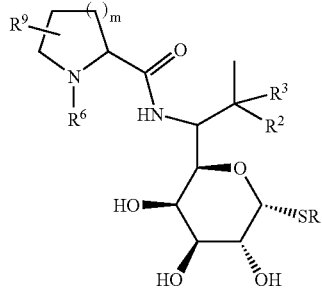

| Ex. # | $R^1$ | $R^2/R^3$ | $R^6$ | $R^{9*}$ | m |
|---|---|---|---|---|---|
| 1 | Methyl | H/methyl | H | ethyl | 2 |
| 2 | Methyl | H/methyl | methyl | propyl | 1 |
| 3 | Methyl | H/cyano-methyl | methyl | propyl | 1 |
| 4 | Methyl | hydroxy/methyl | H | ethyl | 2 |
| 5 | Methyl | hydroxy-imino | methyl | propyl | 1 |
| 6 | Methyl | methoxy-imino | methyl | propyl | 1 |
| 7 | Methyl | H/methyl | H | butyl | 2 |
| 8 | Methyl | H/methyl | H | pentyl | 1 |
| 9 | Methyl | H/methyl | H | isopentyl | 1 |
| 10 | Methyl | H/methyl | H | pentyl | 1 |
| 11 | Methyl | fluoro/fluoro | methyl | propyl | 1 |
| 12 | Methyl | fluoro/fluoro | H | pentyl | 1 |
| 13 | Methyl | H/methyl | H | 2-(4-fluorophenyl)-ethyl | 1 |
| 14 | Methyl | H/methyl | H | 3,3-difluoropropyl | 1 |
| 15 | Methyl | H/methyl | H | 3-(4-chlorophenyl)-propyl | 1 |
| 16 | Methyl | H/methyl | H | 2,2-difluoropentyl | 1 |
| 17 | Methyl | H/methyl | H | propyl | 2 |
| 18 | Methyl | H/methyl | 2-hydroxy-ethyl | pentyl | 1 |
| 19 | Methyl | H/methyl | 2-methyl-2-hydroxyethyl | pentyl | 1 |
| 20 | Methyl | H/methyl | 2-methyl-2-hydroxyethyl | pentyl | 1 |
| 21 | Methyl | H/methyl | 3-hydroxy-propyl | n-pentyl | 1 |
| 22 | Methyl | H/methyl | 2-hydroxyethyl | isopentyl | 1 |

TABLE I-continued

| Ex. # | $R^1$ | $R^2/R^3$ | $R^6$ | $R^{9*}$ | m |
|---|---|---|---|---|---|
| 23 | Methyl | H/methyl | 2-hydroxyethyl | 3,3-difluoropropyl | 1 |
| 24 | Methyl | fluoro/fluoro | 2-hydroxy-ethyl | pentyl | 1 |
| 25 | methyl | H/methyl | H | pentyl | 2 |
| 26 | methyl | H/methyl | H | methoxy | 2 |
| 27 | methyl | H/methyl | H | 1-ethylpropyl | 2 |
| 28 | methyl | H/methyl | H | iso-propyl | 2 |
| 29 | methyl | H/methyl | H | butyl | 2 |
| 30 | methyl | H/methyl | H | cyclohexyl | 2 |
| 31 | methyl | H/methyl | 2-hydroxyethyl | ethyl | 2 |
| 32 | methyl | H/methyl | 2-hydroxyethyl | pentyl | 2 |
| 33 | methyl | H/methyl | 2-hydroxyethyl | propyl | 2 |
| 37 | methyl | H/methyl | H | 4,4-difluoropentyl | 1 |
| 38 | methyl | H/methyl | H | 3,3-difluorobutyl | 1 |
| 39 | methyl | H/methyl | H | 3,3-difluoropentyl | 1 |
| 40 | methyl | H/methyl | 2-hydroxyethyl | 3,3-difluoropentyl | 1 |
| 41 | methyl | H/methyl | H | 3,3-difluoropropyl | 2 |
| 42 | methyl | H/methyl | H | 4,4-difluorobutyl | 2 |
| 43 | methyl | H/methyl | H | 5,5-difluoropentyl | 2 |
| 44 | methyl | H/methyl | H | 5-fluoropentyl | 2 |
| 45 | methyl | H/methyl | H | 4-fluorobutyl | 2 |
| 46 | methyl | H/methyl | H | 3-hydroxy-3-ethylpentyl | 2 |
| 47 | methyl | H/methyl | H | butoxy | 2 |
| 48 | methyl | H/methyl | H | pentoxy | 2 |
| 49 | methyl | H/methyl | H | 4-fluorobutoxy | 2 |
| 50 | Methyl | R2/R3 = methylene | H | butyl | 1 |
| 51 | methyl | H/methyl | Ethyl | ethyl | 2 |
| 52 | methyl | H/methyl | H | 3-fluoropropoxy | 2 |
| 53 | methyl | H/methyl | H | 3,3,3-trifluoropropoxy | 2 |
| 54 | methyl | H/methyl | H | isobutyl | 2 |
| 55 | methyl | fluoro/fluoro | H | propyl | 2 |
| 56 | methyl | H/methyl | H | fluoro/propyl | 1 |
| 57 | methyl | H/methyl | H | fluoro/butyl | 1 |
| 59 | methyl | H/methyl | H | 2-methoxyethoxy | 2 |
| 60 | methyl | H/methyl | H | butyl | 1 |
| 61 | methyl | H/methyl | H | 4,4-difluoropentyl | 2 |
| 62 | methyl | H/methyl | H | 3-fluoropropyl | 2 |
| 63 | methyl | H/methyl | H | fluoro/propyl | 2 |
| 64 | methyl | H/methyl | H | 2-fluoroethoxy | 2 |
| 66 | Methyl | H/methyl | H | 2-cyclopropyl-ethyl | 2 |
| 67 | Methyl | H/methyl | H | Cyclopropyl-methyl | 2 |
| 68 | Methyl | H/methyl | H | 2-cyclobutyl-ethyl | 2 |
| 69 | Methyl | H/methyl | H | Cyclobutyl-methyl | 2 |
| 70 | Methyl | H/methyl | H | n-butyl | 0 |
| 71 | Methyl | H/methyl | H | Cyclopropyl-methyl | 0 |
| 72 | Methyl | H/methyl | H | Propyl | 0 |
| 73 | Methyl | H/methyl | 2-hydroxy-ethyl | n-butyl | 0 |
| 74 | Methyl | H/methyl | H | n-pentyl | 0 |
| 75 | Methyl | H/methyl | H | Isopentyl | 0 |
| 76 | Methyl | H/methyl | H | 3-cyclobutyl-propyl | 0 |
| 77 | Methyl | H/methyl | H | 2-cyclobutyl-ethyl | 0 |
| 78 | Methyl | H/methyl | H | 2-cyclopropyl-ethyl | 0 |
| 79 | Methyl | H/methyl | H | 3-cyclopropyl-propyl | 0 |
| 80 | Methyl | H/methyl | Methyl | N-butyl | 0 |
| 85 | Methyl | H/methyl | H | Cyclopropyl-methyl | 1 |
| 86 | Methyl | H/methyl | H | 2-cyclobutyl-ethyl | 1 |
| 87 | Methyl | H/methyl | H | 2-cyclopropyl-ethyl | 1 |

TABLE I-continued

| Ex. # | R¹ | R²/R³ | R⁶ | R⁹* | m |
|---|---|---|---|---|---|
| 88 | Methyl | H/methyl | H | Propyl | 3 |
| 89 | Methyl | H/methyl | H | n-butyl | 2 |
| 90 | Methyl | H/methyl | H | 3-cyclopentyl-propyl | 2 |
| 91 | Methyl | H/methyl | H | 3-methoxy-propyl | 2 |
| 92 | Methyl | H/methyl | H | 3-ethoxy-propyl | 2 |
| 93 | Methyl | H/methyl | H | 3-propoxy-propyl | 2 |
| 94 | Methyl | H/methyl | H | 3-(cyclopropyl-methoxy)-propyl | 2 |
| 95 | Methyl | H/methyl | H | 3-(2-fluoro-ethoxy)-propyl | 2 |
| 96 | Methyl | H/methyl | H | 3-(3-fluoro-propoxy)-propyl | 2 |
| 97 | Methyl | H/methyl | H | 4-methoxy-butyl | 2 |
| 98 | Methyl | H/methyl | H | Propoxy-methyl | 2 |
| 99 | Methyl | H/methyl | H | 3-fluoro-propoxy-methyl | 2 |
| 115 | Methyl | H/methyl | H | Cyclohexyl-methyl | 2 |
| 116 | Methyl | H/methyl | H | 2-propoxy-ethyl | 2 |
| 117 | Methyl | H/methyl | H | cyclopropyl-methoxy | 2 |
| 118 | Methyl | H/methyl | H | Butyl/fluoro | 2 |
| 119 | Methyl | H/methyl | H | ethyl/fluoro | 2 |
| 120 | Methyl | H/methyl | H | 3-fluoropropyl/fluoro | 2 |
| 121 | Methyl | H/methyl | H | 3,3-difluoropropyl/fluoro | 2 |
| 122 | Methyl | H/methyl | H | 2,2-difluoroethoxy-methyl/fluoro | 2 |

TABLE II

| Ex. # | R¹ | R²/R³ | R⁶ | R⁹* | R¹¹ | m |
|---|---|---|---|---|---|---|
| 34 | methyl | H/methyl | Fluorenyl-methylene-oxy-carbonyl | Propyl | H | 2 |
| 35 | methyl | H/methyl | Ethoxy-carbonyl | Propyl | H | 2 |
| 36 | methyl | H/methyl | Phenoxy-carbonyl | Propyl | H | 2 |
| 81 | Methyl | H/methyl | H | Propyl | —PO₃H₂ | 2 |
| 82 | Methyl | H/methyl | H | Propyl | —C(O)CH₂CH₂COOH | 2 |
| 83 | Methyl | H/methyl | H | Propyl | 2-(N-(2-morpholin-4-yl-ethyl)-amino-carbonyl)-ethyl-carbonyl | 2 |
| 84 | Methyl | H/methyl | H | Propyl | N,N-dimethyl-amino-methyl-carbonyl | 2 |
| 100 | Methyl | H/methyl | 5-methyl-[1,3]dioxol-2-one-4-yl-methyl | Propyl | H | 2 |
| 101 | Methyl | H/methyl | 5-methyl-[1,3]dioxol-2-one-4-yl-methoxy-carbonyl | Propyl | H | 2 |

TABLE II-continued

| Ex. # | R¹ | R²/R³ | R⁶ | R⁹* | R¹¹ | m |
|---|---|---|---|---|---|---|
| 102 | Methyl | H/methyl | H | Propyl | Pentadecyl-carbonyloxy | 2 |
| 103 | Methyl | H/methyl | 1-methyl-3-oxo-but-1-enyl | Propyl | H | 2 |
| 104 | Methyl | H/methyl | 1-(acetyloxy)-ethyl-oxycarbonyl | Propyl | H | 2 |
| 105 | Methyl | H/methyl | 1-amino-2-methyl-butyl-carbonyl-oxy-methyl-oxycarbonyl | Propyl | H | 2 |
| 106 | Methyl | H/methyl | Piperidin-4-yl-carbonyl-oxy-methyl-oxycarbonyl | Propyl | H | 2 |
| 107 | Methyl | H/methyl | Ethyl-carbonylamino-methyl | Propyl | H | 2 |
| 108 | Methyl | H/methyl | Pyridine-3-yl-carbonylamino-methyl | Propyl | H | 2 |
| 109 | Methyl | H/methyl | 1-amino-ethyl-carbonyl | Propyl | H | 2 |
| 110 | Methyl | H/methyl | 1-amino-2-phenyl-ethyl-carbonyl | Propyl | H | 2 |
| 111 | Methyl | H/methyl | 1-amino-2-methyl-butyl-carbonyl | Propyl | H | 2 |
| 112 | Methyl | H/methyl | 1-amino-2-methyl-propyl-carbonyl | Propyl | H | 2 |
| 113 | Methyl | H/methyl | 1-methyl-1,4 dihydro-pyridin-3-yl-carbonyl | Propyl | H | 2 |
| 114 | Methyl | H/methyl | 1-methyl-1,2,3,6 tetrahydro-pyridin-4-yl-oxycarbonyl | Propyl | H | 2 |

*Includes R and/or S isomers as either individual isomers or as a mixture

Specific compounds within the scope of this invention include the following compounds:

4-ethyl-piperidine-2-carboxylic acid [2-methyl-1-(3,4,5-trihydroxy-6-methylsulfanyl-tetrahydro-pyran-2-yl)-propyl]-amide;

1-methyl-4-propyl-pyrrolidine-2-carboxylic acid [2-methyl-1-(3,4,5-trihydroxy-6-methylsulfanyl-tetrahydro-pyran-2-yl)-propyl]-amide;

1-methyl-4-propyl-pyrrolidine-2-carboxylic acid [3-cyano-2-methyl-1-(3,4,5-trihydroxy-6-methylsulfanyl-tetrahydro-pyran-2-yl)-propyl]-amide;

4-ethyl-piperidine-2-carboxylic acid [2-hydroxy-2-methyl-1-(3,4,5-trihydroxy-6-methylsulfanyl-tetrahydro-pyran-2-yl)-propyl]-amide;

1-methyl-4-propyl-pyrrolidine-2-carboxylic acid [2-hydroxyimino-1-(3,4,5-trihydroxy-6-methylsulfanyl-tetrahydro-pyran-2-yl)-propyl]-amide;

1-methyl-4-propyl-pyrrolidine-2-carboxylic acid [2-methoxyimino-1-(3,4,5-trihydroxy-6-methylsulfanyl-tetrahydro-pyran-2-yl)-propyl]-amide;

5-butyl-piperidine-2-carboxylic acid [2-methyl-1-(3,4,5-trihydroxy-6-methylsulfanyl-tetrahydro-pyran-2-yl)-propyl]-amide;

4-pentyl-pyrrolidine-2-carboxylic acid [2-methyl-1-(3,4,5-trihydroxy-6-methylsulfanyl-tetrahydro-pyran-2-yl)-propyl]-amide;

4-(3-methyl-butyl)-pyrrolidine-2-carboxylic acid [2-methyl-1-(3,4,5-trihydroxy-6-methylsulfanyl-tetrahydro-pyran-2-yl)-propyl]-amide;

4-pentyl-pyrrolidine-2-carboxylic acid [2-methyl-1-(3,4,5-trihydroxy-6-methylsulfanyl-tetrahydro-pyran-2-yl)-propyl]-amide;

1-methyl-4-propyl-pyrrolidine-2-carboxylic acid [2,2-difluoro-1-(3,4,5-trihydroxy-6-methylsulfanyl-tetrahydro-pyran-2-yl)-propyl]-amide;

4-pentyl-pyrrolidine-2-carboxylic acid [2,2-difluoro-1-(3,4,5-trihydroxy-6-methylsulfanyl-tetrahydro-pyran-2-yl)-propyl]-amide;

4-[3-(4-fluoro-phenyl)-propyl]-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-propyl)-pyrrolidine-2-carboxylic acid [2-methyl-1-(3,4,5-trihydroxy-6-methylsulfanyl-tetrahydro-pyran-2-yl)-propyl]-amide;

4-[3-(4-chloro-phenyl)-propyl]-pyrrolidine-2-carboxylic acid [2-methyl-1-(3,4,5-trihydroxy-6-methylsulfanyl-tetrahydro-pyran-2-yl)-propyl]-amide;

4-(2,2-difluoro-pentyl)-pyrrolidine-2-carboxylic acid [2-methyl-1-(3,4,5-trihydroxy-6-methylsulfanyl-tetrahydro-pyran-2-yl)-propyl]-amide;

4-propyl-piperidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-hydroxy-propyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-hydroxy-propyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(3-hydroxy-propyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-(3-methyl-butyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-propyl)-1-(2-hydroxy-ethyl)-pyrrolidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-pentyl-pyrrolidine-2-carboxylic acid [2,2-difluoro-1-(3,4,5-trihydroxy-6-methylsulfanyl-tetrahydro-pyran-2-yl)-propyl]-amide;

4-pentyl-piperidine-2-carboxylic acid [2-methyl-1-(3,4,5-trihydroxy-6-methylsulfanyl-tetrahydro-pyran-2-yl)-propyl]-amide;

4-Methoxy-piperidine-2-carboxylic acid [2-methyl-1-(3,4,5-trihydroxy-6-methylsulfanyl-tetrahydro-pyran-2-yl)-propyl]-amide;

4-(1-ethyl-propyl)-piperidine-2-carboxylic acid [2-methyl-1-(3,4,5-trihydroxy-6-methylsulfanyl-tetrahydro-pyran-2-yl)-propyl]-amide;

4-isopropyl-piperidine-2-carboxylic acid [2-methyl-1-(3,4,5-trihydroxy-6-methylsulfanyl-tetrahydro-pyran-2-yl)-propyl]-amide;

4-butyl-piperidine-2-carboxylic acid [2-methyl-1-(3,4,5-trihydroxy-6-methylsulfanyl-tetrahydro-pyran-2-yl)-propyl]-amide;

4-cyclohexyl-piperidine-2-carboxylic acid [2-methyl-1-(3,4,5-trihydroxy-6-methylsulfanyl-tetrahydro-pyran-2-yl)-propyl]-amide;

4-ethyl-1-(2-hydroxy-ethyl)-piperidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-pentyl-piperidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-propyl-piperidine-2-carboxylic acid [2-methyl-1-(3,4,5-trihydroxy-6-methylsulfanyl-tetrahydro-pyran-2-yl)-propyl]-amide;

4-(4,4-difluoro-pentyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-butyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-pentyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-pentyl)-1-(2-hydroxy-ethyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-propyl)-piperidine-2-carboxylic acid [2-methyl-1-(3,4,5-trihydroxy-6-methylsulfanyl-tetrahydro-pyran-2-yl)-propyl]-amide;

4-(4,4-difluoro-butyl)-piperidine-2-carboxylic acid [2-methyl-1-(3,4,5-trihydroxy-6-methylsulfanyl-tetrahydro-pyran-2-yl)-propyl]-amide;

4-(5,5-difluoro-pentyl)-piperidine-2-carboxylic acid [2-methyl-1-(3,4,5-trihydroxy-6-methylsulfanyl-tetrahydro-pyran-2-yl)-propyl]-amide;

4-(5-fluoro-pentyl)-piperidine-2-carboxylic acid [2-methyl-1-(3,4,5-trihydroxy-6-methylsulfanyl-tetrahydro-pyran-2-yl)-propyl]-amide;

4-(4-fluoro-butyl)-piperidine-2-carboxylic acid [2-methyl-1-(3,4,5-trihydroxy-6-methylsulfanyl-tetrahydro-pyran-2-yl)-propyl]-amide;

4-(3-ethyl-3-hydroxy-pentyl)-piperidine-2-carboxylic acid [2-methyl-1-(3,4,5-trihydroxy-6-methylsulfanyl-tetrahydro-pyran-2-yl)-propyl]-amide;

4-butoxy-piperidine-2-carboxylic acid [2-methyl-1-(3,4,5-trihydroxy-6-methylsulfanyl-tetrahydro-pyran-2-yl)-propyl]-amide;

4-pentyloxy-piperidine-2-carboxylic acid [2-methyl-1-(3,4,5-trihydroxy-6-methylsulfanyl-tetrahydro-pyran-2-yl)-propyl]-amide;

4-(4-fluoro-butoxy)-piperidine-2-carboxylic acid [2-methyl-1-(3,4,5-trihydroxy-6-methylsulfanyl-tetrahydro-pyran-2-yl)-propyl]-amide;

4-butyl-pyrrolidine-2-carboxylic acid [2-methyl-1-(3,4,5-trihydroxy-6-methylsulfanyl-tetrahydro-pyran-2-yl)-alkyl]-amide;

1,4-diethyl-piperidine-2-carboxylic acid [2-methyl-1-(3,4,5-trihydroxy-6-methylsulfanyl-tetrahydro-pyran-2-yl)-propyl]-amide;

4-(3-fluoro-propoxy)-piperidine-2-carboxylic acid [2-methyl-1-(3,4,5-trihydroxy-6-methylsulfanyl-tetrahydro-pyran-2-yl)-propyl]-amide;

4-(3,3,3-trifluoro-propoxy)-piperidine-2-carboxylic acid [2-methyl-1-(3,4,5-trihydroxy-6-methylsulfanyl-tetrahydro-pyran-2-yl)-propyl]-amide;

4-isobutyl-piperidine-2-carboxylic acid [2-methyl-1-(3,4,5-trihydroxy-6-methylsulfanyl-tetrahydro-pyran-2-yl)-propyl]-amide;

4-propyl-piperidine-2-carboxylic acid [2,2-difluoro-1-(3,4,5-trihydroxy-6-methylsulfanyl-tetrahydro-pyran-2-yl)-propyl]-amide;

4-fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-butyl-4-fluoro-pyrrolidine-2-carboxylic acid [2-methyl-1-(3,4,5-trihydroxy-6-methylsulfanyl-tetrahydro-pyran-2-yl)-propyl]-amide;

4-(2-methoxyethoxy)-piperidine-2-carboxylic acid [2-methyl-1-(3,4,5-trihydroxy-6-methylsulfanyl-tetrahydro-pyran-2-yl)-propyl]-amide;

4-Butyl-pyrrolidine-2-carboxylic acid [2-methyl-1-(3,4,5-trihydroxy-6-methylsulfanyl-tetrahydro-pyran-2-yl)-propyl]-amide;

4-(4,4-Difluoro-pentyl)-piperidine-2-carboxylic acid [2-methyl-1-(3,4,5-trihydroxy-6-methylsulfanyl-tetrahydro-pyran-2-yl)-propyl]-amide;

4-(3-Fluoro-propyl)-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-methyl-1-(3,4,5-trihydroxy-6-methylsulfanyl-tetrahydro-pyran-2-yl)-propyl]-amide;

4-(2-Fluoroethoxy)-piperidine-2-carboxylic acid [2-methyl-1-(3,4,5-trihydroxy-6-methylsulfanyl-tetrahydro-pyran-2-yl)-propyl]-amide;

4-(2-Cyclopropyl-ethyl)-piperidine-2-carboxylic acid [2-methyl-1-(3,4,5-trihydroxy-6-methylsulfanyl-tetrahydro-pyran-2-yl)-propyl]-amide;

4-Cyclopropylmethyl-piperidine-2-carboxylic acid [2-methyl-1-(3,4,5-trihydroxy-6-methylsulfanyl-tetrahydro-pyran-2-yl)-propyl]-amide;

4-(2-Cyclobutyl-ethyl)-piperidine-2-carboxylic acid [2-methyl-1-(3,4,5-trihydroxy-6-methylsulfanyl-tetrahydro-pyran-2-yl)-propyl]-amide;

4-Cyclobutylmethyl-piperidine-2-carboxylic acid [2-methyl-1-(3,4,5-trihydroxy-6-methylsulfanyl-tetrahydro-pyran-2-yl)-propyl]-amide;

3-Butyl-azetidine-2-carboxylic acid [2-methyl-1-(3,4,5-trihydroxy-6-methylsulfanyl-tetrahydro-pyran-2-yl)-propyl]-amide;

3-Cyclopropylmethyl-azetidine-2-carboxylic acid [2-methyl-1-(3,4,5-trihydroxy-6-methylsulfanyl-tetrahydro-pyran-2-yl)-propyl]-amide;

3-Propyl-azetidine-2-carboxylic acid [2-methyl-1-(3,4,5-trihydroxy-6-methylsulfanyl-tetrahydro-pyran-2-yl)-propyl]-amide;

3-Butyl-1-(2-hydroxy-ethyl)-azetidine-2-carboxylic acid [2-methyl-1-(3,4,5-trihydroxy-6-methylsulfanyl-tetrahydro-pyran-2-yl)-propyl]-amide;

3-Pentyl-azetidine-2-carboxylic acid [2-methyl-1-(3,4,5-trihydroxy-6-methylsulfanyl-tetrahydro-pyran-2-yl)-propyl]-amide;

3-(3-Methyl-butyl)-azetidine-2-carboxylic acid [2-methyl-1-(3,4,5-trihydroxy-6-methylsulfanyl-tetrahydro-pyran-2-yl)-propyl]-amide;

3-(3-Cyclobutyl-propyl)-azetidine-2-carboxylic acid [2-methyl-1-(3,4,5-trihydroxy-6-methylsulfanyl-tetrahydro-pyran-2-yl)-propyl]-amide;

3-(2-Cyclobutyl-ethyl)-azetidine-2-carboxylic acid [2-methyl-1-(3,4,5-trihydroxy-6-methylsulfanyl-tetrahydro-pyran-2-yl)-propyl]-amide;

3-(2-Cyclopropyl-ethyl)-azetidine-2-carboxylic acid [2-methyl-1-(3,4,5-trihydroxy-6-methylsulfanyl-tetrahydro-pyran-2-yl)-propyl]-amide;

3-(3-Cyclopropyl-propyl)-azetidine-2-carboxylic acid [2-methyl-1-(3,4,5-trihydroxy-6-methylsulfanyl-tetrahydro-pyran-2-yl)-propyl]-amide;

3-Butyl-1-methyl-azetidine-2-carboxylic acid [2-methyl-1-(3,4,5-trihydroxy-6-methylsulfanyl-tetrahydro-pyran-2-yl)-propyl]-amide;

4-Cyclopropylmethyl-pyrrolidine-2-carboxylic acid [2-methyl-1-(3,4,5-trihydroxy-6-methylsulfanyl-tetrahydro-pyran-2-yl)-propyl]-amide;

4-(2-Cyclobutyl-ethyl)-pyrrolidine-2-carboxylic acid [2-methyl-1-(3,4,5-trihydroxy-6-methylsulfanyl-tetrahydro-pyran-2-yl)-propyl]-amide;

4-(2-Cyclopropyl-ethyl)-pyrrolidine-2-carboxylic acid [2-methyl-1-(3,4,5-trihydroxy-6-methylsulfanyl-tetrahydro-pyran-2-yl)-propyl]-amide;

5-Propyl-azepane-2-carboxylic acid [2-methyl-1-(3,4,5-trihydroxy-6-methylsulfanyl-tetrahydro-pyran-2-yl)-propyl]-amide;

4-butyl-piperidine-2-carboxylic acid [2-methyl-1-(3,4,5-trihydroxy-6-methylsulfanyl-tetrahydro-pyran-2-yl)-propyl]-amide;

4-(3-Cyclopentyl-propyl)-piperidine-2-carboxylic acid [2-methyl-1-(3,4,5-trihydroxy-6-methylsulfanyl-tetrahydro-pyran-2-yl)-propyl]-amide;

4-(3-Methoxy-propyl)-piperidine-2-carboxylic acid [2-methyl-1-(3,4,5-trihydroxy-6-methylsulfanyl-tetrahydro-pyran-2-yl)-propyl]-amide;

4-(3-Ethoxy-propyl)-piperidine-2-carboxylic acid [2-methyl-1-(3,4,5-trihydroxy-6-methylsulfanyl-tetrahydro-pyran-2-yl)-propyl]-amide;

4-(3-Propoxy-propyl)-piperidine-2-carboxylic acid [2-methyl-1-(3,4,5-trihydroxy-6-methylsulfanyl-tetrahydro-pyran-2-yl)-propyl]-amide;

4-(3-Cyclopropylmethoxy-propyl)-piperidine-2-carboxylic acid [2-methyl-1-(3,4,5-trihydroxy-6-methylsulfanyl-tetrahydro-pyran-2-yl)-propyl]-amide;

4-[3-(2-Fluoro-ethoxy)-propyl]-piperidine-2-carboxylic acid [2-methyl-1-(3,4,5-trihydroxy-6-methylsulfanyl-tetrahydro-pyran-2-yl)-propyl]-amide;

4-[3-(3-Fluoro-propoxy)-propyl]-piperidine-2-carboxylic acid [2-methyl-1-(3,4,5-trihydroxy-6-methylsulfanyl-tetrahydro-pyran-2-yl)-propyl]-amide;

4-(4-Methoxy-butyl)-piperidine-2-carboxylic acid [2-methyl-1-(3,4,5-trihydroxy-6-methylsulfanyl-tetrahydro-pyran-2-yl)-propyl]-amide;

4-Propoxymethyl-piperidine-2-carboxylic acid [2-methyl-1-(3,4,5-trihydroxy-6-methylsulfanyl-tetrahydro-pyran-2-yl)-propyl]-amide;

4-(3-Fluoro-propoxymethyl)-piperidine-2-carboxylic acid [2-methyl-1-(3,4,5-trihydroxy-6-methylsulfanyl-tetrahydro-pyran-2-yl)-propyl]-amide;

4-Cyclohexylmethyl-piperidine-2-carboxylic acid [2-methyl-1-(3,4,5-trihydroxy-6-methylsulfanyl-tetrahydro-pyran-2-yl)-propyl]-amide;

4-(2-Propyloxyethyl)-piperidine-2-carboxylic acid [2-methyl-1-(3,4,5-trihydroxy-6-methylsulfanyl-tetrahydro-pyran-2-yl)-propyl]-amide;

4-Cyclopropylmethoxy-piperidine-2-carboxylic acid [2-methyl-1-(3,4,5-trihydroxy-6-methylsulfanyl-tetrahydro-pyran-2-yl)-propyl]-amide;

4-Fluoro-4-butyl-piperidine-2-carboxylic acid [2-methyl-1-(3,4,5-trihydroxy-6-methylsulfanyl-tetrahydro-pyran-2-yl)-propyl]-amide;

4-Fluoro-4-ethyl-piperidine-2-carboxylic acid [2-methyl-1-(3,4,5-trihydroxy-6-methylsulfanyl-tetrahydro-pyran-2-yl)-propyl]-amide;

4-Fluoro-4-(3-fluoropropyl)-piperidine-2-carboxylic acid [2-methyl-1-(3,4,5-trihydroxy-6-methylsulfanyl-tetrahydro-pyran-2-yl)-propyl]-amide;

4-Fluoro-4-(3,3-difluoropropyl)-piperidine-2-carboxylic acid [2-methyl-1-(3,4,5-trihydroxy-6-methylsulfanyl-tetrahydro-pyran-2-yl)-propyl]-amide;

4-Fluoro-4-(2,2-difluoroethoxymethyl)-piperidine-2-carboxylic acid [2-methyl-1-(3,4,5-trihydroxy-6-methylsulfanyl-tetrahydro-pyran-2-yl)-propyl]-amide;

and prodrugs, tautomers and pharmaceutically acceptable salts thereof.

Specific pro-drug compounds within the scope of this invention include the following compounds:

2-[2-Methyl-1-(3,4,5-trihydroxy-6-methylsulfanyl-tetrahydro-pyran-2-yl)-propylcarbamoyl]-4-propyl-piperidine-1-carboxylic acid 9H-fluoren-9-ylmethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid ethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

Phosphoric acid mono-(4,5-dihydroxy-6-{2-methyl-1-[(4-propyl-piperidine-2-carbonyl)-amino]-propyl}-2-methylsulfanyl-tetrahydro-pyran-3-yl)ester;

Succinic acid mono-(4,5-dihydroxy-6-{2-methyl-1-[(4-propyl-piperidine-2-carbonyl)-amino]-propyl}-2-methylsulfanyl-tetrahydro-pyran-3-yl)ester;

N-(2-Morpholin-4-yl-ethyl)-succinamic acid 4,5-dihydroxy-6-{2-methyl-1-[(4-propyl-piperidine-2-carbonyl)-amino]-propyl}-2-methylsulfanyl-tetrahydro-pyran-3-yl ester;

Dimethylamino-acetic acid 4,5-dihydroxy-6-{2-methyl-1-[(4-propyl-piperidine-2-carbonyl)-amino]-propyl}-2-methylsulfanyl-tetrahydro-pyran-3-yl ester;

1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 5-methyl-2-oxo-[1,3]dioxol-4-ylmethyl ester;

Hexadecanoic acid 4,5-dihydroxy-6-{2-methyl-1-[(4-propyl-piperidine-2-carbonyl)-amino]-propyl}-2-methylsulfanyl-tetrahydro-pyran-3-yl ester;

1-(1-Methyl-3-oxo-but-1-enyl)-4-propyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 1-acetoxy-ethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid 2-amino-3-methyl-pentanoyloxymethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid piperidine-4-carbonyloxymethyl ester;

1-(Propionylamino-methyl)-4-propyl-piperidine-2-carboxylic acid [2-methyl-1-(3,4,5-trihydroxy-6-methylsulfanyl-tetrahydro-pyran-2-yl)-propyl]-amide;

N-{2-[2-Methyl-1-(3,4,5-trihydroxy-6-methylsulfanyl-tetrahydro-pyran-2-yl)-propylcarbamoyl]-4-propyl-piperidin-1-ylmethyl}-nicotinamide;

1-(2-Amino-propionyl)-4-propyl-piperidine-2-carboxylic acid [2-methyl-1-(3,4,5-trihydroxy-6-methylsulfanyl-tetrahydro-pyran-2-yl)-propyl]-amide;

1-(2-Amino-3-phenyl-propionyl)-4-propyl-piperidine-2-carboxylic acid [2-methyl-1-(3,4,5-trihydroxy-6-methylsulfanyl-tetrahydro-pyran-2-yl)-propyl]-amide;

1-(2-Amino-3-methyl-pentanoyl)-4-propyl-piperidine-2-carboxylic acid [2-methyl-1-(3,4,5-trihydroxy-6-methylsulfanyl-tetrahydro-pyran-2-yl)-propyl]-amide;

1-(2-Amino-3-methyl-butyryl)-4-propyl-piperidine-2-carboxylic acid [2-methyl-1-(3,4,5-trihydroxy-6-methylsulfanyl-tetrahydro-pyran-2-yl)-propyl]-amide;

1-(1-Methyl-1,4-dihydro-pyridine-3-carbonyl)-4-propyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 1-methyl-1,2,3,6-tetrahydro-pyridin-4-yl ester;

and tautomers and pharmaceutically acceptable salts thereof.

The compounds, tautomers, prodrugs and pharmaceutically acceptable salts thereof, as defined herein, may have activity against bacteria, protozoa, fungi, and parasites.

In another aspect, this invention provides pharmaceutical compositions comprising a pharmaceutically acceptable carrier and a therapeutically effective amount of a compound defined herein. The pharmaceutical compositions of the present invention may further comprise one or more additional antibacterial agents. One or more of the antibacterial agents may be active against gram negative bacteria. One or more of the antibacterial agents may be active against gram positive bacteria.

In one of its method aspects, this invention is directed to a method for the treatment of a microbial infection in a mammal comprising administering to the mammal a therapeutically effective amount of a compound of this invention. The compound of this invention may be administered to the mammal orally, parenterally, transdermally, topically, rectally, or intranasally.

In another of its method aspects, this invention is directed to a method for the treatment of a microbial infection in a mammal comprising administering to the mammal a pharmaceutical composition comprising a therapeutically effective amount of a compound of this invention. The pharmaceutical compositions of the present invention may further comprise one or more additional antibacterial agents, one of which may be active against gram negative bacteria and/or one of which may be active against gram positive bacteria. The pharmaceutical composition may be administered to the mammal orally, parenterally, transdermally, topically, rectally, or intranasally.

In a preferred embodiment, the microbial infection being treated is a gram positive bacterial infection. In an additional embodiment, the infection may be a gram negative bacterial infection. In a further embodiment, the infection may be a mycobacteria infection, a mycoplasma infection, or a chlamydia infection.

In yet another aspect, the present invention provides novel intermediates and processes for preparing compounds of formula (I), (II), (III) and (IV).

DETAILED DESCRIPTION OF THE INVENTION

As described above, this invention relates to lincomycin derivatives that exhibit antibacterial activity, in particular gram positive antibacterial activity. However, prior to describing this invention in further detail, the following terms will first be defined.

Definitions

Unless otherwise stated, the following terms used in the specification and claims have the meanings given below.

"Acyl" means the group —C(O)R' wherein R' is alkyl, alkenyl, alkynyl, aryl, substituted aryl, heteroaryl, or substituted heteroaryl.

"Acyloxy" means the group —C(O)OR', wherein R' is alkyl, alkenyl, alkynyl, aryl, substituted aryl, heteroaryl, or substituted heteroaryl.

"Alkenyl" means a linear unsaturated monovalent hydrocarbon radical of two to eight carbon atoms or a branched monovalent hydrocarbon radical of three to eight carbon atoms containing at least one double bond, (—C=C—). Examples of alkenyl groups include, but are not limited to, allyl, vinyl, 2-butenyl, and the like.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxyalkoxy" refers to the group alkyl-O-alkylene-O—, wherein alkyl is as defined herein.

"Alkyl" means a linear saturated monovalent hydrocarbon radical of one to eight carbon atoms or a branched saturated monovalent hydrocarbon radical of three to eight carbon atoms. Examples of alkyl groups include, but are not limited to, groups such as methyl, ethyl, n-propyl, isopropyl, n-butyl, isobutyl, sec-butyl, t-butyl, and the like.

"Alkylene" means a linear divalent hydrocarbon radical of one to eight carbon atoms or a branched divalent hydrocarbon group of three to eight carbon atoms. Examples of alkylene groups include, but are not limited to, methylene, ethylene, 2-methylpropylene, and the like.

"Alkylthio" refers to the group "alkyl-S—" which includes, by way of example, methylthio, butylthio, and the like.

"Alkynyl" means a linear monovalent hydrocarbon radical of two to eight carbon atoms or a branched monovalent hydrocarbon radical of three to eight carbon atoms containing at least one triple bond, (—C≡C—). Examples of alkynyl groups include, but are not limited to, ethynyl, propynyl, 2-butynyl, and the like.

"Amino" or "substituted nitrogen" refers to the group "—$NR_aR_b$" wherein $R_a$ and $R_b$ are independently H, alkyl, haloalkyl, alkenyl, cycloalkyl, substituted cycloalkyl, aryl, substituted aryl, heteroaryl, or substituted heteroaryl.

"Aminocarboxyalkyl" means a group "—$R_cC(O)NR_aR_b$" where $R_c$ is an alkylene, as defined above, and $R_a$ and $R_b$ are as defined above.

"Aryl" means a monovalent monocyclic or bicyclic aromatic carbocyclic group of six to fourteen ring atoms. Examples include, but are not limited to, phenyl, naphthyl, and anthryl. The aryl ring may be optionally fused to a 5-, 6-, or 7-membered monocyclic non-aromatic ring optionally containing 1 or 2 heteroatoms independently selected from oxygen, nitrogen, or sulfur, the remaining ring atoms being C where one or two C atoms are optionally replaced by a carbonyl. Representative aryl groups with fused rings include, but are not limited to, 2,5-dihydro-benzo[b]oxepinyl, 2,3-dihydrobenzo[1,4]dioxanyl, chromanyl, isochromanyl, 2,3-dihydrobenzofuranyl, 1,3-dihydroisobenzofuranyl, benzo[1,3]dioxolyl, 1,2,3,4-tetrahydroisoquinolinyl, 1,2,3,4-tetrahydroquinolinyl, 2,3-dihydro-1H-indolyl, 2,3-dihydro-1H-isoindolyl, benzimidazole-2-onyl, 2-H-benzoxazol-2-onyl, and the like.

"Carbonyl" means the group "C(O)."

"Carboxy" means the group "C(O)O."

"Cyanoalkyl" refers to an alkyl, wherein alkyl is as defined above, substituted with one or more cyano (—CN) groups provided that if two cyano groups are present they are not both on the same carbon atom. Examples of cyanoalkyl groups include, for example, cyanomethyl, 2-cyanoethyl, 2-cyanopropyl, and the like.

"Cycloalkyl" refers to cyclic alkyl groups of from 3 to 20 carbon atoms having a single or multiple cyclic rings including, by way of example, cyclopropyl, cyclobutyl, cyclopentyl, cyclooctyl, adamantanyl, and the like. Cycloalkyl groups of the present invention also include fused multicyclic rings wherein one or more of the rings within the multicyclic ring system are aromatic, as long as the point of attachment to the core or backbone of the structure is on the non-aromatic ring, e.g., fluorenyl.

"Cycloalkylalkyl" means a group —$R_cR_d$ where $R_c$ is an alkylene group and $R_d$ is a cycloalkyl group, as defined above. Examples include, but are not limited to, cyclopropylmethylene, cyclohexylethylene, and the like.

"Halo" or "Halogen" means fluoro, chloro, bromo, or iodo.

"Haloalkyl" means an alkyl, wherein alkyl is as defined above, substituted with one or more, preferably one to 6, of the same or different halo atoms. Examples of haloalkyl groups include, for example, trifluoromethyl, 3-fluoropropyl, 2,2-dichloroethyl, and the like.

"Heteroaryl" means a monovalent monocyclic or bicyclic aromatic radical of 5 to 10 ring atoms containing one, two, or three ring heteroatoms selected from N, O, or S, the remaining ring atoms being C. Representative examples include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and the like.

"Heterocycle" or "heterocyclic" refers to a saturated or unsaturated group having a single ring or multiple condensed rings, from 1 to 10 carbon atoms and from 1 to 4 heteroatoms selected from the group consisting of nitrogen, sulfur, or oxygen within the ring, wherein, in fused ring systems one or more of the rings can be aryl or heteroaryl as defined herein. Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

Heterocycles may be optionally substituted with from one to three substituents selected from the group consisting of alkyl, alkenyl, alkynyl, halo, alkoxy, acyloxy, amino, hydroxyl, carboxy, cyano, oxo, nitro, and alkylthio as these terms are defined herein.

"Hydroxy" or "hydroxyl" means the group —OH.

"Hydroxyalkyl" refers to an alkyl, wherein alkyl is as defined above substituted with one or more —OH groups provided that if two hydroxy groups are present they are not both on the same carbon atom. Examples of hydroxyalkyl groups include, for example, hydroxymethyl, 2-hydroxyethyl, 2-hydroxypropyl, and the like.

"Mammal" refers to all mammals including humans, livestock, and companion animals.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

"Pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

"Pharmaceutically acceptable salt" of a compound means a salt that is pharmaceutically acceptable and that possesses the desired pharmacological activity of the parent compound. Such salts include, but are not limited to, (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth metal ion, or an aluminum ion; or coordinates with an organic base such as ethanolamine, diethanolamine, triethanolamine, tromethamine, N-methylglucamine, and the like.

"Prodrugs" mean any compound which releases an active parent drug according to a compound of the subject invention in vivo when such prodrug is administered to a mammalian subject. Prodrugs of a compound of the subject invention are prepared by modifying functional groups present in a compound of the subject invention in such a way that the modifications may be cleaved in vivo to release the parent compound. Prodrugs include compounds of the subject invention wherein a hydroxy, sulfhydryl or amino group in the compound is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of the subject invention, and the like. Specific examples include —C(O)O-alkylene-cycloalkyl, —C(O)O-alkylene-substituted cycloalkyl, —C(O)O-alkyl, —C(O)O-substituted alkyl, —C(O)O-aryl, —C(O)O-substituted aryl, —C(O)O-heteroaryl, —C(O)O-substituted heteroaryl, —[C(O)O]$_p$-alkylene-heterocycle, —[C(O)O]$_p$-alkylene-substituted heterocycle, wherein p is 0 or 1. In one embodiment, the —C(O)O-substituted alkyl does not include the following:

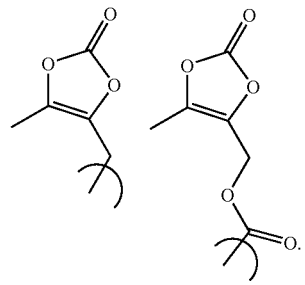

"Substituted alkyl" means an alkyl group, as defined above, in which one or more of the hydrogen atoms has been replaced by a halogen (i.e., Cl, Br, F, or I), oxygen, hydroxy, amine (primary), amine (secondary-amine substituted by alkyl above), amine (tertiary-amine substituted by alkyl as above), sulfur, —SH, phenyl, substituted phenyl, cycloalkyl, alkoxy, substituted alkoxy. Examples of substituted alkyl groups include, but are not limited to, 1-fluoroethyl, 1-chloroethyl, 2-fluoroethyl, 2-chloroethyl, 1-bromopropyl, 2-iodopropyl, 1-chlorobutyl, 4-fluorobutyl, 4-chlorobutyl, 2-cyclopropyl-ethyl, 3-cyclobutyl-propyl, 4-cyclopentyl-butyl, and 4-cyclohexyl-butyl.

"Substituted alkoxy" means substituted alkyl-O—, wherein substituted alkyl is as defined herein.

"Substituted aryl" means an aryl ring substituted with one or more substituents, preferably one to three substituents selected from the group consisting of alkyl, alkenyl, alkynyl, halo, alkoxy, acyloxy, amino, hydroxy, carboxy, cyano, nitro, alkylthio, and thioalkyl. The aryl ring may be optionally fused to a 5-, 6-, or 7-membered monocyclic non-aromatic ring optionally containing 1 or 2 heteroatoms independently selected from oxygen, nitrogen, or sulfur, the remaining ring atoms being carbon where one or two carbon atoms are optionally replaced by a carbonyl.

"Substituted cycloalkyl" means a cycloalkyl substituted with an alkyl group, wherein alkyl is as defined above or a group as defined above for substituted alkyl.

"Substituted heteroaryl" means a heteroaryl ring, wherein heteroaryl is as defined above, substituted with one or more substituents, preferably one to three substituents selected from the group consisting of alkyl, alkenyl, alkynyl, halo, alkoxy, acyloxy, amino, hydroxy, carboxy, cyano, nitro, alkylthio, and thioalkyl, wherein said substituents are as defined herein.

"Substituted oxygen" refers to the group "—O—R$^d$" wherein R$^d$ is alkyl, haloalkyl, alkenyl, cycloalkyl, substituted cycloalkyl, aryl, substituted aryl, heteroaryl, or substituted heteroaryl, wherein said substituents are as defined herein.

"Substituted phenyl" means a phenyl ring wherein one or more of the hydrogen atoms has been replaced by a halogen, hydroxy, alkyl, amine (primary, secondary, and tertiary with the latter two alkyl substituted), —SH, and phenyl. Representative examples include, but are not limited to, p-bromophenyl, m-iodophenyl, o-chlorophenyl, p-ethylphenyl, m-propylphenyl, o-methylphenyl, and p-octylphenyl.

"Thioalkyl" refers to an alkyl, wherein alkyl is as defined above, substituted with one or more —SH groups provided that if two hydroxy groups are present they are not both on the same carbon atom. Examples of thioalkyl groups include, for example, thiomethyl, 2-thioethyl, 2-thiopropyl, and the like.

"Therapeutically effective amount" means the amount of a compound or composition that, when administered to a mammal for treating a disease, is sufficient to effect such treatment for the disease. The "therapeutically effective amount" will vary depending on the compound or composition, the disease and its severity and the age, weight, etc., of the mammal to be treated.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

"Tautomer" refers to an isomer in which migration of a hydrogen atom results in two or more structures.

The compounds of the present invention are generally named according to the IUPAC or CAS nomenclature system. Abbreviations that are well known to one of ordinary skill in the art may be used (e.g. "Ph" for phenyl, "Me" for methyl, "Et" for ethyl, "Bn" for benzyl, "h" for hour and "rt" for room temperature).

General Synthetic Schemes

Compounds of this invention can be made by the methods depicted in the reaction schemes shown below.

The starting materials and reagents used in preparing these compounds are either available from commercial suppliers such as Toronto Research Chemicals (North York, ON Canada), Aldrich Chemical Co. (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991), Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

As it will be apparent to those skilled in the art, conventional protecting groups may be necessary to prevent certain functional groups from undergoing undesired reactions. Suitable protecting groups for various functional groups, as well as suitable conditions for protecting and deprotecting particular function groups are well known in the art. For example, numerous protecting groups are described in T. W. Greene and G. M. Wuts, Protecting Groups in Organic Synthesis, Second Edition, Wiley, New York, 1991, and references cited therein.

The starting materials and the intermediates of the reaction may be isolated and purified if desired using conventional techniques, including but not limited to filtration, distillation, crystallization, chromatography, and the like.

Such materials may be characterized using conventional means, including physical constants and spectral data.

The compounds of this invention will typically contain one or more chiral centers. Accordingly, if desired, such compounds can be prepared or isolated as pure stereoisomers. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Preparation of Compounds of Formula (I)

In general, to prepare the compounds of formula (I) of the present invention, an appropriately 7-substituted lincosamine intermediate and an appropriately substituted pyrrolidinyl or piperidyl carboxylic acid are condensed under reactive conditions, preferably in an inert organic solvent, in the presence of a coupling reagent and an organic base. This reaction can be performed with any number of known coupling reagents, such as O-(7-azabenzotriazol-1-yl)-N,N,N',N'-tetramethyluronium hexafluorophosphate (HATU), 1-hydroxybenzotriazole hydrate (HOBT) with carbodiimides, isobutyl chloroformate, diphenylphosphoryl azide (DPPA), and the like. Suitable organic bases include diisopropylethylamine (DIEA), triethylamine (TEA), pyridine, N-methyl morpholine, and the like. Suitable inert organic solvents which can be used include, for example, N,N-dimethylformamide, acetonitrile, dichloromethane, and the like. This reaction is typically conducted using an excess of carboxylic acid to lincosamine at temperatures in the range of about 0° C. to about 50° C. The reaction is continued until completion, which typically occurs in from about 2 to 12 h.

Appropriately 7-substituted lincosamine intermediates, as defined in the present invention (i.e., $R^2/R^3$), are synthesized by methods well known to those of skill in the art from methyl 6-amino-6,8-dideoxy-1-thio-erythro-β-D-galactooctopyranoside, which can be prepared as described by Hoeksema, et al., Journal of the American Chemical Society, 1967, 89 2448–2452. Illustrative syntheses for 7-substituted lincosamine intermediates are shown below in Schemes 1–5.

Appropriately substituted pyrrolidinyl or piperidyl carboxylic acid intermediates, as defined in the present invention (i.e., $R^9$), are also synthesized by methods well known to those of skill in the art from prolines and pyridines. The prolines and pyridines that can be used in the synthesis of the carboxylic acid intermediates of the present invention include, for example, 4-oxoproline and 4-substituted pyridines. The prolines and pyridines used in the synthesis are commercially available from vendors such as Aldrich and Sigma. Alternatively, these prolines and pyridines can be prepared by methods well known in the art. Illustrative syntheses for appropriately substituted pyrrolidinyl or piperidyl carboxylic acid intermediates are shown below in Schemes 6–10.

Scheme 1 below illustrates a general synthesis of a lincosamine intermediate 1c wherein P is an N-protecting group, preferably either Cbz or Boc, and $R^1$ is as defined for formula (I).

Scheme 1.
General synthesis of lincosamine intermediate 1c.

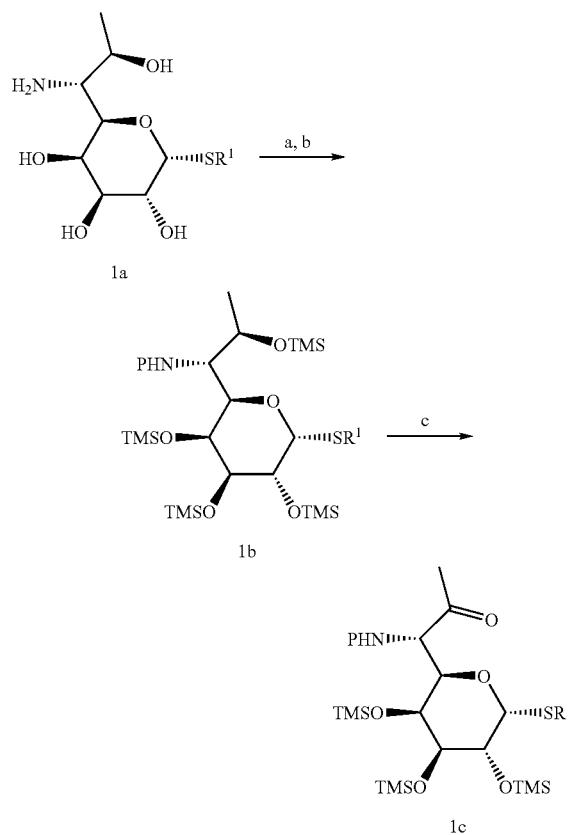

(a) N-Protection (Boc, Cbz); (b) O-silyl protection (TMS); (c) Swern oxidation.

As shown in Scheme 1, methyl 6-amino-6,8-dideoxy-1-thio-erythro-β-D-galacto-octopyranoside, 1a, is prepared as described by Hoeksema, et al., Journal of the American Chemical Society, 1967, 89 2448–2452. The amino functional group and the hydroxy functional groups of the product 1a are then protected with suitable protecting groups. Suitable N-protecting groups can be formed by the addition of di-t-butyldicarbonate, N-(benzyloxycarbonyloxy)succinimide, and the like. The hydroxy groups can be protected as silyl ethers. The hydroxyl group can be converted to trimethylsilyl (TMS) ethers by reaction with N,O-bis-(trimethylsilyl)trifluoroacetamide in the presence of an appropriate organic base such as triethylamine (TEA) or trimethylsilyl chloride in the presence of an organic base such as triethylamine. The N-protection is typically accomplished before the O-protection. Chromatography of the crude product on silica after evaporation of the solvent provides the protected product 1b.

The 7-O-trimethylsilyl group of 1b is chemoselectively deprotected and oxidized to provide the 7-keto-lincosamine derivative 1c. This selective transformation is performed by addition of the protected product 1b to dimethylsulfoxide and oxalyl chloride in an inert organic solvent such as dichloromethane followed by an appropriate organic base such as triethylamine. Alternatively, the transformation may be performed by addition of 1b to dimethylsulfoxide and an appropriate activating agent such as trifluoroacetic anhydride in an inert organic solvent. The reaction is typically conducted at temperatures in the range of approximately −70° C. to −80° C. The resulting reaction mixture is stirred at the low temperature and is then allowed to warm to approximately −50° C. The reaction is maintained at this second temperature for approximately 1 h to 3 h. To the reaction mixture is added a suitable organic base, such as TEA, pyridine, and the like. The reaction mixture is appropriately worked up to provide the product 1c. The general class of conditions used in the transformation of 1b to 1c is known in the art as Swern oxidation conditions.

Scheme 2 below illustrates a general synthesis of a lincosamine intermediate 2b wherein P is an N-protecting group, preferably either Cbz or Boc, $R^1$ is as defined for formula (I), and one of $R^2$ and $R^3$ is hydrogen and the other is as defined for formula (I).

Scheme 2.
General synthesis of lincosamine intermediate 2b.

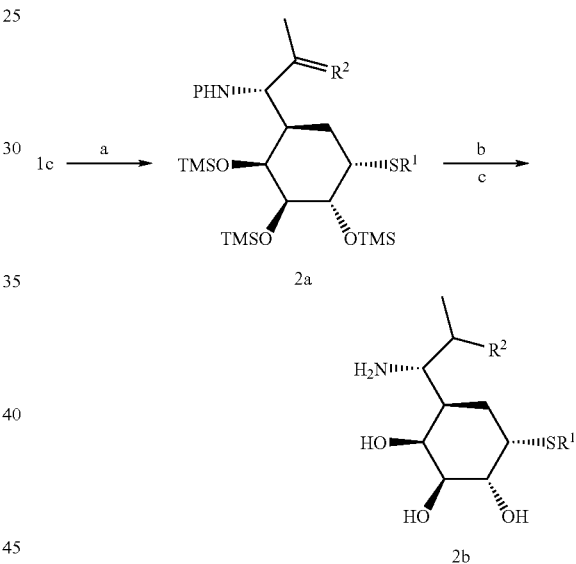

(a) Wittig olefination ($R^2PPh_3^+X^-$, $R^2PO(OEt)_2$, base, solvent); (b) and (c) $H_2$/Pd, Global de-protection As shown in Scheme 2, a keto-lincosamine intermediate 1c is reacted to form an alkene using the Wittig or Horner-Wadsworth-Emmons reaction. In this reaction, a suitable phosphonium salt or phosphonate is deprotonated using a strong base to form a phosphorus ylide. Suitable phosphonium salts which can be used are alkyltriphenylphosphonium halides, which can be prepared by the reaction of triphenylphosphine and an alkyl halide. Suitable phosphorous compounds include, for example, methyltriphenylphosphonium bromide, diethyl(cyanomethyl)phosphonate and the like. Suitable strong bases which can be used to form the ylide include organolithium reagents, potassium tert-butoxide, and the like. The formation of the phosphorus ylide is typically conducted under an inert atmosphere, such as $N_2$, in an inert organic solvent such as toluene, THF, and the like, at low temperatures.

After formation of the phosphorus ylide, the product 1c is added to the reaction. The reaction conveniently can be performed at temperatures between −40° C. and room temperature and is stirred until completion, typically 1 to 4 h. The resulting organic solution is worked-up and chromatography of the crude product on silica provides the alkene product 2a.

Optionally, the product of 2a may be purified using conventional techniques, such as chromatography and said purified product may be used in the subsequent coupling reaction to yield vinyl lincosamine derivatives of the present invention.

The product 2a is then hydrogenated to provide the saturated product 2b. The hydrogenation is typically performed in a polar organic solvent such as methanol, ethanol, and the like, using 10% palladium on carbon in a Parr bottle. The bottle is purged, and charged with $H_2$ to approximately 50 to 70 psi and shaken until completion, typically approximately 12 to 24 h. The resulting reaction mixture is filtered, e.g., through celite, and rinsed with a polar organic solvent such as methanol. The organic solution is worked up by transferring to a resin funnel containing dry, washed Dowex™ 50w-400x $H^+$ form and shaken. After washing the resin with methanol and water, the product 2b is eluted from the resin by washing with 5% TEA in MeOH. The product can also be purified by silica gel column chromatography.

Scheme 3 illustrates a general synthesis of a lincosamine intermediate 3b wherein P is an N-protecting group, preferably either Cbz or Boc, $R^1$ is as defined for formula (I), and one of $R^2$ or $R^3$ is alkyl and the other is —OH.

Scheme 3.
General synthesis of lincosamine intermediate 3b.

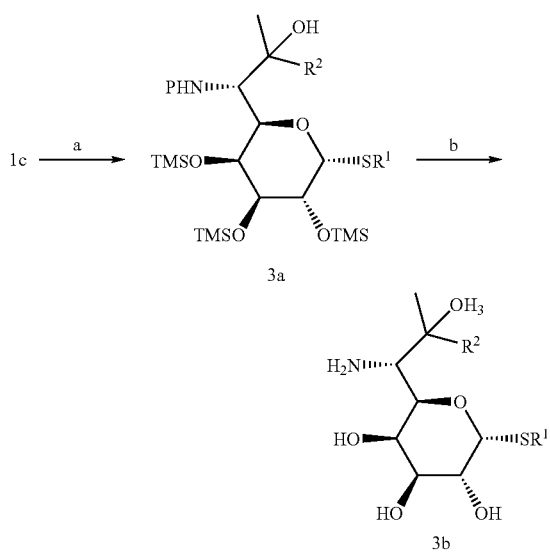

(a) $R^2M$ (carbon nucleophile); (b) (i) TMS de-protection ($H^+$ or $F-$) and (ii) N-deprotection As shown in Scheme 3, suitable carbon nucleophiles add to 7-ketolincosamine intermediate 1c in suitable inert organic solvents to provide a 7-hydroxy lincosamine intermediate 3b. Suitable carbon nucleophiles include methylmagnesium chloride, diethyl zinc, sodium acetylide and the like and suitable inert organic solvents which can be used include THF, diethyl ether, toluene, and the like. The reaction is typically conducted at reduced temperatures, approximately at 0° C., for about 3 to 5 h. The reaction is then quenched with a saturated aqueous acidic solution, such as saturated aqueous $NH_4Cl/H_2O$. The quenched mixture is then worked up and can be purified by chromatography to provide the product 3b.

Scheme 4 below illustrates a general synthesis of a lincosamine intermediate 4b wherein P is a N-protecting group, preferably Boc, $R^1$ is as defined for formula (I), and $R^2/R^3$ is an oxime (=$NOR^7$), wherein $R^7$ is as defined for formula (I).

Scheme 4.
General synthesis of 7-oxime-lincosamines 4b.

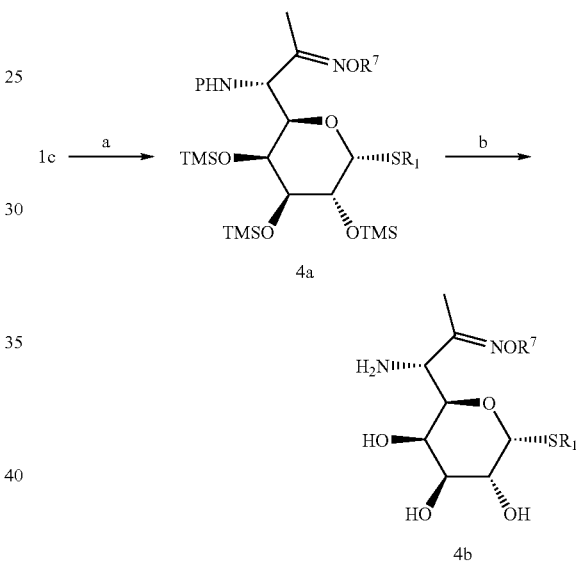

As shown in Scheme 4, the lincosamine intermediate 1c is converted to the oxime by stirring in the presence of a suitable reagent such as O-trimethylsilylhydroxylamine, O-alkylhydroxylamine hydrochloride (for example, O-methylhydroxylamine hydrochloride), and the like. The reaction is typically conducted in a polar organic solvent such as methanol. The reaction conveniently can be conducted at rt in approximately 8 to 24 h. The solvent is removed to provide the N-protected product 4a.

Removal of the protecting group can be carried out with acids, such as trifluoroacetic acid (TFA), hydrochloric acid, p-toluenesulfonic acid, and the like, in an inert organic solvent such as dichloromethane, dichloroethane, dioxane, THF, and the like. The removal is typically conducted at low temperatures, e.g., 0° C., and then gradually allowed to warm to room temperature to provide the product 4b.

Scheme 5 below illustrates a general synthesis of a lincosamine intermediate 5b wherein $R^2$ and $R^3$ are both fluorine, P is an N-protecting group, preferably Cbz or Boc, and $R^1$ is as defined for formula (I).

Scheme 5.
General synthesis of 7-deoxy-7,7-difluorolincosamines 5b.

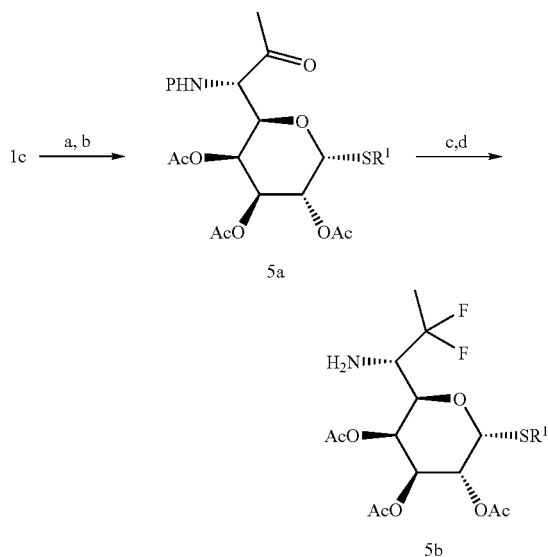

(a) F⁻; (b) Ac₂O, pyridine, DMAP; (c) DAST; (d) TFA

As shown in Scheme 5, the lincosamine intermediate 1c is contacted with a suitable fluoride in an inert organic solvent. Suitable fluorides which can be used include tetrabutylammonium fluoride, Amberlite resin A-26 F form, HF.pyridine and the like. Suitable inert organic solvents include THF, acetonitrile, dichloromethane, dioxane, and the like. The reaction conveniently can be conducted at rt in about 1 to 2 h. The product (not shown) can be purified on a silica gel column.

The O-protecting groups on the product obtained from the column are converted by contact with acetic anhydride and dimethylaminopyridine (DMAP) in a suitable mixture of an inert organic solvent and an organic base, such as, for example, dichloromethane and pyridine. The reaction conveniently can be conducted at rt in approximately 6 to 12 h. The product can be purified on silica gel column to provide product 5a.

The product 5a is contacted with a suitable fluorinating reagent and then the N-protecting group is removed to provide the product 5b. Suitable fluorinating reagents which can be used include, for example, dimethylaminosulfurtrifluoride, [bis(2-methoxyethyl)amino]sulfurtrifluoride, and the like. The reaction is typically conducted in an inert organic solvent such as dichloromethane, ethylacetate, THF, and the like at room temperature in approximately 6 to 12 h.

Removal of the protecting group can be carried out with acids, such as trifluoroacetic acid (TFA), hydrochloric acid, p-toluenesulfonic acid, and the like, in an inert organic solvent such as dichloromethane, dichloroethane, dioxane, THF, and the like. The removal is typically conducted at low temperatures, e.g., 0° C., and then gradually allowed to warm to room temperature to provide the product 5b.

Scheme 6 below illustrates a general synthesis of a proline intermediate 6c wherein $R^9$ is as defined for formula (I).

Scheme 6.
General synthesis of cis/trans $R^9$-proline intermediate mixtures 6c.

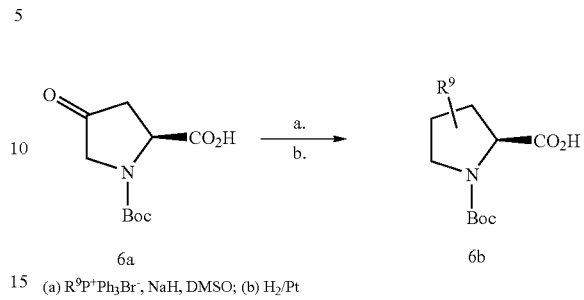

(a) $R^9P^+Ph_3Br^-$, NaH, DMSO; (b) $H_2$/Pt

As shown in Scheme 6, the product 6c is prepared as described in Magerlein, Journal of Medicinal Chemistry 1972, 15, 1255–1259. Compound 6a is commercially available from vendors such as RSP (Scientific Research Consortium, Inc.). Alternatively, 6a can be prepared from commercially available protected hydroxy prolines by methods well known in the art. See, e.g., Demange, et al., Tetrahedron Letters 1998, 39, 1169–1172

Scheme 7 below illustrates a general synthesis of trans-$R^9$-proline intermediates 7d, wherein $R^9$ is alkyl or substituted alkyl.

Scheme 7.
General synthesis of trans-alkylprolines 7d.

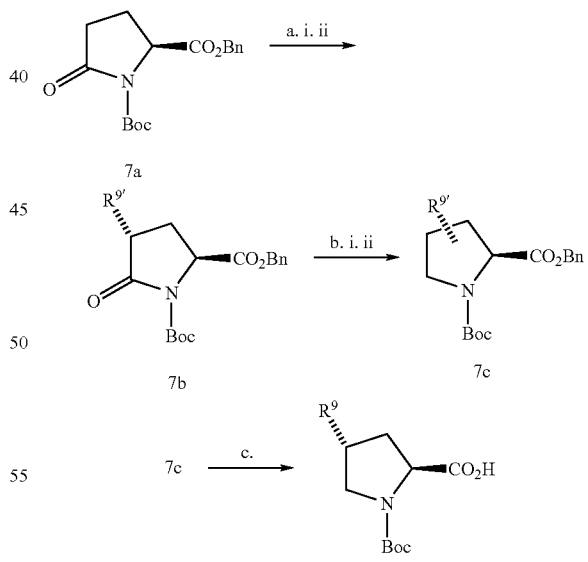

(a) (i) LiHMDS, THF -78° C., (ii) bromoalkene; (b) (i) LiBHEt₃, THF -78° C., (ii) BF₃OEt₂, Et₃SiH; (c) H₂Pd/C.

(a) (i) LiHMDS, THF -78° C., (ii) bromoalkene; (b) (i) LiBHEt₃, THF -78° C., (ii) BF₃OEt₂, Et₃SiH; (c) H₂, Pd/C.

As shown in Scheme 7, a protected 4-oxoproline, 7a, is enolated with a suitable enolation agent and then alkylated with a suitable alkylating agent in an inert organic solvent to provide a lactam 7b (wherein $R^{9'}$ is alkenyl), as described in the literature procedure by Zhang, et al., J.A.C.S. 1998, 120 3894–3902. Compound 7a is commercially available from vendors such as Bachem. Alternatively, 7a can be prepared by methods well known in the art. Suitable enolating agents include LiHMDS, LiN(iPr)$_2$, and the like, and suitable alkylating agents include allylic and benzylic bromides, for example, 4-bromo-2-methyl-2-butene and cis-1-bromo-2-pentene, allylbromide, and the like.

The lactam 7b is reduced using a suitable reducing agent to provide a pyrrolidine 7c, wherein $R^{9'}$ is alkenyl. The reduction is preformed by a two-step sequence involving superhydride reduction of the lactam to the hemiaminal and the subsequent reduction of the hemiaminal. Suitable reducing agents which can be used include $Et_3SiH/BF_3.OEt_2$, $Et_3SiH/TiCl_4$, and the like.

The pyrrolidine 7c is then hydrogenated to simultaneously remove the unsaturation in the $R^{9'}$ substituent and remove the benzyl protecting group from the carboxylic acid to provide the product 7d. The hydrogenation is typically performed in a polar organic solvent such as methanol, ethanol, and the like, using 10% palladium on carbon in a Parr bottle. The bottle is purged, and charged with $H_2$ to approximately 50 to 70 psi and shaken until completion, typically approximately 5 to 24 h. The reaction mixture is filtered, e.g., through a celite pad, and washed with a polar organic solvent, such as methanol. Evaporation of the combined washings and filtrate affords the product 7d, wherein $R^9$ is an alkyl or substituted alkyl.

Scheme 8 below illustrates a general synthesis of trans-$R^9$-proline intermediates 8c, wherein $R^9$ is alkyl or substituted alkyl.

As shown in Scheme 8, the product 7d is ozonolized to provide the aldehyde 8a. The ozonolysis reaction is typically conducted in an anhydrous inert organic solvent, such as dichloromethane, dioxane, THF, and the like, at low temperatures, e.g., −78° C. followed by quenching of the reaction with a reducing agent such as DMS, Ph$_3$P.

The aldehyde, 8a, is reacted with a suitable phosphonium salt in the presence of a strong base in an inert organic solvent. Suitable phosphonium salts which can be used include, for example, fluorobenzyl phosphonium chloride, 4-chlorobenzyl phosphonium chloride, dibromofluoromethane and triphenylphosphine, and the like. Suitable bases which can be used include potassium t-butoxide, organolithium reagents, and activated zinc. Suitable organic solvents which can be used include toluene, THF, dimethylacetamide, and the like. The reaction is typically conducted in an inert atmosphere, such as under nitrogen, with vigorous stirring. The reaction is typically conducted at rt to approximately 110° C. for 1 to 2 h. The resulting reaction mixture is appropriately worked-up and can be purified by chromatography to provide 8b (wherein $R^{9'}$ is alkenyl).

The product 8b is then hydrogenated to provide the product 8c. The hydrogenation is typically performed in a polar organic solvent such as methanol, ethanol, and the like, using 10% Palladium on carbon in a Parr bottle. The bottle is purged, and charged with $H_2$ to approximately 40 to 70 psi and shaken until completion, typically approximately 4 to 24 h. The reaction mixture is filtered, e.g., through a celite pad and washed several times with a polar organic solvent, such as methanol. Evaporation of the combined washings and filtrate affords the product 8c, wherein $R^9$ is an alkyl or substituted alkyl.

Scheme 9 below illustrates a general synthesis of trans-$R^9$-proline intermediates 9d, wherein $R^9$ is substituted alkyl wherein X is halo.

Scheme 8.
General synthesis of trans-$R^9$-substituted prolines 8c, wherein $R^9$ is alkyl or substituted alkyl.

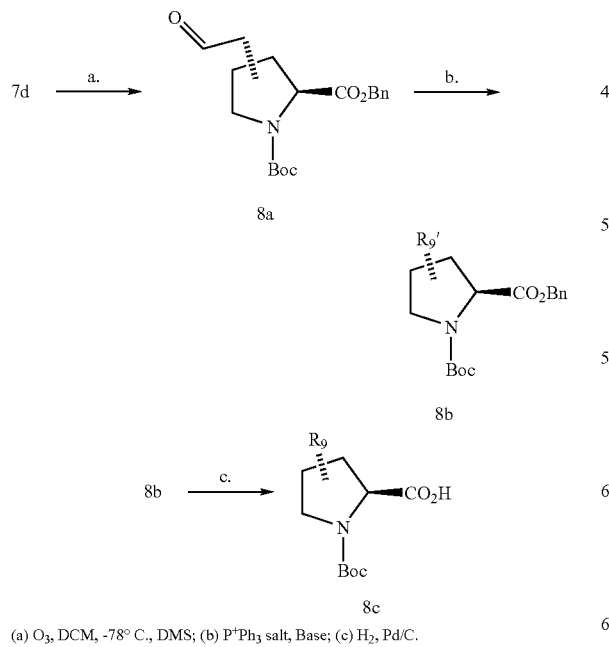

(a) O$_3$, DCM, -78° C., DMS; (b) P$^+$Ph$_3$ salt, Base; (c) H$_2$, Pd/C.

Scheme 9.
Example synthesis of trans-halosubstituted alkyl prolines 9d.

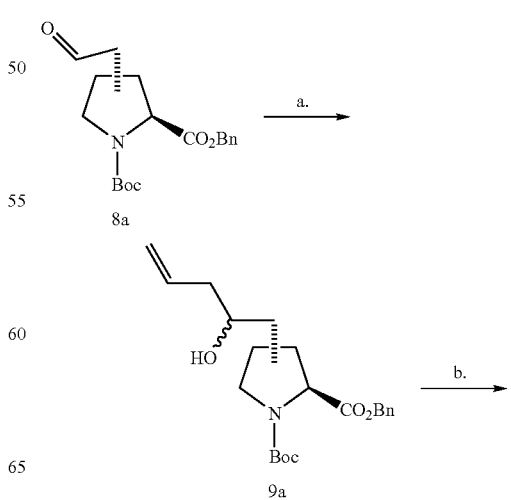

-continued

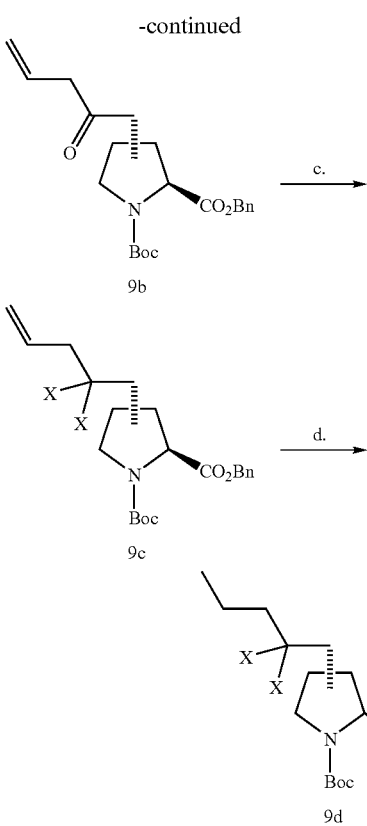

(a) Tetraallyltin, BF$_3$·Et$_2$O; (b) DMSO, (COCl)$_2$, TEA; (c) DAST (d)10%Pd/C, H$_2$ As shown in Scheme 9, aldehyde, 8a, is reduced and alkylated using a suitable reagent in an inert organic solvent to provide a hydroxyalkenyl substituted proline, 9a. Suitable reagents to reduce and alkylate the aldehyde include tetraallyltin/boron trifluoride etherate, allylTMS/boron trifluoride etherate and suitable inert organic solvents which can be used include THF, dichloromethane, and the like. The reaction is typically conducted at low temperatures, e.g., 0° C., for approximately 1 to 2 h. To the reaction mixture is added a solution of a suitable fluoride salt in water, for example potassium fluoride in water, followed by the addition of methanol. The reaction mixture is filtered, for example, over celite. The product can be purified by chromatography to provide 9a.

The hydroxyalkenyl substituted proline, 9a, is oxidized to the ketone by contact with a suitable oxidizing agent in an inert organic solvent. Suitable oxidizing agents include oxalyl chloride/DMSO, Dess Martin periodinane, and the like. Suitable inert organic solvents include dichloromethane, and the like. The reaction is typically conducted at reduced temperatures, e.g., −72° C. to −50° C., for approximately 30 min to 2 h. To the reaction mixture is added a suitable organic base, such as triethylamine. The reaction mixture is worked up to provide product 9b.

The keto-substituted product 9b is halogenated by contact with a suitable halogenating agent in an inert organic solvent. Suitable halogenating agents which can be used include diethylaminosulfur trifluoride, [bis(2-methoxyethyl) amino]sulfur trifluoride, and the like. Suitable inert organic solvents which can be used include dichloromethane, ethyl acetate, THF, and the like. The reaction is typically conducted at low temperatures in the range of approximately −30° C. to −78° C. The reaction mixture is gradually allowed to warm to rt and stirred at rt until completion, typically in 6 to 12 h. The reaction mixture is worked up and can be purified by chromatography to provide 9c.

The product 9c is then hydrogenated to provide the product 9d. The hydrogenation is typically performed in a polar organic solvent such as methanol, ethanol, and the like, using 10% palladium on carbon in a Parr bottle. The bottle is purged, and charged with H$_2$ to approximately 40 to 70 psi and shaken until completion, typically approximately 4 to 24 h. The reaction mixture is filtered, e.g., through a celite pad and washed several times with a polar organic solvent, such as methanol. Evaporation of the combined washings and filtrate affords the product 9d.

Scheme 10 below illustrates a general synthesis, as described in Shuman, Journal of Organic Chemistry. 1990, 55, 741–750, of substituted pyridine carboxylic acid intermediates 10b, wherein R$^9$ is as defined for formula (I).

Scheme 10.
General synthesis of substituted pyridin-2-yl carboxylic acids 10b.

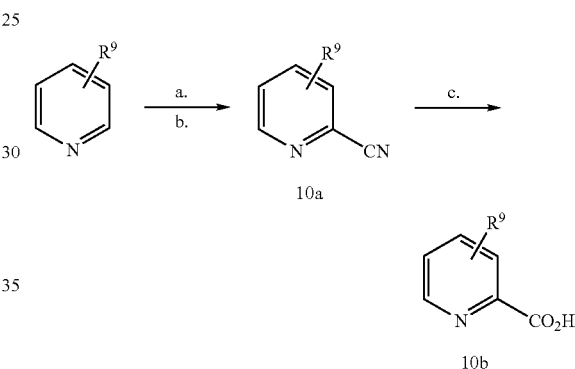

As shown in Scheme 10, an appropriately substituted pyridine, is contacted with a suitable oxidizing agent in an inert organic solvent. The appropriately substituted pyridine starting materials are commercially available from vendors such as Aldrich and Sigma. Alternatively, these pyridines can be prepared by methods well known in the art. Suitable oxidizing agents which can be used include hydrogen peroxide, MCPBA, and the like. The reaction is typically conducted at reflux for 6 to 12 h. The reaction mixture is then contacted with a suitable cyanide reagent to provide the cyano-substituted pyridine, 10a. Suitable cyanide reagents which can be used include trimethylsilyl cyanide, HCN, and the like. Suitable inert organic solvents include dichloromethane, dioxane, THF, and the like. The reaction conveniently can be conducted at rt in approximately 6 to 12 h. The reaction mixture is worked up to provide the cyano-substituted pyridine, 10a.

The cyano-substituted pyridine, 10a, is then hydrolyzed to provide the pyridin-2-yl carboxylic acid 10b by contact with a suitable acid. Suitable acids for hydrolyzing the cyano group to the carboxylic acid include hydrochloric acid, aqueous sulfuric acid, and the like. The reaction is typically conducted at reflux in 6 to 12 h.

Scheme 11 below illustrates the coupling reaction of a lincosamine intermediate, prepared as described above in Schemes 1–5, and a pyrrolidinyl or piperidinyl carboxylic acid, prepared as described above in Schemes 6–10, wherein $R^1$, $R^2$, $R^3$, $R^6$, and $R^9$ are as defined for formula (I) and $P^1$ is a suitable O-protecting group and $P^2$ is a suitable N-protecting group.

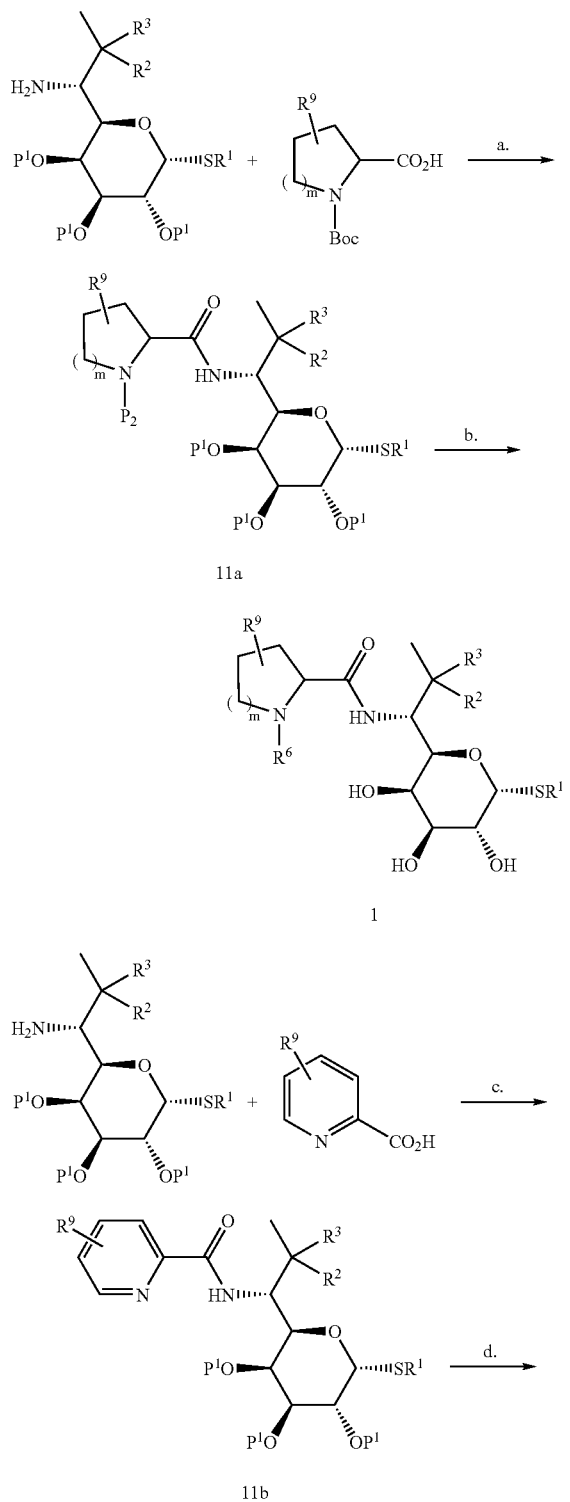

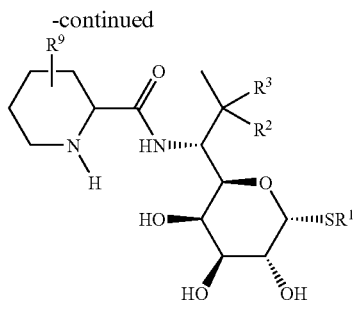

As shown in Scheme 11, an appropriately 7-substituted lincosamine intermediate (prepared, for example, according to any one of Schemes 1–5) and an appropriately substituted pyrrolidinyl or piperidyl carboxylic acid (prepared, for example, according to any one of Schemes 6–10) are condensed under reactive conditions, preferably in an inert organic solvent, in the presence of a coupling reagent and an organic base. This reaction can be performed with any number of known coupling reagents, such as O-(7-azabenzotriazol-1-yl)-N,N,N',N'tetramethyluronium hexafluorophosphate (HATU), 1-hydroxybenzotriazole hydrate (HOBT) with carbodiimides, diphenylphosphoryl azide (DPPA), isobutyl chloroformate, and the like. Suitable organic bases include diisopropylethylamine (DIEA), triethylamine (TEA), pyridine, N-methyl morpholine, and the like. Suitable inert organic solvents which can be used include, for example, N,N-dimethylformamide, acetonitrile, dichloromethane, and the like. This reaction is typically conducted using an excess of carboxylic acid to lincosamine at temperatures in the range of about 0° C. to about 50° C. The reaction is continued until completion, which typically occurs in from about 2 to 12 h.

Removal of the protecting groups can be carried out with acids, such as trifluoroacetic acid (TFA), hydrochloric acid, p-toluenesulfonic acid, and the like, in an inert organic solvent such as dichloromethane, dichloroethane, dioxane, THF, and the like. The removal is typically conducted at low temperatures, e.g., 0° C., and then gradually allowed to warm to room temperature to provide the product.

Also as shown in Scheme 11, an appropriately 7-substituted lincosamine intermediate (prepared, for example, according to any one of Schemes 1–5) and an appropriately substituted pyridin-2-yl carboxylic acid (prepared, for example, according to Scheme 10) are condensed under reactive conditions, preferably in an inert organic solvent, in the presence of a coupling reagent and an organic base, as described above.

The pyridine 11b is hydrogenated to provide the piperidyl product. The hydrogenation is typically performed in a polar organic solvent such as methanol, ethanol, and the like, using platinum(IV)oxide in the presence of an acid such as HCl, acetic acid, and the like, in a Parr bottle. The bottle is purged, and charged with $H_2$ to approximately 40 to 70 psi and shaken until completion, typically approximately 24 h. The reaction mixture is filtered, e.g., through a celite pad, and washed several times with a polar organic solvent such as methanol. Evaporation of the combined washings and filtrate affords the piperidyl product.

The coupling of pyridine carboxylic acids and lincosamines to pyridine 11b followed by reduction to the piperidyl product may also be conducted as described in Birkenmeyer, et al., Journal of Medicinal Chemistry 1984, 27, 216–223.

Scheme 12 below illustrates the alkylation of the nitrogen of the pyrrolidinyl or piperidinyl ring, wherein $R^6$ is alkyl, hydroxyalkyl, alkylene-substituted heterocycle, or alkylene-heterocycle, and $R^1$, $R^2$, $R^3$, and $R^9$ are as defined for formula (I).

Scheme 12.
General synthesis of 1'-N-substituted lincosamines.

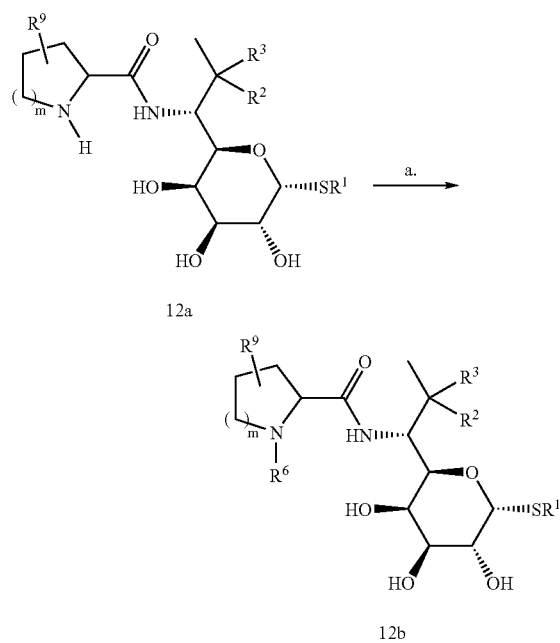

a. alkylating agents

As shown in Scheme 12, the lincosamine 12a can be N-substituted by contact with an alkylating agent in the presence of a suitable base to provide a product 12b. Suitable alkylating agents which can be used include epoxides, alkyl bromides, and the like. Suitable bases which can be used include potassium carbonate, cesium carbonate triethylamine, and the like. The alkylation reaction is typically conducted in a polar organic solvent such as methanol or DMF. The alkylation reaction is typically conducted at low temperatures in the range of 0° C. to –10° C. for 10 to 20 h.

Scheme 13 below illustrates the acylation of the nitrogen of the pyrrolidinyl or piperidinyl ring, wherein $R^6$ is —C(O)O-alkylene-cycloalkyl, —C(O)O-alkylene-substituted cycloalkyl, —C(O)O-alkyl, —C(O)O-substituted alkyl, —C(O)O-aryl, —C(O)O-substituted aryl, —C(O)O-heteroaryl, —C(O)O-substituted heteroaryl, —[C(O)O]-alkylene-heterocycle, —[C(O)O]-alkylene-substituted heterocycle, and $R^1$, $R^2$, $R^3$, and $R^9$ are as defined for formula (I).

Scheme 13.
General synthesis of 1'-N-substituted lincosamines.

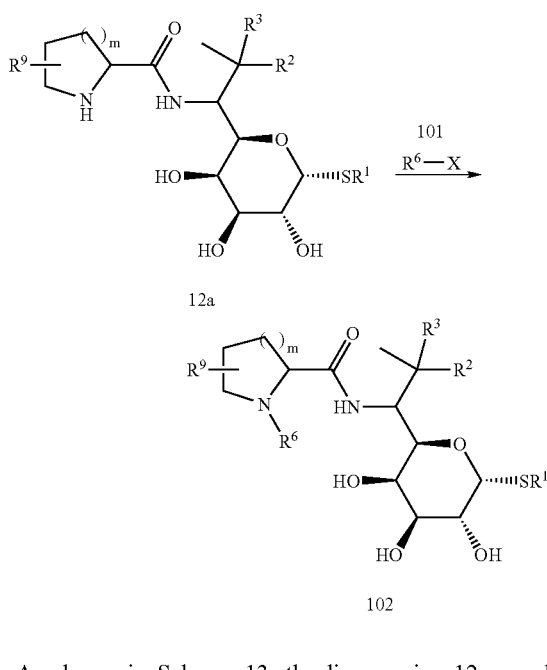

As shown in Scheme 13, the lincosamine 12a can be N-substituted by contact with an acyl chloride 101, such as $R^6$—X, wherein X is a suitable leaving group, and is preferably halogen, even more preferably chloride in the presence of a suitable base to provide a product 102. Examples of compound 101, include bromofluorenyl, Cl—C(O)O-alkyl, Cl—C(O)O-aryl, and the like. Suitable bases which can be used include DCC, TEA, and the like. The reaction is typically conducted in a polar organic solvent such as methanol or DMF. The reaction is typically conducted at low temperatures in the range of –10° C. to 20° C.

Scheme 16 below illustrates the general synthesis of trans-alkylazetidine carboxylic acids.

Scheme 16.
General synthesis of trans-alkylazetidine carboxylic acids.

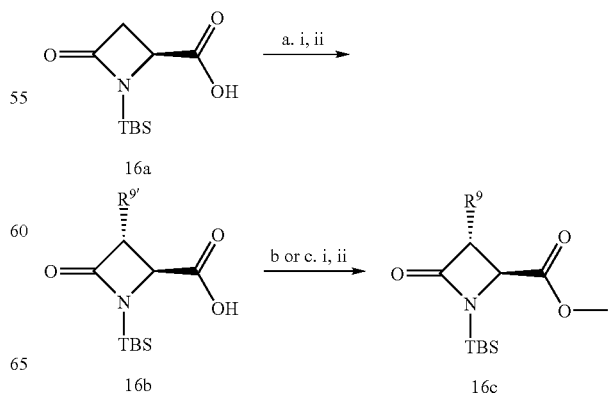

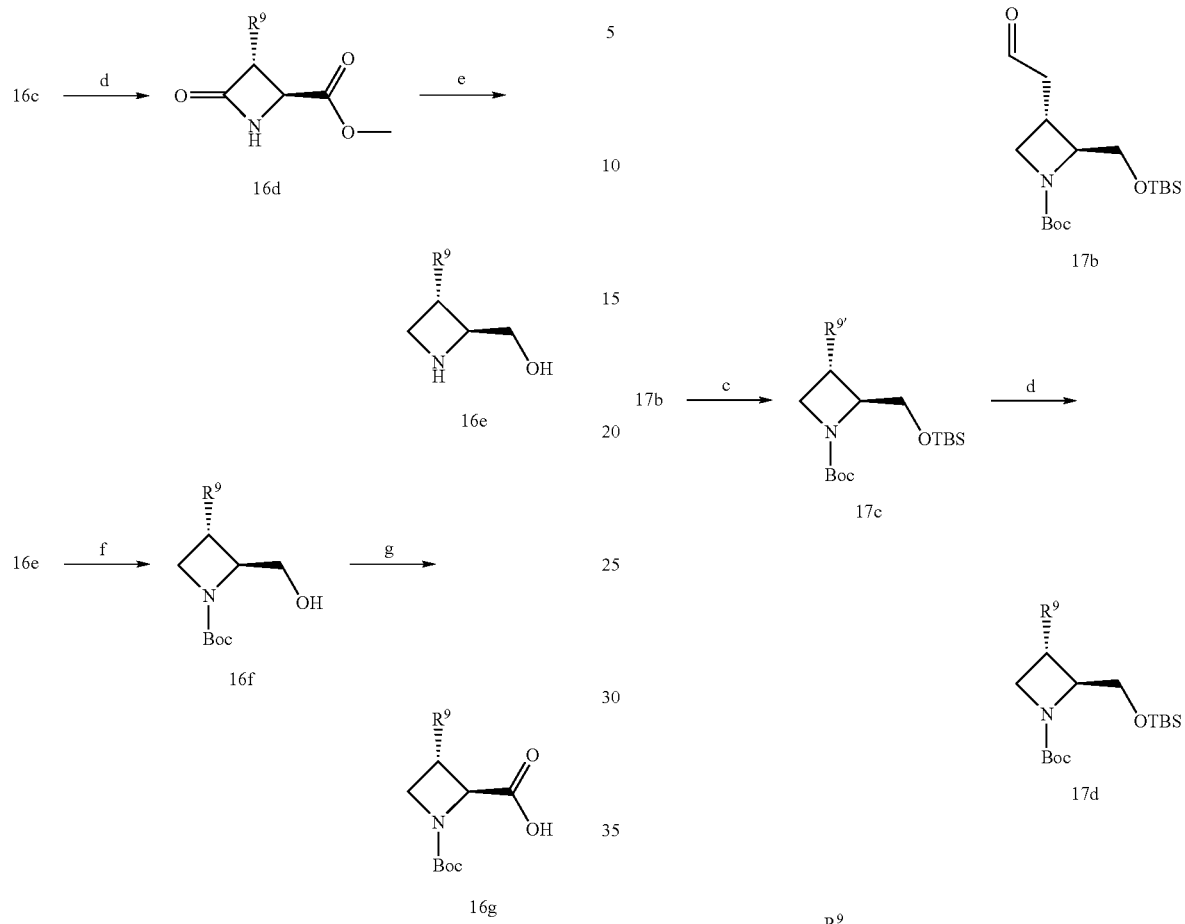

The following reaction scheme may be used in the synthesis of trans-alkylazetidine carboxylic acids, wherein $R^9$ is alkyl: (a) (i) LDA, THF, 0° C., (ii) bromoalkane or bromoalkene; (b) TMSCHN$_2$, MeOH, 23° C.; (c) (i) TMSCHN$_2$, MeOH, 23° C., (ii) H$_2$, Pd/C, EtOAc, 23° C.; (d) Et$_3$N.3HF, THF, 23° C.; (e) LiAlH$_4$, THF, 68° C.; (f) Boc$_2$O, CH$_2$Cl$_2$, 23° C.; (g) RuCl$_3$.xH$_2$O, NaIO$_4$, acetone, H$_2$O, 23° C.

Scheme 17 below illustrates the general synthesis of trans-alkylazetidine carboxylic acids via the aldehyde.

Scheme 17.
General synthesis of trans-alkylazetidine carboxylic acids via aldehyde.

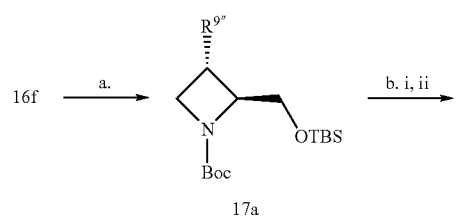

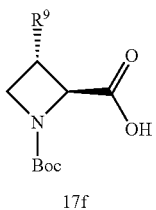

The following reaction scheme may be used in the synthesis of trans-alkylazetidine carboxylic acids: (a) TBSCl, imidazole, DMF, 23° C.; (b) (i) ozone, CH$_2$Cl$_2$, −78° C., (ii) PPh$_3$; (c) olefination: P$^+$Ph$_3$ salt, base, solvent; (d) H$_2$, Pd/C, EtOAc, 23° C. or KO$_2$CN=NCO$_2$K, AcOH, dioxane, 23° C.; (e) TBAF, THF, 23° C.; (f) RuCl$_3$.xH$_2$O, NaIO$_4$, acetone, H$_2$O, 23° C.

Scheme 18 below illustrates a general synthesis of 2-substituted ester prodrug compounds.

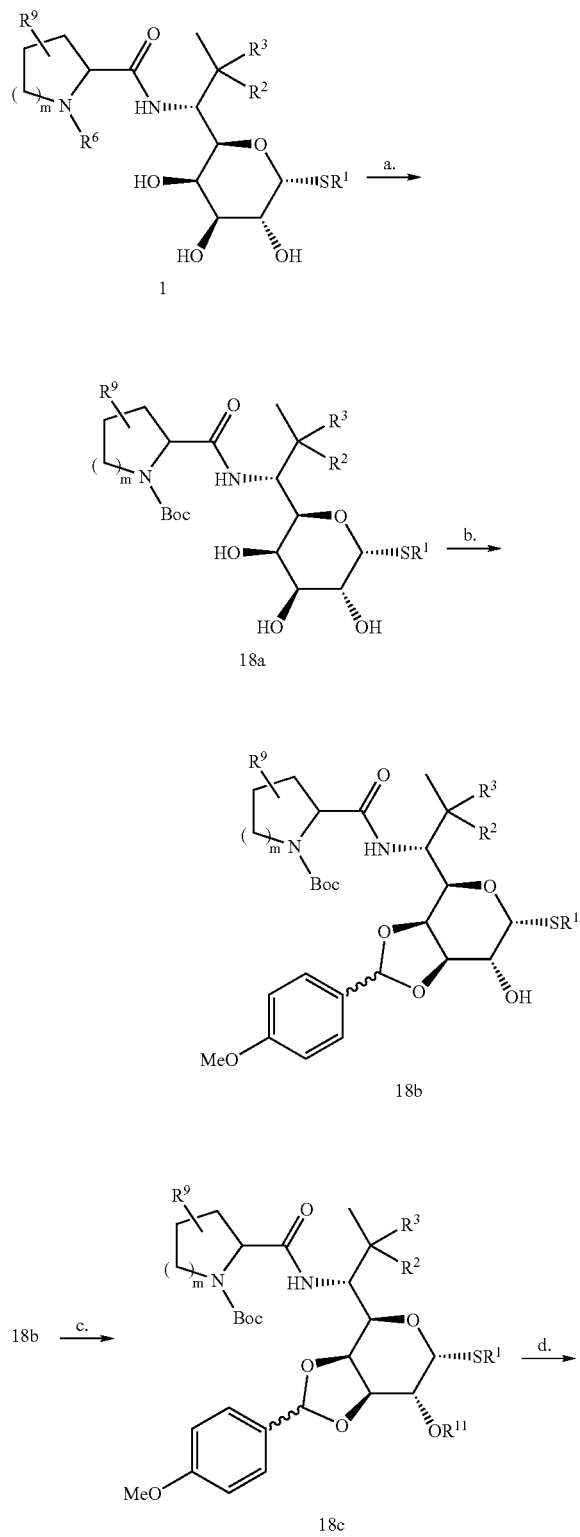

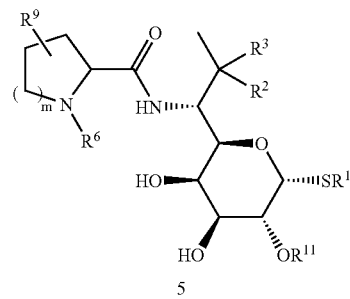

The following representative reaction scheme may be used in the synthesis of 2-substituted prodrug compounds of the invention: a. (Boc)$_2$O, aq. KHCO$_3$ THF b. p-anisaldehyde dimethyl acetal, PPTS, c. R$^{11}$ acylating agent, base d. TFA, DCE, water.

Scheme 19 below illustrates a general method for the synthesis of 4,5-disubstituted-2,3,6,7-tetrahydro-azepine-2-carboxylic acid derivatives.

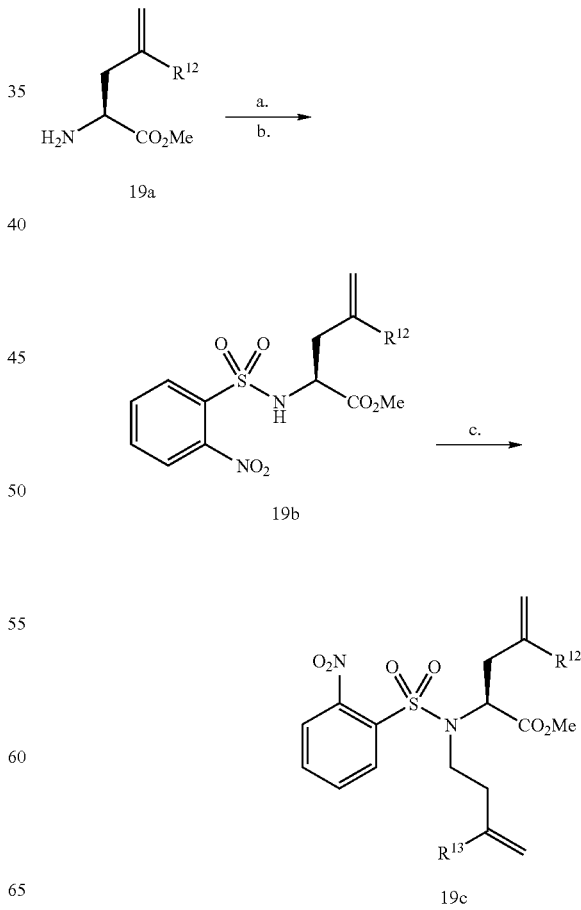

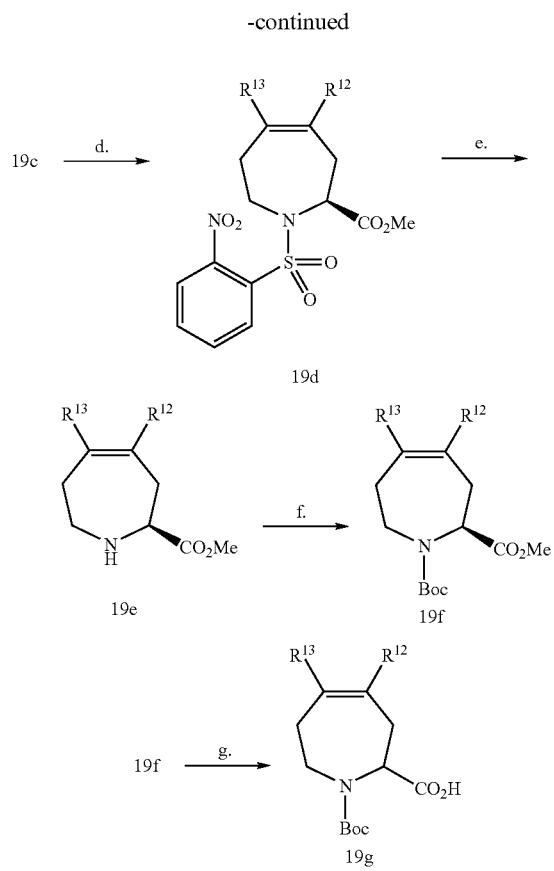

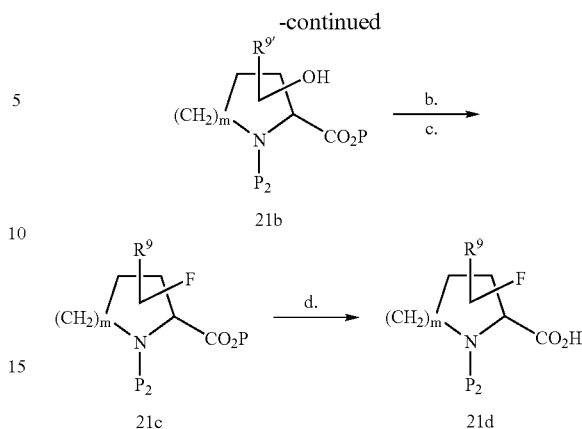

The following general reaction scheme may be used in the preparation of 4,5-disubstituted-2,3,6,7-tetrahydro-azepine-2-carboxylic acid derivatives: a. 2,2-dimethoxypropane, Catalytic HCl, MeOH b. 2-nitrobenzenesulfonyl chloride, 2,4,6-collidine, dichloroethane c. $Cs_2CO_3$, TBABr, DMF, Homoallylic tosylates or halides d. Benzylidene[1,3-bis(2,4,6-trimethylphenyl)-2-imidazolidinylidene]dichloro-(tricyclohexylphosphine)ruthenium e. 7-methyl,1,5,7-triazabicyclo[4.4.0]dec-5-ene, thiophenol f. $(Boc)_2O$, TEA g. Aq. LiOH, Dioxane.

Scheme 21 below illustrates the synthesis of 4,4 di-substituted pyrrolidine and piperidine carboxylic acids, wherein $R^9$ is a suitable substituent and the other substituent is fluorine.

Scheme 21.
Synthesis of intermediate 21d where $R^9$ is defined herein.

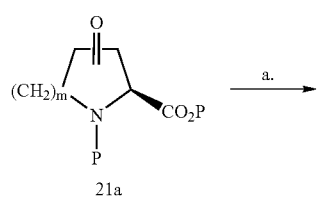

The following representative reaction scheme may be used in Scheme 21: (a) Tetraallyltin, $BF_3.Et_2O$ or $R^9M$ ($R^9$ or $R^{9'}$ carbon nucleophile) (b) $H_2$/Pd (c) DAST (d) aq. LiOH or appropriate carboxylate ester deprotection conditions.

Pharmaceutical Formulations

When employed as pharmaceuticals, the compounds of the subject invention are usually administered in the form of pharmaceutical compositions. These compounds can be administered by a variety of routes including oral, parenteral, transdermal, topical, rectal, and intranasal. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/capsule) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient | 50 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An intravenous formulation may be prepared as follows:

| Ingredient | Quantity |
| --- | --- |
| Active Ingredient | 250 mg |
| Isotonic saline | 1000 mg |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

In general, the compounds of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of symptoms) as determined in cell culture. Such information can be used to more accurately determine useful doses in humans. Levels in plasma may be measured, for example, by high performance liquid chromatography.

Utility

The compounds, prodrugs and pharmaceutically acceptable salts thereof, as defined herein, may have activity against a variety of bacteria, protozoa, fungi, and parasites. By way of example, the compounds, prodrugs and pharmaceutically acceptable salts thereof may be active against gram positive and gram negative bacteria. The compounds, prodrugs and pharmaceutically acceptable salts thereof may be active against a variety of fungi, including fungi from the genus *Mucor* and *Candida*, e.g., *Mucor racemosus* or *Candida albicans*. The compounds, prodrugs and pharmaceutically acceptable salts thereof may be active against a variety of parasites, including malaria and cyptosporidium parasite.

The compounds of the subject invention exhibit activity against a variety of bacterial infections, including, for example, gram positive infections, gram negative infections, mycobacteria infections, mycoplasma infections, and chlamydia infections.

Since the compounds of the subject invention exhibit potent activities a variety of bacteria, such as gram positive bacteria, the compounds of the present invention are useful antimicrobial agents and may be effective against a number of human and veterinary pathogens, including gram positive bacteria. The Gram positive organisms against which the compounds of the present invention are effective include *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron*, and *Clostridium difficile*, and the like.

The compounds of the subject invention may be combined with one or more additional antibacterial agents. One or more of the additional antibacterial agents may be active against gram negative bacteria. Additionally, one or more of the additional antibacterial agents may be active against gram positive bacteria. The combination of the compounds of the subject invention and the one or may additional antibacterial agents may be used to treat a gram negative infection. Additionally, the combination of the compounds of the subject invention and the one or more additional antibacterial agents may be used to treat a gram positive infection. The combination of compounds of the subject invention and the one or more additional antibacterial agents may also be used to treat a mycobacteria infection, mycoplasma infection, or chlamydia infection.

The in vitro activity of compounds of the subject invention may be assessed by standard testing procedures such as the determination of minimum inhibitory concentration (MIC) by agar dilution as described in "Approved Standard. Methods for Dilution Antimicrobial Susceptibility Tests for Bacteria that Grow Aerobically," $3^{rd}$ ed., published 1993 by the National Committee for Clinical Laboratory standards, Villanova, Pa., USA.

The amount administered to the mammalian patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 mg to about 500 mg per kilogram body weight, preferably about 100 mg to about 300 mg per kilogram body weight. Suitable dosage ranges for intranasal administration are generally about 0.1 mg to 1 mg per kilogram body weight. Effective doses can be extrapolated from dose-response curves derived from in vitro or animal model test systems.

The following synthetic and biological examples are offered to illustrate this invention and are not to be construed in any way as limiting the scope of this invention.

EXAMPLES

In the discussion above and in the examples below, the following abbreviations have the following meanings. If an abbreviation is not defined, it has its generally accepted meaning.

7-methyl/MTL=1-methylthio-7-deoxy-7-methyllincosamine
apt=apparent triplet
atm=atmospheres
Bn=benzyl
Boc=tert-butoxycarbonyl protecting group
br s=broad singlet
BSTFA=N,O-bis(trimethylsilyl)trifluoroacetamide
Cbz=carbonyloxybenzyloxy protecting group
$CDCl_3$=deuterated chloroform
$CD_3OD$=deuterated methanol
cfu=colony forming units
D=doublet
DAST=dimethylaminosulfurtrifluoride
d=Doublet
dddd=doublet of doublets of doublet of doublets
dt=doublet of triplets
DCC=dicyclohexylcarbodiimide
DCE=dicholoroethane
DCM=dichloromethane
DIEA=diisopropyethylamine
DMAP=dimethylaminopyridine
DMF=dimethylformamide
DMSO=dimethyl sulfoxide
DPPA=diphenylphosphoryl azide
$ED_{50}$=dose therapeutically effective in 50% of the population
EDC=1-(3-dimethylaminopropyl)-3-ethylcarbodiamide HCl
Equiv=equivalents
ESMS=electrospray mass spectrometry
Et=ethyl
EtOAc=ethyl acetate
$Et_2O$=diethyl ether
g=grams
h=hours
HATU=O-(7-azabenzotriazol-1-yl)-N,N,N',N'-tetramethyluronium hexafluorophosphate
HBTU=O-(Benzotriazol-1-yl)-N,N,N',N'-tetramethyluronium hexafluorophosphate
HOBT=1-hydroxybenzotriazole hydrate
$^1$H NMR=Hydrogen Nuclear Magnetic Resonance spectroscopy
HPLC=high pressure liquid chromatography
Hz=hertz
$IC_{50}$=concentration of the test compound which achieves a half-maximal inhibition of symptoms J=coupling constant in hertz
L=liters
$LD_{50}$=dose lethal to 50% of the population
LDA=lithium diisopropylamide
LiHMDS=lithium hexamethyldisilazide
$LiN(iPr)_2$=lithium diisopropylnitride
m=multiplet
M=molar
MCPBA=2-(4-chloro-o-tolyloxy)acetic acid
Me=methyl
MeCN=acetonitrile
MeOH=methanol
mg=milligrams
MHz=megahertz
min=minutes
mL=milliliters
mm=millimeter
mmol=millimol
MS(ESPOS)=mass spectrometry by positive mode electrospray ionization
MS(ESNEG)=Mass Spectrometry by negative mode electrospray ionization
MTL=1-methylthiolincosamine (methyl 6-amino-6,8-dideoxy-1-thio-erythro-β-D-galacto-octopyranoside)
N=normal
NMR=nuclear magnetic resonance
OBz=benzyloxy protecting group
OtBu=tert-butoxy
Pd/C=palladium/carbon
pg=picograms
Ph=phenyl
PPTS=pyridinium p-toluenesulfonate
Pro=L-proline
psi=pounds per square inch
PTFE=polytetrafluoroethylene
q=quartet
q.v.=quantitative
$R_f$=Retention factor
rt=room temperature
s=singlet
sat. saturated
t=triplet
TBAF=tetrabutylammonium fluoride
TBS=tert-butyldimethylsilyl
TEA=triethylamine
TFA=trifluoroacetic acid
THF=tetrahydrofuran
TLC=thin layer chromatography
TMS=trimethylsilyl
μg=micrograms
μL=microliters
μm=micromolar
v/v=volume by volume
w/w=weight by weight Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates that the compound or reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa., USA; the term "Bachem" indicates that the compound or reagent is commercially available from Bachem Bioscience Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; the term "RSP" indicates that the compound or reagent is commercially available from RSP Amino Acid Analogs, Inc., 106 South St., Hopkinton, Mass. 01748, USA, and the term "TCI" indicates that the compound or reagent is commercially available from TCI America, 9211 North Harborgate St., Portland, Oreg., 97203, OR, USA; the term "Toronto" indicates that the compound or reagent is commercially available from Toronto Reasearch Chemicals, Inc., 2 Brisbane Rd., New York, ON, Canada M3J2J8; the term "Alfa" indicates that the compound or reagent is commercially available from Johnson Matthey Catalog Company, Inc. 30 Bond Street, Ward Hill, Mass. 018350747; and the term "Nova Biochem" indicates that the compound or reagent is commercially available from NovaBiochem USA, 10933 North Torrey Pines Road, P.O. Box 12087, La Jolla Calif. 92039-2087.

In the examples below, all temperatures are in degrees Celsius (unless otherwise indicated) and the following general procedures are used to prepared the compounds as indicated. It will be appreciated by one of skill in the art that the following general procedures are meant to be illustrative only and that the methods may be broadened to synthesize other compounds of the subject invention.

General Procedures

Method A

Methyl 6-amino-6,8-dideoxy-1-thio-erythro-β-D-galacto-octopyranoside 1a ($R^1$=Me) (MTL) was prepared as described by Hoeksema, H. et al., J. Am. Chem. Soc., 1967, 89, 2448–2452. N-(Benzyloxycarbonyloxy)succinimide (5.8 g 23.1 mmol) and 1a (5.0 g, 19.7 mmol) were suspended in pyridine (40 mL) and stirred under $N_2$ atmosphere 36 h. The reaction mixture was cooled to 0° C. and then bis-N,O-trifluoroacetamide (15.7 mL, 59.0 mmol) was added by syringe over 2 min. The reaction mixture was allowed to warm to rt and stirred for 42 h. Toluene (100 mL) was added and the reaction mixture was evaporated to dryness. The residue was taken up in ethyl acetate (400 mL). The organic solution was washed quickly with 10% citric acid (200 mL), $H_2O$ (3×100 mL), saturated $NaHCO_3$ (100 mL), and brine (2×100 mL), and dried over $Na_2SO_4$ and evaporated to dryness. Chromatography of the crude product on silica 10% EtOAc/Hexanes containing 0.2% TEA after co-evaporation from toluene (100 mL) and cyclohexane (2×100 mL) provided the protected product 1b (P=Cbz, $R^1$=Me) (7.2 g, 54%) as a colorless oil.

$^1$H NMR (300 MHz, $CD_3SOCD_3$) δ 7.34–7.31 (m, 5), 7.05 (d, J=8.2, 1), 5.19 (d, J=5.8, 1), 5.01 (d, J=1.6, 2), 3.99 (apt dt, J=5.5, 9.3, 9.3, 2), 3.93–3.86 (m, 3), 3.49 (dd, J=2.5, 9.6, 1), 2.01 (s, 3), 1.03 (d, J=6.3, 3), 0.10 (s, 9), 0.09 (s, 9), 0.04 (m, 18).

To dimethylsulfoxide (413 μL, 5.82 mmol) in DCM (1.5 mL) cooled to −72° C. was added oxalyl chloride 2 M in DCM (1.49 mL, 2.98 mmol) over 1 min. After 25 min the protected product 1b (1.92 g, 2.84 mmol) in DCM (4.0 mL) was added by cannula. The resulting reaction mixture was stirred for 25 min and then allowed to warm to −50° C. (dry ice acetonitrile) and maintained at this temperature for 2 h. To the reaction mixture was added TEA (1.29 mL, 3.30 mmol). After 25 min the reaction mixture was diluted with EtOAc (300 mL). The resulting organic solution was washed quickly with 5% citric acid (300 mL), $H_2O$ (2×300 mL), saturated $NaHCO_3$ (100 mL), brine (100 mL) dried over $Na_2SO_4$ and evaporated to dryness with the aid of toluene (100 mL) to provide the product 1c. The product 1c (P=Cbz, $R^1$=Me) was obtained as a colorless crystalline solid (1.60 g, 94%) after co-evaporation with n-pentane and removal of residual solvent under high vacuum.

$^1$H NMR (300 MHz $CDCl_3$) δ 7.37–7.33 (m, 5), 5.60 (m, 1), 5.21 (d, J=5.2, 1), 5.17 (d, J=12.4, 1), 5.08 (d, J=12.4, 1), 4.74 (m, 1), 4.16–4.12 (m, 2), 3.87 (d, J=2.2, 1), 3.69 (dd, J=2.5, 9.3, 1), 2.01 (br s, 3), 1.90 (s, 3), 0.19 (s, 9), 0.16 (s, 9), 0.15 (s, 9).

Method B

The Boc-protected product 1c (P=Boc, $R^1$=Me) may be prepared in general as outlined above. 1a ($R^1$=Me) (MTL) (Dried at 50° C. high vacuum) (21.8 g, 86 mmol) was suspended in methanol (200 mL) and TEA (26 mL) and was cooled to 0° C. on ice. To this mixture di-t-butyldicarbonate (57.0 g, 0.26 mol) was added. The reaction mixture was then stirred overnight at rt. To the reaction mixture was added toluene (100 mL). The solvents were removed to a total volume of 100 mL, leaving a thick suspension to which cyclohexane (300 mL) was added. The resulting solid precipitate was triturated, then filtered and washed with cyclohexane, ether, and pentane and dried to constant weight. The crude Boc-protected product was used without further purification (87%).

TLC $R_f$=0.75 (10% MeOH/DCM); MS(ESPOS): 354 $[M+H]^+$; $^1$H NMR (300 MHz, $CD_3OD$) δ 0.14 (d, J=6.3, 3), 1.43 (s, 9), 2.07 (s, 3), 3.55 (dd, J=3.3, 10.43, 1), 3.84–4.08 (m, 3), 4.10–4.15 (m, 2), 5.25 (d, J=5.5, 1).

To N-Boc-1-methylthiolincosamide (240 mg, 0.68 mmol) in DMF (5 mL, BSTFA (0.52 mL, 2.0 mmol) and triethylamine (0.14 mL, 1.42 mmol) were added at 0° C. and then stirred at rt overnight. DMF was removed and the crude product was quickly passed through a silica gel column (pretreated with 2% TEA in ethyl acetate) eluting with 10% ethyl acetate in hexanes 1b (P=Boc, $R^1$=Me) (350 mg, 95%). To oxalyl chloride (0.16 mL, 0.78 mmol) in dichloromethane (5 mL) at −60° C., dimethylsulfoxide (0.22 mL, 0.78 mmol) was added slowly and then stirred for 15 min. After which, 1b (370 mg, 0.65 mmol) in DCM (5 mL) was added slowly. The reaction mixture was stirred for 45 min, during which the reaction temperature was raised to −40° C. Triethylamine (0.70 mL, 3.25 mmol) was then added and the stirring continued for an additional 15 min at −40° C. It was then extracted with DCM (100 mL) and washed with 10% citric acid (50 mL). The residue obtained on removal of solvent was then purified on silica gel column using 10% ethyl acetate in hexanes as eluent 1c (P=Boc, $R^1$=Me) as a colorless oil (289 mg, 78%).

TLC: $R_f$=0.60 (10% EtOAc/Hexanes); MS(ESPOS): 590 $[M+Na]^+$; $^1$H NMR (300 MHz, $CDCl_3$) δ 0.11 (s, 18), 0.17 (s, 18), 1.40 (s, 9), 1.84 (s, 3), 2.26 (s,3), 3.63 (dd, J=2.7, 9.34, 1), 3.82 (d, J=1.9, 1), 4.01–4.12 (m, 2), 5.15 (d, J=5.5, 1).

Method C

Triphenylphosphonium bromide (3.29 g, 9.2 mmol) and potassium tert-butoxide (715 mg, 6.4 mmol) under $N_2$ atmosphere were suspended in toluene (31 mL) with vigorous stirring. After 4 h protected product 1c (P=Cbz, $R^1$=Me) (1.4 g, 2.36 mmol) in toluene (20 mL) was added by cannula. The resulting reaction mixture was stirred 2 h and then diluted with EtOAc (250 mL). The resulting organic solution was washed quickly with $H_2O$ (2×100 mL), brine (1×100 mL) dried over $Na_2SO_4$ and evaporated to dryness. Chromatography of the crude product on silica 6% EtOAc/Hexanes containing 0.2% TEA gave the alkene product 2a (P=Cbz, $R^1$=Me, $R^{2'}$=$CH_2$) as a colorless oil that crystallized after co-evaporation from toluene and cyclohexane (0.65 g, 46%).

1H NMR (300 MHz $CDCl_3$) δ 7.35–7.27 (m, 5), 6.36 (d, J=7.1, 1), 5.24 (d, J=5.5, 1), 5.08 (m, 4), 4.34 (m, 1), 4.16 (m, 2), 3.88 (d, J=2.2, 1), 3.61 (dd, J=2.2, 9.3, 1), 2.20 (s, 3), 1.79 (s, 3), 0.17–0.13 (m, 27).

The product 2a (P=Cbz, $R^1$=Me, $R^{2'}$=$CH_2$) (490 mg, 0.82 mmol) in ethanol (50 mL) was added to 10% palladium on carbon (Degussa wet form 50% w/w water) (700 mg) in a par bottle. The bottle was purged, and charged with $H_2$ to 65 psi and shaken 24 h. The reaction mixture was filtered through celite, rinsed with methanol. The organic solution was transferred to a resin funnel containing dry, washed Dowex™ 50w-400x $H^+$ form (0.8 g) and shaken for 10 min. After washing the resin with methanol three times and water two times, the saturated product 2b ($R^1$=Me, $R^2$=Me) was eluted from the resin by washing with 5% TEA in MeOH (35 mL, ×10 min×5). The combined filtrate was evaporated to dryness, co-evaporated from EtOH twice and lyophilized from 1:1 $MeCN/H_2O$ to give the product as a colorless powder (198.4 mg 96%).

$^1$H NMR (300 MHz, $D_2O$) δ 5.17 (d, J=5.8, 1), 3.97–3.84 (m, 3), 3.52 (dd, J=3.0, 10.0, 1), 2.82 (dd, J=4.4, 8.5, 1), 1.94 (s, 3), 1.89–1.81 (m, 1), 0.82 (d, J=6.9, 3), 0.72 (d, J=6.9, 3). MS(ESPOS): 252.2 $[M+H]^+$, (ESNEG): 250.4 $[M-H]^-$.

Method D

In the alternative when a Boc-protecting group is used, methyltriphenylphosphonium bromide (12 g, 33.6 mmol) and potassium t-butoxide (3g. 26.7 mmol) were taken in THF (70 mL) at 0° C., and stirred at rt for 4 h. Then Boc-protected product 1c (P=Boc, $R^1$=Me) (4.7 g, 8.2 mmol) in THF (30 mL) was added and stirred at rt for 2 h. After which it was extracted with EtOAc (300 mL), washed with brine (100 mL) and dried over sodium sulfate. The crude alkene product 2a (P=Boc, $R^1$=Me, $R^{2'}$=$CH_2$) was purified on silica gel column chromatography using 10% EtOAc in Hexane as eluent (4.1 g, 87.6%).

TLC: $R_f$=0.5 (10% of EtOAc in Hexane): $^1$H NMR (300 MHz, $CD_3OD$) δ 7.24 (m, 2), 5.22 (d, J=5.7, 1), 4.21 (m, 1), 4.09 (m, 2), 3.87 (d, J=2.4, 1), 3.60 (dd, J=2.7, 9.3, 1), 1.99 (s, 3), 1.76 (s, 3); 1.43 (s, 9); MS(ESPOS): 444 (M−2TMS+Na).

To the product 2a (P=Boc, $R^1$=Me, $R^{2'}$=$CH_2$) in methanol (30 mL), Dowex™ $H^+$ resin (1 g) was added and stirred at rt for 1 h. The resin was filtered and the product obtained on removal of solvent (2.4 g, 6.8 mmol,) was taken in MeOH (30 mL). Pd/C (2.5 g) was added and hydrogenated at 55 psi overnight. The crude product obtained on filtering and removal of solvent was purified on silica gel column chromatography using 10% MeOH in DCM to provide Boc-protected 7-Methyl MTL as a white solid (2.06 g, 86%).

TLC $R_f$=0.5 (10% of MeOH in DCM).

$^1$H NMR (300 MHz, $CD_3OD$) δ 5.23 (d, J=5.4, 1), 4.11 (m, 1), 3.97 (d, J=10.2, 1), 3.84 (m, 1), 3.52 (m, 1), 2.08 (s,

3), 1.44 (s, 9), 1.14 (m, 1), 0.93 (d, J=6.9, 3), 0.85 (d, J=6.9, 3); MS(ESPOS): 351[M+H]$^+$.

To the Boc-protected 7-Methyl MTL (150 mg, 0.43 mmol) in dichloroethane (6 mL), dimethylsulfide (0.16 mL, 2.5 mmol) was added, followed by TFA (2 mL), water (0.16 mL) and stirred at rt for 1 h. The solvent was removed to obtain the crude product 2b (R$^1$=Me, R$^2$=Me). After purification on silica gel column chromatography using 30% MeOH in DCM as eluent, the product 2b (R$^1$=Me, R$^2$=Me) was obtained identical in all respects to the material obtained from method C.

Method E

Sodium hydride (80 mg, 3.3 mmol) under N$_2$ atmosphere was suspended in THF (4 mL) with vigorous stirring. The suspension was cooled to −30° C. and diethyl(cyanomethyl)phosphonate (805 μL, 5.0 mmol) was added. After 30 min protected product 1c (P=Cbz, R$^1$=Me) (1.0 g, 1.7 mmol) in THF (3 mL) was added by cannula. The resulting reaction mixture was stirred 4 h and then diluted with EtOAc (250 mL). The resulting organic solution was washed quickly saturated aqueous NaHCO$_3$ (1×100 mL), brine (1×50 mL) dried over Na$_2$SO$_4$ and evaporated to dryness. Chromatography of the crude product on silica 6% EtOAc/Hexanes to 10% EtOAc/Hexanes containing 0.2% TEA gave the protected alkene product 2a (P=Cbz, R$^1$=Me, R$^{2'}$=CHCN) as a colorless oil (0.38 g, 37%). MS(ESPOS): 625.5.2 [M+H]$^+$, ES(NEG): 659.5 [M+Cl].

The product 2a (P=Cbz, R$^1$=Me, R$^{2'}$=CHCN) (180 mg, 0.29 mmol) in ethanol (15 mL) was added to 10% palladium on carbon (Degussa wet form 50% w/w water) (300 mg) in a Parr bottle and concentrated HCl (29 μL) was added. The bottle was purged, and charged with H$_2$ to 65 psi and shaken for 24 h. The reaction mixture was filtered through celite, rinsed with methanol. The organic solution was transferred to a resin funnel containing dry, washed Dowex™ 50w-400x H$^+$ form (1 g) and shaken 10 min. After washing the resin with methanol twice and water, the saturated product 2b (R$^1$=Me, R$^2$=CH$_2$CN) was eluted from the resin by washing with 5% TEA in MeOH (20 mL×20 min×3) and MeCN (20 mL×20 min). The combined organic filtrate was evaporated to dryness lyophilized from 1:1 MeCN/H$_2$O to give the product 2b (R$^1$=Me, R$^2$=CH$_2$CN) as a colorless solid (70 mg, 91%). ES(NEG): 275.3 [M−H]$^-$.

Method F

To the protected product 1c (P=Cbz, R$^1$=Me) (0.75 g, 1.3 mmol) in THF (7.3 mL) was added MeMgCl (3M) in THF (7.0 mL 2.1 mmol) at 0° C. Over 30 min the reaction mixture was warmed to 4° C. and after 4 h the reaction mixture was quenched with 1:3 saturated aqueous NH$_4$Cl/H$_2$O (10 mL). The quenched mixture was diluted to 100 mL with water and extracted with DCM (4×50 mL). The combined organic phase was dried and evaporated. The residue was dissolved in 1:2:4 H$_2$O/HOAc/THF (100 mL) and stirred for 20 h, and then evaporated with the aid of toluene (2×100 mL). Chromatography 10:1 to 10:2 DCM/MeOH gave product 3a (P=Cbz, R$^1$=Me, R$^2$=Me) (153 mg, 31%).

(ESNEG): 399.5 [M−H]$^-$.

3a (P=Cbz, R$^1$=Me, R$^2$=Me) (79 mg, 0.2 mmol) in ethanol (10 mL) was added to 10% palladium on carbon (Degussa wet form 50% w/w water) (400 mg) in a Parr bottle. The bottle was purged, and charged with H$_2$ to 65 psi and shaken 6 h. The reaction mixture was filtered through celite, rinsed with methanol. The combined filtrate was evaporated to dryness and lyophilized from 1:1 MeCN/H$_2$O to give the product 3b (R$^1$=Me, R$^2$=Me) as a colorless powder (42 mg, 80%).

$^1$H NMR (300 MHz, D$_2$O) δ 5.33 (d, J=5.8, −1), 4.83–4.06 (m, 3), 3.65–3.60 (m, 1), 3.06–3.03 (m, 1), 2.18 (s, 3), 1.30 (s, 3), 1.23 (s, 3). MS(ESPOS): 268.4 [M+H]$^+$, MS(ESNEG): 266.2 [M−H]$^-$.

Method G

To the Boc-protected product 1c (P=Boc, R$^1$=Me) (100 mg, 0.18 mmol) in methanol (3 mL), O-trimethylsilylhydroxylamine (0.10 mL, 0.88 mmol) was added and stirred at rt overnight. The solvent was removed to obtain the crude Boc-protected product 4a (P=Boc, R$^1$=Me, R$^7$=H). To the crude product 4a (95 mg, 0.15 mmol), 30% trifluoroacetic acid in dichloroethane (10 mL) and dimethyl sulfide (0.5 mL) were added and stirred for 1 h. The solvent was removed and the product 4b (R$^1$=Me, R$^7$=H) was taken as such for the next step.

TLC: R$_f$=0.35 (10% MeOH/DCM); MS(ESPOS): 267 [M+H]$^+$; $^1$H NMR (300 MHz, CD$_3$OD) δ 1.96 (s, 3), 2.09 (s, 3), 3.58 (dd, J=3.3, 10.2, 1), 3.90 (s, 1), 4.11 (dd, J=5.7, 10.20, 1), 4.19 (d, J=5.4, 1), 4.50 (d, J=5.1, 1), 5.36 (d, J=5.7, 1).

Method H

To the Boc-protected product 1c (P=Boc, R$^1$=Me) (100 mg, 0.176 mmol) in methanol (4 mL) and water (1 mL), O-alkylhydroxylamine hydrochloride (for example, O-methylhydroxylamine hydrochloride) (60 mg, 0.70 mmol) and sodium acetate (57 mg, 0.70 mmol) were added and heated at 80° C. for 3 h and then stirred at rt overnight. The solvent was removed under high vacuum to obtain the crude Boc-protected product 4a (P=Boc, R$^1$=H, R$^7$=Me). The crude product 4a was taken in 30% trifluoroacetic acid in dichloroethane (10 mL), dimethylsulfide (0.5 mL) and stirred for 1 h at rt. The solvent was removed and the residue was kept under high vacuum for 1 h and the product 4b (R$^1$=Me, R$^7$=Me) was taken as such for the next step.

TLC: R$_f$=0.63 (10% MeOH/DCM); MS(ESPOS): 281 [M+H]$^+$. $^1$H NMR (300 MHz, CD$_3$OD) δ 1.95 (s, 3), 2.08 (s, 3), 3.60 (dd, J=3.3, 10.20, 1), 3.92 (s, 3), 4.13 (dd, J=4.8, 10.20, 1), 4.49 (d, J=1.2, 1), 5.38 (d, J=5.4, 1).

Method I

To the Boc-protected product 1c (P=Boc, R$^1$=Me) (500 mg, 0.88 mmol) in THF (10 mL), tetrabutylammonium fluoride (2.5 mmol, 1 M in THF) was added and the reaction mixture was stirred at rt for 1 h. The solvent was removed and the residue was purified on silica gel column using 5% methanol in dichloromethane as eluent. The product (111 mg, 0.31 mmol) obtained from the column was then taken in a mixture of dichloromethane (3 mL) and pyridine (3 mL) to which acetic anhydride (0.5 mL, 10.6 mmol) and dimethylaminopyridine (80 mg, 1.7 mmol) were added and stirred at rt overnight. The solvent was removed and the crude product was purified on silica gel column using 30% ethyl acetate in hexanes as eluent to provide 5a (P=Boc, R$^1$=Me) (58 mg, 38%).

TLC: R$_f$=0.73 (50% EtOAc/Hexanes); MS(ESPOS): 500 [M+Na]$^+$. $^1$H NMR (300 MHz, CDCl$_3$) δ 1.38 (s, 9), 1.91 (s, 3), 1.98 (s, 3), 2.07 (s, 3), 2.18 (s, 3), 4.33 (m, 1), 4.72 (m, 1), 4.94 (m, 1), 5.21 (m, 2), 5.45 (s, 1), 5.57 (m, 1).

To product 5a (P=Boc, $R^1$=Me) (158 mg, 0.331 mmol) in DCM (5 mL), dimethylaminosulfurtrifluoride (732 μL, 3.31 mmol) was added and stirred overnight. More DCM was added and the organic portion was washed with sodium bicarbonate. The residue obtained on removal of solvent was purified on silica gel column chromatography using 20% ethyl acetate in hexanes as eluent (100 mg, 60%) to provide the protected product (P=Boc, $R^1$=Me). The Boc-protected product was taken up in 30% trifluoroacetic acid in dichloroethane and dimethylsulfide and stirred for 1 h at rt. The solvent was removed to provide the product 5b ($R^1$=Me).

TLC: $R_f$=0.63 (40% MeOH/Hexanes); MS(ESPOS): 522 [M+Na]$^+$. $^1$H NMR (300 MHz, CDCl$_3$) δ 1.40 (s, 9), 1.69 (t, J=18.9, 3), 1.98 (s, 3), 2.08 (s, 6), 2.13 (s, 3), 4.22–4.30 (m, 1), 4.53 (dd, J=10.9, 25.3, 1), 5.16–5.28 (m, 2), 5.52 (s, 1), 5.63 (d, J=5.2, 1).

Method J

Enolization (LiHMDS) and alkylation of 7a with 4-bromo-2-methyl-2-butenyl afforded a mixture of diastereomers of the lactam 7b ($R^{9'}$=2-methyl-2-butenyl) (61%) according to the literature procedure by Zhang, R.; et al., Journal of the American Chemical Society. 1998, 120, 3894–3902. Compound 7a is commercially available from vendors such as Bachem. Alternatively, 7a can be prepared by methods well known in the art for an example see Baldwin, et al.; Tetrahedron, 1989, 45, 7449–7468.

The lactam 7b was reduced to the pyrrolidine 7c ($R^{9'}$=2-methyl-2-butenyl) (70%) by the two-step sequence involving superhydride reduction of the lactam to the hemiaminal and the subsequent reduction of the hemiaminal with Et$_3$SiH/BF$_3$.OEt$_2$. The pyrrolidine 7c ($R^{9'}$=2-methyl-2-butenyl) (778 mg, 2.08 mmol), 10% palladium on carbon (230 mg), in anhydrous methanol (25 mL) was subjected to Parr hydrogenolysis at 50 psi for 5 h. The reaction mixture was filtered through a celite pad and washed several times with methanol. The combined washings and filtrate were evaporated to dryness, affording, without further purification, a colorless oil 7d ($R^9$=2-methylbutyl).

TLC: $R_f$=0.3 [Solvent system: DCM:hexanes:MeOH(6:5:1)]. MS(ESNEG): 284.5 [M–H]$^-$.

Method K

Enolization (LiHMDS, 33 mmol, 33 mL, 1.1 equiv) and alkylation of 7a (9.47 g, 29.7 mmol, 1 equiv) with cis-1-bromo-2-pentene (4.21 mL, 35.6 mmol, 1.2 equiv), in anhydrous THF at −78° C. under nitrogen, afforded a mixture of diastereomers of the lactam 7b ($R^{9'}$=2-pentenyl) (43.2%) after silica gel purification. The lactam 7b (3.96g, 10.22 mmol) was reduced to the pyrrolidine 7c ($R^{9'}$=2-pentenyl) by the two-step sequence involving superhydride reduction of the lactam to the hemiaminal, at −78° C. in anhydrous THF, and the subsequent reduction of the hemiaminal with Et$_3$SiH/BF$_3$OEt$_2$ in anhydrous DCM at −78° C. affording 7c ($R^{9'}$=2-pentenyl) (71%) after silica gel purification. The pyrrolidine 7c (2.71 g, 7.26 mmol), 10% palladium on carbon (560 mg), in anhydrous methanol (30 mL) was subjected to Parr hydrogenolysis at 50 psi for 5 h. The reaction mixture was filtered through a celite pad and washed several times with methanol. The combined washings and filtrate were evaporated to dryness, affording, without further purification, a colorless oil 7d ($R^9$=pentyl) (1.68 g, 80%).

TLC: $R_f$=0.3 [Solvent system: DCM:hexanes:MeOH (6:5:1)]. MS(ESNEG): 284.5 [M–H]$^-$.

Method L

Ozonolysis of 7d ($R^9$=2-methylbutyl) in anhydrous dichloromethane followed by treatment with DMS at −78° C. afforded aldehyde 8a (77%). 4-Fluorobenzyl phosphonium chloride (0.87 g, 2.13 mmol) and potassium t-butoxide (0.17 g, 1.48 mmol) were suspended in toluene under nitrogen with vigorous stirring. After 4 h, a solution of aldehyde 8a (204 mg, 0.59 mmol) in toluene (4.6 mL) was added drop-wise. The reaction mixture was stirred at rt for 2 h and diluted with ethyl acetate (50 mL). The organic layer was washed with water (2×20 mL), brine, dried and concentrated. The residue was purified by chromatography to give a clear syrup 8b ($R^{9'}$=3-(4-fluorophenyl)prop-2-enyl) (171 mg).

To a solution of 8b ($R^{9'}$=3-(4-fluorophenyl)prop-2-enyl) (171 mg, 0.39 mmol) in MeOH (25 mL) in a Parr bottle was added 10% palladium on carbon (Degussa wet form 50% w/w water) (200 mg). The bottle was purged and charged with H$_2$ to 40 psi, and shaken for 4 h. The reaction mixture was filtered through celite and rinsed with MeOH. The filtrate was concentrated to give a yellow oil 8c ($R^9$=3-(4-fluorophenyl)propyl) (120 mg).

MS(ESPOS): 374.5 [M+Na]$^+$, MS(ESNEG): 350.3 [M–H]$^-$.

Method M

4-Chlorobenzyl phosphonium chloride (0.95 g, 2.24 mmol, 3.9 equiv) and potassium t-butoxide (0.17 g, 1.55 mmol, 2.7 equiv) were suspended in toluene (7.5 mL) under nitrogen with vigorous stirring. After 4 h, a solution of aldehyde 8a (200 mg, 0.58 mmol, 1 equiv) in toluene (4.9 mL) was added dropwise. The reaction mixture was stirred at rt for 2 h and diluted with ethyl acetate (50 mL). The organic layer was washed with water (2×20 mL), brine, dried and concentrated. The residue was purified by chromatography to give a clear syrup 8b ($R^{9'}$=3-(4-chlorophenyl)prop-2-enyl) (216 mg, 82%).

MS(ESPOS): 478.5 [M+Na]$^+$, MS(ESNEG): 454.4 [M–H]$^-$.

To a solution of 8b ($R^{9'}$=3-(4-chlorophenyl)prop-2-enyl) (147 mg, 0.32 mmol) in cyclohexane (50 mL) was added 10% palladium on carbon (Degussa wet form 50% w/w water) (80 mg). The reaction mixture was stirred at rt under 1 atm H$_2$ overnight. The reaction mixture was filtered through celite and rinsed with MeOH. The filtrate was concentrated to give the alkane product 8c ($R^9$=3-(4-chlorophenyl)propyl) as a clear oil (131 mg, 89%). To a solution of the alkane (131 mg, 0.29 mmol, 1 equiv) in THF (3 mL) and water (1 mL) was added lithium hydroxide monohydrate (60 mg, 1.43 mmol, 5 equiv). The reaction mixture was stirred at rt overnight. The THF was removed under vacuum. The residue was diluted with water (5 mL) and washed with ether (10 mL). The aqueous layer was taken up in ethyl acetate (60 mL) and partitioned with 10% citric acid (30 mL). The organic layer was washed with water and brine, dried and concentrated to give a clear syrup 8c ($R^9$=3-(4-chlorophenyl)propyl) (105 mg, 100%).

MS(ESPOS): 390.4 [M+Na]$^+$, 268.4 [M–Boc+H]$^+$.

Method N

To a solution of aldehyde 8a (406.5 mg, 1.17 mmol, 1 equiv) in dimethyl acetamide (0.25 mL) at 0° C. was added dibromodifluoromethane (0.21 mL, 2.34 mmol, 2 equiv). To the stirred mixture was added a solution of triphenylphosphine (0.61 g, 2.34 mmol, 2 equiv) in dimethyl acetamide (0.5 mL) over a period of 20 minutes under nitrogen. The reaction mixture was warmed to rt and stirred for 30 minutes, and then was added to an activated zinc (0.25 g, 3.82 mmol, 3.3 equiv) with the aid of dimethyl acetamide (0.3 mL). The resulting reaction mixture was stirred at 110° C. for 1 h and cooled to rt and filtered with the aid of dimethylacetamide (7 mL). The filtrate was poured into ice water (100 mL) and extracted with ether (150 mL). The ether layer was washed with brine, dried and concentrated. The residue was purified by chromatography to give a clear oil 8b ($R^{9'}$=3,3-difluoroprop-2-enyl) (182 mg, 41%).

MS(ESPOS): 282.4 [M−Boc+H]$^+$.

To a solution of 8b ($R^{9'}$=3,3-difluoroprop-2-enyl) (126 mg, 0.33 mmol) in MeOH (35 mL) was added 10% palladium on carbon (Degussa wet form 50% w/w water) (120 mg). The reaction mixture was stirred at rt under hydrogen (1 atm) overnight and was filtered through celite with the aid of MeOH. The filtrate was concentrated to give a clear syrup 8c ($R^9$=3,3-difluoropropyl) (97 mg, 100%).

MS(ESPOS): 194.4 [M−Boc+H]$^+$, MS(ESNEG): 292.4 [M−H]$^-$.

Method O

To a solution of aldehyde 8a (258 mg, 0.74 mmol, 1 equiv) in THF (3 mL) at 0° C. was added tetraallyltin (178 μL, 0.74 mmol, 1 equiv), followed by the drop-wise addition of boron trifluoride etherate (94.3 μL, 0.74 mmol, 1 equiv) over a period of 15 min. The reaction mixture was stirred at 0° C. for 1.5 h. Then a solution of potassium fluoride (125 mg) in water (1.25 mL) was added. The resulting mixture was warmed to rt and stirred at rt for 20 min. This was followed by the addition of methanol (10 mL) and the resulting mixture was stirred at rt for another 20 mm. The reaction mixture was filtered over celite. The filtrate was evaporated to dryness. The residue was diluted with dichloromethane (100 mL), washed with water (50 mL), dried, concentrated and purified by chromatography to give a clear oil 9a ($R^9$=2-hydroxypent-4-enyl) (261 mg, 90%): MS(ESPOS): 412.5 [M+Na]$^+$, 290.4 [M−Boc+H]$^+$.

To a solution of dimethylsulfoxide (0.17 mL, 2.42 mmol, 3 equiv) in dichloromethane (0.5 mL) at −72° C. was added a 2 M solution of oxalyl chloride in dichloromethane (0.61 mL, 1.21 mmol, 1.5 equiv) over a period of 1 min. The mixture was stirred at −72° C. for 25 min, followed by the drop-wise addition of a solution of the alcohol 9a (314 mg, 0.81 mmol, 1 equiv) in dichloromethane (1.4 mL) over a period of 2 min. The reaction mixture was stirred at −72° C. for 25 min, then warmed to −50° C. and stirred for an additional 2 h. Triethylamine (0.56 mL, 4.04 mmol, 5 equiv) was added and stirred at −50° C. for 25 min. The mixture was diluted with ethyl acetate (100 mL), washed with 5% citric acid (100 mL), water, saturated aqueous NaHCO$_3$ and brine, dried, evaporated and coevaporated with anhydrous toluene to give a clear syrup 9b ($R^9$=2-propenylcarboxymethyl) (287 mg, 92%). MS(ESPOS): 288.5 [M−Boc+H]$^+$; MS(ESNEG): 386.2 [M−H]$^-$.

To a solution of ketone 9b (225.1 mg, 0.58 mmol, 1 equiv) in dichloromethane (2 mL) at −78° C. was added diethylaminosulfur trifluoride (0.46 mL, 3.49 mL, 6 equiv). The reaction mixture was warmed to rt and stirred at rt for 3 h, followed by an addition of additional (diethylamino)sulfur trifluoride (0.46 mL, 3.49 mL, 6 equiv) at −78° C. The mixture was warmed to rt and stirred overnight. Then the mixture was diluted with dichloromethane (60 mL), washed with sat. aqueous NaHCO$_3$ (1×), brine (1×), dried, and evaporated. The residue was purified by chromatography to give a yellow oil 9c (X, X=fluoro, flouro) (75 mg, 32%).

MS(ESPOS): 310.5 [M−Boc+H]$^+$.

To a solution of 9c ($R^9$=2,2-difluoropent-4-enyl) (85 mg, 0.21 mmol) in MeOH (20 mL) was added 10% palladium on carbon (Degussa wet form 50% w/w water) (100 mg). The reaction mixture was stirred at rt under hydrogen (1 atm) overnight, was filtered through celite with the aid of MeOH (10 mL). To the filtrate was added 10% palladium on carbon (Degussa wet form 50% w/w water) (130 mg). The reaction mixture was stirred at rt under hydrogen (1 atm) overnight, was filtered through celite with the aid of MeOH (10 mL). The filtrate was concentrated to give haloalkyl N-Boc-amino acid 9d (X,X=fluoro, fluoro) (67.7 mg, 100%) as a clear syrup.

MS(ESPOS): 344.4 [M+Na]$^+$, 222.4 [M−Boc+H]$^+$+MS (ESNEG): 320.2 [M−H]$^-$.

Method P

To 4-propylpyridine (2.5 g, 20 mmol), 30% hydrogen peroxide (2.4 g) was added and refluxed overnight. The solvent was removed and the resulting residue was taken in DCM (30 mL). Trimethylsilyl cyanide (2.6 g, 26 mmol) was added to the above solution followed by dimethylcarbamyl chloride (2.8 g, 26 mmol), and the reaction mixture was stirred at rt overnight. Potassium carbonate (10%, 100 mL) was added. The organic layer was separated, dried over sodium sulfate and then concentrated to obtain 4-propyl-2-cyanopyridine (2.5 g, 93%). The crude nitrile was dissolved in aqueous hydrochloric acid (6N, 60 mL) and refluxed overnight. The 4-propyl-2-carboxylic acid pyridine 10b ($R^9$=propyl) was obtained after crystallization from acetonitrile (2 g, 71%).

MS(ESPOS): 166 [M+H]$^+$; $^1$H NMR (300 MH$_2$, CD$_3$OD) δ 8.75 (dd, J=9.0, 3.0, 1), 8.42 (s, 1), 8.08 (dd, J=9.0, 3.0, 1), 3.00 (t, J=7.5, 2), 1.82 (m, 2), 1.05 (t, J=7.2, 3).

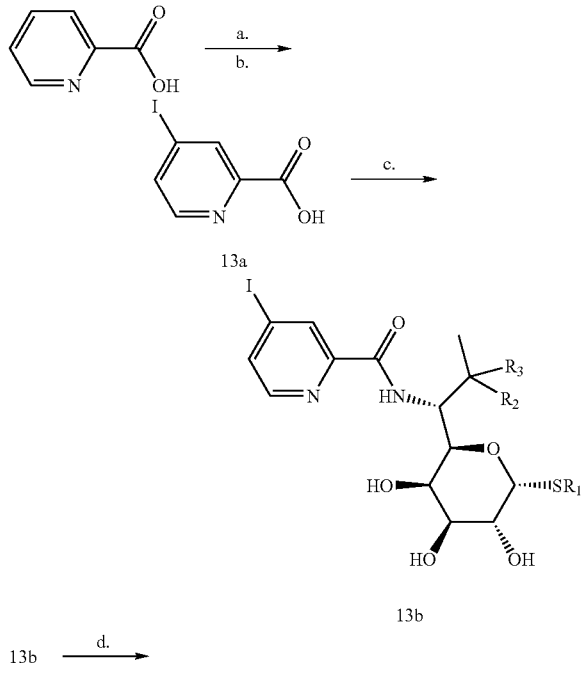

Method Q

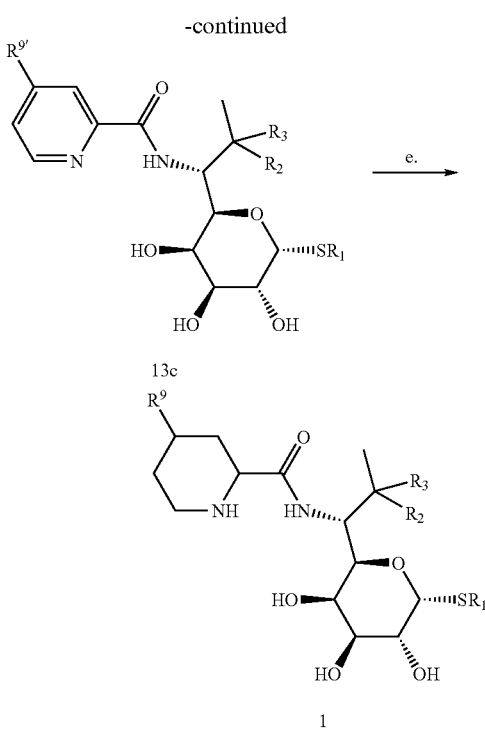

A mixture of picolinic acid (Aldrich) (20 g, 162 mmol, 1 equiv) and sodium bromide (33.43 g, 325 mmol, 2 equiv) in thionyl chloride (81 mL) was refluxed for 5 h. The solvent was removed under vacuum. Absolute methanol (160 mL) was added and the mixture was stirred at rt for 30 minutes. The solvent was evaporated, and the residue was taken up in 5% sodium bicarbonate and extracted with ethyl acetate (3×). The organic layers were combined and dried over $MgSO_4$ and evaporated. The residue was purified by chromatography to give 4-chloropicolinic acid methyl ester as a white solid (19.9 g, 72%): $^1$H NMR (300 MHz, $CDCl_3$) δ 8.63 (d, J=5.4, 1), 8.13 (d, J=2.1, 1), 7.48 (dd, J=2.0, 5.3, 1), 4.00 (s, 3).

A mixture of 4-chloropicolinic acid methyl ester (2.4 g, 14.1 mmol), 57% hydroiodic acid (13.3 mL) and 50% aqueous hypophosphorous acid (0.66 mL) was stirred at 85° C. for 2 h and then was stirred at 107° C. overnight. The mixture was cooled to 95° C. At this temperature over 30 minutes 10 M sodium hydroxide aqueous solution (4.2 mL) was added, followed by the addition of water (15.2 mL). The mixture was cooled to rt and stirred at rt for 1 h. The precipitate was filtered, washed with cold water and dried under high vacuum overnight to give 4-iodopipecolinic acid 13a (3.5 g, 66%): $^1$H NMR (300 MHz, DMSO $d_6$) δ 8.39 (d, J=5.1, 1), 8.35 (d, J=1.8, 1), 8.07 (dd, J=1.7, 5.2, 1); MS (ESPOS): 250.2 [M+H]$^+$.

To a mixture of 7-Me MTL HCl salt 2b ($R^1$=Me, $R^2$=Me) (200 mg, 0.69 mmol, 1 equiv) in dry DMF (1.8 mL) at 0° C. was added triethylamine (0.50 mL, 3.61 mmol, 5.2 equiv), followed by the addition of BSTFA (0.28 mL, 1.04 mmol, 1.5 equiv). The reaction mixture was stirred at 0° C. for 10 minutes, and then was stirred at rt for 50 minutes. To the reaction mixture was added the acid 13a (341 mg, 0.90 mmol, 1.3 equiv) and HATU (423 mg, 1.11 mmol, 1.6 equiv). The reaction mixture was stirred at rt for 3 h. The reaction mixture was evaporated to dryness, taken up in ethyl acetate, washed with water (1×), sat. $NaHCO_3$ (1×) and brine. The organic layer was dried over $Na_2SO_4$ and evaporated to give a yellow residue which was dissolved in methanol (20 mL) to which was added dry Dowex™ resin (250 mg). The reaction mixture was stirred at rt for 1 h. The resin was removed by filtration and the crude product eluted with 2M ammonia in methanol. The methanolic eluent was evaporated, and the resulting residue was purified by chromatography to provide a white solid 13b ($R^1$=Me, $R^2$=Me, $R^3$=H) (250 mg, 75%): $^1$H NMR (300 MHz, $CD_3OD$) δ 8.46 (d, J=1.8, 1), 8.30 (d, J=5.4, 1), 7.98 (dd, J=1.8, 5.1, 1), 5.25 (d, J=6.0, 1), 4.32–4.23(m, 2), 4.09 (dd, J=5.7, 10.2, 1), 3.87 (d, J=3.0, 1), 3.54 (dd, J=3.3, 10.2, 1), 2.24–2.15 (m, 1), 2.11 (s, 3), 0.99–0.96 (m, 6); MS (ESPOS): 483.5 [M+H]$^+$; MS (ESNEG): 481.4 [M-H]$^-$.

To a dry flask was added 13b (R1=Me, R2=Me, R3=H) (133.9 mg, 0.28 mmol, 1 equiv), triphenylphosphine (46.7 mg, 0.18 mmol, 0.64 equiv), copper (I) iodide (33.9 mg, 0.18 mmol, 0.64 equiv), palladium acetate (20 mg, 0.09 mmol, 0.32 equiv) and triethylamine (1.6 mL). The mixture was deaerated with nitrogen, followed by addition of 3-prop-2-ynyl-cyclopentane (120 mg, 1.11 mmol, 4 equiv). The mixture was stirred at 50° C. overnight. The solvent was removed under vacuum to give a dark residue. The residue was purified by chromatography to give 13c (R1=Me, R9'=3-cyclopentyl-prop-1-ynyl, R2=Me, R3=H) as a yellow solid (106 mg, 83%): $^1$H NMR (300 MHz, $CD_3OD$) δ 8.55 (d, J=4.8, 1), 7.98 (s, 1), 7.47 (dd, J=1.7, 5.0, 1), 5.26 (d, J=5.4, 1), 4.33–4.22 (m, 2), 4.10 (dd, J=5.5, 10.4, 1), 3.86 (d, J=3.3, 1), 3.55 (dd, J=3.3, 10.5, 1), 2.49 (d, J=6.9, 2), 2.26–2.12 (m, 2), 2.11 (s, 3), 1.93–1.82 (m, 2), 1.73–1.55 (m, 4), 1.43–1.31 (m, 2), 1.00–0.96 (m, 6); MS (ESPOS): 463.6 [M+H]$^+$; MS (ESNEG): 461.5 [M-H]$^-$.

Method R

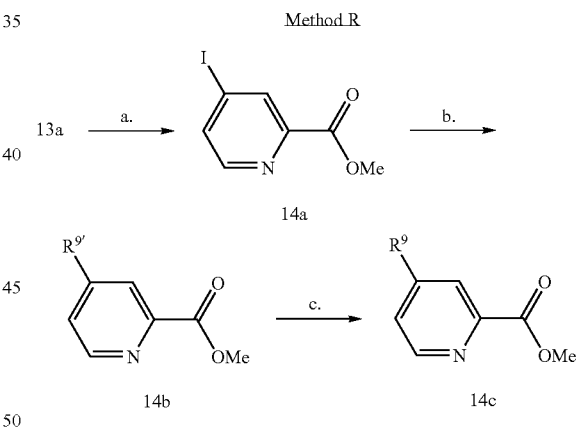

To a solution of 13a prepared in method Q (5 g, 13.26 mmol) in methanol (500 mL) was added a few drops of conc. sulfuric acid. The reaction mixture was refluxed overnight. The solvent was evaporated and the residue was purified by chromatography to give 4-iodopipecolinic acid methyl ester 14a as a yellow solid (3.0 g, 86%): $^1$H NMR (300 MHz, $CDCl_3$) δ 8.49 (d, J=1.5, 1), 8.37 (d, J=5.4, 1), 7.85 (dd, J=1.6, 5.2, 1), 4.00 (s, 3); MS (ESPOS): 264.3 [M+H]$^+$.

To a dry flask were added 14a (1 g, 3.8 mmol, 1 equiv), triphenylphosphine (79.7 mg, 0.3 mmol, 0.08 equiv), copper (I) iodide (57.9 mg, 0.3 mmol, 0.08 equiv), palladium acetate (34.1 mg, 0.15 mmol, 0.04 equiv) and triethylamine (14 mL). The mixture was deaerated with nitrogen, followed by addition of 3-butyn-1-ol (0.53 g, 7.6 mmol, 2 equiv). The mixture was stirred at rt for 3 h. The solvent was removed under vacuum to give a dark residue. The residue was purified by chromatography to give 14b (R$^{9'}$=3-hydroxy-but-1-ynyl) as a yellow oil (0.78 g, 100%): $^1$H NMR (300 MHz, CDCl$_3$) δ 8.66–8.63 (m, 1), 8.09–8.08 (m, 1), 7.43–7.40 (m, 1), 3.99 (s, 3), 3.88–3.82 (m, 2), 2.72 (t, J=6.3, 2). MS (ESPOS): 206.4 [M+H]$^+$.

To a solution of the above 14b (R$^{9'}$=3-hydroxy-but-1-ynyl) (0.78 g, 3.8 mmol) in methanol (40 mL) was added 10% palladium on carbon (0.4 g). The flask containing the reaction mixture was purged and charged with hydrogen (1 atm) and stirred at rt overnight. The palladium was removed by filtration and the filtrate was concentrated to give 14c (R$^{9'}$=3-hydroxybutyl) as an oil (0.77 g, 97%): $^1$H NMR (300 MHz, CDCl$_3$) δ 8.60 (d, J=4.5, 1), 7.97 (d, J=1.2, 1), 7.29 (dd, J=1.6, 5.0, 1), 3.99 (s, 3), 3.67 (t, J=6.3, 2), 2.72 (t, J=7.7, 2), 1.81–1.69 (m, 2), 1.62–1.54 (m, 2); MS (ESPOS): 210.4 [M+H]$^+$.

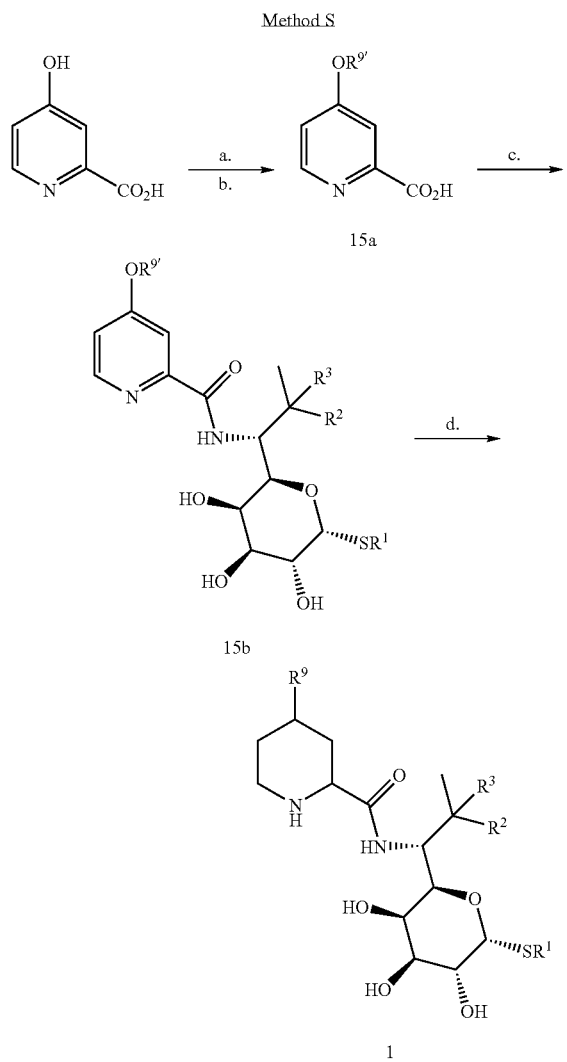

To 4-hydroxypyridine-2-carboxylic acid 10b (R$^9$=hydroxy) (200 mg, 1.4 mmol) in DMF (2 mL), potassium carbonate (397 mg, 2.8 mmol) was added followed by n-bromobutane (197 mg, 1.4 mmol), warmed at 60° C. for overnight. The solvent was removed to obtain the crude ester product. The crude ester (360 mg, 1.4 mmol) was dissolved in THF (4 mL), lithium hydroxide (72 mg, 1.7 mmol) was added, and the reaction mixture stirred at room temperature for 2 hr. The residue obtained on removal of solvent was purified by silica gel chromatography using 10% MeOH in DCM to provide 4-butoxypyridine-2-carboxylic acid 15a (R$^{9'}$=butyl) (100 mg, 43%). $^1$H NMR (300 MHz, CD$_3$OD) δ 8.37 (d, J=6.0, 1), 7.63 (d, J=2.7, 1), 7.07 (dd, J=2.7, 6.0, 1), 4.15 (t, J=6.6, 2), 1.82 (m, 2), 1.54 (m, 2), 1.01 (t, J=7.5, 3). MS (ESNEG): 194 [M−H]$^−$.

To 4-butoxypyridine-2-carboxylic acid 15a (R$^{9'}$=Butyl) (100 mg, 0.5 mmol) in DMF (2 mL), 7-methyl α-thiolincosaminide 2b (R$^1$=Me, R$^2$=Me) (147 mg, 0.5 mmol) was added, followed by HBTU (214 mg, 0.55 mmol) and DIEA (132 mg, 1 mmol). The reaction mixture was stirred at room temperature for 2 hr. The solvent was removed, and purification of the crude material was carried out by silica gel column chromatography to obtain compound 15b (R$^1$=Me, R$^2$=Me, R$^{9'}$=butyl) (201 mg, 91%): $^1$H NMR (300 MHz, CD$_3$OD) δ 8.42 (m, 1), 7.96 (s, 1), 7.09 (m, 1), 5.27 (d, J=5.4, 1), 4.10–4.87 (m, 3), 3.85 (d, J=3.3, 1), 3.76 (m, 1), 2.11 (m, 4), 1.81 (m, 2), 1.49 (m, 4), 0.99 (m, 9). MS (ESPOS): 428 [M+H]$^+$.

To a solution of the pyridine 15b (R$^1$=Me, R$^2$=Me, R$^{9'}$=butyl) (200 mg, 0.46 mmol) in water (10 mL), AcOH (3 mL) and MeOH (2 mL), was added PtO$_2$ (200 mg) and the resulting reaction mixture shaken under 55 psi hydrogen overnight. Residual catalyst was removed by filtration through celite, and the solvent was removed to obtain the crude product. Purification was carried out by silica gel column chromatography using 20% MeOH in DCM to obtain lincosamide analog 1 (R$^1$=Me, R$^2$=Me, R$^3$=H, R$^9$=butoxy) (12 mg, 6%). $^1$H NMR (300 MHz, CD$_3$OD) δ 5.25 (d, J=5.4, 1), 4.22 (dd, J=10.2; 3.3, 1), 4.08 (m, 2), 3.81 (d, J=3.0, 1), 3.70 (m, 1), 3.54 (m, 4), 3.43 (m, 2), 2.90 (m, 1), 2.41 (m, 1), 2.19 (m, 1), 2.10 (s, 3) 1.45 (m, 6), 0.92 (m, 9); MS (ESPOS): 435 [M+H]$^+$.

Method T

Following the general method found in scheme 16, to a solution of β-lactam 16a (2.92 g, 12.8 mmol) 1 equiv; prepared from benzyl (S)-(−)-4-oxo-2-azetidine-carboxylate (Aldrich) as described by Baldwin et al, *Tetrahedron*, 1990, 46, 4733 in THF (30 mL) at 0° C. was added a solution of LDA (2.0 M, 14.0 mL, 28.1 mmol, 2.2 equiv) via syringe pump over 20 min. The reaction was stirred at 0° C. for 30 min., crotyl bromide (85%, 2.89 mL, 28.1 mmol, 2.2 equiv) was added dropwise over ca. 1.5 min, and the mixture was stirred for 2 h at 0° C., and then partitioned between 1.0 M aqueous KHSO$_4$ (100 mL) and EtOAc (100 mL). The organic layer was separated and washed with 1.0 M aqueous KHSO$_4$ (100 mL), brine (100 mL), dried (MgSO$_4$), filtered and concentrated to give 16b (R$^{9'}$=2-butenyl) 3.65 g (100%) of greenish yellow solid. This material was used without further purification.

MS (ESNEG): 282.2 [M−H]$^−$.

(Trimethylsilyl)diazomethane (2.0 M in Et$_2$O, 25.0 mL, 50 mmol, 3.9 equiv) was slowly added to a solution of acid 16b (R$^{9'}$=2-butenyl) (3.65 g, 12.9 mmol, 1 equiv) in methanol (70 mL) at 0° C. Solvent was removed under vacuum to give 3.53 g (11.9 mmol, 92%) of the desired ester product as a yellow oil. This material was used in the subsequent reaction without further purification.

To a solution of alkene 16c (R$^{9'}$=2-butenyl) (3.53 g, 11.9 mmol, 1 equiv) in EtOAc (40 mL) at 23° C. was added Pd/C (10 wt. %, 482 mg). The reaction vessel was charged with hydrogen (balloon), and the mixture stirred vigorously. After 2.5 h, the reaction mixture was filtered through a pad of Celite. Celite was washed, with EtOAc (200 mL) and the filtrate was concentrated to provide 3.51 g (11.7 mmol, 99%) of 16c ($R^9$=butyl) as a yellow oil. This material was used without further purification.

MS (ESPOS): 300.4 [M+H]$^+$.

To a solution of N-TBS β-lactam 16c ($R^9$=butyl) (3.51 g, 11.7 mmol, 1 equiv) in THF (50 mL) at 23° C. was added Et$_3$N.3HF (0.95 mL, 5.85 mmol, 0.5 equiv). After stirring for 60 min at 23° C., the reaction mixture was partitioned between 90% saturated brine (150 mL) and EtOAc (200 mL). The organic layer was separated and washed with brine (150 mL), dried (MgSO$_4$), filtered and concentrated. The product was purified via flash column chromatography on silica gel using 50% EtOAc in hexane as eluent to give 1.48 g (8.0 mmol, 68%) of 16d ($R^9$=butyl) as a clear oil.

MS (ESPOS): 578.3 [3M+H]$^+$.

To a solution of β-lactam 16d ($R^9$=butyl) (2.06 g, 11.1 mmol, 1 equiv) in THF (150 mL) at 23° C. was added a solution of LiAlH$_4$ (1.0 M in THF, 22.9 mL, 22.9 mmol, 2.06 equiv) via syringe over the course of 2 min. After stirring for 10 min at 0° C., the reaction was warmed to 23° C., stirred for 15 min, and then refluxed for 3 h. The mixture was then cooled to 0° C. and quenched via careful addition of H$_2$O (1.0 mL), followed by 15% aqueous NaOH (1.0 mL), and then H$_2$O (2.5 mL). The resulting suspension was stirred at 23° C. for 1.5 h, diluted with Et$_2$O (250 mL), and filtered through Celite, washing with Et$_2$O (250 mL). The filtrate was concentrated to furnish 1.42 g of the desired product 16e ($R^9$=butyl) (9.93 mmol, 89%) as a clear oil. The product was used without further purification.

MS (ESPOS): 287.4 [2M+H]$^+$.

To a solution of amino alcohol 16e ($R^9$=butyl) (1.41 g, 9.86 mmol, 1 equiv) in dichloromethane (50 mL) at 23° C. was added Boc$_2$O (2.59 g, 11.9 mmol, 1.2 equiv). After stirring for 2 h at 23° C., the reaction mixture was concentrated. The product was purified via flash column chromatography on silica gel using 33% EtOAc in hexane as eluent to give 1.53 g (6.31 mmol, 64%) 16f ($R^9$=butyl) as a clear oil.

MS (ESPOS): 266.0 [M+Na]$^+$.

To a solution of NaIO$_4$ (8.81 g, 41.2 mmol, 10 equiv) in H$_2$O (60 mL) at 23° C. was added RuCl$_3$.xH$_2$O (350 mg, catalytic amount) followed by a solution of alcohol 16f ($R^9$=butyl) (1.00 g, 4.12 mmol, 1 equiv) in acetone (60 mL). The biphasic mixture was stirred for 30 min at 23° C., then extracted with EtOAc (250 mL), decanting the organic layer. The aqueous residue was extracted with two further portions of EtOAc (2×150 mL). The combined organic extracts were treated with 2-propanol (75 mL) and stirred at 23° C. After stirring for 2 h the mixture was filtered through Celite, washing with EtOAc (300 mL). The filtrate was concentrated to furnish 0.78 g of the desired product 16g ($R^9$=butyl) (3.04 mmol, 74%) as a dark oil. The product was used without further purification. MS (ESPOS): 280.0 [M+Na]$^+$.

Method U

Following the method shown in general scheme 17, to a solution of alcohol 16f ($R^{9'}$=2-methyl-2-butenyl) (3.31 g, 13.0 mmol, 1 equiv) in DMF (100 mL) at 23° C. was added imidazole (2.21 g, 32.5 mmol, 2.5 equiv) followed by TBSCl (2.93 g, 19.5 mmol, 1.5 equiv). The reaction was stirred for 35 min and then quenched with MeOH (2.0 mL). After stirring for 5 min, the resulting mixture was partitioned between Et$_2$O (500 mL) and H$_2$O (400 mL). The organic layer was separated and washed with H$_2$O (400 mL), brine (200 mL), dried (MgSO$_4$), filtered and concentrated to give 17a ($R^{9''}$=2-methyl-2-butenyl) 4.13 g (11.2 mmol, 86%) of the desired product as a clear oil.

MS (ESPOS): 392.4 [M+Na]$^+$.

A solution of intermediate 17a ($R^{9'}$=2-methyl-2-butenyl) prepared as described in general method T (2.03 g, 5.50 mmol, 1 equiv) in dichloromethane (80 mL) at −78° C. was treated with ozone (1.2 L/min) introduced via a gas dispersion tube until a blue color was observed (20 min). A stream of oxygen (1.2 L/min) was then passed through the reaction mixture to discharge excess ozone. After 15 min, oxygen flow was ceased and PPh$_3$ (2.16 g, 8.25 mmol, 1.5 equiv) was added. The reaction mixture was stirred at −78° C. for 30 min, then at 0° C. for 15 min, and then warmed to 23° C. After stirring for 10 min at 23° C., silica gel was added, and the resulting mixture concentrated to dryness under vacuum to afford a free-flowing powder that was loaded directly onto a silica gel column. Flash column chromatography using 30–33% EtOAc in hexane as eluent gave 1.52 g (4.42 mmol, 80%) of 17b as a clear oil.

MS (ESPOS): 398.0 [M+MeOH+Na]$^+$.

To a suspension of Wittig salt (cyclopropylmethyl triphenyl phosphine) (1.216 g, 3.06 mmol, 1.5 equiv) in THF (10 mL) at 0° C. was added a solution of NaHMDS (1.0 M in THF, 3.06 mL, 3.06 mmol, 1.5 equiv) dropwise via syringe over the course of 1 min. The resulting solution was stirred for 20 min at 0° C. then treated with a solution of aldehyde 17b (700 mg, 2.04 mmol, 1 equiv) in THF (3.0 mL; 2×1.0 mL flush) transferred via cannula. After 15 min at 0° C. the reaction was warmed to 23° C., stirred for a further 10 min then quenched with saturated NH$_4$Cl (30 mL). The resulting mixture was partitioned between Et$_2$O (120 mL) and H$_2$O (50 mL). The organic layer was separated and washed with brine (50 mL), dried (MgSO$_4$) filtered and concentrated. Flash column chromatography using 10% EtOAc in hexane as eluent gave 588 mg (1.54 mmol, 76%) of 17c ($R^{9'}$=2-(3-cyclopropyl)-propen-1-yl) as a clear oil.

MS (ESPOS): 404.3 [M+Na]$^+$.

To a solution of TBS ether 17c ($R^{9'}$=2-(3-cyclopropyl)-propen-1-yl) (190 mg, 0.50 mmol, 1 equiv) in THF (10 mL) at 23° C. was added a solution of TBAF (1.0 M in THF, 0.55 mL, 0.55 mmol, 1.1 equiv). The resulting solution was stirred for 40 min at 23° C. then partitioned between Et$_2$O (50 mL) and H$_2$O (50 mL). The organic layer was separated and washed with brine (50 mL), dried (MgSO$_4$), filtered and concentrated to give 133 mg (0.50 mmol, 100%) of 17c ($R^{9'}$=2-(3-cyclopropyl)-propen-1-yl) as a clear oil.

MS (ESPOS): 290.2 [M+Na]$^+$.

To a solution of alkene 17c ($R^{9'}$=2-(3-cyclopropyl)-propen-1-yl) (191 mg, 0.50 mmol, 1 equiv) in dioxane (5.0 mL) at 23° C. was added dipotassium azodicarboxylate (973 mg, 5.01 mmol, 10 equiv) followed by slow addition of a solution of AcOH (573 μL, 10.0 mmol, 20 equiv) in dioxane (5.0 mL) over the course of 16 h via syringe pump. Following the completion of the addition the reaction was stirred a further 6 h then filtered through a glass frit with the aid of Et$_2$O (150 mL) to remove precipitate. The resulting solution was washed with saturated aqueous NaHCO$_3$ (2×100 mL), brine (80 mL), dried (MgSO$_4$), filtered and concentrated. The above procedure was repeated three times on the crude material obtained to give complete conversion of the alkene, providing 183 mg (0.48 mmol, 96%) of the saturated product 17d ($R^9$=3-cyclopropyl-propyl) as a clear oil.

MS (ESPOS): 406.0 [M+Na]$^+$.

Method V

Following the general method in Scheme 18, to a solution of the compound 1 hydrochloride (wherein $R^1$=R=Me, R=H, $R^6$=H, $R^9$=4-cis-n-Pr, and m=2) (4.00 g, 9.90 mmol, 1 equiv) in THF (70 mL) at 23° C. was added $H_2O$ (70 mL) followed by $KHCO_3$ (1.29 g, 12.9 mmol, 1.3 equiv) followed by $(Boc)_2O$ (2.81 g, 12.9 mmol, 1.3 equiv). After stirring for 5 h, the reaction mixture was partitioned between brine (200 mL) and EtOAc (300 mL). The organic layer was separated and washed with brine (150 mL), and dried ($MgSO_4$). Solvent was removed under vacuum and the crude product purified using Biotage® column chromatography system (40+M cartridge, 40 mm ID×150 mm) using a linear gradient (75% EtOAc/hexanes-100% EtOAc) over 1.2 L total eluent at 50 mL/min to give 4.49 g of the pure carbamate 18a (wherein $R^1$=$R^2$=Me, $R^3$=H, $R^9$=4-cis-n-Pr, and m=2) (8.91 mmol, 90%).

To a solution of carbamate 18a (wherein $R^1$=$R^2$=Me, $R^3$=H, $R^9$=4-cis-n-Pr, and m=2) (7.99 g, 15.9 mmol, 1 equiv) in benzene (300 mL) at 23° C. was added p-anisaldehyde dimethyl acetal (4.06 mL, 23.8 mmol, 1.5 equiv), followed by PPTS (199 mg, 0.79 mmol, 0.05 equiv). The reaction mixture was heated to reflux. After 4 h a second portion of p-anisaldehyde dimethyl acetal (2.0 mL, 11.7 mmol, 0.74 equiv) was added. After a further 17 h a third portion of p-anisaldehyde dimethyl acetal (2.0 mL, 11.7 mmol, 0.74 equiv) was added. Following the final addition the reaction was refluxed a further 3 h then cooled to 23° C. and partitioned between EtOAc (300 mL) and $H_2O$ (300 mL). The organic layer was washed with 50% saturated aqueous $NaHCO_3$ (300 mL), brine (150 mL), dried ($MgSO_4$), filtered and concentrated. The crude product was purified via silica gel flash column chromatography using 40% EtOAc in hexane as eluent to give acetal 18b (wherein $R^1$=$R^2$=Me, $R^3$=H, $R^9$=4-cis-n-Pr, and m=2) 7.00 g (11.3 mmol, 71%) of the desired product as a white foam (1:1 ratio of diastereomers). A small portion of the product was purified on Biotage® column chromatography system (40+S cartridge, 40 mm ID×75 mm) using a linear gradient (5% EtOAc/hexanes-90% EtOAc/hexanes) over 1.2 L total eluent at 50 mL/min to separate the two diastereomers for characterization.

Diastereomer with high $R_f$: MS (ESPOS): 623.0 [M+H]$^+$.
Diastereomer with low $R_f$: MS (ESPOS): 623.0 [M+H]$^+$.

To a solution of alcohol 18b (wherein $R^1$=$R^2$=Me, $R^3$=H, $R^9$=4-cis-n-Pr, and m=2) (3.00 g, 4.82 mmol, 1 equiv) in trimethyl phosphate (60 mL) at 0° C. was added pyridine (3.90 mL, 48.2 mmol, 10 equiv), followed by $POCl_3$ (0.88 mL, 9.65 mmol, 2 equiv) added over the course of 60 sec. Following the addition, the reaction was maintained at 0° C. for 2 h, then triethylammonium bicarbonate buffer (1.0 M, pH 8.5, 40 mL) was added carefully to quench the reaction. $H_2O$ (60 mL) was then added, and the resulting mixture was stirred at 0° C. for 30 min then warmed to 23° C. After stirring the quenched reaction mixture for 2 h at 23° C., volatiles were removed in vacuo with aid of gentle heating in water bath (40–45° C.). The resulting crude product was azeotropically dried by co-evaporation with DMF (3×100 mL), then toluene (150 mL, bath temperature=40–45° C.) to provide 9.4 g of white solid. The crude product 18c (wherein $R^1$=$R^2$=Me, $R^3$=H, $R^9$=4-cis-n-propyl, $R^{11}$=PO(OH)$_2$ and m=2) was substantially contaminated with triethylammonium salts, but was carried forward without purification.

MS (ESNEG): 701.2 [M–H]$^-$.

To a solution of the protected phosphate 18c (wherein $R^1$=$R^2$=Me, $R^3$=H, $R^9$=4-cis-n-propyl, $R^{11}$=PO(OH)$_2$ and m=2) prepared as described above (9.4 g, crude from previous step, approximately 4.8 mmol) in 1,2-dichloroethane (600 mL) at 0° C. was added $H_2O$ (25 mL) followed by TFA (200 mL). Following the additions, the reaction was maintained at 0° C. for 5 min then warmed to 23° C. After stirring for 25 min at 23° C., volatiles were removed in vacuo to give 16.2 g of oil. The crude product was dissolved in 1:1 $H_2O$/MeOH (70 mL), filtered and the resulting solution was purified by preparative HPLC (Waters Nova-Pak® HR $C_{18}$, 6 μm particle size, 60 Å pore size, 40 mm ID×200 mm, 5–60% acetonitrile in $H_2O$ w/0.1% AcOH over 30 min, 75 mL/min flow rate) to give 1.497 g of the desired phosphate 5 (wherein $R^1$=$R^2$=Me, $R^3$=H, $R^9$=4-cis-n-propyl, $R^{11}$=PO(OH)$_2$) (3.10 mmol, 64% from free alcohol) as a white solid.

Method W

Following the general method outlined in Scheme 19, to amino acid 19a ($R^{12}$=H) (Aldrich) (1.0 g, 8.7 mmol) suspended in MeOH (5 mL) and 2,2-dimethoxypropane (15 mL) was added concentrated HCl (1.0 mL), and the mixture was stirred 12 h at r.t. Solvents were removed under vacuum, and the residue was triturated with $Et_2O$ and co-evaporated from dry toluene to furnish the crude methyl ester as an off-white solid which was used without further purification.

To a suspension of crude L-allylglycine methylester in dichloroethane (32 mL) at 0° C. was added 2,4,6-collidine (2.3 mL, 19.1 mmol, 2.2 equiv) and solid 2-nitrobenzenesulfonyl chloride. The reaction was stirred for 3 h at r.t. The solvent was removed under vacuum and the residue was distributed between EtOAc (200 mL) and sat. aqueous $NH_4Cl$. The organic layer was washed with 1.0 M aq. $KHSO_4$, sat. aq. $NaHCO_3$, brine, and dried ($MgSO_4$), and concentrated to give a residue that was purified by column chromatography on silica (gradient 10 to 20% EtOAc/hexanes) to give the desired product 19b ($R^{12}$=H) 0.70 g (26%) as a yellow oil.

$^1$H NMR (300 MHz, CDCl$_3$) δ 8.10–8.06 (m, 1), 7.95–7.92 (m, 1), 7.76–7.73 (m, 2), 6.08 (d, J=8.2, 1), 5.74–5.60 (m, 1), 5.17–5.12 (m, 2), 4.33–4.26 (m, 1), 3.52 (s, 3), 2.58 (dd, J=6.0, 6.0, 1), 3.44–3.30 (m, 2), 2.25–2.10 (m, 2), 2.11 (s, 3), 2.00–1.88 (m, 1), 1.86–1.70 (m, 1), 1.44–1.25 (m, 6), 0.98–0.88 (m, 9H). MS (ESNEG): 313.0 [M–H]$^-$.

To a stirred suspension of sulfonamide 19b ($R^{12}$=H) (685 mg, 2.18 mmol), $Cs_2CO_3$ (710 mg, 2.18 mmol), and tetrabutylammonium bromide (702 mg, 2.18 mmol), in DMF (5.0 mL) was added a solution of 3-methylenehex-1-yl-toluenesulfonate (702 mg, 2.61 mmol; prepared as described by Kelvin H. Yong et al. *Journal of Organic Chemistry*, 2001, 66, 8248) in DMF (1.0 mL), the reaction mixture was heated to 60° C. overnight. The reaction solvent was removed by evaporation, the resulting residue taken up in EtOAc and washed with 10% aqueous citric acid and brine, the organic phase was dried over MgSO$_4$ concentrated to give a residue that was purified by column chromatography on silica (17%–20% EtOAc/hexanes) to give the desired product 19c ($R^{12}$=H, $R^{13}$=propyl), (0.38g, 42%) as an oil.

MS (ESPOS): 433 [M+Na]$^+$.

To a solution of 19c ($R^{12}$=H, $R^{13}$=propyl) (0.38 g, 0.92 mmol) in anhydrous DCM (40 mL) was added benzylidene [1,3-bis(2,4,6-trimethylphenyl)-2-imidazolidinylidene] dichloro(tricyclohexylphosphine)ruthenium (23.3 mg, 0.0276 mmol). The resulting reaction mixture was refluxed under N$_2$ for 2.5 hrs, cooled to room temperature and concentrated. The product was purified by flash column chromatography on silica gel (35% ethyl acetate/hexanes) to give the desired compound 19d ($R^{12}$=H, $R^{13}$=propyl) (0.29 g, 81%).

MS (ESPOS): 383 [M+Na]$^+$.

To a stirred solution of thiophenol (183 µL, 1.79 mmol) and 7-methyl-1,5,7-triazabicyclo-[4,4,0]dec-5-ene (214 µL, 1.49 mmol) in anhydrous DMF (3 mL) was added a solution of alkene 19d ($R^{12}$=H, $R^{13}$=propyl) (228 mg, 0.596 mmol) in anhydrous DMF (3.0 mL) via a cannula. A color change to yellow was observed upon the mixing of the solutions, the resulting reaction mixture was stirred under N$_2$ for one hour then concentrated to a residue. The residue was taken up in ether, stirred with 1N aqueous HCl (15.0 mL) for 5 min. The aqueous phase was washed with ether then made basic with solid potassium carbonate. The resulting basic aqueous phase was extracted with ether three times. The combined organic layer was washed with brine, dried with anhydrous sodium sulfate, concentrated, cooled to 0° C., treated with 2M HCl in ether (0.8 mL), and the resulting mixture was stirred for 5 min and then evaporated to dryness to give the desired product 19d ($R^{12}$=H, $R^{13}$=propyl) as the hydrochloride salt (144 mg, 103%).

MS (ESPOS): 198 [M+H]$^+$.

To a solution of amine 19d ($R^{12}$=H, $R^{13}$=propyl) (143 mg, 0.61 mmol) in anhydrous dichrolomethane (2.0 mL) was added triethylamine (170 µL, 1.22 mmol) and di-t-butyldicarbonate (350 mg, 1.6 mmol). The resulting reaction mixture was stirred over night at room temperature under N$_2$ then evaporated to dryness and purified by flash column chromatography on silica gel using 20% ethylacetate in hexanes as an eluent to give the desired compound 19e ($R^{12}$=H, $R^{13}$=propyl) (176 mg, 86%).

MS (ESPOS): 320 [M+Na]$^+$.

To a solution of ester 19e ($R^{12}$=H, $R^{13}$=propyl) (175 mg, 0.59 mmol) in dioxane/water (6:1) (4 mL) was added 1 M aqueous lithium hydroxide (0.65 mL, 0.648 mmol). The resulting reaction mixture was stirred over night at room temperature under N$_2$ and the solvent was removed under reduced pressure. The residue was taken up in water washed with ether. The aqueous layer was acidified with 10% citric acid and extracted with ether. The organic layer was washed with brine, dried with sodium sulfate, and evaporated to dryness to give the desired protected cyclic amino acid 19f ($R^{12}$=H, $R^{13}$=propyl) (175 mg, 105%).

MS (ESNEG): 292 [M–H]$^-$.

Method X

As shown in Scheme 20 below, suitable amino esters 20g n=1,2 may be appended with psuedoephedrine which serves as a chiral auxiliary, allowing stereospecific alkylation of the α carbon with a suitable allylic bromide 20e. Protection of the secondary amine followed by olefin metathesis and cleavage of the chiral auxiliary leads to 4,5 unsaturated N-protected cyclic amino acids 20l. Reduction of the 2-carboxylic acid to a hydroxymethyl allows stereospecific trans-reduction of the 4,5 unsaturation in which leads to 20n. Re-oxidation of the hydroxymethyl to a carboxylic acid in which $R^{12}$ or $R^{13}$ may be $R^9$ as defined in formula I.

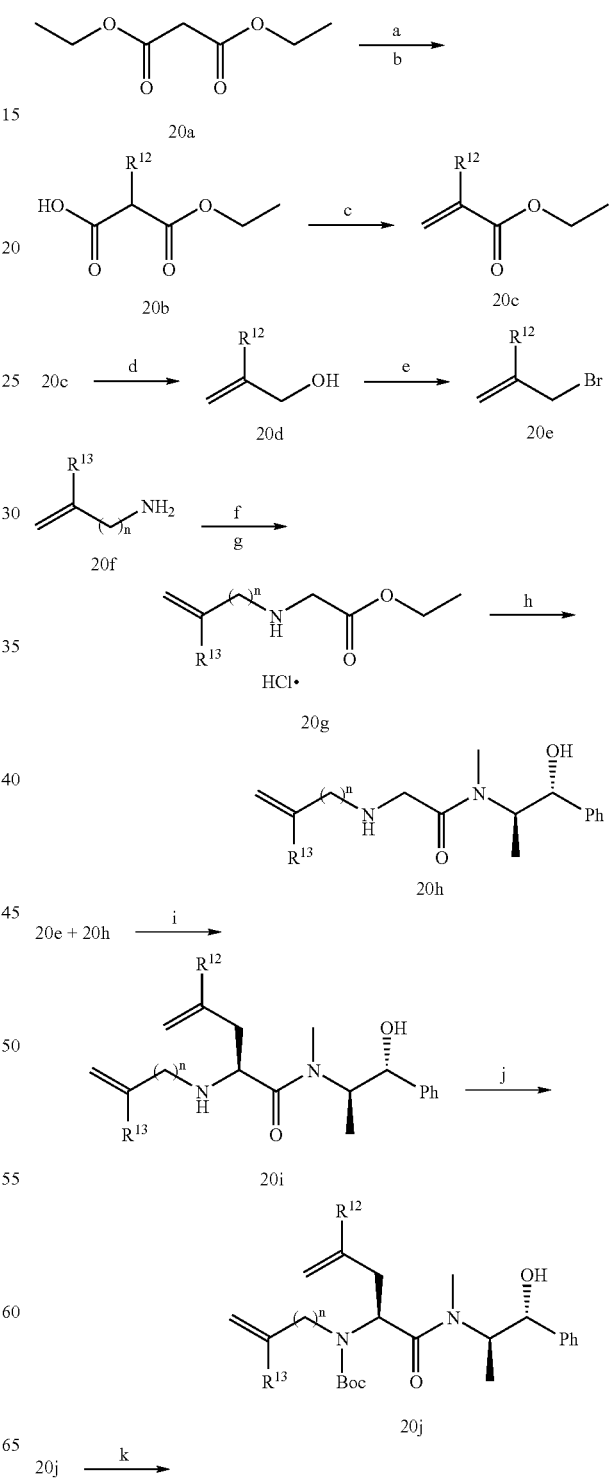

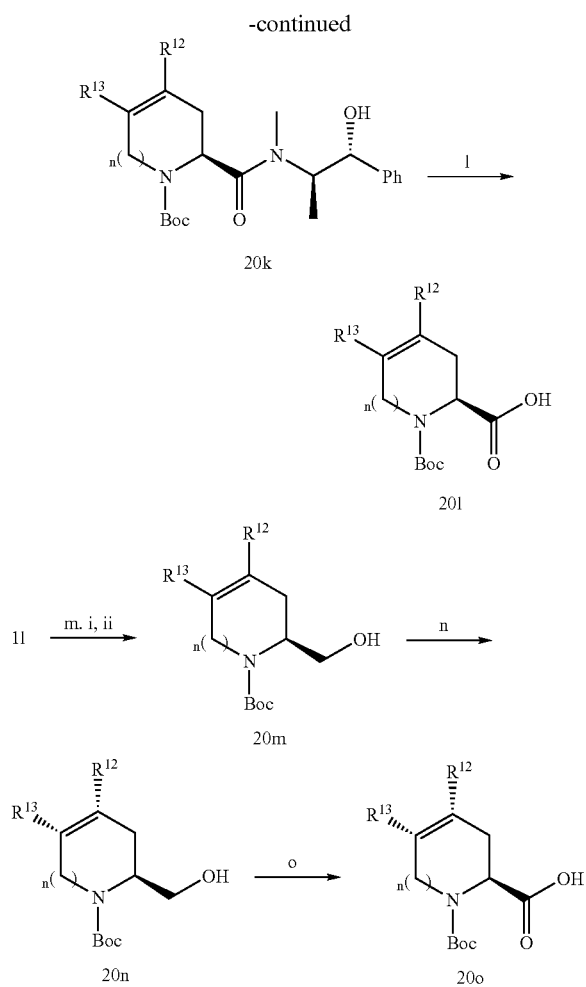

The following general reaction scheme may be used in the preparation of trans-alkylpiperidine-2-carboxylic acids and trans-alkylazapine-2-carboxylic acids: (a) NaH, DMF; R—Br, 65° C.; (b) 1 M aqueous KOH, EtOH, 80° C.; (c) CH$_2$O, piperidine, EtOH, 80° C.; (d) DIBALH, CH$_2$Cl$_2$, −50° C.; (e) PBr$_3$, pyridine, Et$_2$O, 0° C.; (f) Ethyl bromoacetate, Et$_2$O, 23° C.; (g) 4.0 M HCl in dioxane, Et$_2$O, hexane, 23° C.; (h), (1R,2R)-(−)-Pseudoephedrine, t-BuOLi, THF, 23° C.; (i) LiHMDS, LiCl, THF, 0° C.; (j) (Boc)$_2$O, Et$_3$N, CH$_2$Cl$_2$, 23° C.; (k) Benzylidene[1,3-bis(2,4,6-trimethylphenyl)-2-imidazolidinylidene]dichloro(tricyclohexylphosphine)ruthenium, CH$_2$Cl$_2$, 23° C.; (l) 1 M Aq. NaOH, MeOH, 70° C.; (m) (i) Isobutyl chloroformate, 4-methylmorpholine, DME, −15° C., (ii) NaBH$_4$, H$_2$O, 0° C.; (n) H$_2$, IrCODPyPCy$_3$.PF$_6$, CH$_2$Cl$_2$, 23° C.; (o) RuCl$_3$.xH$_2$O, NaIO$_4$, acetone, H$_2$O, 23° C.

As shown in Scheme 20, suitable amino esters 20g n=1,2 may be appended with psudoephedrine which serves as a chiral auxiliary, allowing stereospecific alkylation of the α carbon with a suitable allylic bromide 20e. Protection of the secondary amine followed by olefin metathesis and cleavage of the chiral auxiliary leads to 4,5 unsaturated N-protected cyclic amino acids 20l. Reduction of the 2-carboxylic acid to a hydroxymethyl allows stereospecific trans-reduction of the 4,5 unsaturation in which leads to 20n. Re-oxidation of the hydroxymethyl to a carboxylic acid in which R$^{12}$ or R$^{13}$ may be R$^9$ as defined in general structure.

Method Y

Following the general reaction scheme 21, a rapidly stirred solution of 4-oxo-piperidine-1,2-dicarboxylic acid 1-tert-butyl ester 21a (m=2, P=H, P$_2$=Boc) (16.0 g, 0.066 mol) (prepared by the method described by Bousquet et al. Tetrahedron, 1997, 53, 15671) in DMF (200 mL) was treated with solid cesium carbonate (10.7 g, 0.033 mol) and methyl iodide (4.5 mL, 0.072 mol). The reaction mixture was stirred 5 h, diluted with EtOAc and extracted with sat. aq. sodium bicarbonate, 10% aq. citric acid and brine, the organic layer was separated and dried over sodium sulfate, filtered and evaporated to dryness. The product obtained on removal of solvent was azeotropically dried by evaporation from dry benzene to afford 14.8 g (98%) of the desired product 4-Oxo-piperidine-1,2-dicarboxylic acid 1-tert-butyl ester 2-methyl ester 21a (m=2, P=Me, P$_2$=Boc) as an oil: TLC R$_f$ 0.53 (Hexanes/EtOAc, 1:1); $^1$H NMR (300 MHz, CDCl$_3$) δ 5.33 (broad m, 0.5) rotamer, 5.06 (broad m, 0.5) rotamer, 4.31–4.19 (m, 1), 3.95 (s, 3), 3.95–3.70 (m, 1), 3.16–2.97 (m, 2), 2.71 (m, 2), 1.68 (broad s, 9).

A 0° C. stirred solution of 4-oxo-piperidine-1,2-dicarboxylic acid 1-tert-butyl ester 2-methyl ester 21a (m=2, P=Me, P$_2$=Boc) (5.17 g, 0.02 mol) in DCM (60 mL) was treated with tetraallyltin (Aldrich) (5.3 mL, 0.022 mol) followed by dropwise addition of BF$_3$.OEt$_2$ (2.5 mL, 0.02 mol). The reaction mixture was stirred 1 h, then aq. 1M potassium fluoride (38.0 mL) and celite (5 g) was added and the reaction mixture was stirred 3 h. The reaction mixture was filtered and concentrated to dryness, the residue was dissolved in DCM and washed with water and brine, dried over MgSO$_4$ and evaporated to dryness. The residue obtained was purified by silica gel column chromatography (DCM 100% to DCM:acetone 9:1) to afford 3.85 g (64%) of the desired product 4-allyl-4-hydroxy-piperidine-1,2-dicarboxylicacid 1-tert-butyl ester 2-methyl ester 21b (m=2, P=Me, P$_2$=Boc, R$^{9'}$=allyl) as an oil.

$^1$H NMR (300 MHz, CDCl$_3$) δ 6.11–5.97 (m, 1), 5.42–5.32 (m, 2), 5.06 (broad d, J=6.0, 0.5) rotamer, 4.87 (broad d, J=6.0, 0.5) rotamer, 4.184.03 (m, 1), 3.93 (s, 3), 2.48–2.37 (m, 2), 1.98–1.43 (m, 11); MS (ESPOS): 322.0 [M+Na]$^+$.

A stirred suspension of 21b (m=2, P=Me, P$_2$=Boc, R$^{9'}$=allyl) (3.80 mL, 1.27 mmol) and 10% Pd/C (degusa wet form 50% w/w) (1.35 g, 1.3 mmol) in MeOH (80 mL) was stirred 6 h under 1 atm hydrogen. The reaction mixture was filtered through celite and evaporated to dryness and dried azeotropically by evaporation from toluene the residue obtained (3.15 g) was used in the next step without further purification.

To a stirred −78° C. solution of DAST (1.7 mL, 1.3 mmol) in DCM (50 mL) was added 4-Hydroxy-4-propyl-piperidine-1,2-dicarboxylic acid 1-tert-butyl ester 2-methyl ester in DCM (30 mL). The reaction mixture was then stirred for 1 h, then allowed to warm to −40° C. for 5 h. Additional DAST (0.4 mL) was added and the reaction mixture was stirred an additional 2 h, sat. aq. K$_2$CO$_3$ (20 mL), and water (60 mL) were added followed by diethyl ether (500 mL). The organic layer was separated, washed with brine, dried over sodium sulfate and evaporated to dryness. The resulting crude fluorinated product was purified by silica gel column chromatography (hexanes-EtOAc 9:1). The residue obtained by chromatographic purification was dissolved in dioxane (65 mL) and water (26 mL), cooled to 0° C., and treated with OsO$_4$ (0.65 mL, 4% aq. solution) and 30% H$_2$O$_2$ (10 mL). The reaction mixture was stirred overnight and concentrated to dryness. The residue was dissolved in DCM and the organic layer washed with water (100 mL), 25% aq. Na$_2$SO$_3$ (2×100 mL), and brine (100 mL), dried over Na$_2$SO$_4$ and evaporated to dryness. The residue obtained was purified by silica gel column chromatography (hexanes-EtOAc 9:1) to afford (1.08 g, 34%) of the desired product 4-fluoro-4-propyl-piperidine-1,2-dicarboxylic acid 1-tert-butyl ester 2-methyl ester 21c (m=2, P=Me, P$_2$=Boc, R$^9$=n-propyl) as an oil.

$^1$H NMR (300 MHz, CDCl$_3$) δ 4.59 (dd, J=6.0, 6.0, 1), 3.82–3.69 (m, 1), 3.74 (s, 3), 3.28 (m, 1), 3.29–2.04 (m, 2), 1.91–1.71 (m, 3), 1.60–1.31 (m, 6), 1.45 (s, 9), 0.92 (t, J=7.1, 3); MS (ESPOS): 204.1 (M+H–Boc), 326.3 [M+Na]$^+$.

A stirred solution of 21c (m=2, P$_2$=Boc, R$^9$=n-propyl) (1.06 g, 3.47 mmol) in dioxane-water 6:1 (42 mL) was treated with 1.0 M aq. lithium hydroxide (5.3 mL, 5.3 mmol). The reaction mixture was stirred at room temperature overnight, then treated with additional 1.0 M aq. lithium hydroxide (1.5 mL) and the resulting reaction mixture was stirred 5 h. The reaction solvent was removed, the residue was taken up in ethyl acetate (500 mL), washed with 10% Citric acid and brine and dried over MgSO$_4$. Concentration of organic solution to afford the desired product 4-fluoro-4-propyl-piperidine-1,2-dicarboxylic acid 1-tert-butyl ester 21d (m=2, P$_2$=Boc, R$^9$=n-propyl) (0.88 g, 87%) as a white solid.

$^1$H NMR (300 MHz, CDCl$_3$) δ 4.59 (dd, J=6.0, 6.0, 1), 3.82–3.69 (m, 1), 3.74 (s, 3), 3.28 (m, 1), 3.29–2.04 (m, 2), 1.91–1.71 (m, 3), 1.60–1.31 (m, 6), 1.45 (s, 9), 0.92 (t, J=7.1, 3); MS (ESNEG): 288.4 [M–H]$^-$.

Example 1

Preparation of 4-Ethyl-piperidine-2-carboxylic acid [2-methyl-1-(3,4,5-trihydroxy-6-methylsulfanyl-tetrahydro-pyran-2-yl)-propyl]-amide

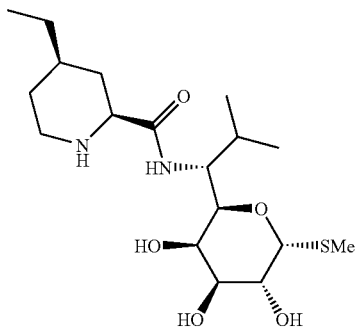

4-Ethyl pyridine-2-carboxylic acid HCl salt (Toronto) (117 mg, 0.64 mmol) was suspended in dry acetonitrile (4 mL). Triethylamine (180 μL, 1.28 mmol) was added and the reaction mixture was cooled to 0° C. Isobutyl chloroformate (129 μL, 0.62 mmol) was added and the reaction mixture was warmed to 4° C. After 1.5 h the activated ester solution was transferred to a solution of 2b (R$^1$=Me, R$^2$=Me), prepared as in Method C, in 1:1 acetone/water (2 mL) and warmed to 30° C. to dissolve. Triethylamine (80 μL, 0.057 mmol) was then added to the reaction mixture. The reaction mixture was stirred for 10 h at rt, then evaporated to dryness and chromatographed on silica 94:5 dichloromethane:0.25% ammonia in methanol to provide 11b (R$^1$=Me, R$^2$=Me R$^3$=H, R$^9$=ethyl) (167 mg 69.7%). MS (ESPOS): 385.2 [M+H]$^+$.

A solution of pyridine 11b (m=2, R$^1$=Me, R$^2$=Me R$^3$=H, R$^9$=ethyl) (167 mg, 0.435 mmol) in 3:2 methanol/water (20 mL) was added to platinum(IV)oxide (339 mg, 0.521 mmol) in a Parr bottle. Concentrated HCl (52 μL, 0.52 mmol) was then added. The bottle was purged, and charged with H$_2$ to 65 psi and shaken for 24 h. The reaction mixture was filtered through celite and rinsed with methanol. The combined filtrate was evaporated to dryness and chromatographed on silica 88:12 to 80:20 dichloromethane: 0.25% ammonia in methanol to give 43 mg of a high R$_f$ product and 49 mg of a mixed fraction. Chromatography of the low R$_f$ fraction on fluorosil 84:16 to 80:20 dichloromethane: 0.25% ammonia in methanol provided the title compound (21.9 mg, 12.9%), which was taken up in 1:1 acetonitrile:water (50 mL), 0.2μ millipore filtered, and cooled to 0° C. 1N HCl (67 μL) in water (20 mL) was added and re-lyophilized to provide the title compound HCl salt (24.0 rug) as a colorless powder.

$^1$H NMR (300 MHz, D$_2$O) δ 5.32 (d, J=5.8, 1), 4.14–4.06 (m, 1), 4.12 (s, 2), 3.85 (d, J=3.30, 1), 3.60 (dd, J=3.3, 10.4, 1), 3.30 (dd, J=2.5, 11.8, 1), 3.09 (m, 1), 2.56 (ddd, J=2.8, 12.9, 15.7, 1), 2.14 (s, 3), 2.14–2.05 (m, 1), 1.96–1.90 (m, 1), 1.74–1.69 (m, 1), 1.45–1.35 (m, 1), 1.33–1.23 (m, 2), 1.08–0.98 (m, 2), 0.86 (m, 9); MS(ESPOS): 391.4 [M+H]$^+$, 803.5.4 [2M+Na], (ESNEG): 389.5 [M–H]$^-$.

Example 2

Preparation of 1-Methyl-4-propyl-pyrrolidine-2-carboxylic acid [2-methyl-1-(3,4,5-trihydroxy-6-methylsulfanyl-tetrahydro-pyran-2-yl)-propyl]-amide

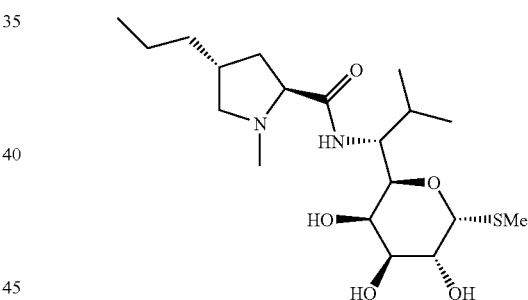

4-n-Propylhygric acid prepared by the method of Hoeksema, H. et. al. Journal of the American Chemical Society, 1967, 89 2448–2452 (157 mg, 0.76 mmol) was suspended in dry acetonitrile (5 mL). Triethylamine (421 μL, 3.02 mmol) was added and the reaction mixture was cooled to 0° C. Isobutyl chloroformate (98 μL, 0.76 mmol) was added and after 10 min the reaction was allowed to warm to 4° C. After 1.5 h a solution of 2b (R$^1$=Me, R$^2$=Me), from Method C (190 mg, 0.76 mmol) in 1:1 acetone:water (5 mL) was added and the reaction mixture was stirred for 10 h at rt. The reaction mixture was evaporated to dryness and chromatographed on silica 94:6 dichloromethane:0.25% ammonia in methanol. Fractions 14–18 contained the product as a colorless oil (50.2 mg, 16.5%).

$^1$H NMR (300 MHz, D$_2$O) δ 5.33 (d, J=6.0, 1), 4.27–4.22 (m, 1), 4.18 (s, 1), 4.09 (dd, J=5.8, 10.2, 1), 3.92–3.81 (m, 1), 3.92–3.81 (m, 1), 3.64–3.59 (m, 1), 2.92 (s, 3), 2.92–2.85 (m, 1), 2.35–2.28 (m, 3), 2.13 (s, 3), 1.46–1.41 (m, 2), 1.40–1.28 (m, 2), 0.89–0.84 (m, 9); MS(ESPOS): 405.5 [M+H]$^+$.

Example 3

Preparation of 1-Methyl-4-propyl-pyrrolidine-2-carboxylic acid [3-cyano-2-methyl-1-(3,4,5-trihydroxy-6-methylsulfanyl-tetrahydro-pyran-2-yl)-propyl]-amide

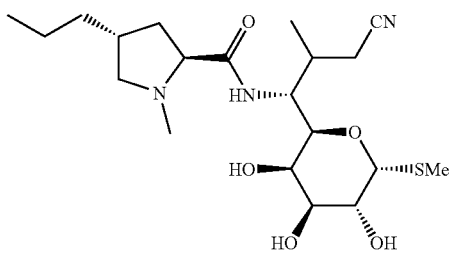

Lincosamine 2b ($R^1$=Me, $R^2$=$CH_2CN$) (54.2 mg, 0.20 mmol) prepared by Method E was dissolved in DMF (0.7 mL). The reaction mixture was cooled to 0° C. and triethylamine (170 μL, 1.2 mmol) and BSTFA (96 μL, 0.36 mmol) was added. The reaction mixture was allowed to warm to rt, and stirred at rt for 1 h. 4-n-Propylhygric acid prepared by the method of Hoeksema, et al., J. Am. Chem. Soc., 1967, 89 2448–2452 (66.4 mg, 0.32 mmol) and HATU (149 mg, 0.39 mmol) were added, and the mixture was stirred at rt for 3 h. DMF was removed and the residue was dissolved in DCM (100 mL), washed with saturated $NaHCO_3$ (30 mL) and brine (30 mL), and dried over sodium sulfate. The residue obtained by removing the solvent was dissolved in methanol (20 mL) and treated with Dowex™ resin $H^+$ (300 mg) for 15 min. The crude product was eluted from the resin by washing with 5% TEA in MeOH (25 ml×15 min×2) and 5% TEA in MeCN (25 mL×15 min). The combined eluent was evaporated to dryness and purified by silica gel column chromatography using 7% 0.25M $NH_3$ in methanol in dichloromethane as the eluent to provide the title compound (24 mg, 28%).

$^1$H NMR (300 MHz, $D_2O$) δ 5.61 (d, J=5.8, 1), 4.59 (d, J=10.2, 1), 4.46 (d, J=10.2, 1), 4.46 (dd, J=6.0, 10.4, 1), 4.05 (d, J=3.0, 1), 3.84 (dd, J=3.3, 10.4, 1), 3.48 (dd, J=5.8, 8.0, 1), 3.34 (dd, J=5.2, 10.2, 1) 2.81–2.61 (m, 2), 2.65 (s, 3), 2.43 (s, 3), 2.31–2.10 (m, 2), 1.32 (d, J=6.0, 1), 1.18 (t, J=7.1, 3); MS(ESPOS): 430.5 [M+H]+MS(ESPOS): 428.5 [M−H]$^-$.

Example 4

Preparation of 4-Ethyl-piperidine-2-carboxylic acid [2-hydroxy-2-methyl-1-(3,4,5-trihydroxy-6-methylsulfanyl-tetrahydro-pyran-2-yl)-propyl]-amide

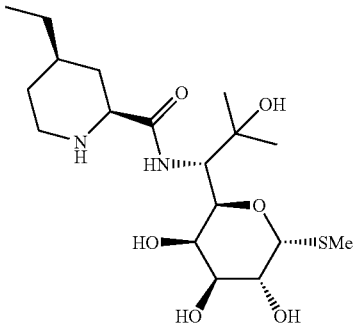

Lincosamine 3b ($R^1$=Me, $R^2$=Me) prepared by Method F (54.2 mg, 0.20 mmol) was dissolved in DMF (1.0 mL). The reaction mixture was cooled to 0° C. and triethylamine (178 μL, 1.3 mmol) and BSTFA (85 μL, 0.32 mmol) were added. The reaction mixture was allowed to warm to rt, and stirred at for 1 h. 4-Ethyl pyridine-2-carboxylic acid HCl salt (Toronto) (55.3 mg, 0.29 mmol) and HATU (122 mg, 0.32 mmol) were added, and the mixture was stirred at rt for 3 h. DMF was removed and the residue was dissolved in THF (10 mL), and treated with (600 mg) Amberlite A-26 F form resin and catalytic TBAF for 5 h. The crude product was obtained by removal of the resin and evaporation of the solvent to dryness and purified by silica gel column chromatography using 10% 0.25M $NH_3$ in methanol in dichloromethane as the eluent to provide the pyridine product 11b (m=2, $R^1$=Me, $R^2$=Me $R^3$=OH, $R^9$=ethyl) (26 mg, 33%).

MS(ESNEG): 399.5 [M−H]$^-$.

A solution of pyridine 11b (m=2, $R^1$=Me, $R^2$=Me $R^3$=OH, $R^9$=ethyl) (26 mg, 0.065 mmol) in 3:2 methanol:water (10 mL) was added to platinum(IV)oxide (51 mg) in a Parr bottle. Concentrated HCl (6.0 μL, 0.072 mmol) was then added. The bottle was purged and charged with $H_2$ to 65 psi and shaken for 24 h. The reaction mixture was filtered through celite and rinsed with methanol. The combined filtrate was evaporated to dryness and chromatographed on silica 80:20 dichloromethane: 0.25% ammonia in methanol to give a high $R_f$ product and the title compound (5.8 mg, 21.8%).

$^1$H NMR (300 MHz, $D_2O$) δ 5.37 (d, J=6.0, 1), 4.41 (d, J=9.6, 1), 4.32 (d, J=9.3, 1), 4.08 (dd, J=6.6, 11.0, 1), 3.93–3.90 (m, 2), 3.59 (dd, J=3.0, 10.7, 1), 3.93–3.90 (m, 2), 3.04 (apt dt, J=7.1, 14.6, 14.6, 1), 2.24–2.18 (m, 1), 2.20 (s, 3), 1.70–1.60 (m, 1), 1.42–1.13 (m, 1), 0.88 (dd, J=6.0, 7.4, 1); MS(ESPOS): 407.4 [M+H]+.

Example 5

Preparation of 1-Methyl-4-propyl-pyrrolidine-2-carboxylic acid [2-hydroxyimino-1-(3,4,5-trihydroxy-6-methylsulfanyl-tetrahydro-pyran-2-yl)-propyl]-amide

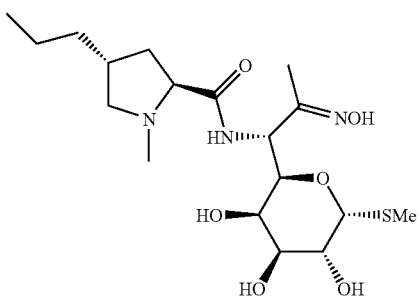

Triethylamine (0.041 mL, 0.28 mmol) and BSTFA (0.24 mL, 0.94 mmol) were added to the crude oxime 4b ($R^1$=Me, $R^7$=H) prepared by Method G (50 mg, 0.19 mmol) in DMF (3 mL) at 0° C. and the mixture was stirred at rt overnight. Next, 4-n-propylhygric acid (63 mg, 0.37 mmol) and HATU (142 mg, 0.37 mmol) were added and the mixture was stirred at rt for 4 h. DMF was removed and the residue was extracted with dichloromethane (100 mL) and washed with saturated bicarbonate (20 mL) and brine (20 mL). The residue obtained on removal of dichloromethane was then treated with 10% TFA in dichloroethane (10 mL) and dimethyl sulfide (0.5 mL) for 1 h. The solvent was then removed to obtain the crude product, which was purified by silica gel column chromatography using 20% methanol in dichloromethane as the eluent to provide the title compound (20 mg, 25%).

TLC: $R_f$=0.67 (20% methanol in dichloromethane); $^1$H NMR (300 MHz, CD$_3$OD) δ 0.93 (t, J=6.8, 3), 1.31–1.44 (m, 4), 1.88 (s, 3), 1.99 (s, 3), 2.09 (m, 2), 2.11 (m, 1), 2.62–2.98 (m, 3), 2.76 (s, 3), 3.60 (m, 2), 4.10 (dd, J=5.7, 10.20, 1), 4.27 (d, J=9.6, 1), 5.23 (d, J=5.5, 1), MS(ESPOS): 420 [M+H]$^+$.

Example 6

Preparation of 1-Methyl-4-propyl-pyrrolidine-2-carboxylic acid [2-methoxyimino-1-(3,4,5-trihydroxy-6-methylsulfanyl-tetrahydro-pyran-2-yl)-propyl]-amide

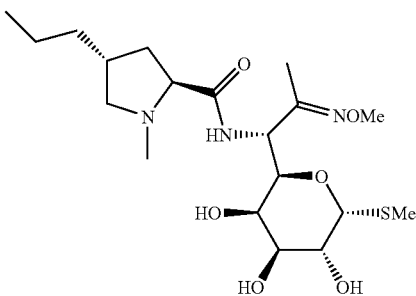

From crude oxime product 4b prepared by Method H (R$^1$=Me, R$^7$=Me), the title compound was prepared as in Example 5 (10 mg, 47%).

TLC: $R_f$=0.55 (10% methanol in dichloromethane); $^1$H NMR (300 MHz, CD$_3$OD) δ 0.91 (m, 3), 1.32 (m, 4), 1.88 (s, 3), 1.98 (s, 3), 1.78–2.04 (m, 2), 2.34 (s, 3), 2.90 (dd, J=5.1, 6.30, 8.10 1), 3.21 (dd, J=6.3, 10.2, 1), 3.57 (dd, J=3.3, 10.2, 1), 4.23 (dd, J=5.4, 10.2, 1), 5.25 (d, J=5.7, 1); MS(ESPOS): 434 [M+H]$^+$.

Example 7

Preparation of 5-Butyl-piperidine-2-carboxylic acid [2-methyl-1-(3,4,5-trihydroxy-6-methylsulfanyl-tetrahydro-pyran-2-yl)-propyl]-amide

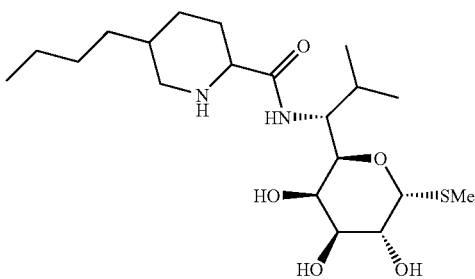

Lincosamine intermediate 2b (R$^1$=Me, R$^2$=Me), prepared by Method C, was dissolved in DMF (2 mL). Triethylamine (80 mg, 1 mmol) and BSTFA (307 mg, 1.1 mmol) were added, and the mixture was stirred at rt for 1.5 h. Next, fusaric acid (143 mg, 0.7 mmol) and HATU (184 mg, 0.5 mmol) were added, and the mixture was stirred at rt for 3 h. DMF was removed and the residue was dissolved in EtOAc (50 mL), washed with sodium bicarbonate (10%, 30 mL) and brine (30 mL), and dried over sodium sulfate. The residue obtained by removing the solvent was dissolved in methanol and treated with Dowex™ resin H$^+$ for 1 h. The crude product obtained by filtering the resin and removing the solvent was purified on silica gel column chromatography using 10% methanol in dichloromethane as the eluent to give the title compound (100 mg, 61%).

TLC $R_f$=0.6 (10% methanol in dichloromethane); $^1$H NMR (300 MHz, CD$_3$OD) δ 8.47 (s, 1), 8.02 (d, J=8.1, 1), 7.80 (d, J=8.1, 1), 5.27 (d, J=5.4, 1), 4.31 (m, 2), 4.12 (dd, J=5.7, 4.2, 1), 3.85 (d, J=3.0, 1), 3.56 (dd, J=3.3, 6.9, 1), 2.80 (m, 2), 2.24 (m, 1), 2.11 (s, 3), 1.67 (m, 2), 1.41 (m, 2), 1.00 (m, 9); MS(ESPOS): 413 [M+H]$^+$.

PtO$_2$ (50 mg, 0.22 mmol) was added to compound 11b (m=2, R$^1$=Me, R$^2$=Me, R$^3$=H, R$^9$=butyl), (70 mg, 0.16 mmol) in methanol (2 mL), water (10 mL), and acetic acid (3 mL), and the mixture was hydrogenated at 50 psi overnight. The product obtained after filtering the catalyst and removing the solvent was purified on silica gel column chromatography using 30% methanol in dichloromethane as the eluent (16 mg, 46%).

TLC $R_f$=0.7 (30% methanol in dichloromethane); $^1$H NMR (300 MHz, CD$_3$OD) δ 5.24 (d, J=5.7, 1), 4.16 (m, 3), 3.82 (d, J=3.3, 1), 3.53 (m, 2), 2.93 (m, 2), 2.09 (s, 3), 1.93 (m, 1), 1.76 (m, 2), 1.50 (m, 1), 1.30 (m, 7), 0.92 (m, 9); MS(ESPOS): 419 [M+H]$^+$.

Example 8

Preparation of 4-Pentyl-pyrrolidine-2-carboxylic acid [2-methyl-1-(3,4,5-trihydroxy-6-methylsulfanyl-tetrahydro-pyran-2-yl)-propyl]-amide

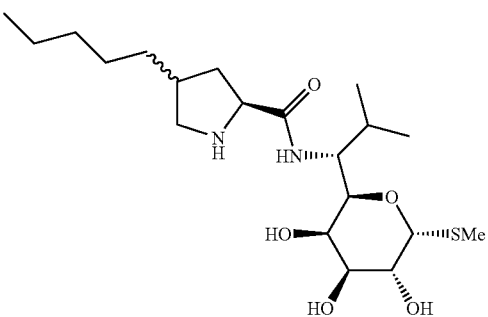

Triethylamine (0.2 mL, 1.44 mmol, 3.6 equiv), followed by BSTFA (0.2 mL, 0.76 mmol, 1.9 equiv), were added to a stirred suspension of 2b (R$^1$=Me, R$^2$=Me) prepared by Method C (100.4 mg, 0.4 mmol, 1 equiv) in anhydrous DMF (2 mL) at 0° C. and under nitrogen. The resulting mixture was stirred at 0° C. for 10 min, and then at rt for 50 min. The resulting solution was cooled to 0° C. and a solution of 6c (R$^9$=pentyl) (Scheme 6) prepared as described in Birkenmeyer, R. D; et al; Journal of Medicinal Chemistry 1972, 15, 1255–1259. (144 mg, 0.51 mmol, 1.2 equiv) in anhydrous DMF (1.5 mL) was added, followed by solid HATU. The reaction mixture was allowed to warm to rt, and after 2 h, the reaction solution was evaporated to dryness under vacuum. The residual oil obtained was diluted with EtOAc (150 mL), washed sequentially with 10% citric acid (2×30 mL), 1:1 saturated aqueous NaHCO₃, water (2×30 mL), and brine (30 mL), dried over Na₂SO₄, and evaporated to dryness.

1,2-Dichloroethane (8 mL), followed by dimethyl sulfide (180.3 µl), TFA (2.7 mL), and water (180.3 µl) were added to the crude product (267.5 mg) obtained above. The resulting mixture was stirred at rt for 1 h and evaporated to a minimal volume, diluted with DCE (3×30 mL), and evaporated to dryness. The residue obtained was purified by chromatography over silica gel, with a gradient eluent of 8–10% methanol ammonia in dichloromethane. The desired fractions were pooled together, evaporated to dryness, and lyophilized to furnish the title compound as a white fluffy powder (35.6 mg, 21.2%).

TLC, $R_f$=0.15 (16% 0.25M methanolic ammonia in dichloromethane). $^1$H NMR (300 MHz, D₂O) δ 5.4 (d, J=5.8, 1), 3.91 (s, 1), 3.69–3.66 (m, 3), 2.1 (s, 3), 1.32–1.15 (m, 3.37), 0.93–0.87 (m, 9.8); MS(ESPOS): 419.5 [M+H]⁺, (ESNEG): 417.45 [M−H]⁻.

Example 9

Preparation of 4-(3-Methyl-butyl)-pyrrolidine-2-carboxylic acid [2-methyl-1-(3,4,5-trihydroxy-6-methylsulfanyl-tetrahydro-pyran-2-yl)-propyl]-amide

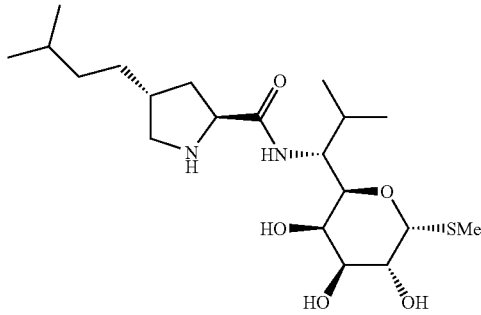

Triethylamine (0.13 mL, 0.96 mmol, 3.2 equiv), followed by BSTFA (0.12 mL, 0.45 mmol, 1.5 equiv), were added to a solution of 2b (R¹=Me, R²=Me) prepared by Method C (75 mg, 0.30 mmol, 1 equiv) in dry DMF (0.8 mL) at 0° C. The reaction mixture was stirred at 0° C. for 10 min, and then at rt for 50 min. To the reaction mixture was added acid 7d (R⁹=2-methylbutyl), prepared by method J (160 mg, 0.56 mmol, 1.9 equiv), in a 25 mL round-bottom flask. Then HATU was added (227 mg, 0.60 mmol, 2 equiv). The reaction mixture was stirred at rt for 3 h. The reaction mixture was evaporated to dryness, taken up in ethyl acetate (100 mL), washed with 10% citric acid (2×60 mL), water (60 mL), half sat. NaHCO₃ (60 mL), and brine. The organic layer was dried over Na₂SO₄ and evaporated to give a yellow syrup.

Trifluoroacetic acid (5 mL) and water (0.33 mL) were added to a solution of the above syrup in dichloromethane (15 mL) with methyl sulfide (0.33 mL). The reaction mixture was stirred at rt for 1 h. The solvent was removed under vacuum and co-evaporated with toluene twice. The residue was purified by chromatography to provide the title compound (75 mg, 60%) as a white solid.

$^1$H NMR (300 MHz, CD₃OD) δ 5.24 (d, J=5.4, 1), 4.18–3.99 (m, 4), 3.75 (d, J=2.4, 1), 3.51 (dd, J=3.3, 10.5, 1), 3.38–3.31 (m, 1), 2.68 (dd, J=8.2, 10.6, 1), 2.23–2.05 (m, 3), 2.10 (s, 3), 1.97–1.87 (m, 1), 1.59–1.47 (m, 1), 1.46–1.34 (m, 2), 1.25–1.16 (m, 2), 0.92–0.88 (m, 12). MS(ESPOS): 419.5 [M+H]⁺, MS(ESNEG): 417.5 [M−H]⁻.

Example 10

Preparation of 4-Pentyl-pyrrolidine-2-carboxylic acid [2-methyl-1-(3,4,5-trihydroxy-6-methylsulfanyl-tetrahydro-pyran-2-yl)-propyl]-amide

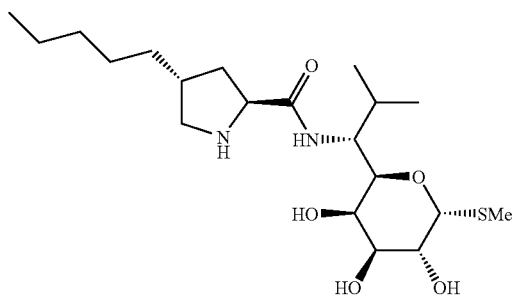

Triethylamine (0.6 mL, 4.33 mmol, 3.6 equiv), followed by BSTFA (0.6 mL, 2.27 mmol, 1.9 equiv), were added to a stirred suspension of 2b (R¹=Me, R²=Me) prepared by Method C (298.8 mg, 1.19 mmol, 1 equiv) in anhydrous DMF (5 mL) at 0° C. and under nitrogen. The resulting mixture was stirred at 0° C. for 10 min, and then at rt for 50 min. The resulting solution was cooled to 0° C. and a solution of 7d (R⁹=n-pentyl) was prepared by Method K (400.1 mg, 1.40 mmol, 1.2 equiv) in anhydrous DMF (5 mL) was added, followed by solid HATU (678.7 mg, 1.79 mmol, 1.5 equiv). The reaction mixture was allowed to warm to rt and after 2 h the reaction solution was evaporated to dryness under vacuum. The residual oil obtained was diluted with EtOAc (400 mL), washed sequentially with 10% citric acid (2×100 mL), 1:1 saturated aqueous NaHCO₃, water (2×100 mL), and brine (100 mL), dried over Na₂SO₄, and evaporated to dryness.

1,2-Dichloroethane (35 mL), followed by dimethylsulfide (768 µL), TFA (11.5 mL), and water (768 µL) were added to the crude product (1.14 g) obtained above. The resulting mixture was stirred at rt for 1 h, evaporated to a minimal volume, diluted with DCE (3×90 mL), and evaporated to dryness. One-third of the residue obtained was purified by chromatography over silica gel, with a gradient eluent of 8–12% methanol ammonia in dichloromethane. The desired fractions were pooled together, evaporated to dryness, treated with deuterium oxide/anhydrous acetonitrile, and lyophilized to furnish a white fluffy powder (68.2 mg, 41.1%); TLC, $R_f$=0.15 {16% 0.25M methanolic ammonia in dichloromethane}. $^1$H NMR (300 MHz, D₂O) δ 5.41 (d, J=5.8, 1H), 4.55 (m, 1), 4.24 (s, 2), 4.14 (m, 1), 3.91 (d, J=3.3, 1), 3.70–3.66 (m, 2), 3.15 (m, 1), 2.36–2.27 (m, 2), 2.19 (s, 5), 1.59–1.13 (m, 9), 0.93–0.88 (m, 9); $^{13}$C NMR (D₂O): δ 170.4, 119.4, 88.4, 70.9, 69.3, 68.8, 68.2, 60.0, 53.4, 51.4, 37.3, 36.7, 31.3, 27.9, 27.2, 22.3, 20.1, 14.8, 13.7, 13.3; MS(ESPOS): 419.6[M+H]⁺; (ESNEG): 417.5[M−H]⁻.

Example 11

Preparation of 1-Methyl-4-propyl-pyrrolidine-2-carboxylic acid [2,2-difluoro-1-(3,4,5-trihydroxy-6-methylsulfanyl-tetrahydro-pyran-2-yl)-propyl]-amide

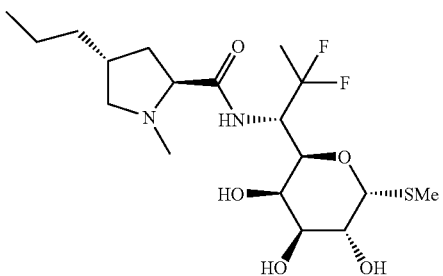

30% Trifluoroacetic acid in dichloroethane (10 mL) and dimethylsulfide (0.5 mL) were added to lincosamine intermediate 5b ($R^1$=Me), prepared by Method H (100 mg, 0.20 mmol). The mixture was stirred at rt for 1 h. The solvent was removed and the residue was kept under high vacuum for 1 h. N-Methyl-4-trans-propylproline (53 mg, 0.4 mmol) and HATU (114 mg, 0.30 mmol) were added to the dried compound in DMF (3 mL), and the mixture was stirred at rt overnight. DMF was removed and the residue obtained was then extracted with ethyl acetate (100 mL) and washed with saturated bicarbonate (50 mL). The organic portion was then dried using magnesium sulfate and the solvent was removed to obtain the crude product. The crude product was purified on silica gel column using ethyl acetate as the eluent (50 mg, 46%). The product (50 mg, 0.09 mmol) was then taken in methanol (2 mL) and water (1 mL), to which solid potassium carbonate (124 mg, 0.90 mmol) was added and the mixture was stirred at rt for 24 h. Solvents were then removed and the crude product was purified on silica gel column using 20% methanol in dichloromethane as the eluent (20 mg, 52%).

TLC: $R_f$=0.57 (20% methanol in dichloromethane); MS(ESPOS): 427 [M+H]$^+$. $^1$H NMR (300 MHz, CD$_3$OD) δ 0.91 (m, 3), 1.34 (m, 4), 1.69 (t, J=19.8, 3), 1.98 (s, 3), 2.20 (m, 2), 2.46 (s, 3), 3.18 (dd, J=5.1, 10.20, 1), 3.93 (d, J=3.0, 1), 4.08 (dd, J=3.3, 10.20, 1), 4.40–4.70 (m, 2), 5.28 (d, J=5.4, 1).

Example 12

Preparation of 4-Pentyl-pyrrolidine-2-carboxylic acid [2,2-difluoro-1-(3,4,5-trihydroxy-6-methylsulfanyl-tetrahydro-pyran-2-yl)-propyl]-amide

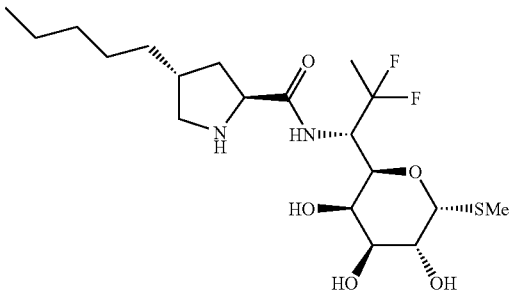

Boc 4-trans-Pentylproline 7d ($R^9$=n-pentyl) (179 mg, 0.631 mmol), HATU (299 mg, 0.789 mmol), and diethylisopropylamine (182 mg, 1.2 mmol) were added to lincosamine intermediate 5b ($R^1$=Me) prepared by method I (210 mg, 0.526 mmol) in DMF (3 mL) at 0° C. The mixture was stirred at rt overnight. After removing DMF, the residue was taken in ethyl acetate and washed with saturated bicarbonate (30 mL). The organic portion was then dried over sodium sulfate and the solvent was removed to obtain the crude product. The crude product was purified by column chromatography using 30% ethyl acetate in hexanes as the eluent (200 mg, 57%). Potassium carbonate (450 mg, 3.0 mmol) was added to the product (200 mg, 0.30 mmol) of the above reaction in methanol (3 mL) and water (1 mL), and the mixture was stirred at rt for 2 h. The solvent was removed and the residue obtained was taken in 30% trifluoroacetic acid in dichloroethane (10 mL) and dimethylsulfide (0.5 mL) and stirred for 1 h. After removing the solvent, the crude product obtained was purified by column using 10% methanol in dichloromethane as the eluent (10 mg, 90%).

TLC: $R_f$=0.56 (20% methanol in dichloromethane); $^1$H NMR (300 MHz, CD$_3$OD) δ 0.90 (m, 3), 1.31 (m, 7), 1.44 (m, 20), 1.73 (t, J=19.5, 3), 2.02 (m, 1), 2.08 (s, 3), 2.24 (m, 2), 2.89 (t, J=9.9, 1), 3.56 (m, 2), 3.86 (s, 1), 4.07 (dd, J=6.0, 9.6, 1), 4.37 (m, 2), 4.63 (m, 1), 5.28 (d, J=5.4, 1); MS(ES-POS): 441 [M+H]$^+$.

Example 13

Preparation of 4-[3-(4-Fluoro-phenyl)-propyl]-pyrrolidine-2-carboxylic acid [2-methyl-1-(3,4,5-trihydroxy-6-methylsulfanyl-tetrahydro-pyran-2-yl)-propyl]-amide

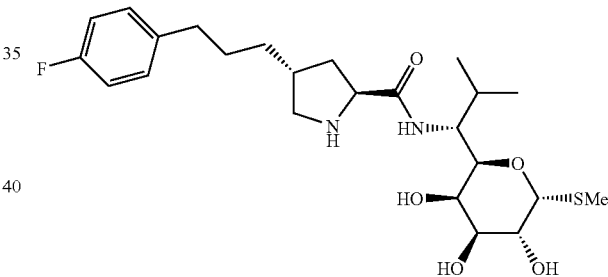

Triethylamine (0.13 mL, 0.96 mmol, 3.2 equiv), followed by BSTFA (0.12 mL, 0.45 mmol, 1.5 equiv), were added to a solution of 2b ($R^1$=Me, $R^2$=Me) prepared by Method C (75 mg, 0.30 mmol, 1 equiv) in dry DMF (0.8 mL) at 0° C. The reaction mixture was stirred at 0° C. for 10 min, and then at rt for 50 min. The reaction mixture was added to acid 8c ($R^9$=3-(4-fluorophenyl)propyl) prepared by Method L (120 mg, 0.34 mmol, 1.1 equiv) in a 25 mL round bottom flask, followed by HATU (160 mg, 0.42 mmol, 1.4 equiv). The reaction mixture was stirred at rt for 3 h. The reaction mixture was evaporated to dryness, taken up in ethyl acetate (100 mL), and washed with 10% citric acid (2×60 mL), water (60 mL), half sat. NaHCO$_3$ (60 mL), and brine. The organic layer was dried over Na$_2$SO$_4$ and evaporated to give a yellow syrup.

Trifluoroacetic acid (5 mL) and water (0.33 mL) were added to a solution of the above syrup in dichloromethane (15 mL) with methylsulfide (0.33 mL). The reaction mixture was stirred at rt for 1 h. The solvent was removed under vacuum and co-evaporated with toluene twice. The residue was purified by chromatography to provide the title compound (90 mg, 62%) as a white solid.

¹H NMR (300 MHz, CDCl₃) δ 7.94 (brs, 1), 7.11–7.06 (m, 2), 6.97–6.90 (m, 2), 5.31 (d, J=5.4, 1), 4.10 (dd, J=5.7, 9.9, 1), 3.96–3.82 (m, 3), 3.68–3.52 (m, 2), 3.10–3.20 (m, 1), 2.70–2.60 (m, 1), 2.56 (dd, J=7.4, 7.4, 2), 2.36–2.24 (m, 1), 2.13 (s, 3), 2.10–1.93 (m, 2), 1.85–1.73 (m, 1), 1.64–1.50 (m, 2), 1.40–1.30 (m, 2), 0.92–0.85 (m, 6). MS(ESPOS): 485.5 [M+H]⁺, MS(ESNEG): 483.5 [M–H]⁻.

Example 14

Preparation of 4-(3,3-Difluoro-propyl)-pyrrolidine-2-carboxylic acid [2-methyl-1-(3,4,5-trihydroxy-6-methylsulfanyl-tetrahydro-pyran-2-yl)-propyl]-amide

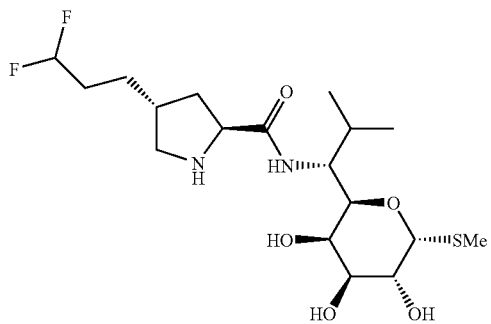

Triethylamine (0.13 mL, 0.96 mmol, 3.2 equiv), followed by BSTFA (0.12 mL, 0.45 mmol, 1.5 equiv), were added to a solution of 2b (R¹=Me, R²=Me) prepared by Method C (75 mg, 0.30 mmol, 1 equiv) in dry DMF (0.8 mL) at 0° C. The reaction mixture was stirred at 0° C. for 10 min, and then at rt for 50 min. The reaction mixture was added to acid 8c (R⁹=3,3-difluoropropyl) prepared by Method N (97 mg, 0.33 mmol, 1.1 equiv) in a 25 mL round bottom flask, followed by HATU (170 mg, 0.45 mmol, 1.5 equiv). The reaction mixture was stirred at rt for 3 h. The reaction mixture was evaporated to dryness, taken up in ethyl acetate (100 mL), and washed with 10% citric acid (2×60 mL), water (60 mL), half sat. NaHCO₃ (60 mL), and brine. The organic layer was dried over Na₂SO₄ and evaporated to give a yellow syrup.

Trifluoroacetic acid (5 mL) and water (0.33 mL) were added to a solution of the above syrup in dichloromethane (15 mL) with methylsulfide (0.33 mL). The reaction mixture was stirred at rt for 1 h. The solvent was removed under vacuum and co-evaporated with toluene twice. The residue was purified by chromatography to provide the title compound (81 mg, 64%) as a white solid.

¹H NMR (300 MHz, CDCl₃) δ 7.92 (d, J=8.1, 1), 5.80 (dddd, J=4.2, 4.2, 57, 57, 1), 5.31 (d, J=5.7, 1), 4.11 (dd, J=5.4, 9.9, 1), 3.96–3.82 (m, 3), 3.64–3.52 (m, 2), 3.23–3.10 (m, 1), 2.73–2.60 (m, 1), 2.36–2.23 (m, 1), 2.13 (s, 3), 2.18–1.95 (m, 2), 1.90–1.73 (m, 3), 1.56–1.43 (m, 2), 0.93–0.85 (m, 6). MS(ESPOS): 427.5 [M+H]⁺, MS(ESNEG): 425.5 [M–H]⁻.

Example 15

Preparation of 4-[3-(4-Chloro-phenyl)-propyl]-pyrrolidine-2-carboxylic acid [2-methyl-1-(3,4,5-trihydroxy-6-methylsulfanyl-tetrahydro-pyran-2-yl)-propyl]-amide

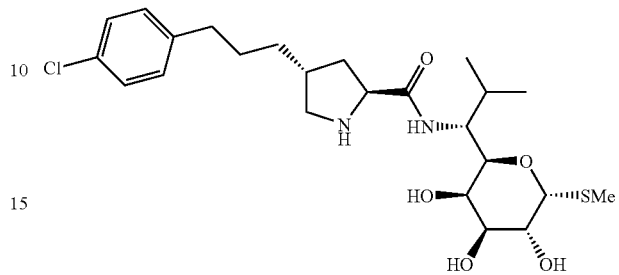

Triethylamine (88.3 µL, 0.64 mmol, 3.2 equiv), followed by BSTFA (79.2 mL, 0.30 mmol, 1.5 equiv), were added to a solution of 2b (R¹=Me, R²=Me) prepared by Method C (50 mg, 0.20 mmol, 1 equiv) in dry DMF (0.5 mL) at 0° C. The reaction mixture was stirred at 0° C. for 10 min, and then at rt for 50 min. The reaction mixture was added to 8c (R⁹=3-(4-chlorophenyl)propyl) prepared by Method M (97.3 mg, 0.26 mmol, 1.3 equiv) in a 25 mL round bottom flask, followed by HATU (123 mg, 0.32 mmol, 1.6 equiv). The reaction mixture was stirred at rt for 3 h. The reaction mixture was evaporated to dryness, taken up in ethyl acetate (60 mL), and washed with 10% citric acid (2×40 mL), water (40 mL), half sat. NaHCO₃ (40 mL), and brine. The organic layer was dried over Na₂SO₄ and evaporated to give a yellow syrup.

Trifluoroacetic acid (3 mL) and water (0.2 mL) were added to a solution of the above syrup in dichloromethane (9 mL) with methylsulfide (0.2 mL). The reaction mixture was stirred at rt for 1 h. The solvent was removed under vacuum and co-evaporated with toluene twice. The residue was purified by chromatography to provide the title compound (41.6 mg, 42%) as a white solid.

¹H NMR (300 MHz, CDCl₃) δ 7.26–7.21 (m, 2), 7.17–7.12 (m, 2), 5.23 (d, J=5.7, 1), 4.10–4.00 (m, 3), 3.83–3.75 (m, 1), 3.74–3.70 (m, 1), 3.54–3.48 (m, 1), 3.25–3.18 (m, 1), 2.63–2.50 (m, 3), 2.20–2.00 (m, 3), 2.09 (s, 3), 1.85–1.74 (m, 1), 1.68–1.55 (m, 2), 1.42–1.33 (m, 2), 0.95–0.85 (m, 6). MS(ESPOS): 501.5 [M+H]⁺ MS(ESNEG): 499.4 [M–H]⁻.

Example 16

Preparation of 4-(2,2-Difluoro-pentyl)-pyrrolidine-2-carboxylic acid [2-methyl-1-(3,4,5-trihydroxy-6-methylsulfanyl-tetrahydro-pyran-2-yl)-propyl]-amide

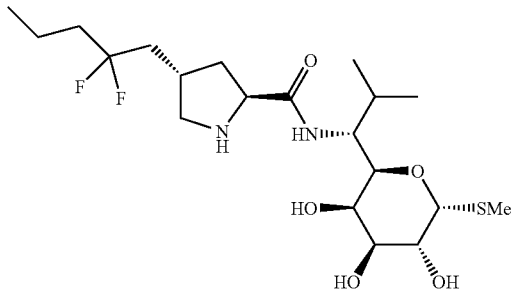

Triethylamine (88.3 mL, 0.64 mmol, 3.2 equiv), followed by BSTFA (79.2 mL, 0.30 mmol, 1.5 equiv), were added to a solution of 2b (R¹=Me, R²=Me) prepared by Method C (50 mg, 0.20 mmol, 1 equiv) in dry DMF (0.5 mL) at 0° C. The reaction mixture was stirred at 0° C. for 10 min, and then at rt for 50 min. The reaction mixture was added to the acid 9d (R⁹=2,2-difluoropentyl) prepared by Method O (67.7 mg, 0.21 mmol, 1.1 equiv) in a 25 mL round bottom flask, followed by HATU (101 mg, 0.27 mmol, 1.3 equiv). The reaction mixture was stirred at rt for 3 h. The reaction mixture was evaporated to dryness, taken up in ethyl acetate (60 mL), and washed with 10% citric acid (2×40 mL), water (40 mL), half sat. NaHCO₃ (40 mL), and brine. The organic layer was dried over Na₂SO₄ and evaporated to give a yellow syrup.

Trifluoroacetic acid (3 mL) and water (0.20 mL) were added to a solution of the above syrup in dichloromethane (9 mL) with methylsulfide (0.20 mL). The reaction mixture was stirred at rt for 1 h. The solvent was removed under vacuum and co-evaporated with toluene twice. The residue was purified by chromatography to provide the title compound (56 mg, 62%) as a white solid.

¹H NMR (300 MHz, CD₃OD) δ 5.24 (d, J=5.7, 1), 4.17–4.04 (m, 3), 3.98 (dd, J=3.3, 9.3, 1), 3.77(d, J=3, 1), 3.51 (dd, J=3.4, 10.3, 1), 3.40(dd, J=6.9, 10.5, 1), 2.71 (dd, J=10.2, 10.2, 1), 2.42–2.33 (m, 1), 2.23–2.11 (m, 2), 2.10 (s, 3), 2.08–1.73 (m, 5), 1.56–1.42 (m, 2), 0.99–0.89 (m, 9). MS(ESPOS): 455.5 [M+H]⁺; MS(ESNEG): 453.5 [M−H]⁻.

Example 17

Preparation of 4-Propyl-piperidine-2-carboxylic acid [2-methyl-1-(3,4,5-trihydroxy-6-methylsulfanyl-tetrahydro-pyran-2-yl)-propyl]-amide

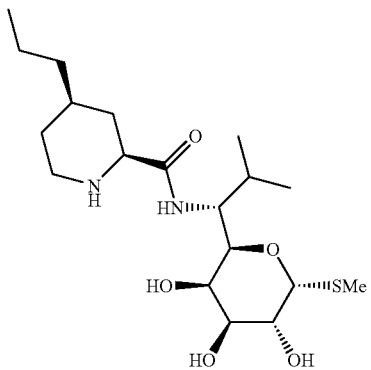

Triethylamine (0.18 mL, 1.26 mmol) and BSTFA (0.549 mL, 2.1 mmol) were added to the lincosamine intermediate 2b (R¹=Me, R²=Me) prepared by Method D (102 mg, 0.42 mmol) in DMF (5 mL) at 0° C., and the mixture was stirred at rt for 3 h. Acid 10b (R⁹=propyl) prepared by Method P (200 mg, 0.84 mmol) and HATU (319 mg, 0.84 mmol) were added and the mixture was stirred for 4 h at rt. DMF was removed and the residue was extracted with ethyl acetate (100 mL) and washed with saturated bicarbonate (40 mL). The product obtained by removal of solvent was taken up in methanol and treated with Dowex™ H⁺ resin for 1 h. After filtering the resin, methanol was removed to obtain the crude product. The crude product was then purified on silica gel column using 10% methanol in dichloromethane as the eluent to provide pyridine 11b (R¹=Me, R²=Me, R³=H, R⁹=propyl) (117 mg, 58%).

TLC: R_f=0.81 (10% methanol in dichloromethane); ¹H NMR (300 MHz, CDCl₃) δ 1.20 (t, J=6.3, 6H), 2.19 (m, 2), 2.32 (s, 3), 2.43 (m, 1), 2.84–2.97 (m, 4), 3.74 (m, 1), 4.06 (m, 1), 4.31 (m, 1), 4.52 (m, 2), 5.42 (d, J=5.7, 1), 7.33–7.61 (m, 5), 7.80 (m, 1), 8.15 (s, 1), 8.69 (d, J=4.8, 1); MS (ESPOS): 475 [M+H]⁺.

PtO₂ (100 mg, 0.44 mmol) was added to pyridine 11b (R¹=Me, R²=Me, R³=H, R⁹=propyl), (150 mg, 0.37 mmol) in methanol (2 mL), water (10 mL), and acetic acid (3 mL), and the mixture was hydrogenated at 50 psi overnight. The product obtained after filtering the catalyst and removing the solvent was purified by silica gel column chromatography using 30% methanol in dichloromethane as the eluent to provide the title compound (20 mg, 14%).

TLC: R_f=0.7 (50% methanol in dichloromethane); ¹H NMR (300 MHz, CD₃OD) δ 5.24 (d, J=6.9, 1), 4.86 (m, 1), 4.13 (m, 2), 3.79 (d, J=3.3, 1), 3.52 (dd, J=3.3, 9.9, 1), 3.32 (m, 1), 3.17 (m, 1), 2.67 (m, 1), 2.17 (m, 1), 2.10 (s, 3), 1.97 (m, 1), 1.74 (m, 1), 1.54 (m, 1), 1.38 (m, 2), 1.31 (m, 2), 1.14 (m, 2), 1.02 (m, 9) MS(ESPOS): 405 [M+H]⁺.

Example 18

Preparation of 1-(2-Hydroxy-ethyl)-4-pentyl-pyrrolidine-2-carboxylic acid [2-methyl-1-(3,4,5-trihydroxy-6-methylsulfanyl-tetrahydro-pyran-2-yl)-propyl]-amide

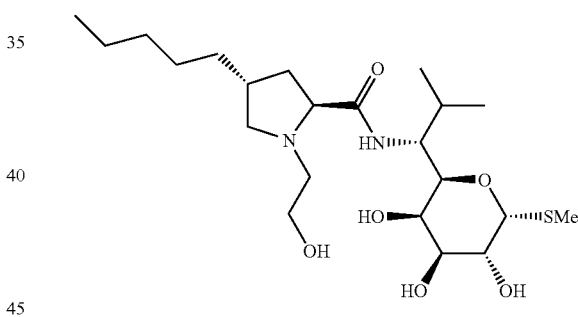

DIEA (0.1 mL, 0.57 mmol) and liquid ethylene oxide (3 mL) were added to a stirred solution of crude 4-pentyl-pyrrolidine-2-carboxylic acid [2-methyl-1-(3,4,5-trihydroxy-6-methylsulfanyl-tetrahydro-pyran-2-yl)-propyl]-amide, prepared as in Example 10 (237.4 mg), in anhydrous methanol (10 mL), at 0° C. and under nitrogen. The resulting solution was stirred at −4° C. for 18 h and evaporated to dryness. The residue obtained was purified by chromatography over silica gel with an eluent of 5% methanolic ammonia in dichloromethane. The desired fractions were evaporated and the residue lyophilized (deuterium oxide/anhydrous acetonitrile, 1:1, v/v, 10 mL) to furnish the title compound as a fluffy white powder (50.1 mg, 30.2%); TLC, R_f=0.68 (14% methanolic ammonia in dichloromethane); ¹H NMR (300 MHz) δ 5.40 (d, J=5.8, 1), 4.55 (m, 1), 4.24 (s, 1), 4.17–4.11 (m, 1), 3.99–3.89 (m, 4), 3.69–3.65 (m, 1), 3.47 (d, J=4.4, 2), 3.01 (m, 1), 2.33 (br s, 4), 2.18 (s, 4), 1.57–1.32 (m, 9), 0.94–0.87 (m, 9).

MS(ESPOS): 464[M+H]⁺; (ESNEG): 497.5 [M−H+HCl].

Example 19

Preparation of 1-(2-Hydroxy-propyl)-4-pentyl-pyrrolidine-2-carboxylic acid [2-methyl-1-(3,4,5-trihydroxy-6-methylsulfanyl-tetrahydro-pyran-2-yl)-propyl]-amide

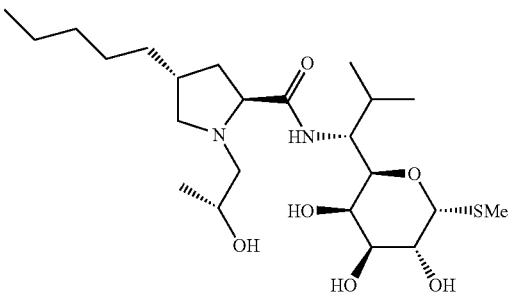

DIEA (0.1 mL, 0.58 mmol, 1 equiv) and R(+)-propylene oxide (3 mL) were added to a stirred cool solution of crude 4-pentyl-pyrrolidine-2-carboxylic acid [2-methyl-1-(3,4,5-trihydroxy-6-methylsulfanyl-tetrahydro-pyran-2-yl)-propyl]-amide (307.6 mg, 0.58 mmol, 1 equiv), prepared as in Example 10, in anhydrous methanol (10 mL), at 0° C. and under nitrogen. The resulting solution was stirred at −4° C. for 18 h and evaporated to dryness. The residue obtained was purified by chromatography over silica gel, with an eluent of 6% methanolic ammonia in dichloromethane. The desired fractions were evaporated, and lyophilized (deuterium oxide/anhydrous acetonitrile, 1:1, v/v, 20 mL) to furnish the title compound as a fluffy white powder (91 mg, 48%).

TLC, $R_f$=0.7 (14% methanolic ammonia in dichloromethane); $^1$H NMR (300 MHz, CD$_3$OD) δ 5.44 (d, J=5.5, 1), 4.31 (s, 2), 4.26–4.11 (m, 1), 3.97 (d, J=3.3, 1.1, 1), 3.75 (dd, J=3.3, 3.3, 1), 3.39 (dd, J=3.8, 3.8, 1), 2.31 (s, 3), 1.5–0.95 (m, 12), 1.34 (d, J=6.0, 4), 1.17–1.10 (m, 13); MS(ESPOS): 477.6 [M+H]$^+$, (ESNEG): 475.6 [M−H]$^−$.

Example 20

Preparation of 1-(2-Hydroxy-propyl)-4-pentyl-pyrrolidine-2-carboxylic acid [2-methyl-1-(3,4,5-trihydroxy-6-methylslfanyl-tetrahydro-pyran-2-yl)-propyl]-amide

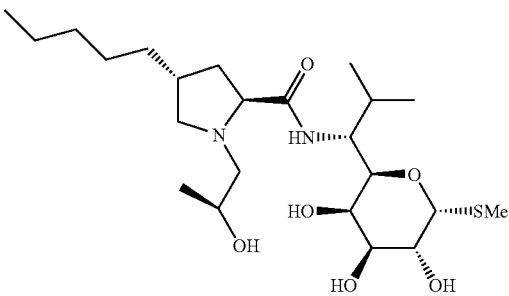

Dimethyl sulfide (62 μL), TFA (1 mL), and water (62 μL) were added to a stirred solution of the Boc-protected 4-pentyl-pyrrolidine-2-carboxylic acid [2-methyl-1-(3,4,5-trihydroxy-6-methylsulfanyl-tetrahydro-pyran-2-yl)-propyl]-amide (92 mg, 0.18 mmol), prepared as in Example 10, in anhydrous dichloroethane (3 mL). The resulting solution was stirred at rt for 1 h and evaporated to dryness. Anhydrous methanol (8 mL) and DIEA (31 μL, 0.18 mmol) were added to the residue obtained. The mixture was cooled to −4° C. and S-(−)-propylene oxide (2 mL) was added. The resulting solution was stirred at −4° C. for 18 h, evaporated to dryness, and purified by chromatography over silica gel, with an eluent of 6% methanolic ammonia in dichloromethane. The desired fractions were evaporated and lyophilized (deuterium/anhydrous acetonitrile, 1:1, v/v, 8 mL) to furnish the title compound as a fluffy white powder (29.8 mg, 31.2%).

TLC, $R_f$=0.7 (12% methanolic ammonia in dichloromethane); 1H NMR (300 MHz, CD$_3$OD) δ 5.44 (d, J=5.5, 1), 4.35–4.19 (m, 4), 4.02 (d, J=3.3, 2), 2.75 (d, J=6.3, 2.2, 3), 2.3 (s, 3), 1.50 (m, 11), 1.4 (d, J=6.0, 3.5, 3), 1.16–1.10 (m, 12). MS(ESPOS): 477.6 [M+H]$^+$; (ESNEG) 475.4 [M−H]$^−$.

Example 21

Preparation of 1-(3-Hydroxy-propyl)-4-pentyl-pyrrolidine-2-carboxylic acid [2-methyl-1-(3,4,5-trihydroxy-6-methylsulfanyl-tetrahydro-pyran-2-yl)-propyl]-amide

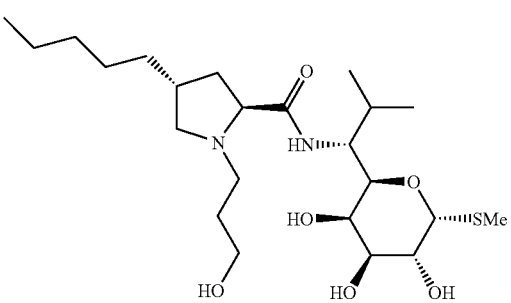

Triethylamine (0.2 mL, 1.38 mmol, 3 equiv), followed by 3-bromo-1-propanol (60 μL, 0.69 mmol, 1.5 equiv), were added to a stirred solution of crude 4-pentyl-pyrrolidine-2-carboxylic acid [2-methyl-1-(3,4,5-trihydroxy-6-methylsulfanyl-tetrahydro-pyran-2-yl)-propyl]-amide (192.5 mg, 0.46 mmol, 1 equiv), prepared as in Example 10, in anhydrous acetonitrile (2 mL), under nitrogen. The resulting mixture was stirred at rt for 18 h and evaporated to dryness. The residue obtained was purified by chromatography over silica gel with an eluent of 5% methanolic ammonia in dichloromethane. The desired fractions were pooled together, evaporated to dryness, and lyophilized to furnish the title compound as a white fluffy powder (13.5 mg, 6%).

TLC, $R_f$=0.75 (14% methanolic ammonia in dichloromethane); $^1$H NMR (300 MHz, CD$_3$OD) δ 5.44 (d, J=5.8, 1), 4.33–4.26 (m, 4), 4.01 (d, J=2.7, 1), 3.85–3.74 (m, 6), 2.29 (s, 3), 2.1 (m, 4), 1.54 (m, 8), 1.16–1.08 (m, 12); MS (ESPOS): 477.6 [M+H]$^+$.

Example 22

Preparation of 1-(2-Hydroxy-ethyl)-4-(3-methyl-butyl)-pyrrolidine-2-carboxylic acid [2-methyl-1-(3,4,5-trihydroxy-6-methylsulfanyl-tetrahydro-pyran-2-yl)-propyl]-amide

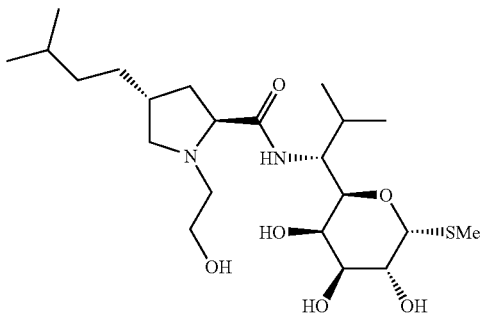

Ethylene oxide (0.6 mL) was added to a solution of 4-(3-methyl-butyl)-pyrrolidine-2-carboxylic acid [2-methyl-1-(3,4,5-trihydroxy-6-methylsulfanyl-tetrahydro-pyran-2-yl)-propyl]-amide (35.1 mg, 0.084 mmol), prepared as in Example 9, in methanol (3 mL), at 0° C. The reaction mixture was stirred at 4° C. overnight. Additional ethylene oxide (0.6 mL) was added and stirred at 4° C. overnight. The reaction mixture was concentrated and purified by chromatography to give the title compound as a white solid (24.1 mg, 62%).

$^1$H NMR (300 MHz, CDCl$_3$) δ 7.68 (d, J=9.0, 1), 5.32 (d, J=5.4, 1), 5.24 (d, J=3.0, 1), 4.13–4.07 (m, 1), 4.01 (ddd, J=2.8, 9.9, 9.9, 1), 3.86 (d, J=10.8, 1), 3.78–3.68 (m, 2), 3.61–3.57 (m, 1), 3.56–3.48 (m, 1), 3.36–3.32 (m, 1), 3.27–3.21 (m, 1), 2.94–2.85 (m, 1), 2.76–2.70 (m, 1), 2.55 (ddd, J=3.6, 3.6, 12.6, 1), 2.41–2.37 (m, 1), 2.36–2.27 (m, 1), 2.15 (s, 3), 2.03–1.95 (m, 2), 1.93–1.81 (m, 1), 1.54–1.42 (m, 1), 1.39–1.26 (m, 2), 1.22–1.10 (m, 2), 0.99–0.92 (m, 6), 0.90–0.84 (m, 6). MS(ESPOS): 463.5 [M+H]$^+$ MS(ESNEG): 461.5 [M−H]$^-$.

Example 23

Preparation of 4-(3,3-Difluoro-propyl)-1-(2-hydroxy-ethyl)-pyrrolidine-2-carboxylic acid [2-methyl-1-(3,4,5-trihydroxy-6-methylsulfanyl-tetrahydro-pyran-2-yl)-propyl]-amide

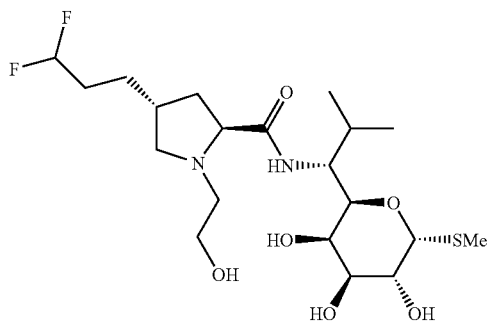

Ethylene oxide (0.4 mL) was added to a solution of 4-(3,3-difluoro-propyl)-pyrrolidine-2-carboxylic acid [2-methyl-1-(3,4,5-trihydroxy-6-methylsulfanyl-tetrahydro-pyran-2-yl)-propyl]-amide, prepared as in Example 14 (29.7 mg, 0.07 mmol), in methanol (2 mL), at 0° C. The reaction mixture was stirred at 4° C. overnight. Additional ethylene oxide (0.4 mL) was added and stirred at 4° C. overnight. The reaction mixture was concentrated and purified by chromatography to give the title compound as a white solid (19.3 mg, 59%).

$^1$H NMR (300 MHz, CDCl$_3$) δ 5.86 (dddd, J=4.3, 4.3, 57, 57, 1), 5.23 (d, J=5.7, 1), 4.13–4.04 (m, 3), 3.75 (d, J=3.3, 1), 3.73–3.57 (m, 2), 3.53 (dd, J=3.3, 10.2, 1), 3.42–3.36 (m, 1), 3.26–3.18 (m, 1), 2.88–2.78 (m, 1), 2.62–2.55 (m, 1), 2.17–2.00 (m, 4), 2.10 (s, 3), 1.94–1.73 (m, 3), 1.55–1.45 (m, 2), 0.98–0.91 (m, 6).

MS (ESPOS): 471.5 [M+H]$^+$, MS (ESNEG): 469.4 [M−H]$^-$.

Example 24

Preparation of 1-(2-Hydroxy-ethyl)-4-pentyl-pyrrolidine-2-carboxylic acid [2,2-difluoro-1-(3,4,5-trihydroxy-6-methylsulfanyl-tetrahydro-pyran-2-yl)-propyl]-amide

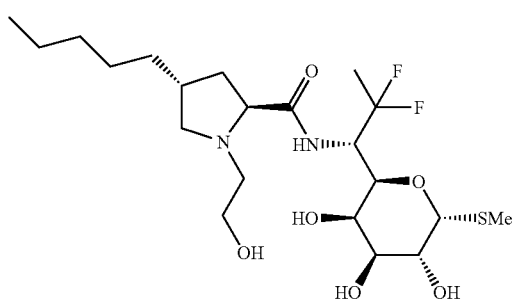

Ethylene oxide (1 mL, excess) was added to the title compound from Example 12 (60 mg, 0.136 mmol) in methanol (5 mL) at 0° C., and the mixture was stirred at 4° C. overnight. The solvent was removed and the crude product was purified by silica gel column chromatography using 10% methanol in dichloromethane as the eluent (25 mg, 38%).

TLC: R$_f$=0.76 (5% methanol in dichloromethane); $^1$H NMR (300 MHz, CD$_3$OD) δ 0.89 (m, 3), 1.30 (m, 8), 1.68 (t, J=19.4, 3), 1.78 (m, 1), 1.99 (m, 2), 2.07 (s, 3), 2.63 (m, 1), 2.73 (m, 1), 3.19 (m, 1), 3.58 (m, 3), 3.95 (m, 1), 4.08 (dd, J=6.0, 9.90, 1), 4.44–4.60 (m, 2), 5.26 (d, J=5.4, 1); MS (ESPOS): 485 [M+H]$^+$.

Example 25

Preparation of 4-Pentyl-piperidine-2-carboxylic acid [2-methyl-1-(3,4,5-trihydroxy-6-methylsulfanyl-tetrahydro-pyran-2-yl)-propyl]-amide

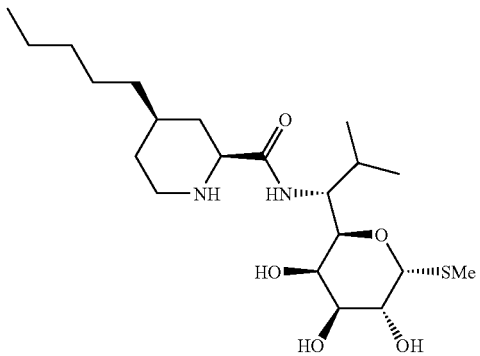

4-Pentylpyridine-2-carboxylic acid (10b) ($R^9$=pentyl) was made by employing Method P. To 4-pentylpyridine (3 g, 20 mmol) in acetic acid (30 mL), hydrogen peroxide (0.7 g, 30%, 20 mmol) was added and refluxed overnight. Removal of solvent resulted in residue which was dissolved in DCM (100 mL) dried over $MgSO_4$ and filtered. Removal of DCM resulted in a brown liquid, 4-pentylpyridine-N-oxide, (3.3 g, 100%). To trimethylsilyl cyanide (2.37 g, 24 mmol), 4-pentylpyridine N-oxide (3.3 g, 20 mmol) in DCM (10 mL) was added followed by dropwise addition of dimethylcarbamoyl chloride (2.56 g, 24 mmol) in DCM (10 mL). After stirring at room temperature overnight, sodium bicarbonate (100 mL, 10%) was added and the organic layer was separated. The aqueous layer was extracted twice with DCM (50 mL) and the combined organic layer was dried over magnesium sulfate. Removal of solvent resulted in compound 10a ($R^9$=pentyl) (4.1 g, 100%).

$^1$H NMR (300 MHz, $CD_3OD$) δ 8.52 (m, 1), 7.46 (s, 1), 7.27 (m, 1), 3.00 (m, 2), 2.60 (m, 2), 1.60 (m, 2), 1.27 (m, 2), 0.86 (m, 3). MS (ESPOS): 175 [M+H]$^+$.

The 4-Pentyl-2-cyanopyridine (10a) ($R^9$=pentyl) (3.4 g, 19.5 mmol) from the previous step was dissolved in HCl (6 N, 100 mL) and refluxed overnight. The residue obtained on removal of HCl was purified by column chromatography using 20% MeOH in DCM (3.7 g, 100%) to give product compound 10(b). $^1$H NMR (300 MHz, $CD_3OD$) δ 8.74 (d, J=6.3, 1), 8.39 (s, 1), 8.06 (d, J=6.3, 1), 2.98 (t, J=7.2, 2), 1.77(m, 2), 1.39 (m, 4), 0.95 (t, J=7.2, 3H). MS (ESNEG): 192 [M−H]$^−$.

Then to 7-methyl α-thiolincosaminide 2b ($R^1$=Me, $R^2$=Me) (90 mg, 0.35 mmol) in DMF (2 ml), TEA (72 mg, 0.7 mmol), BSTFA (276 mg, 1.05 mmol) were added at 0° C. and stirred at room temperature for 1.5 hr. Then the acid (10b) ($R^9$=pentyl) (138 mg, 0.7 mmol) and HATU (165 mg, 0.53 mmol) was added to the reaction mixture, and stirred at room temperature overnight. DMF was completely removed, the residue was taken up in EtOAc (50 mL), washed with sodium bicarbonate (10%, 50 mL), brine (50 mL). The product obtained after drying over magnesium sulfate and concentration was taken up in methanol (10 mL) and treated with Dowex™ polymeric sulfonic acid H$^+$ resin (150 mg) for 3 hr. The resin was filtered and the solvent was removed. Purification of the crude product was carried out by silica gel column chromatography using 3% MeOH in DCM as eluent to obtain compound 11b ($R^1$=Me, $R^2$=Me $R^3$=H, $R^9$=pentyl) (90 mg, 59%):

$^1$H NMR (300 MHz, $CD_3OD$) δ 8.50 (d, J=5.1, 1), 7.95 (s, 1), 7.11 (m, 1), 5.25 (d, J=5.7, 1), 4.20–4.87 (m, 3), 3.85 (d, J=3.3, 1), 3.55 (dd, J=3.3, 7.2, 1), 2.72 (m, 2), 2.16 (m, 4), 1.67 (m, 2), 1.35 (m, 4), 0.96 (m, 9). MS (ESPOS): 427 [M+H]$^+$.

To pyridine 11b ($R^1$=Me, $R^2$=Me $R^3$=H, $R^9$=pentyl) (90 mg, 0.7 mmol) in water (10 mL), AcOH (3 mL) and MeOH (2 mL), $PtO_2$ (100 mg) was added, hydrogenated at 55 psi overnight. The solvent was removed to obtain the crude product. Purification of the crude product was carried out by silica gel column chromatography using 20% MeOH in DCM to obtain the title compound (35 mg, 38%).

$^1$H NMR (300 MHz, $CD_3OD$) δ 5.23 (d, J=5.1, 1), 4.17 (m, 3), 3.79 (d, J=3.3, 1), 3.52 (m, 1), 3.38 (m, 1), 3.07 (m, 1), 2.68 (m, 1), 2.14 (m, 4), 1.88 (m, 1), 1.71 (m, 1), 1.52 (m, 1), 1.30 (m, 8), 1.07 (m, 3), 0.90 (m, 9); MS (ESPOS): 433 [M+H]$^+$.

Example 26

Preparation of 4-Methoxy-piperidine-2-carboxylic acid [2-methyl-1-(3,4,5-trihydroxy-6-methylsulfanyl-tetrahydro-pyran-2-yl)-propyl]-amide

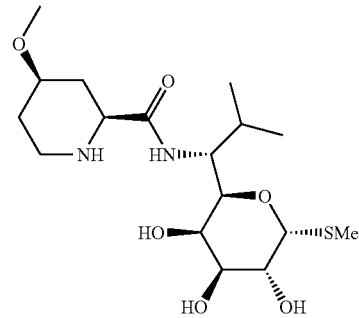

4-Methoxypyridine-2-carboxylic acid, compound 10(b) ($R^9$=methoxy), was made employing Method P. To trimethylsilyl cyanide (0.95 g, 9.6 mmol), 4-methoxypyridine N-oxide (1 g, 8 mmol) in DCM (10 mL) was added, followed by dimethylcarbamoyl chloride (1.03 g, 9.6 mmol) in DCM (10 mL), dropwise. After stirring at room temperature overnight, sodium bicarbonate (100 mL, 10%) was added, and the organic layer was separated. The aqueous layer was extracted twice by DCM (50 mL each). The combined organic layer was dried over magnesium sulfate and the solvent was removed to obtain product, compound 10a (0.97 g, 90%):

$^1$H NMR (300 MHz, $CD_3OD$) δ 8.52 (m, 1), 7.22 (m, 1), 7.01 (m, 1), 3.92 (s, 3H); MS (ESPOS): 135 [M+H]$^+$.

4-Methoxy-2-cyanopyridine, compound 10a ($R^9$=methoxy), (0.97 g, 7.2 mmol) was dissolved in HCl (6N, 50 mL), and refluxed overnight. The HCl was evaporated and the resulting product was crystallized from acetonile, to give compound 10b ($R^9$=methoxy) (0.6 g, 60%).

$^1$H NMR (300 MHz, $CD_3OD$) δ 8.65 (m, 1), 7.99 (m, 1), 7.68 (m, 1), 4.21 (s, 3H). MS (ESNEG): 152 [M−H]$^−$.

To 7-methyl α-thiolincosaminide, compound 2b ($R^1$=Me, $R^2$=Me), (90 mg, 0.35 mmol) in DMF (2 mL), TEA (72 mg, 0.7 mmol), BSTFA (276 mg, 1.05 mmol) were added at 0° C. and left stirred at room temperature for 1.5 hr. Then compound 10b (R$^9$=methoxy) (109 mg, 0.7 mmol) and HATU (165 mg, 0.53 mmol) were added to the reaction mixture, and stirred at room temperature overnight. The DMF was completely removed and the residue was taken up in EtOAc (50 mL), washed with sodium bicarbonate (10%, 30 mL), brine (30 mL), and dried over magnesium sulfate. The solvent was removed to obtain a brown oil-like liquid, which was dissolved in methanol (10 mL) and treated with Dowex™ polymeric sulfonic acid H$^+$ resin for 1 hr. The resin was filtered, and the solvent was removed to obtain the crude material. Purification was carried out on silica gel column chromatography using EtOAc as eluent to obtain compound 11b (R$^1$=Me, R$^2$=Me R$^3$=H, R$^9$=methoxy) (100 mg, 72%).

$^1$H NMR (300 MHz, CD$_3$OD) δ 8.42 (m, 1), 7.64 (m, 1), 7.07 (m, 1), 5.25 (d, J=5.4, 1), 4.07–4.87 (m, 3), 3.94 (m, 4), 3.56 (m, 1), 2.99 (m, 2), 2.80 (m, 1), 2.22 (m, 1), 2.11 (s, 3), 0.96 (m, 3). MS (ESPOS): 387 [M+H]$^+$.

To compound 11b (R$^1$=Me, R$^2$=Me, R$^3$=H, R$^9$=methoxy) (100 mg, 0.26 mmol) in water (10 mL), AcOH (3 mL) and MeOH (2 mL), PtO$_2$ (100 mg) were added and hydrogenated at 55 psi overnight. The solvent was removed to obtain the crude product. Purification of the crude product was carried out by silica gel column chromatography using 20% MeOH in DCM to obtain the title compound. (9 mg, 9%).

$^1$H NMR (300 MHz, CD$_3$OD) δ 5.24 (d, J=5.7, 1), 4.17 (dd, J=9.9; 3.3, 1), 4.07 (m, 2), 3.79 (m, 1), 3.52 (dd, J=10.5; 3.3, 1), 3.35 (s, 3), 3.18 (m, 2), 2.72 (m, 1), 2.16 (m, 1), 2.12 (s, 3) 1.99 (m, 2), 1.50 (m, 1), 1.24 (m, 2), 0.90 (d, J=6.9, 6); MS (ESPOS): 393 [M+H]$^+$.

Example 27

Preparation of 4-(1-Ethyl-propyl)-piperidine-2-carboxylic acid [2-methyl-1-(3,4,5-trihydroxy-6-methylsulfanyl-tetrahydro-pyran-2-yl)-propyl]-amide

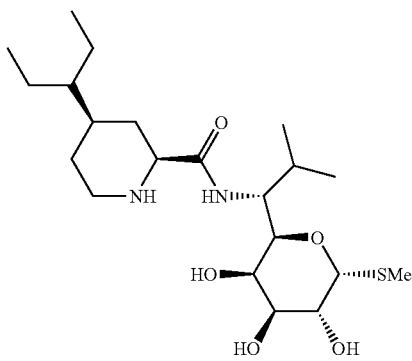

4-Isopentylpyridine-2-carboxylic acid, compound 10b (R$^9$=1-ethyl-propyl), was made by employing Method P. To 4-(1-ethyl-propyl)-pyridine (8.5 g, 57 mmol) in acetic acid (30 mL), hydrogen peroxide (17.8 g, 30%, 57 mmol) was added. The resulting reaction mixture was refluxed overnight. The residue obtained on removal of solvent was dissolved in DCM (100 mL), dried over MgSO$_4$. After filtering, the solvent was removed to obtain a brown liquid, 4-(1-ethyl-propyl)-pyridine-N-oxide (9 g, 95%).

To a solution of trimethylsilyl cyanide (6.5 g, 65 mmol) and 4-(1-ethyl-propyl)-pyridine-N-oxide (9 g, 54 mmol) in DCM (25 mL) was added a solution of dimethylcarbamoyl chloride (7 g, 65 mmol) in DCM (10 mL), dropwise. After stirring at room temperature overnight, sodium bicarbonate (100 mL, 10%) was added, and the organic layer was separated. The aqueous layer was extracted twice with DCM (50 mL). The combined organic layer was dried over magnesium sulfate and the solvent was removed to obtain the product, compound 10a (R$^9$=1-ethyl-propyl) (9.6 g, 100%).

$^1$H NMR (300 MHz, CD$_3$OD) δ 8.58 (m, 1), 7.46 (m, 1), 7.26 (m, 1), 2.42 (m, 1), 1.77 (m, 4)), 0.78 (t, J=7.5, 6). MS (ESPOS): 175 [M+H]$^+$.

Compound 10a (R$^9$=1-ethyl-propyl) (9.5 g, 54 mmol) was dissolved in HCl (6N, 50 mL) and refluxed overnight. HCl was evaporated and the resulting product, compound 10b (R$^9$=1-ethyl-propyl), was crystallized from acetonitrile (10 g, 100%).

$^1$H NMR (300 MHz, CD$_3$OD) δ 8.86 (m, 1), 8.45 (m, 1), 8.20 (m, 1), 2.92 (m, 1), 1.87 (m, 4), 0.84 (t, J=7.5, 6). MS (ESNEG): 192 [M−H]$^-$.

To the acid 10b (77 mg, 0.4 mmol) in DMF (2 mL), 7-methyl α-thiolincosaminide, compound 2b (R$^1$=Me, R$^2$=Me), (100 mg, 0.4 mmol) was added, followed by HBTU (166 mg, 0.44 mmol) and DIEA (205 mg, 0.8 mmol). The mixture was stirred at room temperature for 2 hr. The product was obtained on removal of DMF and purified by silica gel column chromatography using ethyl acetate to provide compound 11b (R$^1$=Me, R$^2$=Me R$^3$=H, R$^9$=1-ethyl-propyl) (150 mg, 89%).

$^1$H NMR (300 MHz, CD$_3$OD) δ 8.42 (d, J=5.1, 1), 7.37 (s, 1), 7.32 (m, 1), 5.27 (d, J=4.8, 1), 4.21–4.88 (m, 3), 3.85 (d, J=3.6, 1), 3.56 (dd, J=3.3, 10.2, 1), 2.48 (m, 1), 2.11 (m, 4), 1.00 (m, 12). MS (ESPOS): 427 [M+H]$^+$.

To compound 11b (R$^1$=Me, R$^2$=Me R$^3$=H, R$^9$=1-ethyl-propyl) (130 mg, 0.3 mmol) in water (10 mL), AcOH (2 mL) and MeOH (2 mL), PtO$_2$ (150 mg) was added and hydrogenated at 55 psi overnight. The solvent was removed to obtain the crude product. Purification was carried by silica gel column chromatography using 20% MeOH in DCM to obtain the title compound (40 mg, 30%).

$^1$H NMR (300 MHz, CD$_3$OD) δ 5.24 (d, J=5.7, 1), 4.17 (dd, J=9.9; 3.3, 1), 4.10 (m, 2), 3.78 (m, 1), 3.51 (m, 2), 2.81 (m, 2), 2.16 (m, 1), 2.10 (s, 3) 1.90 (m, 2), 1.76 (m, 3), 1.40 (m, 8), 0.91 (m, 9); MS (ESPOS): 433 [M+H]$^+$.

Example 28

Preparation of 4-Isopropyl-piperidine-2-carboxylic acid [2-methyl-1-(3,4,5-trihydroxy-6-methylsulfanyl-tetrahydro-pyran-2-yl)-propyl]-amide

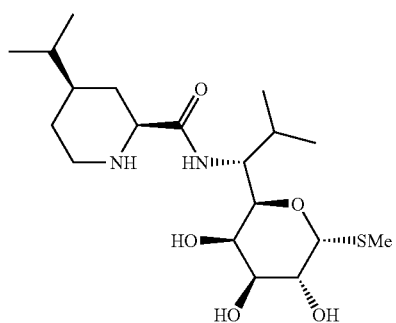

4-Isopropylpyridine-2-carboxylic acid, compound (10b) (R⁹=isopropyl), was made by employing Method P. To 4-isopropylpyridine (5 g, 0.041 mol) in acetic acid (60 mL), hydrogen peroxide (30%, 4.7 g, 0.13 mol) was added and refluxed over night. After removing the solvent, the residue was dissolved in DCM dried over magnesium sulfate and taken as such for the next step. To the resulting compound in dichloromethane (10 mL) trimethylsilyl cyanide (7.0 mL, 0.07 mol) and dimethylcarbamyl chloride (5.6 mL, 0.05 mol) were added and stirred at room temperature for 24 hours. Aqueous potassium carbonate (10%, 50 mL) was added and extracted with dichloromethane (100 mL). The crude product obtained on removal of solvent was taken up in hydrochloric acid (6N, 30 mL) and refluxed for 24 hours. Removal of acid followed by crystallization of the crude product from acetonitrile resulted in acid 10b (R⁹=isopropyl) (5 g, 75%).

$^1$H NMR (300 MHz, CD$_3$OD): δ 8.78 (d, J=6, 1), 8.42 (s, 1), 8.16 (d, J=6.0, 1), 3.25 (m, 1), 1.33 (d, J=9.0, 6) MS (ESNEG): 164 [M−H]⁻.

To the amine, compound 2b (R¹=Me, R²=Me), (140 mg, 0.56 mmol) in DMF (3 mL), BSTFA (0.59 mL, 2.24 mmol) and triethylamine (0.18 mL, 1.26 mmol) were added at 0° C. and the reaction mixture was stirred at room temperature for 3 hours. Acid 10b (R⁹=isopropyl) (188 mg, 1.13 mmol) and HATU (319 mg, 0.84 mmol) were combined and left stirred for further 4 hours at room temperature. The DMF was removed and the residue was extracted with ethyl acetate (100 mL) and washed with saturated bicarbonate (40 mL). The product obtained on removal of solvent was taken up in methanol and treated with Dowex™ H⁺ resin for 1 hour. After filtering the resin, methanol was removed to obtain the crude product. It was then purified on silica gel column using 10% methanol in dichloromethane as eluent to provide compound 11b (R¹=Me, R²=Me R³=H, R⁹=isopropyl) (120 mg, 53%).

$^1$H NMR (300 MHz, CD$_3$OD): δ 8.42 (d, J=5.1, 1), 7.37 (s, 1), 7.32 (m, 1), 5.27 (d, J=4.8, 1), 4.21–4.88 (m, 3), 3.85 (d, J=3.6, 1), 3.56 (dd, J=3.3, 10.2, 1), 2.48 (m, 1), 2.11 (m, 1), 2.10 (s, 3), 1.20 (m, 12). MS (ESPOS): 399 [M+H]⁺.

To 11b (R¹=Me, R²=Me R³=H, R⁹=isopropyl) (100 mg, 0.257 mmol) in methanol (5 mL), water (10 mL) and acetic acid (5 mL), platinum dioxide (100 mg, 0.44 mmol) was added and hydrogenated at 60 psi for 16 h. After filtering the catalyst, the solvent was stripped off to obtain the crude product which was then purified on silica gel column chromatography using 10% methanol in dichloromethane as eluent. The lower R$_f$ compound was the title compound (10 mg, 9%).

$^1$H NMR (300 MHz, CD$_3$OD): δ 5.24 (d, J=5.7, 1), 4.17 (dd, J=9.9; 3.3, 1), 4.10 (m, 2), 3.80 (m, 1), 3.51 (m, 1), 3.16 (m, 1), 2.61 (m, 1), 2.16 (m, 1), 2.10 (s, 3) 1.90 (m, 1), 1.76 (m, 1), 1.50–1.09 (m, 5), 0.91 (m, 12); MS (ESPOS): 405 [M+H]⁺.

Example 29

Preparation of 4-Butyl-piperidine-2-carboxylic acid [2-methyl-1-(3,4,5-trihydroxy-6-methylsulfanyl-tetrahydro-pyran-2-yl)-propyl]-amide

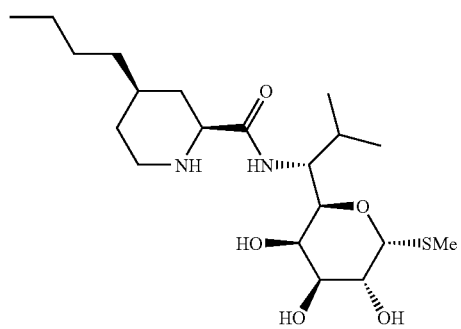

4-Butylpyridine was prepared by adding potassium-t-butoxide (0.68 g, 6 mmol) to propylphosphonium bromide (Aldrich) (2.4 g, 6.0 mmol) in THF (10 mL), at 0° C. and stirring at room temperature for 1 hour. Pyridine-4-carbaldehyde (428 mg, 4 mmol) was added and the reaction mixture stirred for 2 h. The reaction mixture was then poured into water and extracted with ethyl acetate. The product obtained after removing the solvent was taken as such in methanol (30 mL) to which palladium on carbon (10%, 300 mg) was added and hydrogenated at 1 atm pressure over night. Removal of solvent and purification on column chromatography using ethyl acetate resulted in pure product 4-butylpyridine (500 mg, 92%):

$^1$H NMR (CDCl$_3$): δ 8.42 (d, J=6.0, 2), 7.05 (d, J=6.0, 1), 2.60 (t, J=6.5, 2), 1.62 (m, 2), 1.37 (m, 2), 0.93 (t, J=7.0, 3). MS (ESPOS): 136 [M+H]⁺.

4-Butylpyridine-2-carboxylic acid, compound (10b) (R⁹=butyl), was made employing Method P. To 4-butylpyridine (2 g, 0.014 mol) in acetic acid (15 mL), hydrogen peroxide (30%, 5 mL, 0.056 mol) was added and refluxed over night. After removing the solvent, the residue was dissolved in DCM dried over magnesium sulfate and taken as such for the next step. To the compound from the previous step in dichloromethane (10 mL) trimethylsilyl cyanide (3.92 mL, 0.029 mol) and dimethylcarbamoyl chloride (2.67 mL, 0.028 mol) was added and stirred at room temperature for 24 hours. Aqueous potassium carbonate (10%, 50 mL) was added and extracted with dichloromethane (100 mL). The crude product obtained on removal of solvent was taken up in hydrochloric acid (6N, 30 mL) and refluxed for 24 hours. Removal of acid followed by crystallization of the crude product from acetonitrile resulted in acid 10b (R⁹=butyl) (1.5 g, 60%).

$^1$H NMR (CDCl$_3$): δ 8.92 (d, J=6.0, 1), 8.65 (s, 1), 8.27 (m, 1), 3.23 (t, J=6.5, 2), 1.98 (m, 2), 1.67 (m, 2), 1.20 (t, J=7.0, 3). MS (ESNEG): 178 [M−H]⁻.

To the amine, compound 2b (R¹=Me, R²=Me), (140 mg, 0.56 mmol) in DMF (3 mL), BSTFA (0.59 mL, 2.24 mmol) and triethylamine (0.18 mL, 1.26 mmol) were added at 0° C. and then stirred at room temperature for 3 hours. Acid 10b (R⁹=butyl) (203 mg, 1.13 mmol) and HATU (319 mg, 0.84 mmol) were added and the reaction mixture was stirred for 4 more hours at room temperature. The DMF was removed and the residue was extracted with ethyl acetate (100 mL) and washed with saturated bicarbonate (40 mL). The product obtained on removal of solvent was taken up in methanol and treated with Dowex™ H+ resin for 1 hour. After filtering the resin, methanol was removed to obtain the crude product. The product was then purified on silica gel column using ethyl acetate as eluent to provide for compound 11b ($R^1$=Me, $R^2$=Me $R^3$=H, $R^9$=butyl) (200 mg, 86%).

$^1$H NMR (CDCl$_3$) δ 8.40 (d, J=4.2, 1), 8.01 (s, 1), 7.29 (m, 1), 5.40 (d, J=5.4, 1), 4.02–4.36 (m, 3), 4.80 (s, 1), 3.48–3.60 (m, 1), 3.72 (t, J=6.0, 2), 2.49 (m, 1), 2.20 9s, 3), 1.67 (m, 4), 1.40 (m, 3), 0.98–1.18 (m, 9). Mass 413 [M+H]+.

To compound 11b ($R^1$=Me, $R^2$=Me $R^3$=H, $R^9$=butyl) (200 mg, 0.49 mmol) in methanol (5 mL), water (10 mL) and acetic acid (5 mL), platinum dioxide (100 mg, 0.44 mmol) was added and hydrogenated at 60 psi for 16 h. After filtering the catalyst, the solvent was stripped off to obtain the crude product, which was then purified on silica gel column chromatography using 20% methanol in dichloromethane as eluent. The lower $R_f$ fractions provided the title compound (60 mg, 29%).

$^1$H NMR (CDCl$_3$): δ 5.20 (d, J=3.6, 1), 4.20 (dd, J=3.0, 4.8, 1), 4.04 (m, 2), 3.80 (d, J=3.0, 1), 3.61–3.66 (m, 1), 3.52 (dd, J=3.3, 10.2), 2.88 (m, 1), 2.17 (m, 1), 2.14 (s, 3), 1.87 (m, 2), 1.62 (m, 2), 1.32 (m, 6), 0.89 (m, 9); MS (ESPOS): 419 [M+H]+.

Example 30

Preparation of 4-Cyclohexyl-piperidine-2-carboxylic acid [2-methyl-1-(3,4,5-trihydroxy-6-methylsulfanyl-tetrahydro-pyran-2-yl)-propyl]-amide

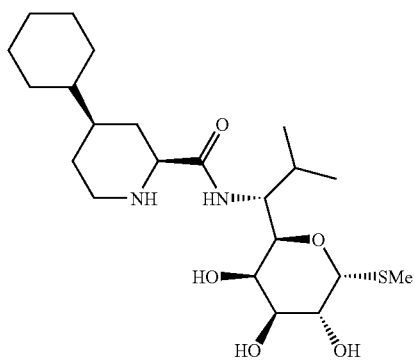

4-phenylpyridine-2-carboxylic acid, compound 10b ($R^9$=phenyl), was made by employing Method P. To 4-phenylpyridine-N-oxide (1 g, 5.84 mmol) in dichloromethane (10 mL) trimethylsilyl cyanide (1.5 mL, 11.6 mmol) and dimethylcarbamoyl chloride (1 mL, 11.6 mmol) were added and the reaction mixture was stirred at room temperature for 24 hours. An aqueous potassium carbonate solution (10%, 10 mL) was added and extracted with dichloromethane (100 mL). The crude product obtained on removal of solvent was taken up in hydrochloric acid (6N, 30 mL) and refluxed for 24 hours. Removal of acid followed by crystallization of the crude product from acetonitrile resulted in acid 10b ($R^{9'}$=phenyl) (1 g, 86%).

MS(ESNEG): 198 [M–H]–; $^1$H NMR (300 MHz, CD$_3$OD) δ 7.64–7.67 (m, 3), 8.02–8.06 (m, 2), 8.53–8.56 (m, 1), 8.82 (s, 1), 8.82–8.90 (m, 1).

To the amine 2b ($R^1$=Me, $R^2$=Me) (102 mg, 0.42 mmol) in DMF (5 mL), BSTFA (0.549 mL, 2.1 mmol) and triethylamine (0.183 mL, 1.26 mmol) was added at 0° C. and then stirred at room temperature for 3 hours. Acid 10b ($R^9$=phenyl) (158 mg, 0.80 mmol) and HATU (302 mg, 0.80 mmol) were added and the reaction was stirred for an additional 4 hours at room temperature. The DMF was removed and the residue was extracted with ethyl acetate (100 mL) and washed with saturated bicarbonate (40 mL). The product obtained on removal of solvent was taken up in methanol and treated with Dowex™ H+ resin for 1 hour. After filtering the resin, methanol was removed to obtain the crude product. The resulting residue was then purified by silica gel chromatography using 10% methanol in dichloromethane as eluent to provide compound 11b($R^1$=Me, $R^2$=Me $R^3$=H, $R^{9'}$=phenyl) (50 mg, 58%).

TLC: $R_f$=0.70 (10% MeOH/DCM); MS (ESPOS): 435 [M+H]+; $^1$H NMR (300 MHz, CDCl$_3$) δ 1.01 (t, J=6.6, 6), 2.12 (s, 3), 2.28 (m, 1), 3.56 (dd, J=3.3, 10.5, 1), 3.90 (d, J=3.3, 1), 4.12 (dd, J=5.4, 10.5, 1), 4.27–4.36 (m, 2), 4.52 (m, 2), 5.26 (d, J=5.7, 1), 7.48–7.55 (m, 3), 7.77–7.80 (m, 2), 7.83–7.85 (m, 1), 8.37 (s, 1), 8.69 (d, J=5.4, 1).

To compound 11b ($R^1$=Me, $R^2$=Me $R^3$=H, $R^{9'}$=phenyl) (40 mg, 0.09 mmol) in methanol (5 mL), water (10 mL) and acetic acid (5 mL), platinum dioxide (100 mg, 0.44 mmol) was added and the reaction mixture shaken at 60 psi hydrogen for 16 h. The catalyst was removed by filtration, and the solvent was evaporated to obtain the crude product, which was then purified on silica gel column chromatography using 10% methanol in dichloromethane to provide the title compound (10 mg, 25%).

TLC: $R_f$=0.22 (20% MeOH/DCM); MS (ESPOS): 447 [M+H]+; $^1$H NMR (300 MHz, CD$_3$OD) δ 0.90 (d, J=6.8, 6), 0.93–1.05 (m, 5), 1.20 (m, 6), 1.33–1.47 (m, 4), 1.75 (m, 6), 2.10 (s, 3), 2.18–2.22 (m, 1), 2.97 (t, J=12.3, 1), 3.39–3.52 (m, 2), 3.70–3.78 (m, 2), 4.05–4.21 (m, 3), 5.23 (d, J=5.7, 1).

Example 31

Preparation of 4-Ethyl-1-(2-hydroxy-ethyl)-piperidine-2-carboxylic acid [2-methyl-1-(3,4,5-trihydroxy-6-methylsulfanyl-tetrahydro-pyran-2-yl)-propyl]-amide

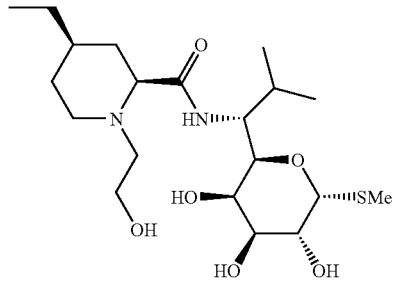

To the product of Example 1 (28 mg, 0.07 mmol) in methanol (2 mL), ethylene oxide (0.5 mL) was added and stirred at 4° C. overnight. The solvent was removed and the resulting product was purified by column chromatography using 20% MeOH in DCM as eluent to obtain the title compound (16 mg, 51%) as a white powder.

$^1$H NMR (300 MHz, CD$_3$OD) δ 5.24 (d, J=6, 1), 4.27 (m, 1), 4.10 (m, 2), 3.95 (m, 1), 3.79–3.50 (m, 4), 3.85 (m, 1) 3.74 (m, 1), 3.26 (m, 1), 2.91 (m, 2), 2.33 (m, 1), 2.13 (m, 4), 1.92 (m, 1), 1.71 (m, 1), 1.17 (m, 7), 0.94 (m, 9); MS (ESPOS): 435 [M+H]+.

Example 32

Preparation of 1-(2-Hydroxy-ethyl)-4-pentyl-piperidine-2-carboxylic acid [2-methyl-1-(3,4,5-trihydroxy-6methylsulfanyl-tetrahydro-pyran-2-yl)-propyl]-amide

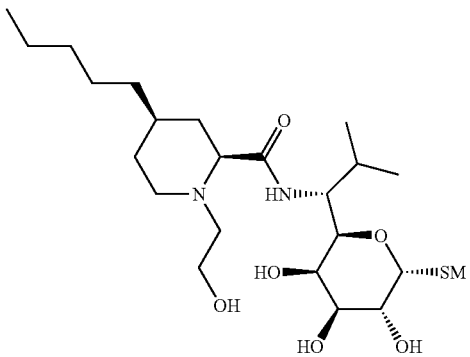

The title compound was prepared using the procedures of Example 32 with the product from Example 25 as the starting material.

$^1$H NMR (300 MHz, CD$_3$OD) δ 5.24 (d, J=6.0, 1), 4.19 (m, 3), 3.79 (d, J=3.3, 1), 3.74 (m, 1), 3.65 (m, 1), 3.54 (dd, J=3.0, 10.2, 1), 3.25 (m, 2), 2.82 (m, 2), 2.14 (m, 4), 1.89 (m, 1), 1.72 (m, 1), 1.28 (m, 12), 0.94 (m, 9); MS (ESPOS): 477 [M+H]$^+$.

Example 33

Preparation of 1-(2-Hydroxy-ethyl)-4-propyl-piperidine-2-carboxylic acid [2-methyl-1-(3,4,5-trihydroxy-6-methylsulfanyl-tetrahydro-pyran-2-yl)-propyl]-amide

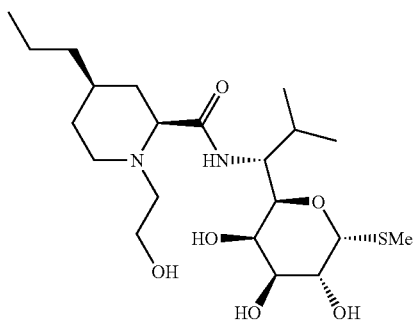

The title compound was made using the procedures of Example 32 with the product of Example 17 as the starting material.

$^1$H NMR (300 MHz, CD$_3$OD) δ 5.24 (d, J=6.0, 1), 4.19 (dd, J=9.6; 3.3, 1), 4.11 (m, 2), 3.79 (d, J=3.3, 1), 3.75 (m, 1), 3.65 (m, 1), 3.54 (m, 1), 3.28 (m, 1), 2.82 (m, 2), 2.27 (m, 5) 1.90 (m, 1), 1.71 (m, 1), 1.36 (m, 8), 0.94 (m, 9); MS (ESPOS): 449 [M+H]$^+$.

Example 34

Preparation of 2-[2-Methyl-1-(3,4,5-trihydroxy-6-methylsulfanyl-tetrahydro-pyran-2-yl)-propylcarbamoyl]-4-propyl-piperidine-1-carboxylic acid 9H-fluoren-9-ylmethyl ester

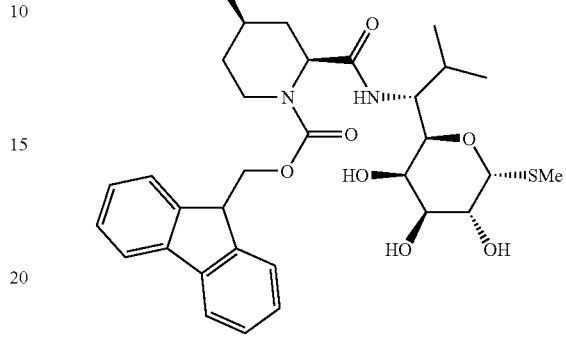

To the product of Example 17 (50 mg, 0.123 mmol) in water (3 mL) and dioxane (3 mL), Fmoc-Cl (38 mg, 0.197 mmol) and sodium carbonate (25 mg, 0.246 mmol) were added and the reaction mixture was stirred over night at room temperature. The solvents were removed and the crude material was loaded into a silica gel column and eluted with ethyl acetate to obtain the title compound as a white solid (30 mg, 51%).

TLC: Rf=0.5 (EtOAc). MS (ESPOS): 627 [M+H]$^+$, 649 [M+Na]$^+$; $^1$H NMR (CD$_3$OD, 200 MHz): 7.79 (d, J=4.6 Hz, 2), 7.59–7.62 (m, 2), 7.28–7.41 (m, 4), 5.19 (d, J=3.8 Hz, 1), 4.45 (m, 2), 4.24 (t, J=4.2, 1), 3.99–4.15 (m, 4), 3.93 (m, 1), 3.47–3.50 (m, 2), 2.05 (s, 3), 1.87 (m, 1), 1.67 (s, 2), 1.50 (m, 1), 1.30 (m, 4), 0.86–0.91 (m, 9).

Example 35

Preparation of 2-[2-Methyl-1-(3,4,5-trihydroxy-6-methylsulfanyl-tetrahydro-pyran-2-yl)-propylcarbamoyl]-4-propyl-piperidine-1-carboxylic acid ethyl ester

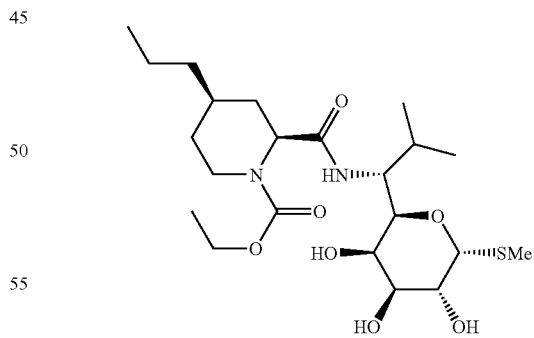

To the product of Example 17 (50 mg, 0.123 mmol) in water (3 mL) and dioxane (3 mL), ethyl chloroformate (20 mg, 0.147 mmol) and sodium carbonate (25 mg, 0.246 mmol) were added and stirred over night at room temperature. The solvents were removed and the crude material was loaded into a silica gel column and eluted with ethyl acetate to obtain the title compound as a white solid (40 mg, 52%).

TLC: Rf=0.28 (EtOAc). MS (ESPOS): 477 [M+H]$^+$; 499 [M+Na]$^+$; $^1$H NMR (CD$_3$OD, 200 MHz): 5.22 (d, J=3.6 Hz,

1), 4.27 (m, 1), 4.03–4.14 (m, 5), 3.96 (bs, 1), 3.62 (m, 1), 3.54 (d, J=2.2 Hz, 1), 3.52 (d, J=2.2 Hz, 1), 2.08 (s, 3), 1.93–2.03 (m, 2), 1.75–1.85 (m, 3), 1.61 (m, 2), 1.33 (m, 4), 1.22–1.28 (m, 3), 0.90–0.94 (m, 9).

Example 36

Preparation of 2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester

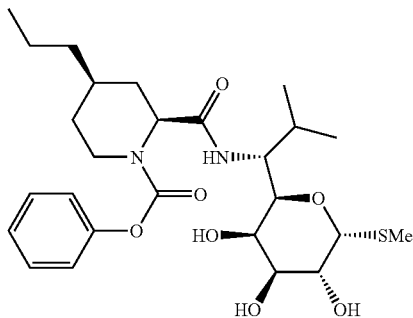

To the product of Example 17 (50 mg, 0.123 mmol) in water (3 mL) and dioxane (3 mL), phenyl chloroformate (40 mg, 0.246 mmol) and sodium carbonate (25 mg, 0.246 mmol) were added and the reaction mixture was stirred overnight at room temperature. The solvents were removed and the crude material was loaded into a silica gel column and eluted with ethyl acetate to obtain the title compound as a white solid (30 mg, 47%).

TLC: Rf=0.4 (EtOAc). MS (ESPOS): 526 [M+H]$^+$, 548 [M+Na]$^+$; $^1$H NMR (CD$_3$OD, 200 MHz): 7.36 (t, J=3.8 Hz, 2), 7.17–7.23 (m, 10), 7.10 (d, J=3.6 Hz, 2), 5.20 (d, J=3.6 Hz, 1), 4.09 (m, 3), 3.93 (d, J=2.2 Hz, 1), 3.82 (m, 2), 3.46 (m, 2), 2.01 (s, 3), 2.00 (m, 1), 1.71 (m, 1), 1.46–1.36 (m, 4), 0.96–0.90 (m, 9).

Example 37

Preparation of 4-(4,4-Difluoro-pentyl)-pyrrolidine-2-carboxylic acid [2-methyl-1-(3,4,5-trihydroxy-6-methylsulfanyl-tetrahydro-pyran-2-yl)-propyl]-amide

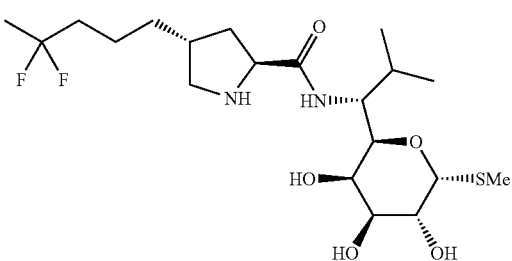

To a solution of aldehyde 8a, prepared by first step in Method L, (510 mg, 1.47 mmol, 1 equiv) in benzene (8 mL) was added 1-triphenylphosphoranylidene-2-propanone (Aldrich) (702 mg, 2.2 mmol, 1.5 equiv). The reaction mixture was refluxed overnight and the solvent was removed under vacuum. The residue was purified by chromatography to give 4-(4-oxo-pent-2-enyl)-pyrrolidine-1,2-dicarboxylic acid 1-tert-butyl ester 2-methyl ester as an oil (237 mg, 42%).

MS (ESPOS): 410.2 [M+Na]$^+$, 288.3 [M–Boc+H]$^+$; MS (ESNEG): 386.2 [M–H]$^-$.

To a solution of 4-(4-oxo-pent-2-enyl)-pyrrolidine-1,2-dicarboxylic acid 1-tert-butyl ester 2-methyl ester (193 mg, 0.5 mmol, 1 equiv) in benzene (0.9 mL) was added a solution of triphenylphosphine-copper (I) hydride hexamer in benzene (3.6 mL). The mixture was stirred at rt overnight and hexane (13 mL) was added. The mixture was filtered and the filtrate was evaporated. The residue was purified by chromatography to give 4-(4-oxo-pentyl)-pyrrolidine-1,2-dicarboxylic acid 1-tert-butyl ester 2-methyl ester (127 mg, 65%).

$^1$H NMR (300 MHz, CDCl$_3$) δ 7.35–7.30 (m, 5), 5.25–5.04 (m, 2), 4.42–4.25 (m, 1), 3.77–3.62 (m, 1), 3.00–2.85 (m, 1), 2.39 (t, J=7, 2), 2.34–1.47 (m, 7), 2.10 (s, 3), 1.43 (s, 3H), 1.31 (s, 6H); MS (ESPOS): 412.3 [M+Na]$^+$, 290.3 [M–Boc+H]$^+$; MS (ESNEG): 388.4 [M–H]$^-$.

To a solution of 4-(4-oxo-pentyl)-pyrrolidine-1,2-dicarboxylic acid 1-tert-butyl ester 2-methyl ester (155 mg, 0.40 mmol, 1 equiv) in dichloromethane (1.5 mL) at −78° C. was added DAST (0.21 mL, 1.60 mmol, 4 equiv). The reaction mixture was warmed to rt and stirred at rt for 3 h, followed by additional DAST (0.32 mL, 2.4 mmol, 6 equiv) at −78° C. The mixture was warmed to rt and stirred overnight. Then the mixture was diluted with dichloromethane, washed with sat. aqueous NaHCO$_3$ (1×), dried, and evaporated. The residue was purified by chromatography to give 4-(4,4-difluoro-pentyl)-pyrrolidine-1,2-dicarboxylic acid 1-tert-butyl ester 2-methyl ester as a yellow oil (88 mg, 54%).

MS (ESPOS): 434.2 [M+Na]$^+$, 312.3 [M–Boc+H]$^+$.

To a solution of 4-(4,4-difluoro-pentyl)-pyrrolidine-1,2-dicarboxylic acid 1-tert-butyl ester 2-methyl ester (88 mg, 0.21 mmol, 1 equiv) in THF (1.2 mL) and water (0.4 mL) was added lithium hydroxide monohydrate (45 mg, 1.07 mmol, 5 equiv). The reaction mixture was stirred at rt overnight. The THF was removed under vacuum. The residue was diluted with water and washed with ether. The aqueous layer was taken up in ethyl acetate, partitioned with 10% citric acid. The organic layer was washed with water (1×), brine (1×), dried and concentrated to give 4-(4,4-difluoro-pentyl)-pyrrolidine-1,2-dicarboxylic acid 1-tert-butyl ester (66 mg, 96%).

$^1$H NMR (300 MHz, CDCl$_3$) δ 4.39–4.34 (m, 1), 3.57–3.48 (m, 1), 2.92–2.83 (m, 1), 2.57–2.50 (m, 1), 2.30–2.18 (m, 1), 1.91–1.73 (m, 3), 1.64–1.36 (m, 7), 1.48 (s, 9); MS (ESPOS): 344.3 [M+Na]$^+$, 222.3 [M–Boc+H]$^+$; MS (ESNEG): 320.2 [M–H]$^-$.

To a solution of compound 2b (R$^1$=Me, R$^2$=Me) (50 mg, 0.20 mmol, 1 equiv) in dry DMF (0.5 mL) at 0° C. was added triethylamine (88.3 up, 0.64 mmol, 3.2 equiv), followed by the addition of BSTFA (79.2 µL, 0.30 mmol, 1.5 equiv). The reaction mixture was stirred at 0° C. for 10 minutes, and then was stirred at rt for 50 minutes. The reaction mixture was added to the acid (66 mg, 0.21 mmol, 1 equiv) in a 25 mL round bottom flask, followed by the addition of HATU (96.8 mg, 0.25 mmol, 1.25 equiv). The reaction mixture was stirred at rt for 3 h. The reaction mixture was evaporated to dryness, taken up in ethyl acetate, washed with 10% citric acid, water, sat. NaHCO$_3$ and brine. The organic layer was dried over Na$_2$SO$_4$ and evaporated and used in the next step without additional purification.

To a solution of the above Boc protected lincosamide in DCM (9 mL) with methyl sulfide (0.20 mL) were added trifluoroacetic acid (3 mL) and water (0.20 mL). The reaction mixture was stirred at rt for 1 h. The solvent was removed under vacuum and co-evaporated with toluene twice. The residue was purified by chromatography to provide the title compound (68 mg, 75%) as a white solid.

$^1$H NMR (300 MHz, CD$_3$OD) δ 5.24 (d, J=5.4, 1), 4.16 (dd, J=3.3, 9.9, 1), 4.11–4.00 (m, 3), 3.75 (d, J=3.3, 1), 3.51 (dd, J=3.3, 10.2, 1), 3.40–3.32 (m, 1), 2.71 (dd, J=8.2, 10.6, 1), 2.23–2.05 (m, 3), 2.10 (s, 3), 1.98–1.76 (m, 3), 1.63–1.39 (m, 7), 0.94–0.87 (m, 6). MS (ESPOS): 455.3 [M+H]$^+$.

Example 38

Preparation of 4-(3,3-Difluoro-butyl)-pyrrolidine-2-carboxylic acid [2-methyl-1-(3,4,5-trihydroxy-6-methylsulfanyl-tetrahydro-pyran-2-yl)-propyl]-amide

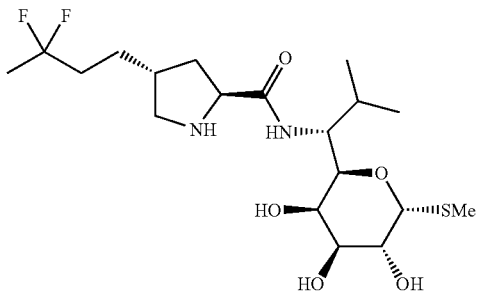

Ethyl triphenylphosphonium bromide (Aldrich) (2.92 g, 7.86 mmol, 3.9 equiv) and potassium-t-butoxide (0.61 g, 5.44 mmol, 2.7 equiv) were suspended in toluene (26 mL) under nitrogen with vigorous stirring. After 4 h, a solution of aldehyde 8a prepared by the first step in Method L (700 mg, 2.01 mmol, 1 equiv) in toluene (17 mL) was added dropwise. The reaction mixture was stirred at rt for 2 h and diluted with ethyl acetate (150 mL). The organic layer was washed with water (2×), brine, dried and concentrated. The residue was purified by chromatography to give a clear oil 4-but-2-enyl-pyrrolidine-1,2-dicarboxylic acid 1-tert-butyl ester 2-methyl ester (360 mg, 50%).

MS (ESPOS): 260.3 [M+H–Boc]$^+$.

To a solution of 4-but-2-enyl-pyrrolidine-1,2-dicarboxylic acid 1-tert-butyl ester 2-methyl ester (149 mg, 0.42 mmol, 1 equiv) in DMF (1.4 mL) and water (0.2 mL) were added palladium(II)chloride (7.4 mg, 0.042 mmol, 0.1 equiv) and copper(I) chloride (41.1 mg, 0.42 mmol, 1 equiv). The mixture was stirred at 50° C. overnight with oxygen bubbling into the mixture. The mixture was filtered and the filtrate was concentrated under high vacuum. The residue was diluted with ethyl acetate, washed with water (1×), brine (1×), dried and concentrated. The residue was purified by preparative TLC to give 4-(3-oxo-butyl)-pyrrolidine-1,2-dicarboxylic acid 1-tert-butyl ester 2-methyl ester (110 mg, 71%).

$^1$H NMR (300 MHz, CDCl$_3$) δ 7.35–7.28 (m, 5), 5.24–5.03 (m, 2), 4.43–4.25 (m, 1), 3.75–3.61 (m, 1), 3.01–2.87 (m, 1), 2.44–2.35 (m, 2), 2.28–2.15 (m, 1), 2.11 (s, 3), 2.09–1.98 (m, 1), 1.91–1.51 (m, 3), 1.43 (s, 3.4H), 1.31 (s, 5.6H). MS (ESPOS): 398.3 [M+Na]$^+$, 276.3 [M–Boc+H]$^+$.

To a solution of the 4-(3-oxo-butyl)-pyrrolidine-1,2-dicarboxylic acid 1-tert-butyl ester 2-methyl ester (110 mg, 0.29 mmol, 1 equiv) in dichloromethane (1.1 mL) at −78° C. was added DAST (0.16 mL, 1.17 mmol, 4 equiv). The reaction mixture was warmed to rt and stirred at rt for 3 h, followed by additional DAST (0.23 mL, 1.76 mmol, 6 equiv) at −78° C. The mixture was warmed to rt and stirred overnight. Then the mixture was diluted with dichloromethane, washed with sat. aqueous NaHCO$_3$ (1×), dried, evaporated. The residue was purified by chromatography to give 4-(3,3-Difluoro-butyl)-pyrrolidine-1,2-dicarboxylic acid 1-tert-butyl ester 2-methyl ester (92.7 mg, 80%).

MS (ESPOS): 420.3 [M+Na]$^+$.

To a mixture of 4-(3,3-difluoro-butyl)-pyrrolidine-1,2-dicarboxylic acid 1-tert-butyl ester 2-methyl ester (92.7 mg, 0.23 mmol, 1 equiv) in THF (1.2 mL) and water (0.4 mL) was added lithium hydroxide monohydrate (49 mg, 1.17 mmol, 5 equiv). The reaction mixture was stirred at rt overnight. the THF was removed under vacuum. The residue was diluted with water, washed with ether. The aqueous layer was taken up in ethyl acetate, partitioned with 10% citric acid. The organic layer was washed with water (1×), brine (1×), dried and concentrated to give a white solid, 4-(3,3-difluoro-butyl)-pyrrolidine-1,2-dicarboxylic acid 1-tert-butyl ester (59.7 mg, 83%).

$^1$H NMR (300 MHz, CDCl$_3$) δ 4.40–4.36 (m, 1), 3.59–3.52 (m, 1), 2.94–2.86 (m, 1), 2.55–2.48 (m, 1), 2.33–2.15 (m, 1), 1.92–1.73 (m, 3), 1.66–1.40 (m, 5), 1.47 (s, 9); MS (ESPOS): 330.2 [M+Na]$^+$, 208.2 [M−Boc+H]$^+$; MS (ESNEG): 306.1 [M−H]$^−$.

To a solution of compound 2b (R$^1$=Me, R$^2$=Me) (50 mg, 0.20 mmol, 1 equiv) in dry DMF (0.5 mL) at 0° C. was added triethylamine (88.3 up, 0.64 mmol, 3.2 equiv), followed by the addition of BSTFA (79.2 μL, 0.30 mmol, 1.5 equiv). The reaction mixture was stirred at 0° C. for 10 minutes, and then was stirred at rt for 50 minutes. The reaction mixture was added to the acid 4-(3,3-difluoro-butyl)-pyrrolidine-1,2-dicarboxylic acid 1-tert-butyl ester (59.7 mg, 0.20 mmol, 1 equiv) in a 25 mL round bottom flask, followed by the addition of HATU (93.3 mg, 0.25 mmol, 1.25 equiv). The reaction mixture was stirred at rt for 3 h. The reaction mixture was evaporated to dryness, taken up in ethyl acetate, washed with 10% citric acid, water, sat. NaHCO$_3$ and brine. The organic layer was dried over Na$_2$SO$_4$ and evaporated to give a syrup.

To a solution of the above syrup in DCM (9 mL) with methyl sulfide (0.20 mL) were added trifluoroacetic acid (3 mL) and water (0.20 mL). The reaction mixture was stirred at rt for 1 h. The solvent was removed under vacuum and co-evaporated with toluene twice. The residue was purified by chromatography to provide the title compound (63 mg, 72%) as a white solid.

$^1$H NMR (300 MHz, CD$_3$OD) δ 5.24 (d, J=5.7, 1), 4.22–4.13 (m, 2), 4.10–4.04 (m, 2), 3.76 (d, J=2.4, 1), 3.54–3.42 (m, 2), 2.84–2.76 (m, 1), 2.29–1.83 (m, 5), 2.10 (s, 3), 1.67–1.51 (m, 6), 0.95–0.87 (m, 6). MS (ESPOS): 441.3 [M+H]$^+$

Example 39

Preparation of 4-(3,3-Difluoro-pentyl)-pyrrolidine-2-carboxylic acid [2-methyl-1-(3,4,5-trihydroxy-6-methylsulfanyl-tetrahydro-pyran-2-yl)-propyl]-amide

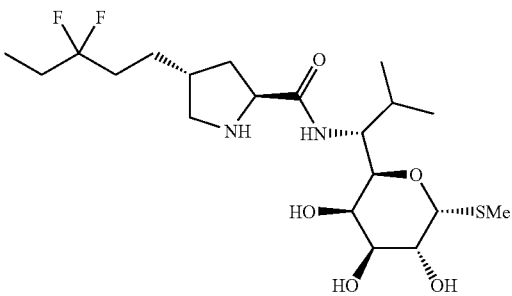

To a solution of compound 7c ($R^{9'}$=2-penteneyl) prepared using methods of Method K (323.7 mg, 0.87 mmol, 1 equiv) in DMF (2.8 mL) and water (0.4 mL) at 0° C. were added palladium (II) chloride (15.4 mg, 0.087 mmol, 0.1 equiv) and copper(I) chloride (85.9 mg, 0.87 mmol, 1 equiv). The mixture was stirred at 50° C. overnight with oxygen bubbling into the mixture. The mixture was filtered and the filtrate was concentrated under high vacuum. The residue was diluted with ethyl acetate, washed with water (1×), brine (1×), dried and concentrated. The residue was purified by preparative TLC to provide 4-(3-oxo-pentyl)-pyrrolidine-1,2-dicarboxylic acid 1-tert-butyl ester 2-methyl ester (242 mg, 72%).

MS (ESPOS): 412.3 [M+Na]$^+$, 290.3 [M−Boc+H]$^+$.

To 4-(3-oxo-pentyl)-pyrrolidine-1,2-dicarboxylic acid 1-tert-butyl ester 2-methyl ester (242 mg, 0.62 mmol, 1 equiv) in dichloromethane (2.3 mL) at −78° C. was added DAST (0.33 mL, 2.49 mmol, 4 equiv). The reaction mixture was warmed to rt and stirred at rt for 3 h, followed by an addition of more DAST (0.49 mL, 3.73 mmol, 6 equiv) at −78° C. The mixture was warmed to rt and stirred overnight. Then the mixture was diluted with dichloromethane, washed with sat. aqueous NaHCO$_3$ (1×), dried, evaporated. The residue was purified by chromatography to 4-(3,3-Difluoro-pentyl)-pyrrolidine-1,2-dicarboxylic acid 1-tert-butyl ester 2-methyl ester (117 mg, 46%).

$^1$H NMR (300 MHz, CDCl$_3$) δ 7.35–7.26 (m, 5), 5.25–5.04 (m, 2), 4.44–4.27 (m, 1), 3.79–3.64 (m, 1), 3.02–2.89 (m, 1), 2.32–2.17 (m, 1), 2.13–2.02 (m, 1), 1.91–1.68 (m, 5), 1.57–1.47 (m, 2), 1.44 (s, 3.5H), 1.31 (s, 5.5H), 0.97 (t, J=7.5, 3).

MS (ESPOS): 434.3 [M+Na]$^+$, 312.3 [M−Boc+H]$^+$.

To a solution of 4-(3,3-difluoro-pentyl)-pyrrolidine-1,2-dicarboxylic acid 1-tert-butyl ester 2-methyl ester (106 mg, 0.26 mmol, 1 equiv) in THF (2.4 mL) and water (0.8 mL) was added lithium hydroxide monohydrate (54 mg, 1.29 mmol, 5 equiv). The reaction mixture was stirred at rt overnight. THF was removed under vacuum. The residue was diluted with water (10 mL), washed with ether (20 mL). The aqueous layer was taken up in ethyl acetate (50 mL), partitioned with 10% citric acid (25 mL). The organic layer was washed with water (1×), brine (1×), dried and concentrated to give 4-(3,3-difluoro-pentyl)-pyrrolidine-1,2-dicarboxylic acid 1-tert-butyl ester as a clear oil (82.1 mg, 99%).

$^1$H NMR (300 MHz, CDCl$_3$) δ 4.40–4.36 (m, 1), 3.58–3.51 (m, 1), 2.94–2.86 (m, 1), 2.57–2.51 (m, 1), 2.30–2.15 (m, 1), 1.92–1.72 (m, 5), 1.62–1.53 (m, 2), 1.48 (s, 9), 0.99 (t, J=7.5, 3); MS (ESPOS): 344.3 [M+Na]$^+$, 222.3 [M−Boc+H]$^+$.

To a solution of compound 2b ($R^1$=Me, $R^2$=Me) (50 mg, 0.20 mmol, 1 equiv) in dry DMF (0.5 mL) at 0° C. was added triethylamine (88.3 μL, 0.64 mmol, 3.2 equiv), followed by the addition of BSTFA (79.2 μL, 0.30 mmol, 1.5 equiv). The reaction mixture was stirred at 0° C. for 10 minutes, and then was stirred at rt for 50 minutes. The reaction mixture was added to the acid 4-(3,3-difluoro-pentyl)-pyrrolidine-1,2-dicarboxylic acid 1-tert-butyl ester (76.6 mg, 0.24 mmol, 1.2 equiv) in a 25 mL round bottom flask, followed by the addition of HATU (111.9 mg, 0.29 mmol, 1.5 equiv). The reaction mixture was stirred at rt for 3 h. The reaction mixture was evaporated to dryness, taken up in ethyl acetate (60 mL), washed with 10% citric acid (30 mL), water (30 mL), sat. NaHCO$_3$ (30 mL) and brine. The organic layer was dried over Na$_2$SO$_4$ and evaporated to give a yellow oil.

To a solution of the above oil in DCM (9 mL) with methyl sulfide (0.20 mL) were added trifluoroacetic acid (3 mL) and water (0.20 mL). The reaction mixture was stirred at rt for 1 h. The solvent was removed under vacuum and co-evaporated with toluene twice. The residue was purified by chromatography to provide the title compound (72 mg, 80%) as a white solid.

$^1$H NMR (300 MHz, CD$_3$OD) δ 5.24 (d, J=5.7, 1), 4.20–4.04 (m, 4), 3.76 (d, J=2.7, 1), 3.51 (dd, J=3.4, 10.3, 1), 3.43 (dd, J=6.9, 10.8, 1), 2.77 (dd, J=8.4, 10.8, 1), 2.30–2.05 (m, 3), 2.10 (s, 3), 2.03–1.76 (m, 5), 1.64–1.54 (m, 2), 1.03–0.89 (m, 9); MS (ESPOS): 455.4 [M+H]$^+$.

Example 40

Preparation of 4-(3,3-Difluoro-pentyl)-1-(2-hydroxy-ethyl)-pyrrolidine-2-carboxylic acid [2-methyl-1-(3,4,5-trihydroxy-6-methylsulfanyl-tetrahydro-pyran-2-yl)-propyl]-amide

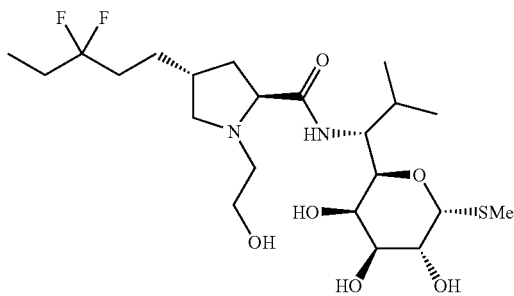

To a solution of the title compound of Example 39 (17.9 mg, 0.039 mmol) in MeOH (2 mL) at 0° C. was added ethylene oxide (0.4 mL). The reaction mixture was stirred at 4° C. overnight. The reaction mixture was concentrated and purified by chromatography to give the title compound as a white solid (8.2 mg, 42%).

$^1$H NMR (300 MHz, CD$_3$OD) δ 5.23 (d, J=5.7, 1), 4.13–4.05 (m, 3), 3.75 (d, J=3.6, 1), 3.72–3.57 (m, 2), 3.53 (dd, J=3.3, 10.2, 1), 3.41–3.36 (m, 1), 3.22 (dd, J=3.3, 10.8, 1), 2.88–2.78 (m, 1), 2.63–2.54 (m, 1), 2.18–1.99 (m, 4), 2.10 (s, 3), 1.93–1.75 (m, 5), 1.57–1.46 (m, 2), 1.01–0.90 (m, 9); MS (ESPOS): 499.6 [M+H]$^+$; MS (ESNEG): 497.5 [M–H]$^-$.

Example 41

Preparation of 4-(3,3-Difluoro-propyl)-piperidine-2-carboxylic acid [2-methyl-1-(3,4,5-trihydroxy-6-methylsulfanyl-tetrahydro-pyran-2-yl)-propyl]-amide

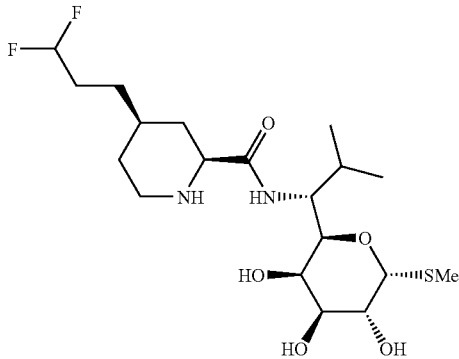

Compound 14c (R$^9$=3,3-difluoro-propyl) is prepared using the methods described in Method R.

To a dry flask were added compound 14a (1.4 g, 5.32 mmol, 1 equiv), triphenylphosphine (111.6 mg, 0.43 mmol, 0.08 equiv), copper (I) iodide (81 mg, 0.43 mmol, 0.08 equiv), palladium acetate (47.7 mg, 0.21 mmol, 0.04 equiv) and triethylamine (20 mL). The mixture was deaerated with nitrogen, followed by addition of propiolaldehyde diethyl acetyl (1.36 g, 10.65 mmol, 2 equiv). The mixture was stirred at rt for 3 hrs. The solvent was removed under vacuum to give a dark residue. The residue was purified by chromatography to give a yellow oil, compound 14b (R$^{9'}$=3,3-Diethoxy-prop-1-ynyl) (1.4 g, 100%).

$^1$H NMR (300 MHz, CDCl$_3$) δ 8.69 (dd, J=0.8, 5.0, 1), 8.15 (dd, J=0.8, 1.4, 1), 7.49 (dd, J=1.7, 5.0, 1), 5.48 (s, 1), 3.99 (s, 3), 3.82–3.73 (m, 2), 3.71–3.62 (m, 2), 1.26 (t, J=7.2, 6). MS (ESPOS): 264.5 [M+H]$^+$.

To a solution of 14b (R$^{9'}$=3,3-Diethoxy-prop-1-ynyl) (1.4 g, 5.32 mmol) in methanol (100 mL) was added 10% palladium on carbon (0.3 g). The mixture was purged and charged with hydrogen (1 atm) and shaken at rt overnight. The palladium was removed by filtration and the filtrate was concentrated to give 14c (R$^9$=3,3-diethoxy propyl) as an oil (1.39 g, 98%).

$^1$H NMR (300 MHz, CDCl$_3$) δ 8.60 (d, J=5.1, 1), 7.98 (d, J=0.9, 1), 7.31–7.28 (m, 1), 4.45 (t, J=5.4, 1), 3.98 (s, 3), 3.72–3.58 (m, 2), 3.52–3.39 (m, 2), 2.79–2.72 (m, 2), 1.99–1.90 (m, 2), 1.22–1.15 (m, 6).

To a mixture of 14c (R$^9$=3,3-diethoxy propyl) (0.68 g, 2.55 mmol) in acetic acid (8 mL) and water (2 mL) was added conc. hydrochloric acid (2 drops). The mixture was stirred at rt overnight and the solvent was removed under high vacuum. The residue was diluted with ethyl acetate, washed with sat. sodium bicarbonate (1×), brine (1×). The organic layer was dried and concentrated to give 4-(3-Oxo-propyl)-pyridine-2-carboxylic acid methyl ester as a yellow oil (0.27 g, 55%).

To a solution of aldehyde 4-(3-oxo-propyl)-pyridine-2-carboxylic acid methyl ester (0.27 g, 1.4 mmol, 1 equiv) in DCM (5 mL) at –78° C. was added DAST (0.91 g, 5.6 mmol, 4 equiv). The mixture was warmed to rt and stirred overnight. The mixture was diluted with dichloromethane (60 mL), washed with sat. aqueous NaHCO$_3$ (1×), dried, and evaporated. The residue was purified by prep. TLC (5% MeOH in DCM) to 4-(3,3-difluoro-propyl)-pyridine-2-carboxylic acid methyl ester (137 mg, 45%): $^1$H NMR (300 MHz, CDCl$_3$) δ 8.64 (d, J=5.1, 1), 8.00–7.98 (m, 1), 7.33–7.29 (m, 1), 5.85 (dddd, J=4.1, 4.1, 56.4, 56.4, 1), 3.99 (s, 3), 2.90–2.83 (m, 2), 2.28–2.09 (m, 2); MS (ESPOS): 216.4 [M+H]$^+$.

To a solution of 4-(3,3-difluoro-propyl)-pyridine-2-carboxylic acid methyl ester (130 mg, 0.6 mmol) (compound 14c R$^9$=3,3-difluoro-propyl in MeOH (3 mL) and water (3 mL) were added cons. HCl (0.25 mL, 3.0 mmol, 5 equiv) and platinum oxide (65 mg). The mixture was purged and charged with hydrogen (1 atm) and stirred overnight. The platinum oxide was removed by filtration and the filtrate was evaporated to give a clear syrup. To the above residue were added 2N NaOH (1.21 mL) and t-butyl alcohol (0.7 mL). The mixture was stirred at rt for 2 hrs. Then di-t-butyl dicarbonate (0.16 g, 0.73 mmol) was added. The mixture was stirred at rt overnight. The solvent was removed under vacuum. The residue was diluted with water (10 mL), was washed with ether (20 mL). The aqueous layer was acidified with 2N HCl to pH=2.0, and extracted with ethyl acetate (2×). The combined organic layers were dried and concentrated to give 4-(3,3-difluoro-propyl)-piperidine-1,2-dicarboxylic acid 1-tert-butyl ester as a clear syrup (163 mg, 88%)

$^1$H NMR (300 MHz, CDCl$_3$) δ 5.77 (dddd, J=4.2, 4.2, 56.6, 56.6, 1), 4.34 (t, J=6.4, 1), 3.62–3.50 (m, 1), 3.41–3.30 (m, 1), 2.05–1.96 (m, 1), 1.92–1.73 (m, 4), 1.70–1.60 (m, 1), 1.52–1.32 (m, 3), 1.43 (s, 9); MS (ESPOS): 330.5 [M+Na]$^+$; MS (ESNEG): 306.5 [M–H]$^-$.

To a mixture of the HCl salt of compound 2b (R$^1$=Me, R$^2$=Me) (140 mg, 0.49 mmol, 1 equiv) in dry DMF (1.2 mL) at 0° C. was added triethylamine (0.34 mL, 2.43 mmol, 5 equiv), followed by the addition of BSTFA (0.20 mL, 0.74 mmol, 1.5 equiv). The reaction mixture was stirred at 0° C. for 10 minutes, and then was stirred at rt for 50 minutes. To the reaction mixture were added the 4-(3,3-Difluoro-propyl)-piperidine-1,2-dicarboxylic acid 1-tert-butyl ester (153 mg, 0.50 mmol, 1.0 equiv) and HATU (235 mg, 0.62 mmol, 1.26 equiv). The reaction mixture was stirred at rt for 3 h. The reaction mixture was evaporated to dryness, taken up in ethyl acetate, washed with 10% citric acid (1×), water (1×), sat. NaHCO$_3$ (1×) and brine. The organic layer was dried over Na$_2$SO$_4$ and evaporated to give a pink syrup which was used without purification.

To a solution of the above syrup in DCM (15 mL) with methyl sulfide (0.33 mL) were added trifluoroacetic acid (5 mL) and water (0.33 mL). The reaction mixture was stirred at rt for 1 h. The solvent was removed under vacuum and co-evaporated with toluene twice. The residue was purified by chromatography to provide the title compound (lower isomer, 93 mg, 43%) as a white solid.

$^1$H NMR (300 MHz, CD$_3$OD) δ 5.90 (dddd, J=4.2, 4.2, 56.7, 56.7, 1), 5.24 (d, J=6, 1), 4.21 (dd, J=3.5, 9.8, 1), 4.11–4.04 (m, 2), 3.84–3.77 (m, 2), 3.51 (dd, J=3.2, 10.3, 1), 3.45–3.37 (m, 1), 3.07–2.98 (m, 1), 2.23–2.12 (m, 2), 2.11 (s, 3), 1.98–1.66 (m, 4), 1.52–1.26 (m, 4), 0.94–0.88 (m, 6). MS (ESPOS): 441.7 [M+H]$^+$.

Example 42

Preparation of 4-(4,4-Difluoro-butyl)-piperidine-2-carboxylic acid [2-methyl-1-(3,4,5-trihydroxy-6-methylsulfanyl-tetrahydro-pyran-2-yl)-propyl]-amide

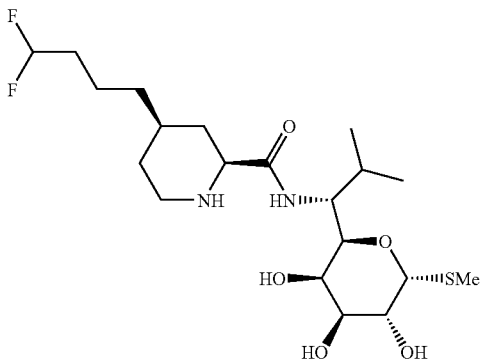

To a solution of methyl sulfoxide (0.58 mL, 8.16 mmol, 2.4 equiv) in dichloromethane (1.8 mL) at −72° C. was added a 2 M solution of oxalyl chloride in dichloromethane (2.04 mL, 4.08 mmol, 1.2 equiv) over a period of 1 minute. The mixture was stirred at −72° C. for 25 minutes, followed by the dropwise addition of a solution of the alcohol 14c ($R^9$=4-hydroxybutyl), prepared using the procedures in Method R, (0.71 g, 3.4 mmol, 1 equiv) in dichloromethane (4.8 mL) over a period of 2 minutes. The reaction mixture was stirred at −72° C. for 25 minutes, then warmed to −50° C. and stirred for an additional 2 h. Triethylamine (1.89 mL, 13.6 mmol, 4.0 equiv) was added and stirred at −50° C. for 25 minutes. The mixture was diluted with ethyl acetate, washed with water (1×), sat. aqueous NaHCO$_3$ (1×), brine (1×), dried, evaporated and co-evaporated with anhydrous toluene to give aldehyde 4-(4-oxo-butyl)-pyridine-2-carboxylic acid methyl ester as an oil (0.66 mg, 94%).

$^1$H NMR (300 MHz, CDCl$_3$) δ 9.78 (s, 1), 8.62 (d, J=5.1, 1), 7.97 (s, 1), 7.29 (d, J=5.1, 1), 3.99 (s, 3), 2.72 (t, J=7.8, 2), 2.50 (t, J=7.2, 2), 2.04–1.93 (m, 2); MS (ESPOS): 230.4 [M+Na]$^+$.

To a solution of 4-(4-oxo-butyl)-pyridine-2-carboxylic acid methyl ester (0.66 g, 3.19 mmol, 1 equiv) in DCM (12 mL) at −78° C. was added DAST (1.69 mL, 12.75 mmol, 4 equiv). The mixture was warmed to rt and stirred overnight. The mixture was diluted with dichloromethane, washed with sat. aqueous NaHCO$_3$ (1×), brine (1×), dried, evaporated. The residue was purified by chromatography to provide 4-(4,4-difluorobutyl)-pyridine-2-carboxylic acid methyl ester (0.54 g, 74%).

$^1$H NMR (300 MHz, CDCl$_3$) δ 8.62 (d, J=5.1, 1), 7.97–7.95 (m, 1), 7.29–7.26 (m, 1), 5.81 (dddd, J=3.9, 3.9, 56.6, 56.6, 1), 3.98 (s, 3), 2.74 (t, J=7.2, 2), 1.93–1.77 (m, 4). MS (ESPOS): 230.4 [M+H]$^+$, 252.4 [M+Na]$^+$.

To a mixture 4-(4,4-difluorobutyl)-pyridine-2-carboxylic acid methyl ester (0.54 g, 2.36 mmol, 1 equiv) in MeOH (8 mL) and water (8 mL) were added conc. HCl (0.59 mL, 7.07 mmol, 3 equiv) and platinum oxide (0.2 g). The mixture was purged and charged with hydrogen (1 atm) and stirred overnight. The platinum oxide was removed by filtration and the filtrate was evaporated to give a residue:

MS (ESPOS): 236.6 [M+H]$^+$.

To the residue prepared above were added 2N NaOH (4.72 mL) and t-butyl alcohol (2.5 mL). The mixture was stirred at rt for 2 hrs. Then di-t-butyl dicarbonate (0.77 g, 3.54 mmol) was added. The mixture was stirred at rt overnight. The solvent was removed under vacuum. The residue was diluted with water (10 mL), was washed with ether (20 mL). The aqueous layer was acidified with 2N HCl to pH=2.0, extracted with ethyl acetate (2×). The combined organic layers were dried and concentrated to give 4-(4,4-difluoro-butyl)-piperidine-1,2-dicarboxylic acid 1-tert-butyl ester (0.67 g, 89%).

$^1$H NMR (300 MHz, CDCl$_3$) δ 5.77 (dddd, J=4.3, 4.3, 56.8, 56.8, 1), 4.30 (t, J=6.8, 1), 3.58–3.47 (m, 1), 3.41–3.31 (m, 1), 2.05–1.96 (m, 1), 1.87–1.68 (m, 4), 1.65–1.56 (m, 1), 1.51–1.30 (m, 5), 1.43 (s, 9); MS (ESPOS): 344.5 [M+Na]$^+$.

To a mixture of the HCl salt of compound 2b ($R^1$=Me, $R^2$=Me) (153 mg, 0.53 mmol, 1 equiv) in dry DMF (1.3 mL) at 0° C. was added triethylamine (0.37 mL, 2.66 mmol, 5 equiv), followed by the addition of BSTFA (0.21 mL, 0.80 mmol, 1.5 equiv). The reaction mixture was stirred at 0° C. for 10 minutes, and then was stirred at rt for 50 minutes. To the reaction mixture were added the 4-(4,4-difluoro-butyl)-piperidine-1,2-dicarboxylic acid 1-tert-butyl ester (196 mg, 0.61 mmol, 1.15 equiv) and HATU (293 mg, 0.77 mmol, 1.45 equiv). The reaction mixture was stirred at rt for 3 h. The reaction mixture was evaporated to dryness, taken up in ethyl acetate, washed with 10% citric acid (1×), water (1×), sat. NaHCO$_3$ (1×) and brine. The organic layer was dried over Na$_2$SO$_4$ and evaporated to give the crude product as a syrup. The residue was dissolved in methanol (20 mL), then dried and washed Dowex™ resin (100 mg) was added. The mixture was stirred at rt for 30 minutes, and filtered. The filtrate was concentrated to give a clear syrup, which was purified by chromatography to give a clear syrup (0.25 g, 85%).

MS (ESPOS): 555.8 [M+H]$^+$.

To a solution of the above syrup in DCM (15 mL) with methyl sulfide (0.33 mL) were added trifluoroacetic acid (5 mL) and water (0.33 mL). The reaction mixture was stirred at rt for 1 h. The solvent was removed under vacuum and co-evaporated with toluene twice. The residue was purified by chromatography to provide the title compound (lower isomer, 70 mg, 34%) as a white solid.

$^1$H NMR (300 MHz, CD$_3$OD) δ 5.88 (dddd, J=4.4, 4.4, 57, 57, 1), 5.24 (d, J=5.4, 1), 4.20 (dd, J=3.2, 10.1, 1), 4.12–4.03 (m, 2), 3.90–3.80 (m, 2), 3.52 (dd, J=3.5, 10.3, 1), 3.46–3.39 (m, 1), 3.09–2.98 (m, 1), 2.25–2.12 (m, 2), 2.11 (s, 3), 1.98–1.67 (m, 4), 1.56–1.30 (m, 6), 0.95–0.87 (m, 6); MS (ESPOS): 455.7 [M+H]$^+$.

Example 43

Preparation of 4-(5,5-Difluoro-pentyl)-piperidine-2-carboxylic acid [2-methyl-1-(3,4,5-trihydroxy-6-methylsulfanyl-tetrahydro-pyran-2-yl)-propyl]-amide

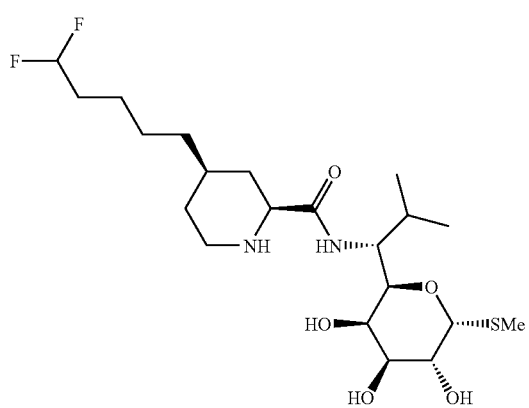

Method R is used to prepare compound 14c (R$^{9'}$=5-hydroxypentyl) (To a dry flask was added compound 14a (2 g, 7.60 mmol, 1 equiv), triphenylphosphine (159.4 mg, 0.61 mmol, 0.08 equiv), copper (I) iodide (115.8 mg, 0.61 mmol, 0.08 equiv), palladium acetate (68.2 mg, 0.30 mmol, 0.04 equiv) and triethylamine (28 mL). The mixture was deaerated with nitrogen, followed by addition of 4-pentyn-1-ol (1.28 g, 15.21 mmol, 2 equiv). The mixture was stirred at rt overnight. The solvent was removed under vacuum to give a dark residue. The residue was purified by chromatography to give 14b (R$^{9'}$=5-hydroxypent-1-yn-yl).

To a solution of 14b (R$^{9'}$=5-hydroxypent-1-yn-yl) in methanol (60 mL) was added 10% palladium on carbon (0.62 g). The mixture was purged and charged with hydrogen (1 atm) and stirred at rt overnight. The palladium was removed by filtration and the filtrate was concentrated to give a yellow oil 14c (R$^9$=5-hydroxypentyl) (1.34 g, 79%).

$^1$H NMR (300 MHz, CDCl$_3$) δ 8.62 (d, J=4.8, 1), 7.97 (s, 1), 7.31 (dd, J=1.6, 5, 1), 3.99 (s, 3), 3.63 (t, J=6.5, 2), 2.70 (t, J=7.7, 2), 1.74–1.53 (m, 4), 1.46–1.34 (m, 2).

To a solution of methyl sulfoxide (0.46 mL, 6.42 mmol, 2.6 equiv) in dichloromethane (1.4 mL) at −72° C. was added a 2 M solution of oxalyl chloride in dichloromethane (1.61 mL, 3.21 mmol, 1.3 equiv) over a period of 1 minute. The mixture was stirred at −72° C. for 25 minutes, followed by the dropwise addition of a solution of pyridine 14c (R$^9$=5-hydroxypentyl) (0.55 g, 2.47 mmol, 1 equiv) in dichloromethane (3.8 mL) over a period of 2 minutes. The reaction mixture was stirred at −72° C. for 25 minutes, then warmed to −50° C. and stirred for an additional 2 h. Triethylamine (1.48 mL, 10.7 mmol, 4.33 equiv) was added and stirred at −50° C. for 25 minutes. The mixture was diluted with ethyl acetate, washed with water (2×), sat. aqueous NaHCO$_3$ (1×), brine (1×), dried, evaporated and co-evaporated with anhydrous toluene to 4-(5-oxo-pentyl)-pyridine-2-carboxylic acid methyl ester (0.48 mg, 88%).

$^1$H NMR (300 MHz, CDCl$_3$) δ 9.75 (t, J=1.4, 1), 8.61 (d, J=5.1, 1), 7.97–7.95 (m, 1), 7.28 (dd, J=1.7, 5, 1), 3.99 (s, 3), 2.73–2.67 (m, 2), 2.50–2.44 (m, 2), 1.71–1.63 (m, 4).

To a solution of the to 4-(5-oxo-pentyl)-pyridine-2-carboxylic acid methyl ester oil (0.48 g, 2.19 mmol, 1 equiv) in DCM (8 mL) at −78° C. was added DAST (1.41 g, 8.74 mmol, 4 equiv). The mixture was warmed to rt and stirred overnight. The mixture was diluted with dichloromethane, washed with sat. aqueous NaHCO$_3$ (1×), dried, and evaporated. The residue was purified by chromatography to 4-(5,5-Difluoro-pentyl)-pyridine-2-carboxylic acid methyl ester (278 mg, 52%)

$^1$H NMR (300 MHz, CDCl$_3$) δ 8.61 (dd, J=0.6, 4.8, 1), 7.97–7.95 (m, 1), 7.28 (dd, J=1.5, 4.8, 1), 5.78 (dddd, J=4.3, 4.3, 57, 57, 1), 3.99 (s, 3), 2.70 (t, J=7.7, 2), 1.94–1.66 (m, 4), 1.55–1.43 (m, 2).

MS (ESPOS): 244.2 [M+H]$^+$

To a mixture of 4-(5,5-difluoro-pentyl)-pyridine-2-carboxylic acid methyl ester (278 mg, 1.14 mmol) in MeOH (5 mL) and water (5 mL) were added conc. HCl (0.286 mL, 3.43 mmol, 3 equiv) and platinum oxide (140 mg). The mixture was purged and charged with hydrogen (1 atm) and stirred overnight. The platinum oxide was removed by filtration and the filtrate was evaporated to 4-(5,5-difluoro-pentyl)-piperidine-2-carboxylic acid 2-methyl ester.

MS (ESPOS): 250.2 [M+H]$^+$.

To the above residue 4-(5,5-difluoro-pentyl)-piperidine-2-carboxylic acid-2-methyl ester were added 2N NaOH (2.3 mL) and t-butyl alcohol (1.2 mL). The mixture was stirred at rt for 2 hrs. Then di-t-butyl dicarbonate (0.37 g, 1.72 mmol) was added. The mixture was stirred at rt overnight. The solvent was removed under vacuum. The residue was diluted with water, was washed with ether. The aqueous layer was acidified with 2N HCl to pH=2.0, extracted with ethyl acetate (2×). The combined organic layers were dried and concentrated to 4-(5,5-Difluoro-pentyl)-piperidine-1,2-dicarboxylic acid 1-tert-butyl ester (310 mg, 81%).

$^1$H NMR (300 MHz, CD$_3$OD) δ 5.84 (dddd, J=4.5, 4.5, 57, 57, 1), 4.31 (t, J=6.3, 1), 3.65–3.56 (m, 1), 3.35–3.25 (m, 1), 2.03–1.63 (m, 5), 1.48–1.30 (m, 8), 1.43 (s, 9).

To a mixture of the HCl salt of compound 2b (R$^1$=Me, R$^2$=Me) (223.7 mg, 0.78 mmol, 1 equiv) in dry DMF (1.9 mL) at 0° C. was added triethylamine (0.54 mL, 3.89 mmol, 5 equiv), followed by the addition of BSTFA (0.31 mL, 1.17 mmol, 1.5 equiv). The reaction mixture was stirred at 0° C. for 10 minutes, and then was stirred at rt for 50 minutes. To the reaction mixture were added 4-(5,5-difluoro-pentyl)-piperidine-1,2-dicarboxylic acid 1-tert-butyl ester (272 mg, 0.81 mmol, 1.05 equiv) and HATU (391 mg, 1.03 mmol, 1.32 equiv). The reaction mixture was stirred at rt for 3 h. The reaction mixture was evaporated to dryness, taken up in ethyl acetate, washed with 10% citric acid (1×), water (1×), sat. NaHCO$_3$ (1×) and brine. The organic layer was dried over Na$_2$SO$_4$ and evaporated to give a residue. The residue was dissolved in methanol (30 mL), then dry and washed Dowex™ resin (150 mg) was added. The mixture was stirred at rt for 1 h and filtered. The filtrate was concentrated to give a clear syrup, which was purified by chromatography to give a clear syrup (0.26 g, 72%).

To a solution of the above syrup in DCM (15 mL) with methyl sulfide (0.33 mL) were added trifluoroacetic acid (5 mL) and water (0.33 mL). The reaction mixture was stirred at rt for 1 h. The solvent was removed under vacuum and co-evaporated with toluene twice. The residue was purified by chromatography to provide the title compound (lower isomer, 40 mg, 15%) as a white solid.

$^1$H NMR (300 MHz, CD$_3$OD) δ 5.86 (dddd, J=4.5, 4.5, 57, 57, 1), 5.24 (d, J=5.7, 1), 4.21 (dd, J=3.3, 9.9, 1), 4.11–4.04 (m, 2), 3.86–3.78 (m, 2), 3.51 (dd, J=3.5, 10.4, 1), 3.47–3.38 (m, 1), 3.07–2.97 (m, 1), 2.23–2.12 (m, 2), 2.11 (s, 3), 1.98–1.64 (m, 4), 1.50–1.27 (m, 8), 0.94–0.87 (m, 6); MS (ESPOS): 469.4 [M+H]$^+$.

Example 44

Preparation of 4-(5-Fluoro-pentyl)-piperidine-2-carboxylic acid [2-methyl-1-(3,4,5-trihydroxy-6-methylsulfanyl-tetrahydro-pyran-2-yl)-propyl]-amide

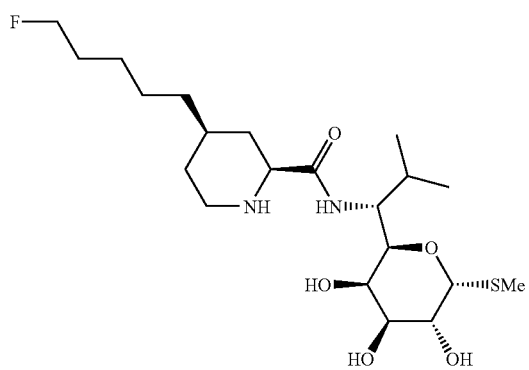

To a solution of compound 14c (R$^9$=5-hydroxypentyl) (0.66 g, 2.96 mmol, 1 equiv), prepared as described in Method R and in the synthesis of Example 47, in DCM (11 mL) at −78° C. was added DAST (1.91 g, 11.85 mmol, 4 equiv). The mixture was warmed to rt and stirred overnight.

The mixture was diluted with dichloromethane, washed with sat. aqueous NaHCO$_3$ (1×), dried, and evaporated. The residue was purified by chromatography to give 4-(5-fluoro-pentyl)-pyridine-2-carboxylic acid methyl ester (254 mg, 38%)

$^1$H NMR (300 MHz, CDCl$_3$) δ 8.62 (d, J=4.8, 1), 7.97 (d, J=1.2, 1), 7.30 (dd, J=1.7, 5, 1), 4.50 (t, J=5.9, 1), 4.34 (t, J=6, 1), 3.99 (s, 3), 2.70 (t, J=7.7, 2), 1.80–1.62 (m, 4), 1.50–1.41 (m, 2).

To a mixture of 4-(5-fluoro-pentyl)-pyridine-2-carboxylic acid methyl ester (254 mg, 1.13 mmol) in MeOH (5 mL) and water (5 mL) were added conc. HCl (0.28 mL, 3.39 mmol, 3 equiv) and platinum oxide (130 mg). The mixture was purged and charged with hydrogen (1 atm) and stirred overnight. The platinum oxide was removed by filtration and the filtrate was evaporated to give 4-(5-fluoro-pentyl)-piperidine-2-carboxylic acid 2-methyl ester.

MS (ESPOS): 232.4 [M+H]$^+$.

To 4-(5-fluoro-pentyl)-piperidine-2-carboxylic acid 2-methyl ester was added 2N NaOH (2.43 mL) and t-butyl alcohol (1.3 mL). The mixture was stirred at rt for 2 hrs. Then di-t-butyl dicarbonate (0.40 g, 1.82 mmol) was added. The mixture was stirred at rt overnight. The solvent was removed under vacuum. The residue was diluted with water, was washed with ether. The aqueous layer was acidified with 2N HCl to pH=2.0, extracted with ethyl acetate (2×). The combined organic layers were dried and concentrated to give 4-(5-fluoro-pentyl)-piperidine-1,2-dicarboxylic acid 1-tert-butyl ester as a syrup (254 mg, 71%).

$^1$H NMR (300 MHz, CDCl$_3$) δ 4.52–4.06 (m, 3), 3.55–3.30 (m, 2), 2.03–1.94 (m, 1), 1.81–1.54 (m, 4), 1.45–1.20 (m, 8), 1.43 (s, 9). MS (ESPOS): 218.3 [M+Na–Boc]$^+$

To a mixture of the HCl salt of compound 2b (R$^1$=Me, R$^2$=Me) (213.8 mg, 0.74 mmol, 1 equiv) in dry DMF (1.8 mL) at 0° C. was added triethylamine (0.52 mL, 3.72 mmol, 5 equiv), followed by the addition of BSTFA (0.30 mL, 1.12 mmol, 1.5 equiv). The reaction mixture was stirred at 0° C. for 10 minutes, and then was stirred at rt for 50 minutes. To the reaction mixture were added the 4-(5-fluoro-pentyl)-piperidine-1,2-dicarboxylic acid 1-tert-butyl ester as a syrup (244 mg, 0.77 mmol, 1.04 equiv) and HATU (370 mg, 0.97 mmol, 1.31 equiv). The reaction mixture was stirred at rt for 3 h. The reaction mixture was evaporated to dryness, taken up in ethyl acetate, washed with 10% citric acid (1×), water (1×), sat. NaHCO$_3$ (1×) and brine. The organic layer was dried over Na$_2$SO$_4$ and evaporated to give a residue. The residue was dissolved in methanol (30 mL), then dry and washed Dowex™ resin (140 mg) was added. The mixture was stirred at rt for 1 h and filtered. The filtrate was concentrated to give a clear syrup, which was purified by chromatography to give a clear syrup (212 mg, 52%).

To a solution of the above syrup in DCM (15 mL) with methyl sulfide (0.33 mL) were added trifluoroacetic acid (5 mL) and water (0.33 mL). The reaction mixture was stirred at rt for 1 h. The solvent was removed under vacuum and co-evaporated with toluene twice. The residue was purified by chromatography to provide the title compound (lower isomer, 40 mg, 17%) as a white solid.

$^1$H NMR (300 MHz, CD$_3$OD) δ 5.24 (d, J=5.7, 1), 4.49 (t, J=5.9, 1), 4.33 (t, J=6, 1), 4.20 (dd, J=3.5, 10.1, 1), 4.11–4.04 (m, 2), 3.83–3.77 (m, 2), 3.51 (dd, J=3.3, 10.2, 1), 3.44–3.36 (m, 1), 3.06–2.94 (m, 1), 2.23–2.13 (m, 2), 2.11 (s, 3), 1.98–1.88 (m, 1), 1.77–1.59 (m, 3), 1.45–1.27 (m, 8), 0.94–0.87 (m, 6).

MS (ESPOS): 451.4 [M+H]$^+$

Example 45

Preparation of 4-(4-Fluoro-butyl)-piperidine-2-carboxylic acid [2-methyl-1-(3,4,5-trihydroxy-6-methylsulfanyl-tetrahydro-pyran-2-yl)-propyl]-amide

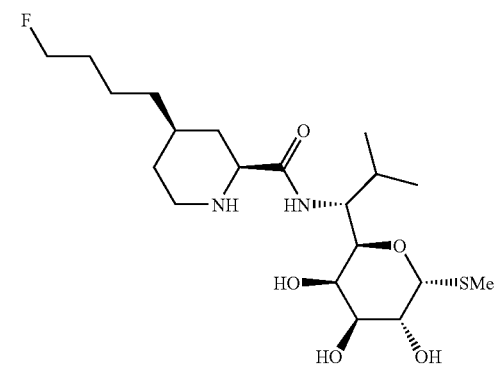

To a solution of compound 14c (R$^9$=4-hydroxybutyl) (0.76 g, 3.62 mmol, 1 equiv), prepared as described in Method R and in the synthesis of Example 47, in DCM (14 mL) at −78° C. was added DAST (1.9 mL, 14.47 mmol, 4 equiv). The mixture was warmed to rt and stirred overnight. The mixture was diluted with dichloromethane, washed with sat. aqueous NaHCO$_3$ (1×), brine (1×), dried, evaporated. The residue was purified by chromatography to provide 4-(4-Fluoro-butyl)-pyridine-2-carboxylic acid methyl ester as a yellow oil (0.24 g, 31%).

$^1$H NMR (300 MHz, CDCl$_3$) δ 8.57 (d, J=4.8, 1), 7.92 (d, J=1.2, 1), 7.27–7.23 (m, 1), 4.49 (t, J=5.6, 1), 4.33 (t, J=5.6, 1), 3.94 (s, 3), 2.69 (t, J=7.5, 2), 1.79–1.59 (m, 4).

To a mixture of 4-(4-fluoro-butyl)-pyridine-2-carboxylic acid methyl ester (0.24 g) in THF (3 mL) and water (1 mL) was added lithium hydroxide monohydrate (71.3 mg, 1.7 mmol, 1.5 equiv). The mixture was stirred at rt overnight and diluted with methanol (20 mL). Then H$^+$ resin was added and the mixture was shaken for 10 minutes. The resin was washed with methanol (1×), 1:1 acetonitrile/water (1×), and acetonitrile (1×). The product was eluted with 5% TEA in methanol (4×) and acetonitrile (1×). The combined organic solvents were evaporated and co-evaporated with toluene to provide 4-(4-Fluoro-butyl)-pyridine-2-carboxylic acid (0.22 g, 65%).

$^1$H NMR (300 MHz, CD$_3$OD) δ 8.46 (d, J=4.8, 1), 7.95 (s, 1), 7.39–7.35 (m, 1), 4.52 (t, J=5.6, 1), 4.36 (t, J=5.9, 1), 3.22 (q, J=7.3, 2.5H, TEA), 2.77 (t, J=7.5, 2), 1.84–1.62 (m, 4), 1.28 (t, J=7.2, 3.8H, TEA).

To a solution of 4-(4-fluoro-butyl)-pyridine-2-carboxylic acid (0.22 g, 0.73 mmol, 1 equiv) in dry acetonitrile (4 mL) at 0° C. was added triethylamine (74 mg, 0.73 mmol, 1 equiv), followed by the addition of isobutyl chloroformate (100 mg, 0.73 mmol, 1 equiv). The reaction mixture was stirred at 0° C. for 15 minutes, and then was stirred at 4° C. for 2 h. To the reaction mixture was added a solution of the HCl salt of compound 2b (R$^1$=Me, R$^2$=Me) (263 mg, 0.91 mmol, 1.25 equiv) and triethylamine (93 mg, 0.91 mmol, 1.25 equiv) in a 1:1 acetone/water (4 mL). The reaction mixture was stirred at 4° C. overnight. The reaction mixture was evaporated to dryness, taken up in DCM, washed with sat. NaHCO$_3$ (1×). The organic layer was dried over Na$_2$SO$_4$ and evaporated. The residue was purified by chromatography to give a clear solid (110 mg, 35%).

To a solution of the above solid (110 mg, 0.25 mmol, 1 equiv) in MeOH (6 mL) and water (4 mL) were added conc. HCl (20.2 µL, 0.24 mmol, 0.95 equiv) and platinum oxide (220 mg). The mixture was purged and charged with hydrogen (65 psi) and shaken overnight. The platinum oxide was removed by filtration and the filtrate was evaporated to give a residue, which was purified by chromatography to provide the title compound (lower isomer, 33 mg, 30%) as a white solid.

$^1$H NMR (300 MHz, CD$_3$OD) δ 5.25 (d, J=5.4, 1), 4.51 (t, J=6, 1), 4.35 (t, J=5.9, 1), 4.21 (dd, J=3.3, 10.2, 1), 4.10–4.04 (m, 2), 3.93–3.80 (m, 2), 3.52 (dd, J=3.3, 10.2, 1), 3.46–3.38 (m, 1), 3.11–2.98 (m, 1), 2.26–2.13 (m, 2), 2.11 (s, 3), 2.00–1.92 (m, 1), 1.80–1.60 (m, 3), 1.54–1.27 (m, 6), 0.95–0.87 (m, 6).

MS (ESPOS): 437.4 [M+H]$^+$

Example 46

Preparation of 4-(3-Ethyl-3-hydroxy-pentyl)-piperidine-2-carboxylic acid [2-methyl-1-(3,4,5-trihydroxy-6-methylsulfanyl-tetrahydro-pyran-2-yl)-propyl]-amide

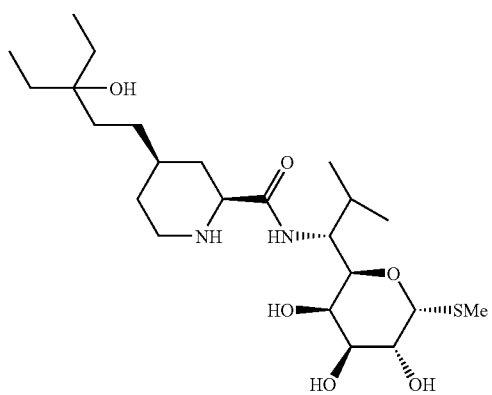

To a dry flask was added compound 13b (R$^1$=Me, R$^2$=Me, and R$^3$=H) made using Method Q (130 mg, 0.27 mmol, 1 equiv), triphenylphosphine (45.3 mg, 0.17 mmol, 0.64 equiv), copper (I) iodide (32.9 mg, 0.17 mmol, 0.64 equiv), palladium acetate (19.4 mg, 0.086 mmol, 0.32 equiv) and triethylamine (1.5 mL). The mixture was deaerated with nitrogen, followed by addition of 3-ethyl-1-pentyn-3-ol (174 µL, 1.35 mmol, 5 equiv). The mixture was stirred at 50° C. overnight. The solvent was removed under vacuum to give a dark residue. The residue was purified by chromatography to give 13c (R$^1$=Me, R$^2$=Me, R$^3$=H, R$^9$=3-Ethyl-3-hydroxypent-1-ynyl).

MS (ESPOS): 467.7 [M+H]$^+$; MS (ESNEG): 465.5 [M–H]$^-$.

To a mixture of the above syrup in MeOH (12 mL) and water (8 mL) were added platinum oxide (300 mg) and conc. HCl (26 µL). The mixture was purged and charged with hydrogen (65 psi) and shaken overnight. The platinum oxide was removed by filtration and the filtrate was evaporated. The residue was purified by chromatography to give the title compound as a white solid (19 mg, 15%).

$^1$H NMR (300 MHz, CD$_3$OD) δ 5.24 (d, J=5.7, 1), 4.17 (dd, J=3.1, 10.0, 1), 4.10–4.02 (m, 2), 3.80 (d, J=3, 1), 3.53–3.48 (m, 1), 3.42–3.35 (m, 1), 3.23–3.15 (m, 1), 2.75–2.64 (m, 1), 2.22–2.11 (m, 1), 2.10 (s, 3), 2.04–1.97 (m, 1), 1.80–1.72 (m, 1), 1.50–1.40 (m, 6), 1.31–1.06 (m, 5), 0.94–0.80 (m, 12); MS (ESPOS): 477.8 [M+H]$^+$; MS (ES-NEG): 475.6 [M–H]$^-$.

Example 47

Preparation of 4-Butoxy-piperidine-2-carboxylic acid [2-methyl-1-(3,4,5-trihydroxy-6-methylsulfanyl-tetrahydro-pyran-2-yl)-propyl]-amide

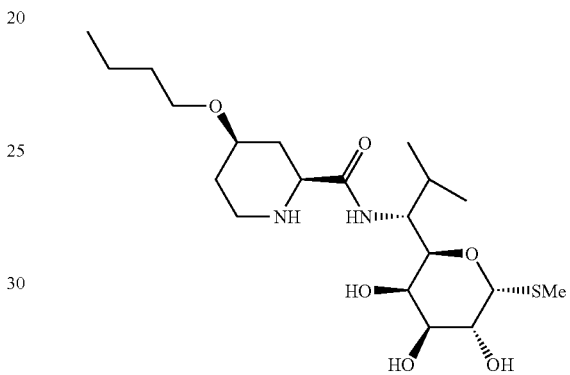

To trimethylsilyl cyanide (5.2 g, 52 mmol), 4-benzyloxypyridine 1-oxide (8.8 g, 44 mmol) in DCM (20 mL) was added, followed by dimethylcarbamoyl chloride (5.6 g, 52 mmol) in DCM (10 mL), dropwise, stirred at room temperature overnight. Sodium bicarbonate (100 mL, 10%) was added, stirred for 10 minutes and extracted twice with DCM (50 mL). The combined organic layer was dried over magnesium sulfate, solvent was removed to obtain the product, compound 10a (R$^9$=Benzyloxy) (10.5 g, 100%).

$^1$H NMR (300 MHz, CDCl$_3$) δ 8.34 (d, J=5.7, 1), 7.24 (m, 5), 7.11 (t, J=2.4, 1), 6.90 (dd, J=5.7, 2.4, 1), MS (ESPOS): 211[M+H]$^+$.

Compound 10a (R$^9$=Benzyloxy) (5 g, 23 mmol) was dissolved in HCl (6N, 70 mL) and refluxed overnight. The crude product 4-hydroxypyridine-2-carboxylic acid, compound 10b (R$^9$=hydroxy) obtained on removal of HCl was crystallized from acetonitrile (2.6 g, 80%).

$^1$H NMR (300 MHz, CD$_3$OD) δ 8.55 (d, J=6.6, 1), 7.78 (d, J=3.0, 1), 6.90 (dd, J=2.7, 6.9, 1), MS (ESNEG): 138 [M–H]$^-$.

The synthesis of title compound was completed using the synthetic sequence found in Method S starting from 4-hydroxypyridine-2-carboxylic acid, as prepared above.

$^1$H NMR (300 MHz, CD$_3$OD) δ 5.25 (d, J=5.4, 1), 4.22 (dd, J=10.2; 3.3, 1), 4.08 (m, 2), 3.81 (d, J=3.0, 1), 3.70 (m, 1), 3.54 (m, 4), 3.43 (m, 2), 2.90 (m, 1), 2.41 (m, 1), 2.19 (m, 1), 2.10 (s, 3) 1.45 (m, 6), 0.92 (m, 9); MS (ESPOS): 435 [M+H]$^+$.

Example 48

Preparation of 4-Pentyloxy-piperidine-2-carboxylic acid [2-methyl-1-(3,4,5-trihydroxy-6-methylsulfanyl-tetrahydro-pyran-2-yl)-propyl]-amide

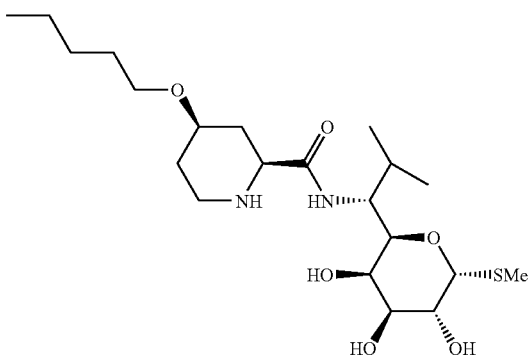

The title compound was made using the synthetic sequence found in Method S starting from 4-hydroxypyridine-2-carboxylic acid 10b ($R^9$=hydroxy) substituting n-pentyl bromide as the alkylating agent.

Compound 15a ($R^9$=pentoxy): $^1$H NMR (300 MHz, CD$_3$OD) δ 8.38 (d, J=5.1, 1), 7.64 (s, 1), 7.10 (d, J=3.3, 1), 4.18 (t, J=6.6, 2), 1.85 (m, 2), 1.49 (m, 4), 0.96 (t, J=7.2, 3). MS (ESNEG): 208 [M–H]$^-$.

Compound 15b ($R^1$=Me, $R^2$=Me, $R^9$=pentoxy): $^1$H NMR (300 MHz, CD$_3$OD) δ 8.41 (d, J=5.7, 1), 7.61 (d, J=2.4, 1), 7.07 (dd, J=2.4, 5.4, 1), 5.27 (d, J=5.4, 1), 4.05–4.31 (m, 5), 3.85 (d, J=3.0, 1), 3.57 (dd, J=3.3, 7.2, 1), 2.11 (m, 4), 1.81 (m, 2), 1.49 (m, 4), 1.00 (m, 9). MS (ESPOS): 443 [M+H]$^+$.

Title compound (20 mg, 10%): $^1$H NMR (300 MHz, CD$_3$OD) δ 5.24 (d, J=5.7, 1), 4.22 (dd, J=9.9; 3.3, 1), 4.10 (m, 2), 3.76 (m, 3), 3.51 (m, 3), 3.39 (m, 1), 3.02 (m, 2), 2.43 (m, 1), 2.15 (m, 1), 2.10 (s, 3) 1.95 (m, 2), 1.69 (m, 2), 1.53 (m, 2), 1.34 (m, 2), 0.93 (m, 9); MS (ESPOS): 449 [M+H]$^+$.

Example 49

Preparation of 4-(4-Fluoro-butoxy)-piperidine-2-carboxylic acid [2-methyl-1-(3,4,5-trihydroxy-6-methylsulfanyl-tetrahydro-pyran-2-yl)-propyl]-amide

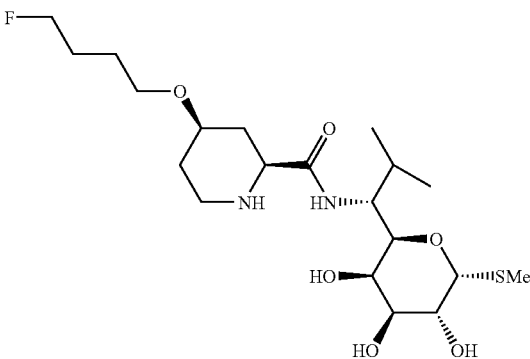

The title compound was made using the synthetic sequence found in Method S starting from 4-hydroxypyridine-2-carboxylic acid 10b ($R^9$=hydroxy) substituting 1-bromo-4-fluoro-butane as the alkylating agent.

$^1$H NMR (300 MHz, CD$_3$OD) δ 5.25 (d, J=5.7, 1), 4.53 (t, J=5.7, 1), 4.37 (t, J=5.7, 1), 4.21 (dd, J=3.3, 6.6, 1), 4.07 (m, 2), 3.80 (d, J=3.3, 2), 3.60 (m, 5), 2.88 (m, 1), 2.38 (m, 1), 2.18 (m, 1), 2.10 (s, 3) 1.33–1.83 (m, 8), 0.92 (m, 6); MS (ESPOS): 453 [M+H]$^+$.

Example 50

Preparation of 4-Butyl-pyrrolidine-2-carboxylic acid [2-methyl-1-(3,4,5-trihydroxy-6-methylsulfanyl-tetrahydro-pyran-2-yl)-allyl]-amide

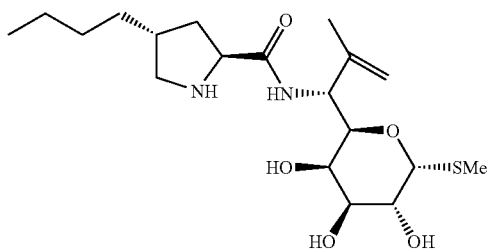

To a solution of Boc 7-Methylene MTL (P=Boc, $R^1$=Me, $R^{2'}$=CH$_2$) prepared from compound 2a (P=Boc, $R^1$=Me) by Method D (391 mg, 1.1 mmol) in a solution of dichloroethane (10 mL) and dimethylsulfide (0.4 mL, 2.5 mmol) was added, TFA (5 mL) containing water (0.4 mL) and the reaction mixture stirred at rt for 45 min. The solvent was removed and the residue evaporated twice from DCE to obtain the crude product. The product was obtained as an HCl salt by precipitation from ethyl acetate (4 mL) at 0° C. by addition of 2M HCl in ether, and dried under vacuum (351 mg g, 86%). The white solid product was used in the next reaction without additional purification.

MS (ESPOS): 350 [M+H]$^+$.

Triethylamine (0.68 mL, 4.9 mmol, 4.0 equiv), followed by BSTFA (0.58 mL, 2.20 mmol, 1.8 equiv), were added to a stirred suspension of compound prepared above (351 mg, 1.22 mmol, 1 equiv) in anhydrous DMF (5 mL) at 0° C. and under nitrogen. The resulting mixture was stirred at 0° C. for 10 min, and then at rt for 50 min. The resulting solution was cooled to 0° C. and a solution of compound 7d ($R^9$=n-butyl) prepared by Method K (400 mg, 1.47 mmol, 1.2 equiv) in anhydrous DMF (5 mL) was added, followed by solid HATU (741 mg, 1.95 mmol, 1.6 equiv). The reaction mixture was allowed to warm to rt and after 2 h the reaction solution was evaporated to dryness under vacuum. The residual oil obtained was diluted with EtOAc (200 mL), washed sequentially with 10% citric acid, 1:1 saturated aqueous NaHCO$_3$, water, and brine dried over Na$_2$SO$_4$, and evaporated to dryness.

To a solution of 50 mg crude coupling product in 1,2-dichloroethane (6 mL), was added dimethylsulfide (200 μL), followed by TFA (11.5 mL), and water (768 μL). The resulting mixture was stirred at rt for 1 h, evaporated to a minimal volume, diluted with DCE (3×10 mL), and evaporated to dryness. The residue was purified by column chromatography 8% to 12% 0.25M methanolic ammonia in dichloromethane to provide the title compound (10.0 mg, 25%).

$^1$H NMR (300 MHz, CD$_3$OD) δ 5.22 (d, J=5.8, 1), 5.00 (s, 1), 4.95 (s, 1), 4.58 (d, J=8.8, 1) 4.19 (d, J=8.8, 1), 4.09

(dd, J=5.8, 10.1, 1) 3.85–3.77 (m, 2), 3.57–3.52 (m, 1), 3.26–3.29 (m, 1), 2.59–2.53 (m, 1), 2.10–1.98 (m, 4), 1.80 (s, 3), 1.36–1.51–1.11 (m, 7), 0.91(t, J=6.9, 3); MS (ESPOS): 403.6 [M+H]+.

Example 51

Preparation of 1,4-Diethyl-piperidine-2-carboxylic acid [2-methyl-1-(3,4,5-trihydroxy-6-methylsulfanyl-tetrahydro-pyran-2-yl)-propyl]-amide

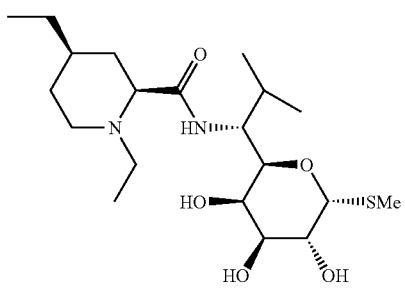

To the product of Example 1 (30 mg, 0.07 mmol) in DMF (1 mL), DIEA (43 mg, 0.35 mmol) was added at room temperature and stirred overnight. Then removed the solvent and the resulting product was purified by column chromatography using 20% MeOH in DCM to obtain the title compound (20 mg, 66%) as a white powder.

$^1$H NMR (300 MHz, CD$_3$OD) δ 5.24 (d, J=6.0, 1), 4.26 (dd, J=3.6, 9.6, 1), 3.79 (d, J=3.0, 1), 3.55 (dd, J=3.3, 10.2, 1) 2.85 (m, 2), 2.13 (m, 4), 1.37 (m, 12), 0.94 (m, 9); MS (ESPOS): 420 [M+H]+.

Example 52

Preparation of 4-(3-Fluoro-propoxy)-piperidine-2-carboxylic acid [2-methyl-1-(3,4,5-trihydroxy-6-methylsulfanyl-tetrahydro-pyran-2-yl)-propyl]-amide

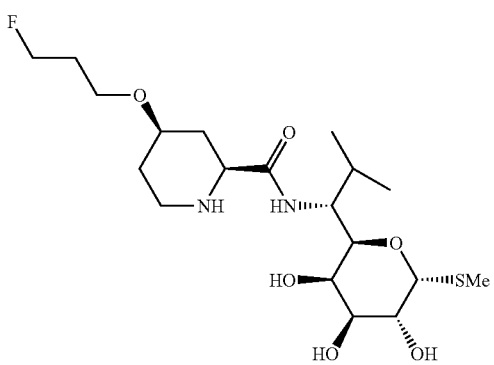

The title compound was made using the synthetic sequence found in Method S starting from 4-hydroxypyridine-2-carboxylic acid substituting 1-bromo-3-fluoro-propane as the alkylating agent.

Compound 15a (R$^9$=3-fluoropropoxy): $^1$H NMR (300 MHz, CD$_3$OD) δ 8.41 (d, J=5.1, 1), 7.65 (d, J=2.1, 1), 7.14 (dd, J=2.1, 5.7, 1), 4.59 (m, 2), 4.24 (t, J=6.0, 2), 1.91 (m, 2). MS (ESNEG): 212 [M–H]−.

Compound 15b (R$^1$=Me, R$^2$=Me, R$^9$=3-fluoropropoxy): $^1$H NMR (300 MHz, CD$_3$OD) δ 8.44 (d, J=5.7, 1), 7.65 (d, J=2.4, 1), 7.12 (dd, J=2.4, 5.7, 1), 5.48 (d, J=5.7, 1), 4.87 (m, 2), 4.30 (m, 2), 4.12 (dd, J=3.0, 10.2, 1), 3.85 (d, J=3.3, 1), 3.56 (dd, J=9.9, 3.3, 1), 2.26 (m, 1), 2.11 (s, 3), 1.37 (m, 4), 1.00 (t, J=5.1, 6). MS (ESPOS): 443 [M+H]+.

Title compound (60 mg, 31%): $^1$H NMR (300 MHz, CD$_3$OD) δ 5.25 (d, J=5.7, 1), 4.50 (m, 2), 4.21 (dd, J=3.3, 9.9, 1), 4.06 (m, 2), 3.80 (d, J=2.7, 1), 3.66 (m, 3), 3.59 (m, 1), 3.33 (m, 1), 2.87 (m, 1), 2.41 (m, 1), 2.18 (m, 1), 2.10 (s, 3) 1.91 (m, 4), 1.51 (m, 2), 0.92 (m, 6); MS (ESPOS): 439 [M+H]+.

Example 53

Preparation of 4-(3,3,3-Trifluoro-propoxy)-piperidine-2-carboxylic acid [2-methyl-1-(3,4,5-trihydroxy-6-methylsulfanyl-tetrahydro-pyran-2-yl)-propyl]-amide

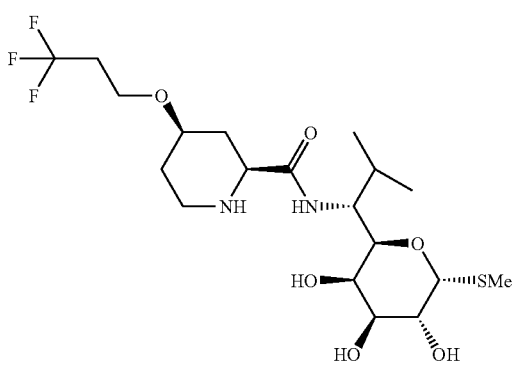

The title compound was made using the synthetic sequence found in general Method S starting from 4-hydroxypyridine-2-carboxylic acid substituting 3-bromo-1,1,1-trifluoro-propane as the alkylating agent.

Compound 15a (R$^9$=3,3,3-trifluoropropoxy): $^1$H NMR (300 MHz, CD$_3$OD) δ 8.67 (m, 1), 7.92 (s, 1), 7.43 (m, 1), 4.65 (m, 2), 3.01 (m, 2). MS (ESNEG): 234[M–H]−.

Compound 15b (R$^1$=Me, R$^2$=Me, R$^9$=3,3,3-trifluoropropoxy): $^1$H NMR (300 MHz, CD$_3$OD) δ 8.46 (d, J=6.0, 1), 7.65 (d, J=2.7, 1), 7.13 (dd, J=2.7, 6.0, 1), 5.27 (d, J=5.7, 1), 4.39 (t, J=6.0, 2), 4.30 (m, 2), 4.11 (m, 1), 3.85 (d, J=3.0, 1), 3.57 (dd, J=3.0, 10.2, 1), 2.88 (m, 2), 2.25 (m, 1), 2.11 (s, 3), 1.00 (t, J=6.9, 6). MS (METHOD ESPOS): 469 [M+H]+.

Title compound (10 mg, 10%): $^1$H NMR (300 MHz, CD$_3$OD) δ 5.24 (d, J=5.7, 1), 4.18 (dd, J=3.0, 9.9, 1), 4.15 (m, 2), 3.80 (d, J=3.6, 1), 3.74 (m, 2), 3.52 (dd, J=3.3, 10.2, 2), 3.38 (m, 2), 3.18 (m, 1), 2.66 (m, 1), 2.66 (m, 1), 2.44 (m, 2), 2.22 (m, 1), 2.10 (s, 3) 1.34 (m, 2), 0.91 (d, J=7.2, 6); MS (ESPOS): 475 [M+H]+.

Example 54

Preparation of 4-Isobutyl-piperidine-2-carboxylic acid [2-methyl-1-(3,4,5-trihydroxy-6-methylsulfanyl-tetrahydro-pyran-2-yl)-propyl]-amide

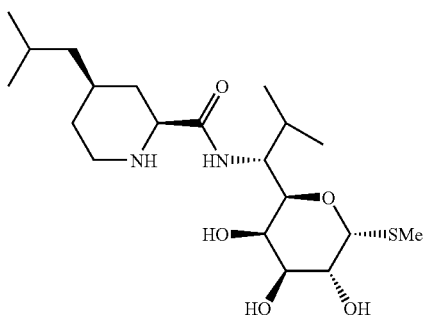

4-Isobutyl-2-cyanopyridine is prepared as follows. To isobutyltriphenylphosphonium iodide (Aldrich) (8 g, 18.5 mmol) in THF (20 mL) at 0° C., potassium-tert-butoxide (1.8 g, 16 mmol) was added, stirred at room temperature for 1 hr. pyridine-4-carboxlaldehyde (1 g, 9.3 mmol) was added, stirred at room temperature for overnight. Reaction mixture was then poured to water (100 mL) and extracted with EtOAc (100 mL). The product obtained on removal of solvent was purified by column chromatography using 40% EtOAc in hexane as eluent (1.05 g, 84%). To the resulting product (4.2 g, 31.5 mmol), 10% Pd/C (0.4 g) was added and hydrogenated at 1 atm pressure overnight. Removal of solvent and purification on column chromatography using 30% EtOAc in hexanes resulted in 4-isobutylpyridine (3.8 g, 90%).

The intermediate, 4-isobutylpyridine-2-carboxylic acid, compound 10b, ($R^9$=isobutyl) was made by employing Method P. To 4-isobutylpyridine (2 g, 14.8 mmol) in acetic acid (20 mL), hydrogen peroxide (3.35 g, 30%, 30 mmol) was added and refluxed overnight. After removing the solvent, the residue was dissolved in DCM dried over magnesium sulfate and taken as such for the next step. To the compound in DCM (10 mL) trimethylsilyl cyanide (1.73 g, 17.4 mmol) and dimethylcarbonyl chloride (1.89 g, 17.4 mmol) was added and stirred at room temperature for 24 hours. Aqueous potassium bicarbonate (100 mL, 10%) was added and extracted twice with DCM (50 mL each). The crude product obtained on removal of solvent was taken in HCl (6N, 100 mL) and refluxed for 24 hours. Removal of acid and purification of crude product by column chromatography using 30% MeOH in DCM resulted in acid 10b ($R^9$=isobutyl) (1.5 g, 100%).

$^1$H NMR (300 MHz, $CD_3OD$) δ 8.78 (d, J=5.7, 1), 8.44 (s, 1), 8.13 (d, J=5.7, 1), 2.92 (d, J=7.5, 1), 2.15 (m, 1), 0.98 (d, J=6.6, 6). MS (ESNEG): 178 [M−H]⁻.

To the amine 2b ($R^1$=Me, $R^2$=Me) (200 mg, 0.79 mmol) in DMF (2 ml), TEA (161 mg, 1.6 mmol), BSTFA (614 mg, 2.4 mmol) was added at 0° C. and stirred at room temperature for 1.5 hr. Acid 10b ($R^9$=isobutyl) (214 mg, 1.2 mmol) and HATU (368 mg, 1.2 mmol) was added and let stirred at room temperature for 4 hours. DMF was removed and the residue was extracted with EtOAc (50 mL), washed with sodium bicarbonate (10%, 50 mL), brine (50 mL) and dried over magnesium sulfate. The product obtained on removal of solvent was dissolved in methanol (10 mL) and treated with Dowex™ polymeric sulfonic acid H⁺ resin (300 mg) for 3 hr. After filtering the resin, methanol was removed to obtain the crude product. It was then purified on silica gel column chromatography using 3% MeOH in DCM to obtain compound 11b ($R^1$=Me, $R^2$=Me, $R^3$=H, $R^9$=isobutyl) (200 mg, 60%).

$^1$H NMR (300 MHz, $CD_3OD$) δ 8.41 (d, J=4.8, 1), 8.28 (d, J=9.6, 1), 7.95 (s, 1), 5.35 (d, J=5.4, 1), 4.25 (m, 2), 3.99 (d, J=10.8, 1), 3.78 (d, J=3.6, 1), 3.55 (dd, J=3.6, 10.8, 1), 2.52 (m, 3), 2.15 (s, 3), 1.93 (m, 1), 1.02 (m, 12). MS (ESPOS): 413 [M+H]⁺.

To compound 11b ($R^1$=Me, $R^2$=Me, $R^3$=H, $R^9$=isobutyl) (200 mg, 0.48 mmol) in water (10 mL), AcOH (2 mL) and MeOH (2 mL), $PtO_2$ (200 mg), was added, hydrogenated at 55 psi for 16 hours. After filtering the catalyst, the solvent was removed to obtain the crude material which on purification over silica gel column using 20% MeOH in DCM as eluent. The lower $R_f$ fraction provided the title compound (70 mg, 34%).

$^1$H NMR (300 MHz, $CD_3OD$) δ 5.25 (d, J=5.7, 1), 4.20 (dd, J=9.9; 3.3, 1), 4.07 (m, 2), 3.80 (d, J=3.0, 1), 3.60 (m, 2), 3.34 (m, 2), 2.84 (m, 1), 2.17 (m, 1), 2.10 (s, 3) 2.01 (m, 1), 1.77 (m, 3), 1.40 (m, 4), 0.91 (m, 12); MS (ESPOS): 419 [M+H]⁺.

Example 55

Preparation of 4-Propyl-piperidine-2-carboxylic acid [2,2-difluoro-1-(3,4,5-trihydroxy-6-methylsulfanyl-tetrahydro-pyran-2-yl)-propyl]-amide

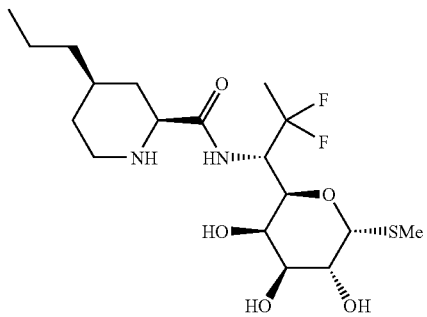

To acid 10b ($R^9$=propyl) prepared by Method P (53 mg, 0.32 mmol) in DMF (3 mL), lincosamide intermediate, compound 5b ($R^1$=Me), prepared by Method I (63 mg, 0.16 mmol) and HATU (121 mg, 0.32 mmol), triethylamine (70 mg, 0.48 mmol) was added at 0° C. and stirred at room temperature 16 hours. DMF was removed and the residue was taken in ethyl acetate and washed with saturated bicarbonate (30 mL). The product obtained on removal of solvent was purified on silica gel column using 30% ethyl acetate in hexanes (40 mg, 45%). To the pure product in methanol (5 mL), water (5 mL), acetic acid (5 mL) and platinum dioxide (50 mg, mmol) was added and hydrogenated at 60 psi for 16 hours. After filtering the catalyst, the solvent was removed to obtain the crude product which was taken in methanol (3 mL). Potassium carbonate (125 mg, 0.83 mmol) in water (1 mL) was added to it and stirred 16 hours. Solvents were then removed and the crude product purified on column chromatography using 20% methanol in dichloromethane. The lower Rf fraction resulted in the title compound (10 mg, 33%).

¹H NMR (300 MHz, CD₃OD) δ 5.28 (d, J=5.4, 1), 4.73 (s, 1), 4.57–4.65 (m, 1), 4.33–4.42 (m, 1), 4.05 (m, 1), 3.89 (s, 1), 3.53–3.57 (m, 2), 2.83 (t, J=12.3, 1), 2.09 (s, 3), 1.63–1.84 (m, 5), 1.16–1.37 (m, 6), 0.93 (m, 3). MS(ES-POS): 427 [M+H]⁺.

Example 56

Preparation of 4-Fluoro-4-propyl-pyrrolidine-2-carboxylic acid [2-methyl-1-(3,4,5-trihydroxy-6-methylsulfanyl-tetrahydro-pyran-2-yl)-propyl]-amide

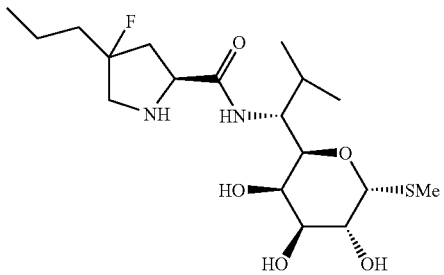

To a stirred solution of (2S, 4R)-4-hydroxyproline (Aldrich) (25 g, 108 mmol) in methanol (50 mL) at 0° C. was added trimethylsilyldiazomethene (24.6 g, 216 mmol). The mixture was stirred at 0° C. for 1 hour. The residue obtained on removal of solvent and purification by column chromatography using 50% ethyl acetate in hexanes (27 g, 100%) was used in the next step. To oxalyl chloride (15 g, 118 mmol) in DCM (15 mL) at −78° C., DMSO (18.6 mL, 236 mmol) was added slowly over 15 minutes. After the completion of addition, the above product (2S, 4R)-N-Boc-4-hydroxyproline methylester (26.5 g, 108 mmol) in DCM (100 mL) was added at −78° C. dropwise over 20 minutes. Triethylamine (54.6 g, 540 mmol) was added followed by stirring at room temperature for 2 hours. The reaction mixture was then washed with 10% aq HCl (200 mL) and the organic layer was separated and dried over sodium sulfate. The crude product obtained on removal of solvent was purified on silica gel column chromatography using 50% EtoAc in hexanes to obtain 4-oxo-pyrrolidine-1,2-dicarboxylic acid 1-tert-butyl ester 2-methyl ester (20 g, 78%).

¹H NMR (300 MHz, CDCl₃) δ 4.80 (m, 1), 3.88 (d, J=8.7, 2), 3.77 (s, 3), 2.98 (m, 1), 2.58 (m, 1), 1.45 (s, 9); MS (ESPOS): 244 [M+H]⁺.

To a stirred solution of 4-oxo-pyrrolidine-1,2-dicarboxylic acid 1-tert-butyl ester 2-methyl ester (1 g, 4.11 mmol) in THF (10 mL), tetraallyltin (1.08 mL, 4.52 mmol) in dry THF was added, then cooled to 0° C. before borontrifluoride etherate (0.520 mL, 4.11 mmol) was added drop wise. The mixture was stirred at 0° C. for 1 h and then at room temperature for an additional 2 hours. Potassium fluoride (360 mg in 5 mL water) and celite (1 g) was added and the reaction mixture was stirred for an hour. The reaction mixture was filtered and concentrated to dryness and the residue was dissolved in DCM (200 mL), washed with water (100 mL) and brine 100 mL), dried over MgSO₄ and evaporated to dryness. The residue obtained on removal of solvent was purified by silica gel column chromatography using 50% EtOAc in hexanes to obtain 4-allyl-4-hydroxy-pyrrolidine-1,2-dicarboxylic acid 1-tert-butyl ester 2-methyl ester (0.94 g, 80%).

¹H NMR (300 MHz, CDCl₃) δ 5.87 (m, 1), 5.19 (m, 2), 4.34 (m, 1), 3.75 (d, J=4.8, 3), 3.50 (m, 3), 2.37 (m, 1), 2.21 (m, 1), 1.39 (d, J=12.9, 9); MS (ESPOS): 308 [M+Na]⁺.

To a stirred solution of DAST (1.06 g, 6.58 mmol) in DCM (10 mL) at −78° C., 4-allyl-4-hydroxy-pyrrolidine-1,2-dicarboxylic acid 1-tert-butyl ester 2-methyl ester (940 mg, 3.3 mmol) in dry DCM (10 mL) was added slowly. The mixture was then stirred at −78° C. for 1 h, then at −10° C. for an additional 1 h. DCM (50 mL) was added, quenched with NH₄Cl (10%, 150 mL) and the organic layer was separated, dried over sodium sulfate and evaporated to dryness. The residue obtained on removal of solvent was purified by silica gel column chromatography using 5% EtOAc in hexanes as eluent to obtain 4-allyl-4-fluoro-pyrrolidine-1,2-dicarboxylic acid 1-tert-butyl ester 2-methyl ester (330 mg, 34%).

¹H NMR (300 MHz, CDCl₁₃) δ 5.82 (m, 1), 5.12 (m, 2), 4.43 (m, 1), 3.66 (s, 3), 3.47 (m, 1), 2.37 (m, 1), 2.43 (m, 4), 1.37 (dd, J=4.5, 13.8, 9); MS (ESPOS): 310 [M+Na]⁺.

¹H NMR (300 MHz, CD₃OD) δ 4.43 (m, 1), 3.71 (m, 6), 2.51 (m, 2), 1.98 (m, 3), 1.45 (m, 9), 0.96 (m, 3); MS (ESNEG): 274 [M−H]⁻.

To a solution of 4-allyl-4-propyl-pyrrolidine-1,2-dicarboxylic acid 1-tert-butyl ester-4- (310 mg, 1.15 mmol) in DMF (3 mL) at 0° C., 7-Methyl MTL 2b (R¹=Me, R²=Me) (272 mg, 1.15 mmol), HBTU (469 mg, 1.3 mmol) and DIEA (290 mg, 2.3 mmol) was added, left stirred at room temperature for 16 hours. DMF was removed and the residue obtained was purified by 3% MeOH in DCM(40 mg, 93%). The product from the column purification was taken in DCE (6 mL), to which triethylsilane (0.16 mL), TFA (2 mL) and water (0.16 mL) was added and stirred at room temperature for 1.5 hours. Removal of solvent followed by purification on silica gel column chromatography using 10% MeOH in DCM resulted in the title compound as isomeric mixtures with lower R_f fraction (160 mg, 50%).

¹H NMR (300 MHz, CD₃OD) δ 5.25 (d, J=5.7, 1), 4.46 (m, 1), 4.24 (dd, J5.7, 10.2, 1), 4.08 (m, 2), 3.81 (d, J=2.4, 1), 3.52 (m, 3), 2.73 (m, 1), 2.10 (m, 4), 1.88 (m, 2), 1.50 (m, 2), 0.99 (t, J=7.5, 3), 0.91 (dd, J=3.0, 6.9, 6); MS (ESPOS): 409 [M+H]⁺; and higher Rf fraction (40 mg, 12%). ¹H NMR (300 MHz, CD₃OD) δ 5.38 (d, J=5.4, 1), 4.46 (m, 1), 4.24 (dd, J=2.7, 7.2, 1), 4.08 (m, 2), 3.81 (d, J=2.4, 1), 3.64 (m, 3), 2.73 (m, 1), 2.11 (m, 4), 1.84 (m, 2), 1.47 (m, 2), 0.98 (t, J=7.5, 3), 0.91 (dd, J=3.0, 6.9, 6); MS (ESPOS): 409 [M+H]⁺.

To ethyl acetylene (140 mg, 2.6 mmol) in THF (5 mL) at −78° C., n-butyllithium (1.1 mL, 2.6 mmol) was added with stirring at −78° C. for 1 hour. Then 4-oxo-pyrrolidine-1,2-dicarboxylic acid 1-tert-butyl ester 2-methyl ester (prepared as described in the example 56) (570 mg, 2.3 mmol) in THF (5 mL) was added at −78° C. with stirring for 2 h, the reaction mixture was then allowed to warm to −40° C. over 1 h. The reaction mixture was extracted with EtOAc (20 mL), washed with saturated NH₄Cl (5 mL) and dried over sodium sulfate. Purification of the crude product was carried out by silica gel chromatography using 50% EtOAc in hexane to obtain the 4-butyl-4-hydroxy-pyrrolidine-1,2-dicarboxylic acid 1-tert-butyl ester 2-methyl ester (520 mg, 73%). To the DAST (556 mg, 3.4 mmol) in DCM (5 mL) at −78° C., was added a solution of the above ester (520 mg, 1.7 mmol) in DCM (5 mL) at −78° C. and stirred for 1 hour. The reaction mixture was extracted with DCM (50 mL) and washed with NaHCO₃ (30 mL, 10%). The product obtained after removal of solvent was purified by silica gel chromatography using 5% EtOAc in hexanes to obtain 4-butyl-4-fluoro-pyrrolidine-1,2-dicarboxylic acid 1-tert-butyl ester 2-methyl ester (276 mg, 52%).

Example 57

Preparation of 4-Butyl-4-fluoro-pyrrolidine-2-carboxylic acid [2-methyl-1-(3,4,5-trihydroxy-6-methylsulfanyl-tetrahydro-pyran-2-yl)-propyl-amide

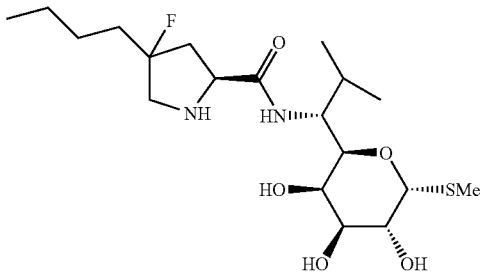

To ethyl acetylene (140 mg, 2.6 mmol) in THF (5 mL) at −78° C., n-butyllithium (1.1 mL, 2.6 mmol) was added with stirring at −78° C. for 1 hour. Then n-(tert-Butoxycarbonyl)-L-proline-4-ketone (described in the example 56) (570 mg, 2.3 mmol) in THF (5 mL) was added at −78° C. with stirring for 2 hours and then let it warm to −40° C. over 1 hour. The reaction mixture was extracted with EtOAc (20 mL), washed with saturated NH₄Cl (5 mL) and dried over sodium sulfate. Purification of the crude product was carried out by silica gel chromatography using 50% EtOAc in hexane to obtain the N-boc-4-butyl-4-hydroxy-prolinemethyl ester (520 mg, 73%). To the DAST (556 mg, 3.4 mmol) in DCM (5 mL) at −78° C., was added a solution of the above ester (520 mg, 1.7 mmol) in DCM (5 mL) at −78° C. and stirred for 1 hour. The reaction mixture was extracted with DCM (50 mL) and washed with NaHCO₃ (30 mL, 10%). The product obtained after removal of solvent was purified by silica gel chromatography using 5% EtOAc in hexanes to obtain N-(tert-butoxycarbonyl)-L-proline-4-fluoro-4-butane (276 mg, 52%).

$^1$H NMR (300 MHz, CD$_3$OD) δ 4.41 (m, 1), 3.83 (m, 1), 3.71 (s, 3), 3.45 (m, 1), 2.55–1.54 (m, 8), 1.39 (m, 9), 0.89 (m, 3); MS (ESPOS): 326 [M+Na]$^+$.

To a solution of 4-butyl-4-fluoro-pyrrolidine-1,2-dicarboxylic acid 1-tert-butyl ester 2-methyl ester (270 mg, 0.89 mmol) in THF (12 mL) and water (4 mL), was added lithium hydroxide monohydrate (45 mg, 1.07 mmol). The reaction mixture was stirred at room temperature for 16 hours. THF was removed under vacuum and the residue was taken up in ethyl acetate (150 mL), washed with 10% citric acid (100 mL) and brine (20 mL). Removal of solvent provided 4-butyl-4-fluoro-pyrrolidine-1,2-dicarboxylic acid 1-tert-butyl ester (260 mg, 100%).

$^1$H NMR (300 MHz, CD$_3$OD) δ 4.32 (m, 1), 3.72 (m, 2), 2.58 (m, 2), 2.10–1.63 (m, 6), 1.42 (m, 9), 0.93 (t, J=6.6, 3); MS (ESNEG): 288 [M−H]$^-$.

To a solution of 4-butyl-4-fluoro-pyrrolidine-1,2-dicarboxylic acid 1-tert-butyl ester (135 mg, 0.46 mmol) in DMF (3 mL) at 0° C., 7-Methy MTL 2b (R$^1$=Me, R$^2$=Me) (135 mg, 0.46 mmol), HBTU (194 mg, 0.51 mmol), DIEA (120 mg, 0.93 mmol) was added, left it at room temperature for 16 hours. The product obtained after removing DMF and purification by column chromatography using 5% MeOH in DCM (189 mg, 77%) was taken in DCE (6 mL). Triethylsilane (0.16 mL), TFA (2 mL) and water (0.16 mL) was added, stirred at room temperature for 1.5 hours. The residue obtained on removal of solvent was purified by column chromatography using 10% MeGH in DCM to obtain the title compound (156 mg, 96%).

$^1$H NMR (300 MHz, CD$_3$OD) δ 5.26 (d, J=5.7, 1), 4.55 (m, 1), 4.27 (dd, J=3.3, 10.2, 1), 4.08 (m, 2), 3.82 (d, J=3.0, 1), 3.58 (m, 3), 2.79 (m, 1), 2.22 (m, 1), 2.10 (s, 3), 1.89 (m, 3), 1.40 (m, 4), 0.91 (m, 9); MS (ESPOS): 423 [M+H]$^+$.

Example 58

4-Fluoro-4-propyl-pyrrolidine-2-carboxylic acid [2-hydroxy-1-(3,4,5-trihydroxy-6-methylsulfanyl-tetrahydro-pyran-2-yl)-propyl]-amide

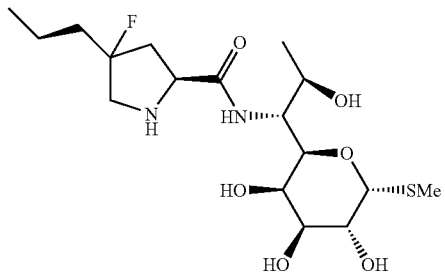

N-(tert-butoxycarbonyl)-4-fluoro-4-propyl-L-proline was prepared as described in the previous example (except using n-propyl lithium in the place of n-butyl lithium) (164 mg, 0.57 mmol) was suspended in dry acetonitrile (4 mL). Triethylamine (332 µL, 3.02 mmol) was added and the reaction mixture was cooled to 0° C. Isobutyl chloroformate (78 µL, 0.57 mmol) was added and after 10 min the reaction was allowed to warm to 4° C. After 1.5 h a solution of MTL (151 mg, 0.57 mmol) in 1:1 acetone: water (4 mL) was added and the reaction mixture was stirred for 10 h at rt. The reaction mixture was evaporated to dryness and chromatographed on silica 95:5 dichloromethane/MeOH to 95:8 dichloromethane/MeOH to provide the product as a colorless oil (137 mg, 45%): TLC Rf 0.32 (9:1 dichloromethane/MeOH).

To a solution of the above boc protected lincosamide (125 mg,) in DCM (2.0 mL) was added a solution of DCE (10.0 mL), trifluoroacetic acid (5 mL) methyl sulfide (0.3 mL), and water (0.3 mL). The reaction mixture was stirred at rt for 40 min then diluted with DCE (25.0 mL). The solvent was removed under vacuum and co-evaporated with DCE twice. The residue was purified by chromatography on fluorosil 20% MeOH (0.25M NH$_3$) in DCM to provide the product as a colorless solid (30.0 mg, 30%).

Example 59

Preparation of 4-(2-methoxyethoxy)-piperidine-2-carboxylic acid [2-methyl-1-(3,4,5-trihydroxy-6-methylsulfanyl-tetrahydro-pyran-2-yl)-propyl]-amide

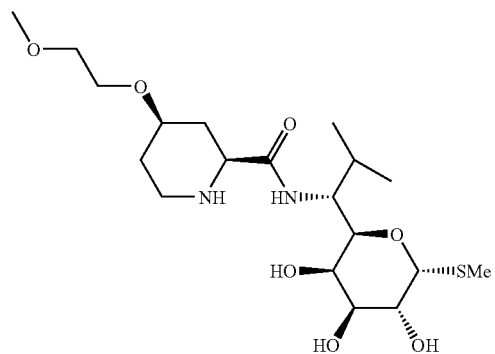

The title compound was made using the synthetic sequence found in Method S starting from 4-hydroxypyridine-2-carboxylic acid, substituting 1-bromo-2-methoxyethane as the alkylating agent.

Compound 15a ($R^9$=2-methoxyethoxy): $^1$H NMR (300 MHz, CD$_3$OD) δ 8.40 (d, J=6.0, 1), 7.69 (d, J=2.4, 1), 7.20 (dd, J=2.7, 6.3, 1), 4.35 (m, 2), 3.80 (m, 2), 3.40 (s, 3). MS (ESNEG): 196 [M−H]$^−$.

Compound 15b ($R^1$=Me, $R^2$=Me, $R^9$=2-methoxyethoxy): $^1$H NMR (300 MHz, CD$_3$OD) δ 8.43 (d, J=5.7, 1), 7.65 (d, J=2.4, 1), 7.12 (dd, J=2.4, 5.7, 1), 5.27 (d, J=5.4, 1), 4.10–4.87 (m, 4), 3.85 (d, J=3.3, 1), 3.77 (m, 2), 3.55 (m, 1), 3.41 (s, 3), 2.26 (m, 1), 2.11 (s, 1), 0.998 (m, 6). MS (ESPOS): 431 [M+H]$^+$.

Title compound (10 mg, 10%). $^1$H NMR (300 MHz, D$_2$O) δ 5.18 (d, J=6.0, 1), 4.00 (m, 3), 3.70 (m, 1), 3.56 (m, 1), 3.45 (m, 3), 3.26 (m, 1), 3.16 (m, 3), 3.10 (m, 1), 2.80 (m, 1), 2.48 (m, 1), 2.22 (m, 1), 1.96 (m, 4), 1.17–1.72 (m, 4), 0.70 (m, 6); MS(ESPOS): 437 [M+H]$^+$.

Examples 60–62

Example 60

Preparation of 4-Butyl-pyrrolidine-2-carboxylic acid [2-methyl-1-(3,4,5-trihydroxy-6-methylsulfanyl-tetrahydro-pyran-2-yl)-propyl]-amide

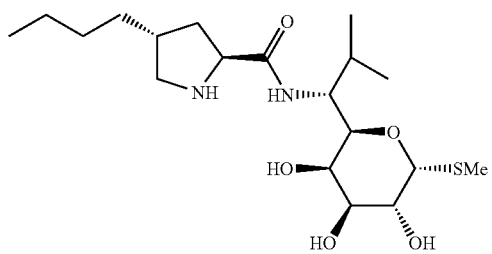

Example 61

Preparation of 4-(4,4-Difluoro-pentyl)-piperidine-2-carboxylic acid [2-methyl-1-(3,4,5-trihydroxy-6-methylsulfanyl-tetrahydro-pyran-2-yl)-propyl]-amide

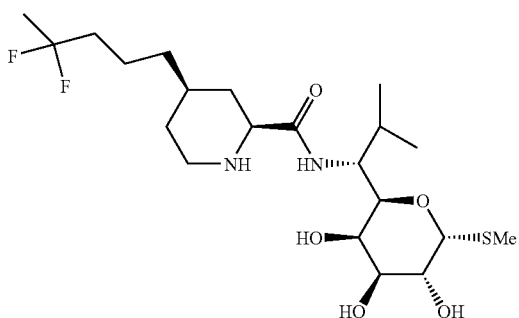

Example 62

Preparation of 4-(3-Fluoro-propyl)-piperidine-2-carboxylic acid [2-methyl-1-(3,4,5-trihydroxy-6-methylsulfanyl-tetrahydro-pyran-2-yl)-propyl]-amide

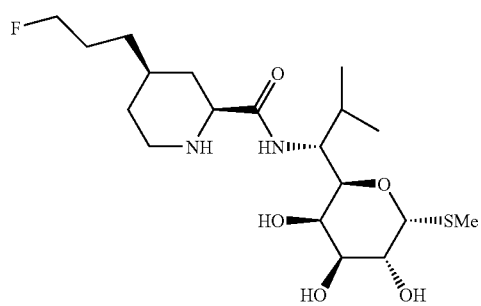

Examples 60 to 62 were prepared using methods and techniques describe herein utilizing commercially available starting materials where appropriate.

Example 63

Preparation of 4-Fluoro-4-propyl-piperidine-2-carboxylic acid [2-methyl-1-(3,4,5-trihydroxy-6-methylsulfanyl-tetrahydro-pyran-2-yl)-propyl]-amide

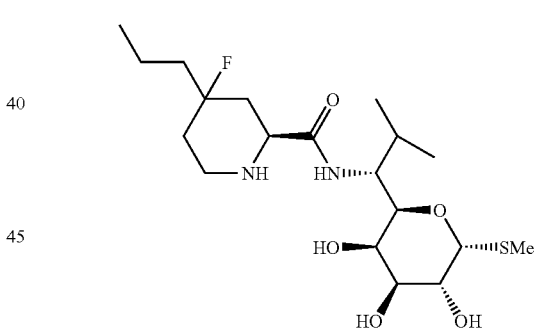

Lincosamine 2b ($R^1$=Me, $R^2$=Me) was coupled to carbamate 21d ($P_2$=Boc, m=2, $R^9$=n-propyl) as depicted in general coupling scheme 11 to provide intermediate 11a ($R^1$=$R^2$=Me, $R^3$=H, $R^9$=propyl/fluoro, $P^1$=H, $P_2$=carboxylic acid-t-butyl ester, m=2) which was deprotected under acidic conditions to provide the title compound.

HPLC: C$_{18}$ 3.5 μm, 4.6×30 mm Column; gradient eluent 2%–98% MeCN over 10 min; 1.5 mL/min): $R_t$=3.696 min); $^1$H NMR (300 MHz, CD$_3$OD) δ 5.36 (d, J=5.8, 1), 4.24 (dd, J=3.3, 12.9, 1), 4.20 (s, 2), 4.12 (dd, J=6.0, 10.4, 1), 3.88 (d, J=3.3, 1), 3.65 (dd, J=3.0, 10.4, 1), 3.48 (dd, J=4.1, 13.1, 1), 3.33 (ddd, J=3.6, 3.6, 13.5, 1), 2.43–2.45 (m, 1), 2.22–1.58 (m, 6), 2.16 (s, 3), 1.48 (m, 2), 0.94 (t, J=7.1, 3), 0.88 (d, J=6.9, 6); $^{19}$F NMR (CD$_3$OD) δ-158.8-δ-159.0 (sextuplet), MS (ESPOS): 423.2.

Example 64

Preparation of 4-(2-Fluoroethoxy)-piperidine-2-carboxylic acid [2-methyl-1-(3,4,5-trihydroxy-6-methylsulfanyl-tetrahydro-pyran-2-yl)-propyl]-amide

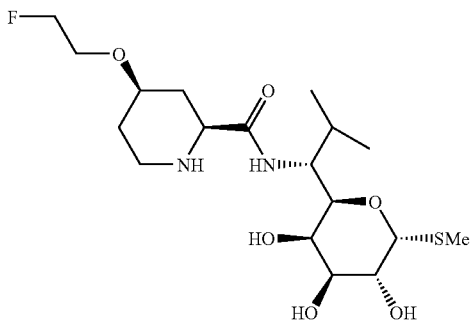

The title compound was made using the synthetic sequence found in general method S starting from 4-hydroxypyridine-2-carboxylic acid 10b (R$^9$=hydroxy) substituting 2-fluoroethyl bromide as the alkylating agent.

15a (R$^{9'}$=2-fluoroethoxy): $^1$H NMR (300 MHz, CD$_3$OD) δ 8.40 (d, J=6.0, 1), 7.73 (d, J=2.7, 1), 7.24 (dd, J=2.4, 6.0, 1), 4.87 (m, 2), 4.50 (m, 2). MS (ESNEG): 184 [M−H]$^-$.

15b (R$^1$=R$^2$=Me, R$^3$=H, R$^{9'}$=2-fluoroethoxy): $^1$H NMR (300 MHz, CD$_3$OD) δ 8.45 (d, J=5.7, 1), 7.67 (d, J=2.4, 1), 7.14 (dd, J=2.7, 5.7, 1), 5.27 (d, J=5.7, 1), 4.68 (m, 1), 4.43 (m, 1), 4.12–4.33 (m, 3), 4.10 (dd, J=6.0, 10.2, 1), 3.18–3.84 (m, 3), 2.26 (m, 1), 2.11 (s, 3), 1.00 (t, J=5.1, 6). MS (ESPOS): 419 [M+H]$^+$.

Title compound (20 mg, 14%): $^1$H NMR (300 MHz, CD$_3$OD) δ 5.24 (d, J=5.7, 1), 4.59 (t, J=4.2, 1), 4.43 (t, J=4.2, 1), 4.18 (dd, J=3.3, 6.6, 1), 4.07 (m, 2), 3.80 (m, 2), 3.73 (m, 1), 3.55 (m, 2), 3.48 (m, 1), 3.21 (m, 1), 2.74 (m, 1), 2.32 (m, 1), 2.18 (m, 1), 2.10 (s, 3) 1.38 (m, 3), 0.93 (m, 6); MS (ESPOS): 425 [M+H]$^+$.

Example 65

There is no Example 65.

Example 66

Preparation of 4-(2-Cyclopropyl-ethyl)-piperidine-2-carboxylic acid [2-methyl-1-(3,4,5-trihydroxy-6-methylsulfanyl-tetrahydro-pyran-2-yl)-propyl]-amide

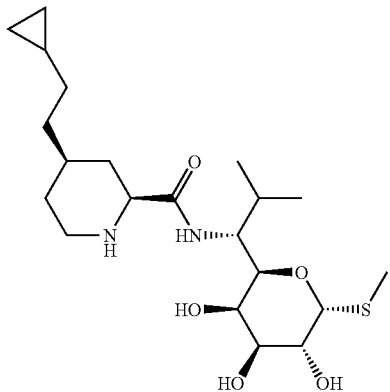

Compound 14c (R$^9$=2-cyclopropylethyl) was prepared using the methods described in general method R.

To a stirred suspension of 14a (0.5 g, 1.9 mmol, 1 equiv), triphenylphosphine (39.9 mg, 0.15 mmol, 0.08 equiv), copper (I) iodide (28.9 mg, 0.15 mmol, 0.08 equiv), palladium acetate (17 mg, 0.076 mmol, 0.04 equiv) in triethylamine (7 mL) under dry nitrogen, was added cyclopropyl acetylene (Aldrich) (0.25 g, 3.8 mmol, 2 equiv). The mixture was stirred at rt overnight. The solvent was removed under vacuum to give a dark residue. The residue was purified by column chromatography to give 14b (R$^{9'}$=2-cyclopropyl-eth-1-ynyl) (0.39 g, 100%) as a yellow oil.

$^1$H NMR (300 MHz, CDCl$_3$) δ 8.65–8.56 (m, 1), 8.06–7.99 (m, 1), 7.40–7.32 (m, 1), 3.98 (s, 3), 1.50–1.40 (m, 1), 0.96–0.81 (m, 4). MS (ESPOS): 202.0 [M+H]$^+$.

To a solution of 14b (R$^{9'}$=2-cyclopropyl-eth-1-ynyl) (0.39 g, 1.9 mmol) in methanol (15 mL) was added 10% palladium on carbon (0.2 g). The mixture was purged and charged with hydrogen (1 atm) and stirred at rt overnight. The palladium was removed by filtration and the filtrate was concentrated to give 14c (R$^9$=2-cyclopropylethyl) (0.38 g, 97%) as a yellow oil.

$^1$H NMR (300 MHz, CDCl$_3$) δ 8.60 (d, J=4.5, 1), 8.00–7.96 (m, 1), 7.34–7.29 (m, 1), 3.99 (s, 3), 2.78 (t, J=7.6, 2), 1.58–1.49 (m, 2), 0.71–0.59 (m, 1), 0.47–0.38 (m, 2), 0.06–0.02 (m, 2); MS (ESPOS): 228.2 [M+Na]$^+$.

To a mixture of 14c (R$^9$=2-cyclopropylethyl) (0.38 g) in MeOH (8 mL) and water (8 mL) were added conc. HCl (158 μL) and platinum oxide (0.2 g). The mixture was purged and charged with hydrogen (1 atm) and stirred overnight. The platinum oxide was removed by filtration and the filtrate was evaporated to give a light yellow solid.

To the above residue was added 2N NaOH (3.8 mL) and t-butylalcohol (2 mL). The reaction mixture was stirred at rt for 2 h, di-t-butyl dicarbonate (0.62 g, 2.85 mmol) was then added and the mixture stirred overnight. The solvent was removed under vacuum and the resulting residue was diluted with water, then washed with ether. The aqueous layer was acidified with 2N HCl to pH=2.0, and extracted with ethyl acetate (2×). The combined organic layers were dried and concentrated to give 4-(2-cyclopropylethyl)-piperidine-1,2-dicarboxylic acid 1-tert-butyl ester (0.42 g, 77%) as a clear syrup.

MS (ESPOS): 320.3 [M+Na]$^+$. MS (ESNEG): 296.2 [M−H]$^-$.

To a solution of 4-(2-cyclopropylethyl)-piperidine-1,2-dicarboxylic acid-1-tert-butyl ester (115 mg, 0.387 mmol, 1 equiv) and 2b (R$^1$=Me, R$^2$=Me) HCl salt (111.4 mg, 0.387 mmol, 1 equiv) in DMF (2.4 mL) at r.t. was added DIEA (100 μL, 0.774 mmol, 2 equiv), followed by HBTU (162 mg, 0.426 mmol, 1.1 equiv). The reaction mixture was stirred at rt for 3 hrs then evaporated under high vacuum to dryness. The residue was diluted with ethyl acetate, washed with 1:1 10% citric acid/brine (1×), sat. aqueous sodium bicarbonate (1×), brine (1×), dried and concentrated. The residue was purified by chromatography to give the desired 1'-Boc protected lincosamide product 11a (R$^1$=R$^2$=Me, R$^3$=H, R$^9$=2-cyclopropylethyl, P$^1$=H, P$^2$=carboxylic acid-t-butyl ester) (126 mg, 61%) as a clear syrup.

MS (ESPOS): 531.3 [M+H]$^+$.

To a solution of the above 11a (R$^1$=R$^2$=Me, R$^3$=H, R$^9$=2-cyclopropylethyl, P$^1$=H, P$^2$=carboxylic acid-t-butyl ester, m=2) in DCE (12 mL) at 0° C. was added a solution of trifluoroacetic acid (3 mL) and water (0.375 mL). The reaction mixture was stirred at 0° C. for 5 min and at rt for 35 min. The reaction solvent was removed under vacuum and co-evaporated with toluene twice, and the resulting residue was purified by semi-preparative HPLC (Waters Nova-Pak® HR $C_{18}$, 6 μm particle size, 60 Å pore size, 20 mm ID×100 mm, 5–60% acetonitrile in $H_2O$ w/0.1% AcOH over 30 min, 20 mL/min flow rate) to provide the title compound of example 66 (25 mg, 27%) as a white solid.

$^1$H NMR (300 MHz, $CD_3OD$) δ 5.24 (d, J=6, 1), 4.19 (dd, J=3.4, 10, 1), 4.10–4.04 (m, 2), 3.81–3.72 (m, 2), 3.51 (dd, J=3.3, 10.2, 1), 3.42–3.33 (m, 1), 3.02–2.90 (m, 1), 2.20–2.12 (m, 1), 2.11 (s, 3), 1.94–1.86 (m, 1), 1.76–1.64 (m, 1), 1.48–1.20 (m, 7), 0.94–0.85 (m, 6), 0.73–0.62 (m, 1), 0.47–0.38 (m, 2), 0.05–0.02 (m, 2). MS (ESPOS): 431.3 $[M+H]^+$.

Example 67

Preparation of 4-Cyclopropylmethyl-piperidine-2-carboxylic acid [2-methyl-1-(3,4,5-trihydroxy-6-methylsulfanyl-tetrahydro-pyran-2-yl)-propyl]-amide

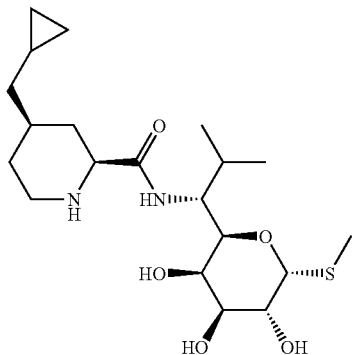

4-Cyclopropylmethylpyridine-2-carboxylic acid, compound 10b ($R^9$=cyclopropylmethyl), was made by employing Method P using the starting material 4-Cyclopropylmethylpyridine prepared as described by Osuch et al, *Journal of the American Chemical Society*, 1955, 78, 1723.

To a –78° C. solution of 4-picoline (1.1 g, 11.8 mmol) in THF (5 mL) was added a solution of LDA 2M in THF/heptane/ethylbenzene (Aldrich) (5.9 mL, 11.8 mmol). The resulting reaction mixture was stirred at –78° C. for 3 h then –40° C. for 1 h. Cyclopropyl bromide (1.43 g, 11.8 mmol) was added at –78° C., the reaction mixture was allowed to warm up to room temperature and was stirred at room temperature for 1 h. To the reaction mixture was added saturated aqueous $NH_4Cl$ (10 mL), the aqueous phase was extracted with EtOAc (10×2 mL), and the combined organic extracts dried over $Na_2SO_4$. 4-Cyclopropylmethylpyridine-2-carboxylic acid (0.5 g, 31%) was obtained after the solvent was removed and used without further purification.

To a 0° C. solution of 4-Cyclopropylmethylpyridine-2-carboxylic acid (10b) ($R^9$=cyclopropylmethyl) (147 mg, 0.83 mmol), 2b ($R^1$=Me, $R^2$=Me) HCl salt (238 mg, 0.83 mmol) and TEA (231 μL, 1.66 mmol) in DMF (2 mL) was added solid HBTU (346 mg, 0.91 mmol), and the resulting reaction mixture was stirred overnight. Reaction solvents were removed, and the residue purified by silica gel column chromatography at 50–100% EtOAc/Hexane to provide the desired lincosamide product 11b ($R^1$=$R^2$=Me, $R^3$=H, $R^9$=cyclopropylmethyl, $P^1$=H) (260 mg, 76%).

To a solution of 11b ($R^1$=$R^2$=Me, $R^3$=H, $R^9$=cyclopropylmethyl, $P^1$=H) (250 mg, 0.6 mmol) in water (10 mL), AcOH (2 mL), MeOH (3 mL) was added $PtO_2$ (200 mg), and the reaction mixture was hydrogenated at 50 psi for 5 hr. The solvent was removed to obtain the crude lincosamide product. Purification was carried by silica gel column chromatography (20% MeOH/DCM), then HPLC (Waters Nova-Pak® HR $C_{18}$, 6 μm particle size, 60 Å pore size, 20 mm ID×100 mm, 5–60% acetonitrile in $H_2O$ w/0.1% AcOH over 30 min, 20 mL/min flow rate) to provide the title compound (13 mg, 5%) as a colorless solid.

$^1$H NMR (300 MHz, $CD_3OD$) δ 5.23 (d, J=6, 1), 4.26–4.10 (m, 3), 3.83–3.78 (m, 2), 3.55–3.33 (m, 2), 3.07–2.95 (m, 1), 2.34–2.17 (m, 2), 2.12 (s, 3), 2.00–1.80 (m, 4), 1.42–1.15 (m, 4), 1.00–0.90 (m, 6), 0.79–0.66 (m, 1), 0.53–0.45 (m, 2), 0.12–0.04 (m, 2); MS (ESPOS): 417.3 $[M+H]^+$.

Example 68

Preparation of 4-(2-Cyclobutyl-ethyl)-piperidine-2-carboxylic acid [2-methyl-1-(3,4,5-trihydroxy-6-methylsulfanyl-tetrahydro-pyran-2-yl)-propyl]-amide

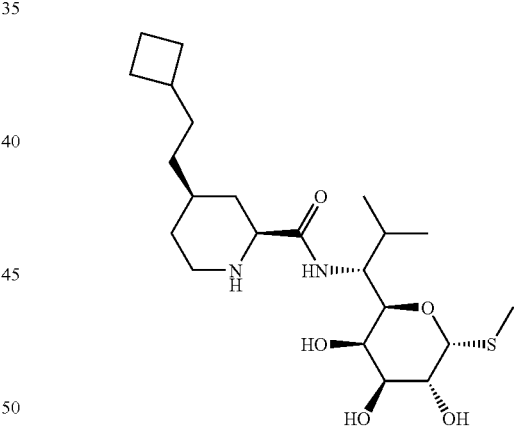

4-(2-Cyclobutyl-ethyl)-pyridine-2-carboxylic acid, compound 10b ($R^9$=2-cyclobutyl-ethyl), was made by employing Method P using the starting material 4-(2-Cyclobutyl-ethyl)-pyridine prepared as described by Osuch et al, *Journal of the American Chemical Society*, 1955, 78, 1723.

Lincosamine 2b ($R^1$=Me, $R^2$=Me) was coupled to 4-(2-cyclobutyl-ethyl)-pyridine-2-carboxylic acid 10b ($R^9$=cyclobutyl-ethyl) as depicted in general coupling scheme 11 to provide intermediate 11b ($R^1$=$R^2$=Me, $R^3$=H, $R^9$=2-cyclobutyl-ethyl, $P^1$=H) which was reduced by catalytic hydrogenation to the title compound.

MS (ESPOS): 445.2 $[M+H]^+$.

Example 69

Preparation of 4-Cyclobutylmethyl-piperidine-2-carboxylic acid [2-methyl-1-(3,4,5-trihydroxy-6-methylsulfanyl-tetrahydro-pyran-2-yl)-propyl]-amide

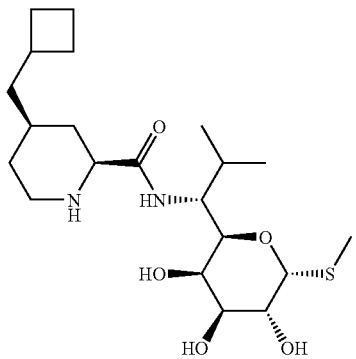

4-Cyclobutylmethylpyridine-2-carboxylic acid, compound (10b) (R⁹=4-cyclobutylmethyl) was made by employing Method P using the starting material 4-cyclobutylmethylpyridine prepared as described by Osuch et al, *Journal of the American Chemical Society*, 1955, 78, 1723.

Lincosamine 2b (R$^1$=Me, R$^2$=Me) was coupled to 4-cyclobutylmethylpyridine-2-carboxylic acid, compound 10b (R$^9$=4-cyclobutylmethyl), as depicted in general coupling scheme 11 to provide intermediate 11b (R$^1$=R$^2$=Me, R$^3$=H, R$^9$=cyclobutyl-methyl, P$^1$=H), which was reduced by catalytic hydrogenation to the title compound.

MS (ESPOS): 431.3 [M+H]$^+$.

Example 70

Preparation of 3-Butyl-azetidine-2-carboxylic acid [2-methyl-1-(3,4,5-trihydroxy-6-methylsulfanyl-tetrahydro-pyran-2-yl)-propyl]-amide

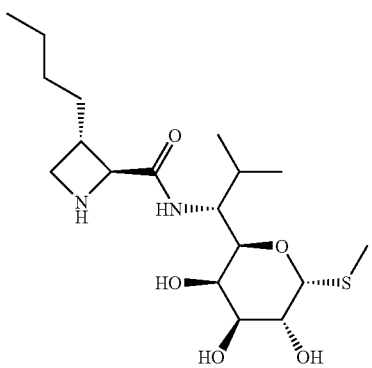

To a solution of azetedine acid 16f (R$^9$=butyl) (52 mg, 0.20 mmol, 1 equiv), aminosugar (58 mg, 0.20 mmol, 1 equiv) and HBTU (84 mg, 0.22 mmol, 1.1 equiv) in DMF (2.0 mL) at 23° C. was added DIPEA (88 μL, 0.51 mmol, 2.5 equiv). After stirring for 12 h at 23° C., DMF was removed in vacuo, then the residue was partitioned between EtOAc (100 mL) and 1:1 brine: 10% aqueous citric acid (100 mL). The organic layer was separated and washed with 1:1 brine/saturated aqueous NaHCO$_3$ (100 mL), brine (50 mL), dried (MgSO$_4$), filtered and concentrated to furnish 82 mg (0.17 mmol, 84%) 11a (R$^1$=R$^2$=Me, R$^3$=H, R$^9$=butyl, P$^1$=H, P$^2$=carboxylic acid-t-butyl ester, m=0) as a glassy solid.

MS (ESPOS): [M+H]$^+$.

To a solution of carbamate 11a (R$^1$=R$^2$=Me, R$^3$=H, R$^9$=butyl, P$^1$=H, P$^2$=carboxylic acid-t-butyl ester, m=0) (82 mg, 0.17 mmol, 1 equiv) in 1,2-dichloroethane (10 mL) at 23° C. was added H$_2$O (0.40 mL) followed by TFA (4.0 mL). After stirring for 20 min at 23° C., toluene (50 mL) was added and the resulting solution was concentrated to dryness. The residue was purified by semi-preparative HPLC (Waters Nova-Pak® HR C$_{18}$, 6 μm particle size, 60 Å pore size, 20 mm ID×100 mm, 5–60% acetonitrile in H$_2$O w/0.1% HCl over 30 min, 20 mL/min flow rate) to give 41 mg of title compound as a white solid.

$^1$H NMR (300 MHz, CD$_3$OD) δ 5.25 (d, J=5.7, 1), 4.60 (d, J=7.2, 1), 4.25 (dd, J=3.3, 9.9, 1), 4.16–4.05 (m, 2), 3.99 (t, J=9.0, 1), 3.81 (d, J=3.0, 1), 3.74 (dd, J=8.4, 9.9, 1), 3.50 (dd, J=3.3, 10.2, 1), 2.90–2.74 (m, 1), 2.23–2.10 (m, 1), 2.10 (s, 3), 1.90–1.67 (m, 2), 1.44–1.24 (m, 4), 1.00–0.86 (m, 9H). MS (ESPOS): 391.4 [M+H]$^+$.

Example 71

Preparation of 3-Cyclopropylmethyl-azetidine-2-carboxylic acid [2-methyl-1-(3,4,5-trihydroxy-6-methylsulfanyl-tetrahydro-pyran-2-yl)-propyl]-amide

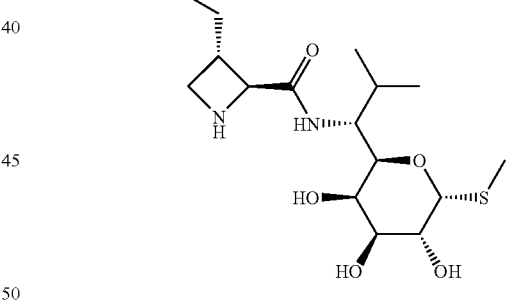

Lincosamine 2b (R$^1$=Me, R$^2$=Me) was coupled to azetedine acid 16f (R$^9$=cyclopropylmethyl) as depicted in general coupling scheme 11 to provide intermediate 11a (R$^1$=R$^2$=Me, R$^3$=H, R$^9$=cyclopropylmethyl, P$^1$=H, P$^2$=carboxylic acid-t-butyl ester, m=0) which was deprotected under acidic conditions to provide the title compound.

$^1$H NMR (300 MHz, CD$_3$OD) δ 5.25 (d, J=5.7, 1), 4.65 (d, J=7.5, 1), 4.25 (dd, J=3.9, 9.6, 1), 4.13–3.99 (m, 3), 3.86–3.79 (m, 2), 3.51 (dd, J=3.3, 10.2, 1), 3.00–2.87 (m, 1), 2.21–2.09 (m, 1), 2.11 (s, 3), 1.83–1.72 (m, 1), 1.62–1.51 (m, 1), 0.94 (d, J=6.9, 3), 0.89 (d, J=6.9, 3), 0.82–0.70 (m, 1), 0.58–0.47 (m, 2), 0.18–0.08 (m, 2H). MS (ESPOS): 389.2 [M+H]$^+$.

Example 72

Preparation of 3-Propyl-azetidine-2-carboxylic acid [2-methyl-1-(3,4,5-trihydroxy-6-methylsulfanyl-tetrahydro-pyran-2-yl)-propyl]-amide

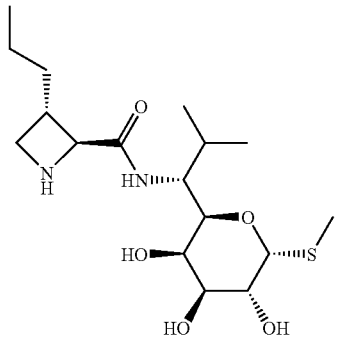

Lincosamine 2b ($R^1$=Me, $R^2$=Me) was coupled to azetedine acid 16f ($R^9$=propyl) as depicted in general coupling scheme 11 to provide intermediate 11a $R^1$=$R^2$=Me, $R^3$=H, $R^9$=propyl, $P^1$=H, $P^2$=carboxylic acid-t-butyl ester, m=0) which was deprotected under acidic conditions to provide the title compound.

$^1$H NMR (300 MHz, CD$_3$OD) δ 5.26 (d, J=5.4, 1), 4.60 (d, J=7.5, 1), 4.26 (dd, J=3.3, 9.6, 1), 4.13–3.99 (m, 3), 3.81 (d, J=3.3, 1), 3.76 (dd, J=5.1, 10.2, 1), 3.51 (dd, J=3.3, 9.9, 1), 2.93–2.76 (m, 1), 2.24–2.09 (m, 1), 2.11 (s, 3), 1.84–1.67 (m, 2), 1.48–1.30 (m, 2), 1.01–0.87 (m, 9H). MS (ESPOS): 377.0 [M+H]$^+$.

Example 73

Preparation of 3-Butyl-1-(2-hydroxy-ethyl)-azetidine-2-carboxylic acid [2-methyl-1-(3,4,5-trihydroxy-6-methylsulfanyl-tetrahydro-pyran-2-yl)-propyl]-amide

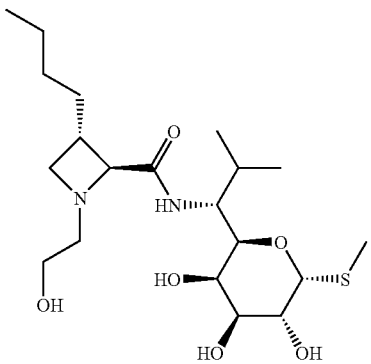

A sample of 3-Butyl-azetidine-2-carboxylic acid [2-methyl-1-(3,4,5-trihydroxy-6-methylsulfanyl-tetrahydro-pyran-2-yl)-propyl]-amide prepared in example 70 was alkylated with ethyleneoxide as depicted in scheme 12 ($R^6$=2-hydroxyethyl) to provide the title compound.

$^1$H NMR (300 MHz, CD$_3$OD) δ 5.25 (d, J=5.4, 1), 4.13–4.05 (m, 3), 3.83–3.77 (m, 2), 3.64 (t, J=9.9, 1), 3.58–3.48 (m, 2), 3.37–3.30 (m, 1), 2.78–2.55 (m, 2), 2.44–2.34 (m, 1), 2.25–2.10 (m, 2), 2.11 (s, 3), 1.80–1.40 (m, 2), 1.39–1.20 (m, 4), 0.95–0.84 (m, 9H). MS (ESPOS): 435.1 [M+H]$^+$.

Example 74

Preparation of 3-Pentyl-azetidine-2-carboxylic acid [2-methyl-1-(3,4,5-trihydroxy-6-methylsulfanyl-tetrahydro-pyran-2-yl)-propyl]-amide

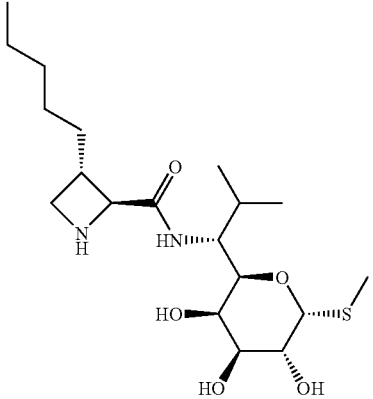

Lincosamine 2b ($R^1$=Me, $R^2$=Me) was coupled to azetedine acid 16f ($R^9$=pentyl) as depicted in general coupling scheme 11 to provide intermediate 11a ($R^1$=$R^2$=Me, $R^3$=H, $R^9$=pentyl, $P^1$=H, $P^2$=carboxylic acid-t-butyl ester, m=0) which was deprotected under acidic conditions to provide the title compound.

$^1$H NMR (300 MHz, CD$_3$OD) δ 5.25 (d, J=5.7, 1), 4.55 (d, J=6.9, 1), 4.25 (dd, J=3.3, 9.9, 1), 4.13–4.04 (m, 2), 4.00 (t, J=9.3, 1), 3.80 (d, J=3.0, 1), 3.73 (dd, J=7.8, 9.9, 1), 3.51 (dd, J=3.3, 10.5, 1), 2.88–2.75 (m, 1), 2.23–2.10 (m, 1), 2.11 (s, 3), 1.84–1.60 (m, 2), 1.44–1.26 (m, 6), 0.97–0.86 (m, 9H). MS (ESPOS): 405.4 [M+H]$^+$.

Example 75

Preparation of 3-(3-Methyl-butyl)-azetidine-2-carboxylic acid [2-methyl-1-(3,4,5-trihydroxy-6-methylsulfanyl-tetrahydro-pyran-2-yl)-propyl]-amide

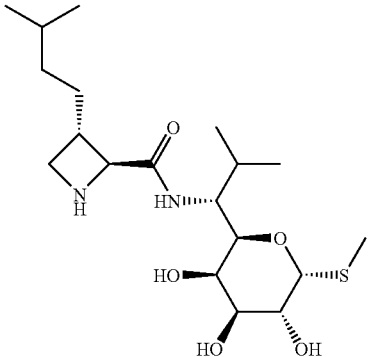

Lincosamine 2b ($R^1$=Me, $R^2$=Me) was coupled to azetedine acid 16f ($R^9$=3-methyl-butyl) as depicted in general coupling scheme 11 to provide intermediate 11a ($R^1$=$R^2$=Me, $R^3$=H, $R^9$=3-methyl-butyl, $P^1$=H, $P^2$=carboxylic acid-t-butyl ester, m=0) which was deprotected under acidic conditions to provide the title compound.

$^1$H NMR (300 MHz, CD$_3$OD) δ 5.25 (d, J=6.0, 1), 4.55 (d, J=7.5, 1), 4.26 (dd, J=3.6, 10.2, 1), 4.13–4.04 (m, 2), 4.00 (t, J=9.3, 1), 3.80 (d, J=3.3, 1), 3.73 (dd, J=8.1, 10.2, 1), 3.51 (dd, J=3.3, 10.2, 1), 2.87–2.72 (m, 1), 2.24–2.10 (m, 1), 2.11

(s, 3), 1.84–1.70 (m, 2), 1.66–1.50 (m, 1), 1.26–1.10 (m, 2), 0.97–0.86 (m, 12H). MS (ESPOS): 405.0 [M+H]+.

Example 76

Preparation of 3-(3-Cyclobutyl-propyl)-azetidine-2-carboxylic acid [2-methyl-1-(3,4,5-trihydroxy-6-methylsulfanyl-tetrahydro-pyran-2-yl)-propyl]-amide

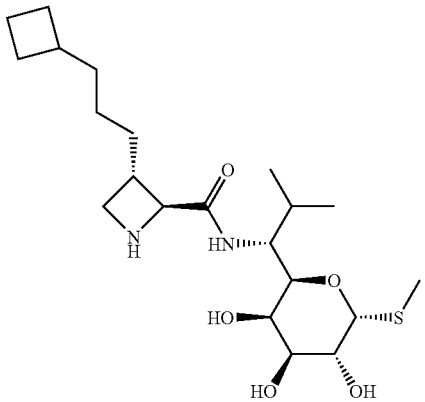

Lincosamine 2b ($R^1$=Me, $R^2$=Me) was coupled to azetedine acid 16f ($R^9$=3-cyclobutyl-propyl) as depicted in general coupling scheme 11 to provide intermediate 11a ($R^1$=$R^2$=Me, $R^3$=H, $R^9$=(3-cyclobutyl-propyl), $P^1$=H, $P^2$=carboxylic acid-t-butyl ester, m=0) which was deprotected under acidic conditions to provide the title compound.

$^1$H NMR (300 MHz, CD$_3$OD) δ 5.24 (d, J=5.7, 1), 4.24–4.14 (m, 2), 4.11–4.04 (m, 2), 3.78 (d, J=3.3, 1), 3.71 (t, J=9.0, 1), 3.54–3.43 (m, 1), 2.76–2.60 (m, 1), 2.34–2.10 (m, 2), 2.10 (s, 3), 2.09–1.97 (m, 2), 1.90–1.51 (m, 7), 1.44–1.11 (m, 3), 0.90 (d, J=2.1, 3), 0.88 (d, J=2.1, 3H). MS (ESPOS): 431.3 [M+H]+.

Example 77

Preparation of 3-(2-Cyclobutyl-ethyl)-azetidine-2-carboxylic acid [2-methyl-1-(3,4,5-trihydroxy-6-methylsulfanyl-tetrahydro-pyran-2-yl)-propyl]-amide

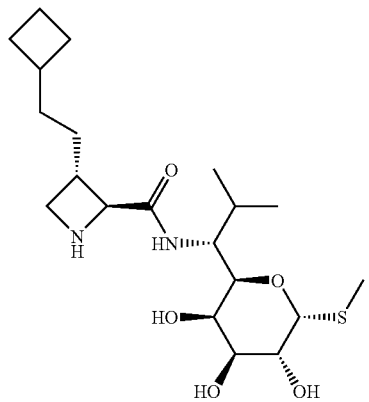

Lincosamine 2b ($R^1$=Me, $R^2$=Me) was coupled to azetedine acid 16f ($R^9$=2-cyclobutyl-ethyl) as depicted in general coupling scheme 11 to provide intermediate 11a ($R^1$=$R^2$=Me, $R^3$=H, $R^9$=2-cyclobutyl-ethyl, $P^1$=H, $P^2$=carboxylic acid-t-butyl ester, m=0) which was deprotected under acidic conditions to provide the title compound.

$^1$H NMR (300 MHz, CD$_3$OD) δ 5.24 (d, J=6.0, 1), 4.51 (d, J=10.2, 1), 4.25 (dd, J=3.3, 9.9, 1), 4.12–4.03 (m, 2), 3.96 (t, J=9.3, 1), 3.79 (d, J=3.0, 1), 3.69 (dd, J=8.1, 10.2, 1), 3.50 (dd, J=3.3, 10.2, 1), 2.85–2.69 (m, 1), 2.36–2.10 (m, 2), 2.10 (s, 3), 2.09–2.00 (m, 2), 1.95–1.33 (m, 10), 0.92 (d, J=6.9, 3), 0.89 (d, J=6.9, 3H). MS (ESPOS): 417.3 [M+H]+.

Example 78

Preparation of 3-(2-Cyclopropyl-ethyl)-azetidine-2-carboxylic acid [2-methyl-1-(3,4,5-trihydroxy-6-methylsulfanyl-tetrahydro-pyran-2-yl)-propyl]-amide

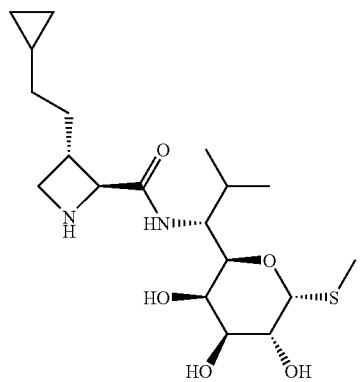

Lincosamine 2b ($R^1$=Me, $R^2$=Me) was coupled to azetedine acid 16f ($R^9$=2-cyclopropyl-ethyl) as depicted in general coupling scheme 11 to provide intermediate 11a ($R^1$=$R^2$=Me, $R^1$=H, $R^9$=2-cyclopropyl-ethyl, $P^1$=H, $P^2$=carboxylic acid-t-butyl ester, m=0) which was deprotected under acidic conditions to provide the title compound.

$^1$H NMR (300 MHz, CD$_3$OD) δ 5.24 (d, J=5.7, 1), 4.53 (d, J=7.2, 1), 4.24 (dd, J=3.3, 9.9, 1), 4.11–4.03 (m, 2), 3.98 (t, J=9.6, 1), 3.79 (d, J=3.0, 1), 3.73 (dd, J=8.1, 9.9, 1), 3.50 (dd, J=3.3, 10.2, 1), 2.92–2.77 (m, 1), 2.22–2.09 (m, 1), 2.10 (s, 3), 1.95–1.77 (m, 2), 1.33–1.18 (m, 2), 0.91 (d, J=6.9, 3), 0.88 (d, J=6.9, 3), 0.73–0.60 (m, 1), 0.48–0.40 (m, 2), 0.08–0.01 (m, 2H). MS (ESPOS): 403.3 [M+H]+.

Example 79

Preparation of 3-(3-Cyclopropyl-propyl)-azetidine-2-carboxylic acid [2-methyl-1-(3,4,5-trihydroxy-6-methylsulfanyl-tetrahydro-pyran-2-yl)-propyl]-amide

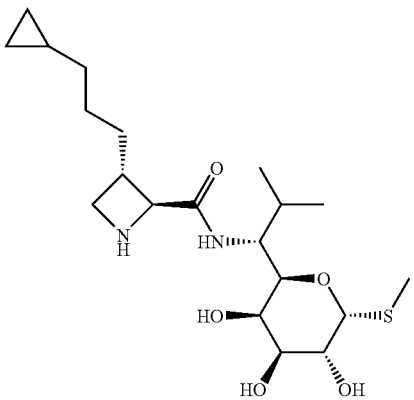

Lincosamine 2b (R¹=Me, R²=Me) was coupled to azetedine acid 16f (R⁹=3-cyclopropyl-propyl) as depicted in general coupling scheme 11 to provide intermediate 11a (R¹=R²=Me, R³=H, R⁹=3-cyclopropyl-propyl, P¹=H, P²=carboxylic acid-t-butyl ester, m=0) which was deprotected under acidic conditions to provide the title compound.

¹H NMR (300 MHz, CD₃OD) δ 5.24 (d, J=5.7, 1), 4.54 (d, J=7.5, 1), 4.24 (dd, J=3.3, 9.9, 1), 4.11–4.03 (m, 2), 3.97 (t, J=9.6, 1), 3.79 (d, J=3.0, 1), 3.71 (dd, J=7.8, 9.9, 1), 3.50 (dd, J=3.0, 10.2, 1), 2.88–2.74 (m, 1), 2.23–2.09 (m, 1), 2.10 (s, 3), 1.90–1.68 (m, 2), 1.57–1.33 (m, 2), 1.23 (q, J=6.9, 2), 0.91 (d, J=6.9, 3), 0.89 (d, J=6.9, 3), 0.75–0.60 (m, 1), 0.45–0.38 (m, 2), 0.04–0.02 (m, 2H). MS (ESPOS): 417.3 [M+H]⁺.

Example 80

Preparation of 3-Butyl-1-methyl-azetidine-2-carboxylic acid [2-methyl-1-(3,4,5-trihydroxy-6-methylsulfanyl-tetrahydro-pyran-2-yl)-propyl]-amide

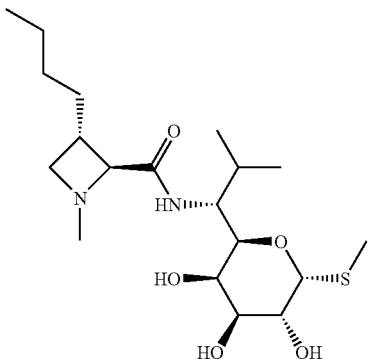

Azetedine acid 16f (R⁹=butyl) was deprotected and N-methylated by treatment with formic acid and formaldehyde under conditions known to persons skilled in the art to provide 3-butyl-1-methyl-azetidine-2-carboxylic acid. Lincosamine 2b (R¹=Me, R²=Me) was coupled to 3-butyl-1-methyl-azetidine-2-carboxylic acid as depicted in general coupling scheme 11 to provide the title compound.

¹H NMR (300 MHz, D₂O) δ 5.36 (d, J=6.0, 1), 4.67 (d, J=8.7, 1), 4.31 (t, J=9.3, 1), 4.22 (s, 2), 4.10 (dd, J=6.0, 10.5, 1), 3.86 (d, J=3.3, 1), 3.79 (t, J=9.6, 1), 3.64 (dd, J=3.3, 10.2, 1), 3.04–2.84 (m, 1), 2.93 (s, 3), 2.25–2.05 (m, 1), 2.14 (s, 3), 1.87–1.68 (m, 2), 1.40–1.20 (m, 4), 0.87 (t, J=7.5, 9H). MS (ESPOS): 405.4 [M+H]⁺.

Example 81

Preparation of Phosphoric acid mono-(4,5-dihydroxy-6-{2-methyl-1-[(4-propyl-piperidine-2-carbonyl)-amino]-propyl}-2-methylsulfanyl-tetrahydro-pyran-3-yl) ester

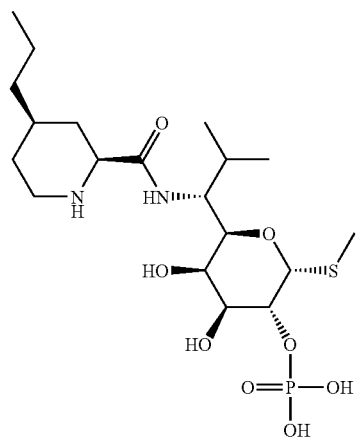

Synthesis of the title compound, 5 (wherein R¹=R²=Me, R³=H, R⁹=4-cis-n-propyl, R¹¹=PO(OH)₂) is detailed in Method V.

¹H NMR (300 MHz, CD₃OD) δ 5.41 (d, J=5.7, 1), 4.53–4.43 (m, 1), 4.10–3.88 (m, 4), 3.73 (dd, J=3.0, 9.6, 1), 3.44–3.30 (m, 2), 2.25–2.10 (m, 2), 2.11 (s, 3), 2.00–1.88 (m, 1), 1.86–1.70 (m, 1), 1.44–1.25 (m, 6), 0.98–0.88 (m, 9). MS (ESPOS): 485.1 [M+H]⁺. MS (ESNEG): 483.0 [M−H]⁻.

Example 82

Preparation of Succinic acid mono-(4,5-dihydroxy-6-{2-methyl-1-[(4-propyl-piperidine-2-carbonyl)-amino]-propyl}-2-methylsulfanyl-tetrahydro-pyran-3-yl)ester

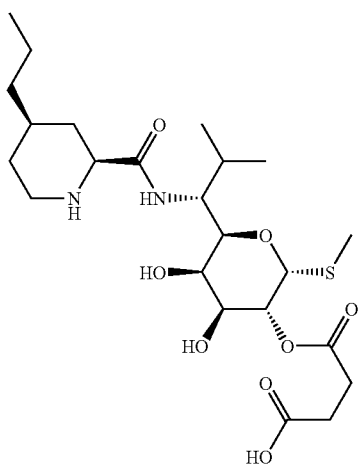

To a suspension of alcohol 18b (wherein $R^1=R^2=Me$, $R^3=H$, $R^9=$4-cis-n-propyl, m=2) (721 mg, 1.16 mmol, 1 equiv), succinic anhydride (174 mg, 1.74 mmol, 1.5 equiv) and DMAP (71 mg, 0.58 mmol, 0.5 equiv) in 1,2-dichloroethane (3.0 mL) at 23° C. was added $Et_3N$ (0.34 mL, 2.43 mmol, 2.1 equiv). After stirring for 2 h at 23° C., the reaction mixture was partitioned between EtOAc (100 mL) and 10% aqueous citric acid (100 mL). The organic layer was separated, washed with brine (50 mL), dried ($MgSO_4$) filtered and concentrated to furnish 840 mg of the desired product 18c (wherein $R^1=R^2=Me$, $R^3=H$, $R^9=$4-cis-n-propyl, $R^{11}=$succinic acid mono ester) (1.16 mmol, 100%) as a white foam. The product was used without further purification.

MS (ESPOS): 745.2 $[M+Na]^+$. MS (ESNEG): 721.2 $[M-H]^-$.

To a solution of protected succinate 18c (wherein $R^1=R^2=Me$, $R^3=H$, $R^9=$4-cis-n-propyl, $R^{11}=$succinic acid mono ester) (251 mg, 0.35 mmol, 1 equiv) in 1,2-dichloroethane (20 mL) at 23° C. was added $H_2O$ (1.0 mL) followed by TFA (8.0 mL). After stirring for 25 min at 23° C., toluene (30 mL) was added and the resulting solution was concentrated to 20 mL volume. This solution was further diluted with toluene (30 mL) then concentrated to dryness. The product was purified by semi-preparative HPLC (Waters Nova-Pak® HR $C_{18}$, 6 μm particle size, 60 Å pore size, 20 mm ID×100 mm, 5–60% acetonitrile in $H_2O$ w/0.1% AcOH over 30 min, 20 mL/min flow rate) to give 94 mg of the title compound as a white solid.

$^1$H NMR (300 MHz, $D_2O$) δ 5.55 (d, J=6.0, 1), 5.15 (dd, J=6.0, 10.5, 1), 4.26–4.16 (m, 2), 3.98–3.87 (m, 3), 3.51 (br d, J=13.5, 1), 3.07 (br t, J=9.9, 1), 2.69 (t, J=7.2, 2), 2.56 (t, J=7.2, 2), 2.28–2.21 (m, 1), 2.16–2.06 (m, 1), 2.13 (s, 3), 2.04–1.96 (m, 1), 1.84–1.70 (m, 1), 1.54–1.28 (m, 6), 0.94–0.84 (m, 9H). MS (ESPOS): 505.1 $[M+H]^+$. MS (ESNEG): 503.2 $[M-H]^-$.

Example 83

Preparation of N-(2-Morpholin-4-yl-ethyl)-succinamic acid 4,5-dihydroxy-6-{2-methyl-1-[(4-propyl-piperidine-2-carbonyl)-amino]-propyl}-2-methylsulfanyl-tetrahydro-pyran-3-yl ester

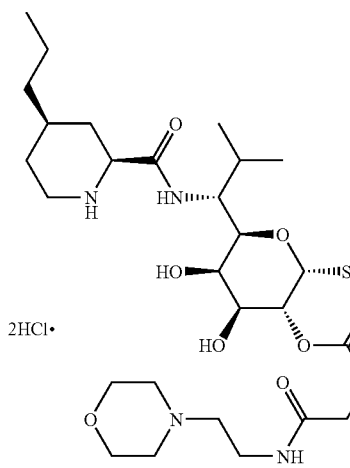

To a solution of protected succinate 18c (wherein $R^1=R^2=Me$, $R^3=H$, $R^9=$4-cis-n-propyl, $R^{11}=$succinic acid mono ester) (222 mg, 0.31 mmol, 1 equiv) in DMF (3.0 mL) at 0° C. was added 4-(2-aminoethyl)morpholine (60 μL, 0.46 mmol, 1.5 equiv) followed by EDC.HCl (89 mg, 0.46 mmol, 1.5 equiv) followed by HOBt.$H_2O$ (56 mg, 0.37 mmol, 1.2 equiv). After stirring for 20 min at 0° C. the reaction was warmed to 23° C. After stirring for a further 16 h, volatiles were removed in vacuo and the residue was partitioned between EtOAc (100 mL) and 1:1 brine/10% aqueous citric acid (100 mL). The organic layer was separated, washed with brine (80 mL), dried ($MgSO_4$) filtered and concentrated to furnish 242 mg (0.29 mmol, 94%) of 18c (wherein $R^1=R^2=Me$, $R^3=H$, $R^9=$4-cis-n-propyl, $R^{11}=$N-(2-Morpholin-4-yl-ethyl)-succinic acid mono ester) as a clear oil. The product was used without further purification.

MS (ESPOS): 835.5 $[M+H]^+$.

To a solution of protected succinate 18c (wherein $R^1=R^2=Me$, $R^3=H$, $R^9=$4-cis-n-propyl, $R^{11}=$N-(2-Morpholin-4-yl-ethyl)-succinic acid mono ester) (242 mg, 0.29 mmol, 1 equiv) in 1,2-dichloroethane (20 mL) at 23° C. was added $H_2O$ (1.0 mL) followed by TFA (8.0 mL). After stirring for 25 min at 23° C., toluene (70 mL) was added and the resulting solution was concentrated to dryness. The product was purified by semi-preparative HPLC (Waters Nova-Pak® HR $C_{18}$, 6 μm particle size, 60 Å pore size, 20 mm ID×100 mm, 5–60% acetonitrile in $H_2O$ w/0.1% HCl over 30 min, 20 mL/min flow rate) to give 47 mg of the title compound as a white solid.

$^1$H NMR (300 MHz, $D_2O$) δ 5.52 (d, J=6.0, 1), 5.12 (dd, J=6.0, 10.5, 1), 4.24–4.16 (m, 2), 3.95–3.85 (m, 3), 3.63 (t, J=6.0, 2), 3.50 (br d, J=13.5, 1), 3.34 (t, J=6.0, 2), 3.05 (dt, J=3.0, 13.5, 1), 2.76 (t, J=6.0, 2), 2.61 (t, J=6.0, 2), 2.28–2.21 (m, 1), 2.16–2.06 (m, 1), 2.11 (s, 3), 2.04–1.96 (m, 1), 1.84–1.70 (m, 1), 1.54–1.28 (m, 6), 0.94–0.84 (m, 9H); morpholine protons are visible but very broad, causing baseline humps between δ4.15–3.14 (8H). MS (ESPOS): 617.5 $[M+H]^+$. MS (ESNEG): 651.2 $[M+Cl]^-$.

Example 84

Preparation of Dimethylamino-acetic acid 4,5-dihydroxy-6-{2-methyl-1-[(4-propyl-piperidine-2-carbonyl)-amino]-propyl}-2-methylsulfanyl-tetrahydro-pyran-3-yl ester

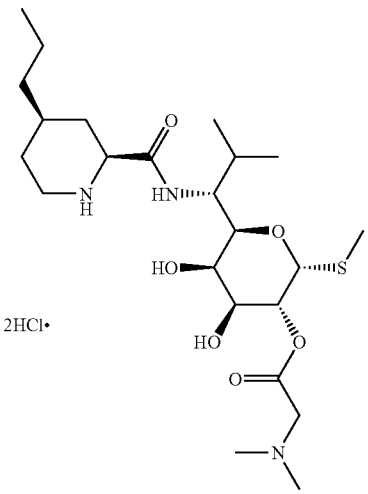

145

To a solution of alcohol 18b (wherein $R^1=R^2=Me$, $R^3=H$, $R^9$=4-cis-n-propyl, m=2) (393 mg, 0.63 mmol, 1 equiv) in $CH_2Cl_2$ (5.0 mL) at 23° C. was added N,N-dimethylglycine (72 mg, 0.70 mmol, 1.1 equiv) followed by DCC (390 mg, 1.90 mmol, 3 equiv) followed by DMAP (54 mg, 0.44 mmol, 0.7 equiv). After stirring for 12 h at 23° C., the reaction mixture was filtered through a PTFE membrane (0.45 µm) with the aid of $CH_2Cl_2$ (20 mL). The filtrate was partitioned between EtOAc (100 mL) and saturated aqueous $NaHCO_3$ (80 mL). The organic layer was separated, washed with 1:1 brine: 10% aqueous citric acid (60 mL), brine (50 mL), dried ($MgSO_4$) filtered and concentrated to furnish 600 mg of brown solid which was determined to contain the desired product. The crude product was used without further purification.

MS (ESPOS): 708.5 $[M+H]^+$.

To a solution of protected glycinate (600 mg, crude) in 1,2-dichloroethane (20 mL) at 23° C. was added $H_2O$ (1.0 mL) followed by TFA (8.0 mL). After stirring for 20 min at 23° C., toluene (100 mL) was added and the resulting solution was concentrated to dryness. The residue was dissolved/suspended in $H_2O$ (10 mL) and filtered through a PTFE membrane (0.45 µm) with the aid of $H_2O$ (10 mL). The resulting solution was purified by semi-preparative HPLC (Waters Nova-Pak® HR $C_{18}$, 6 µm particle size, 60 Å pore size, 20 mm ID×100 mm, 5–60% acetonitrile in $H_2O$ w/0.1% HCl over 30 min, 20 mL/min flow rate) to give 189 mg the title compound as a white solid.

$^1H$ NMR (300 MHz, $D_2O$) δ 5.62 (d, J=6.3, 1), 5.30–5.23 (m, 1), 4.27–4.16 (m, 4), 3.95–3.89 (m, 3), 3.50 (br d, J=12.3, 1), 3.04 (br t, J=13.2, 1), 3.00 (s, 6), 2.28–2.19 (m, 1), 2.16–2.06 (m, 1), 2.13 (s, 3), 2.04–1.96 (m, 1), 1.84–1.70 (m, 1), 1.54–1.28 (m, 6), 0.93–0.83 (m, 9H). MS (ESPOS): 490.4 $[M+H]^+$. MS (ESNEG): 524.2 $[M+Cl]^-$.

Example 85

Preparation of 4-Cyclopropylmethyl-pyrrolidine-2-carboxylic acid [2-methyl-1-(3,4,5-trihydroxy-6-methylsulfanyl-tetrahydro-pyran-2-yl)-propyl]-amide

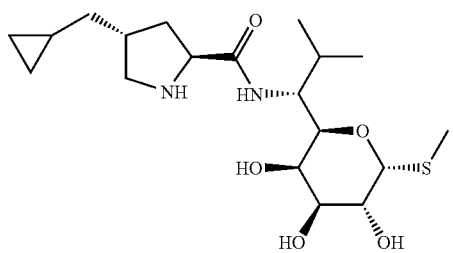

Amino acid intermediate (2S, 4R)-4-cyclopropylmethyl-pyrrolidine-1,2-dicarboxylic acid-1-tert-butyl ester was prepared by the synthetic sequence described by Goodman et al. *Journal of Organic Chemistry*, 2003, 68, 3923.

Lincosamine 2b ($R^1=Me$, $R^2=Me$) was coupled to (2S, 4R)-4-cyclopropylmethyl-pyrrolidine-1,2-dicarboxylic acid-1-tert-butyl ester as depicted in general coupling scheme 11 to provide intermediate 11a ($R^1=R^2=Me$, $R^3=H$, $R^9$=cyclopropylmethyl, $P^1=H$, $P^2$=carboxylic acid-t-butyl ester, m=1) which was deprotected under acidic conditions to provide the title compound.

MS (ESPOS): 403.3 $[M+H]^+$.

146

Example 86

Preparation of 4-(2-Cyclobutyl-ethyl)-pyrrolidine-2-carboxylic acid [2-methyl-1-(3,4,5-trihydroxy-6-methylsulfanyl-tetrahydro-pyran-2-yl)-propyl]-amide

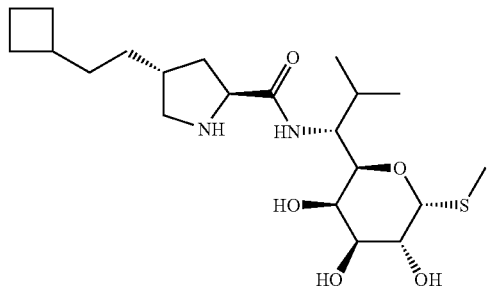

Amino acid intermediate (2S, 4R)-4-(2-cyclobutyl-ethyl)-pyrrolidine-1,2-dicarboxylic acid-1-tert-butyl ester was prepared by general method K by alkylation of pyroglutamic acid ester 7a with (2-bromo-ethylidene)-cyclobutane. The allylic halide (2-bromo-ethylidene)-cyclobutane starting material was prepared from cyclobutanone in two steps as disclosed in U.S. Pat. No. 3,711,555.

Lincosamine 2b ($R^1=Me$, $R^2=Me$) was coupled to protected amino acid 7d ($R^9$=2-cyclobutyl-ethyl) to provide intermediate carbamate 11a ($R^1=R^2=Me$, $R^3=H$, $R^9$=2-cyclobutyl-ethyl, $P^1=H$, $P^2$=carboxylic acid-t-butyl ester, m=1) which was deprotected under acidic conditions to provide the title compound.

MS (ESPOS): 432.3 $[M+H]^+$.

Example 87

Preparation of 4-(2-Cyclopropyl-ethyl)-pyrrolidine-2-carboxylic acid [2-methyl-1-(3,4,5-trihydroxy-6-methylsulfanyl-tetrahydro-pyran-2-yl)-propyl]-amide

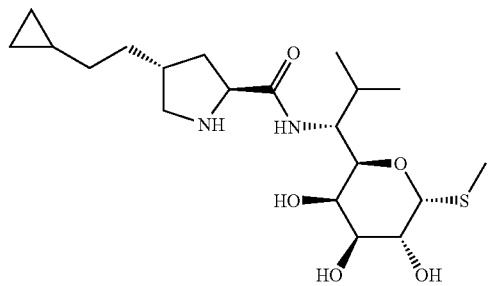

Lincosamine 2b ($R^1=Me$, $R^2=Me$) was coupled to protected amino acid 8c ($R^9$=2-cyclopropyl-ethyl) prepared by method M to provide intermediate carbamate 11a ($R^1=R^2=Me$, $R^3=H$, $R^9$=2-cyclopropyl-ethyl, $P^1=H$, $P^2$=carboxylic acid-t-butyl ester, m=1) which was deprotected under acidic conditions to provide the title compound.

MS (ESPOS): 417.3 $[M+H]^+$.

Example 88

Preparation of 5-Propyl-azepane-2-carboxylic acid [2-methyl-1-(3,4,5-trihydroxy-6-methylsulfanyl-tetrahydro-pyran-2-yl)-propyl]-amide

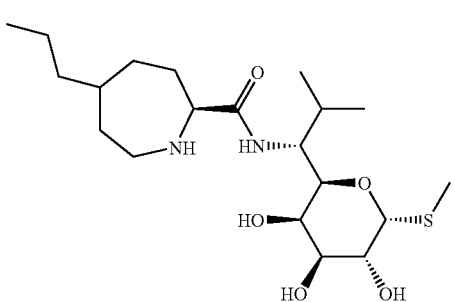

To a solution of protected cyclic amino acid 19f ($R^{12}$=H, $R^{13}$=propyl), (81.4 mg, 0.29 mmol) prepared by general method W, DIEA (100 µL, 0.57 mmol) and 2b ($R^1$=Me, $R^2$=Me) HCl salt (83 mg, 0.29 mmol) in anhydrous DMF (2 mL) and HBTU (120 mg, 0.32 mmol) were added. The resulting reaction mixture was stirred for 6 hours at room temperature under $N_2$ then concentrated to a residue. The residue was taken up in ethyl acetate and washed with 10% citric acid, saturated sodium bicarbonate, and brine. The organic layer was dried and evaporated to dryness to give the desired 1'-N protected lincosamide 11a ($R^1$=Me, $R^2$=Me, $R^3$=H, $R^9$=propyl, $P^1$=H, $P^2$=carboxylic acid-t-butyl ester) (148 mg, 100%).

To a solution of 1'-N protected lincosamide 11a ($R^1$=Me, $R^2$=Me, $R^3$=H, $R^9$=propyl, $P^1$=H, $P^2$=carboxylic acid t-butyl ester) (147 mg, 0.285 mmol) in anhydrous DCE (2.0 mL) was added a solution of TES (10 µL, 0.13 mmol) in TFA (7.5% by weight water) 0.44 mL,). The resulting reaction mixture was stirred for one hour at room temperature under $N_2$. The reaction mixture was concentrated and co-evaporated with toluene to furnish the desired product 5-Propyl-2,3,6,7-tetrahydro-1H-azepine-2-carboxylic acid [2-methyl-1-(3,4,5-trihydroxy-6-methylsulfanyl-tetrahydro-pyran-2-yl)-propyl]-amide (151 mg, 100%) as a white solid which was used in the subsequent reaction without further purification.

MS(ESPOS): 517 [M+H]$^+$.

To a solution of 5-Propyl-2,3,6,7-tetrahydro-1H-azepine-2-carboxylic acid [2-methyl-1-(3,4,5-trihydroxy-6-methylsulfanyl-tetrahydro-pyran-2-yl)-propyl]-amide (112.4 mg, 0.212 mmol) in methanol (8.0 mL) was added 10% Pd/C degusa wet form (100 mg). The resulting suspension was hydrogenated at 50 psi for two days. The reaction mixture was filtered through celite, then a 0.45 µm PTFE membrane and evaporation to dryness to furnish the crude product (96 mg, 88%). The crude product was purified by semi-preparative HPLC (Waters Nova-Pak® HR $C_{18}$, 6 µm particle size, 60 Å pore size, 20 mm ID×100 mm, 5–60% acetonitrile in $H_2O$ w/0.1% AcOH over 30 min, 20 mL/min flow rate) to provide the title compound (23.5 mg, 21.5%) as a white solid.

$^1$H NMR (300 MHz, $CD_3OD$) δ 5.24 (d, 1). 4.20–4.27 (m, 1), 4.04–4.15 (m, 2), 3.84 (d, 1), 3.41–3.55 (m, 2), 3.10–3.18 (t, 1), 1.88–2.20 (m, 6), 1.50–1.61 (m, 2), 1.25–1.39 (m, 3), 0.88–0.89 (m, 6); MS (ESPOS): 419.4 [M+H]$^+$.

Example 89

Preparation of 4-butyl-piperidine-2-carboxylic acid [2-methyl-1-(3,4,5-trihydroxy-6-methylsulfanyl-tetrahydro-pyran-2-yl)-propyl]-amide

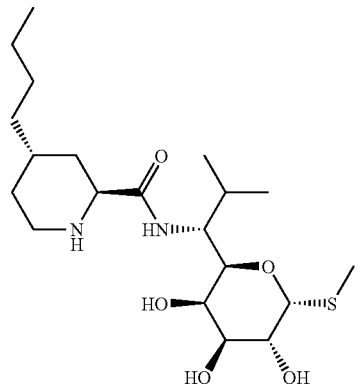

Lincosamine 2b ($R^1$=Me, $R^2$=Me) was coupled to amino acid intermediate 20o, (wherein $R^{13}$=H, $R^{12}$=4-trans-n-butyl, n=1) as prepared by method X, as depicted in general coupling scheme 11 to provide intermediate carbamate 11a ($R^1$=$R^2$=Me, $R^3$=H, $R^9$=4-trans-n-butyl, $P^1$=H, $P^2$=carboxylic acid-t-butyl ester, m=2) which was deprotected under acidic conditions to provide the title compound.

MS (ESPOS): 420 [M+H]$^+$.

Example 90

Preparation of 4-(3-Cyclopentyl-propyl)-piperidine-2-carboxylic acid [2-methyl-1-(3,4,5-trihydroxy-6-methylsulfanyl-tetrahydro-pyran-2-yl)-propyl]-amide

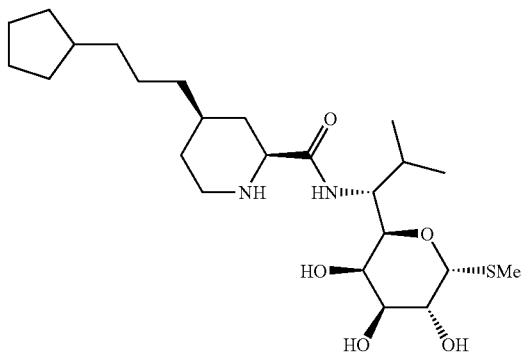

To a mixture of 13c ($R^1$=$R^2$=Me, $R^1$=H, $R^{9'}$=3-Cyclopentyl-prop-1-ynyl) prepared by method Q (100 mg, 0.22 mmol) in MeOH (6 mL) and water (4 mL) were added platinum oxide (200 mg) and conc. HCl (25 µL). The mixture was purged and charged with hydrogen (65 psi) and shaken overnight. The platinum oxide was removed by filtration and the filtrate was evaporated. The residue was purified by column chromatography to give the title compound (26.8 mg, 26%) as a white solid.

$^1$H NMR (300 MHz, $CD_3OD$) δ 5.24 (d, J=5.4, 1), 4.17 (dd, J=3.3, 10.2, 1), 4.10–4.03 (m, 2), 3.81 (d, J=3.3, 1), 3.57–3.48 (m, 2), 3.27–3.20 (m, 1), 2.84–2.74 (m, 1), 2.19–2.13 (m, 1), 2.10 (s, 3), 2.07–2.00 (m, 1), 1.82–1.70

(m, 4), 1.64–1.50 (m, 5), 1.38–1.25 (m, 6), 1.23–1.04 (m, 4), 0.94–0.88 (m, 6). MS (ESPOS): 473.7 [M+H]+.

Example 91

Preparation of 4-(3-Methoxy-propyl)-piperidine-2-carboxylic acid [2-methyl-1-(3,4,5-trihydroxy-6-methylsulfanyl-tetrahydro-pyran-2-yl)-propyl]-amide

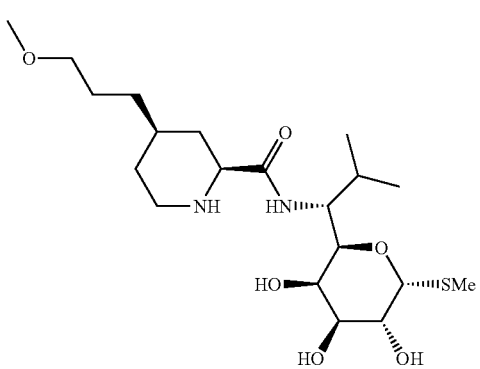

To a dry flask was added 13b ($R^1=R^2$=Me, $R^3$=H) (130 mg, 0.27 mmol, 1 equiv), triphenylphosphine (45.3 mg, 0.17 mmol, 0.64 equiv), copper (I) iodide (32.9 mg, 0.17 mmol, 0.64 equiv), palladium acetate (19.4 mg, 0.086 mmol, 0.32 equiv) and triethylamine (1.5 mL). The mixture was deaerated with nitrogen, followed by addition of methyl propargyl ether (Aldrich) (114 μL, 1.35 mmol, 5 equiv). The mixture was stirred at 50° C. overnight. The solvent was removed under vacuum to give a dark residue. The residue was purified by column chromatography to give 13c ($R^1=R^2$=Me, $R^3$=H, $R^{9'}$=3-Methoxy-prop-1-ynyl) as a yellow syrup (105 mg, 92%).

$^1$H NMR (300 MHz, CDCl$_3$) δ 8.52–8.49 (m, 1), 8.20 (bs, 1), 8.16 (s, 1), 7.46 (dd, J=1.7, 5.0, 1), 5.36 (d, J=5.4, 1), 5.03 (d, J=3, 1), 4.33 (s, 2), 4.27–4.10 (m, 2), 3.98 (d, J=10.2, 1), 3.75 (t, J=3.6, 1), 3.55–3.45 (m, 1), 3.44 (s, 3), 2.67 (d, J=9.9, 1), 2.47–2.40 (m, 1), 2.38 (d, J=5.1, 1), 2.17 (s, 3), 1.04 (d, J=7.2, 3), 0.96 (d, J=6.9, 3); MS (ESPOS): 425.6 [M+H]+; MS (ESNEG): 423.5 [M–H]−.

To a mixture of 13c ($R^1$=Me, $R^{9'}$=3-Methoxy-prop-1-ynyl) (95 mg, 0.22 mmol) in MeOH (6 mL) and water (4 mL) were added platinum oxide (200 mg) and conc. HCl (26 μL). The mixture was purged and charged with hydrogen (65 psi) and shaken overnight. The platinum oxide was removed by filtration and the filtrate was evaporated. The residue was purified by chromatography to give the title compound (8 mg, 8%) as a white solid.

$^1$H NMR (300 MHz, CD$_3$OD) δ 5.23 (d, J=5.7, 1), 4.17 (dd, J=3.2, 10.1, 1), 4.10–4.02 (m, 2), 3.80 (d, J=3.3, 1), 3.53–3.43 (m, 2), 3.39 (t, J=6.5, 2), 3.31 (s, 3), 3.27–3.18 (m, 1), 2.80–2.70 (m, 1), 2.21–2.11 (m, 1), 2.10 (s, 3), 2.06–1.98 (m, 1), 1.82–1.74 (m, 1), 1.65–1.54 (m, 3), 1.38–1.28 (m, 2), 1.23–1.08 (m, 2), 0.93–0.88 (m, 6); MS (ESPOS): 435.7 [M+H]+; MS (ESNEG): 433.6 [M–H]−.

Example 92

Preparation of 4-(3-Ethoxy-propyl)-piperidine-2-carboxylic acid [2-methyl-1-(3,4,5-trihydroxy-6-methylsulfanyl-tetrahydro-pyran-2-yl)-propyl]-amide

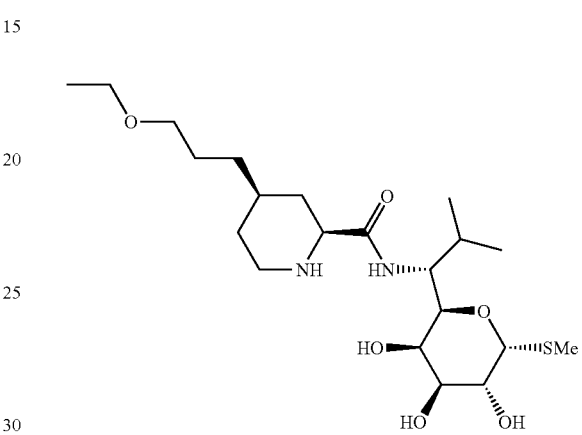

To a dry flask were added 13b ($R^1=R^2$=Me, $R^3$=H) made using method Q (130 mg, 0.27 mmol, 1 equiv), triphenylphosphine (45.3 mg, 0.17 mmol, 0.64 equiv), copper (I) iodide (32.9 mg, 0.17 mmol, 0.64 equiv), palladium acetate (19.4 mg, 0.086 mmol, 0.32 equiv) and triethylamine (1.5 mL). The mixture was deaerated with nitrogen, followed by addition of ethyl propargyl ether (113 mg, 1.35 mmol, 5 equiv). The mixture was stirred at 50° C. overnight. The solvent was removed under vacuum to give a dark residue. The residue was purified by chromatography to give 13c ($R^1=R^2$=Me, $R^3$=H, $R^{9'}$=3-Ethoxy-prop-1-ynyl) (78.1 mg, 66%). MS (ESPOS): 439.6 [M+H]+; MS (ESNEG): 437.5 [M–H]−.

To a mixture of the above syrup in MeOH (6 mL) and water (4 mL) were added platinum oxide (150 mg) and conc. HCl (14 μL). The mixture was purged and charged with hydrogen (65 psi) and shaken overnight. The platinum oxide was removed by filtration and the filtrate was evaporated. The residue was purified by chromatography to give the title compound (20 mg, 25%) as a white solid.

$^1$H NMR (300 MHz, CD$_3$OD) δ 5.25 (d, J=5.7, 1), 4.21 (dd, J=3, 9.9, 1), 4.11–4.04 (m, 2), 3.89–3.80 (m, 2), 3.54–3.38 (m, 6), 3.10–2.98 (m, 1), 2.25–2.12 (m, 2), 2.11 (s, 3), 2.00–1.90 (m, 1), 1.78–1.56 (m, 2), 1.44–1.27 (m, 5), 1.17 (t, J=6.9, 3), 0.94–0.88 (m, 6). MS (ESPOS): 449.6 [M+H]+; MS (ESNEG): 447.7 [M–H]−.

Example 93

Preparation of 4-(3-Propoxy-propyl)-piperidine-2-carboxylic acid [2-methyl-1-(3,4,5-trihydroxy-6-methylsulfanyl-tetrahydro-pyran-2-yl)-propyl]-amide

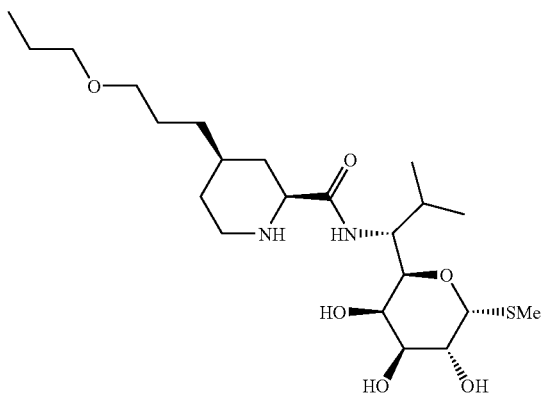

To a dry flask were added 13b ($R^1=R^2$=Me, $R^3$=H) made using method Q (150 mg, 0.31 mmol, 1 equiv), triphenylphosphine (52.4 mg, 0.2 mmol, 0.64 equiv), copper (I) iodide (38.1 mg, 0.2 mmol, 0.64 equiv), palladium acetate (22.4 mg, 0.1 mmol, 0.32 equiv) and triethylamine (1.7 mL). The mixture was deaerated with nitrogen, followed by addition of propargyl ether (117 mg, 1.24 mmol, 4 equiv). The mixture was stirred at 50° C. overnight. The solvent was removed under vacuum to give a dark residue. The residue was purified by chromatography to give 13c ($R^1=R^2$=Me, $R^3$=H, $R^{9'}$=3-prop-1-ynyl-oxy-prop-1-ynyl) (40.9 mg, 29%). MS (ESPOS): 449.2 [M+H]$^+$.

To a mixture of the above syrup in MeOH (6 mL) and water (4 mL) were added platinum oxide (100 mg) and 0.1037 N HCl (0.86 mL, 0.089 mmol, 0.98 equiv). The mixture was purged and charged with hydrogen (65 psi) and shaken overnight. The platinum oxide was removed by filtration and the filtrate was evaporated. The residue was purified by chromatography to give a white solid, the title compound (11 mg, 26%).

$^1$H NMR (300 MHz, CD$_3$OD) δ 5.24 (d, J=5.7, 1), 4.17 (dd, J=3.2, 10.1, 1), 4.10–4.02 (m, 2), 3.79 (d, J=3, 1), 3.53–3.32 (m, 6), 3.25–3.18 (m, 1), 2.80–2.68 (m, 1), 2.22–2.12 (m, 1), 2.10 (s, 3), 2.06–1.98 (m, 1), 1.83–1.74 (m, 1), 1.66–1.08 (m, 9), 0.97–0.86 (m, 9); MS (ESPOS): 463.4 [M+H]$^+$.

Example 94

Preparation of 4-(3-Cyclopropylmethoxy-propyl)-piperidine-2-carboxylic acid [2-methyl-1-(3,4,5-trihydroxy-6-methylsulfanyl-tetrahydro-pyran-2-yl)-propyl]-amide

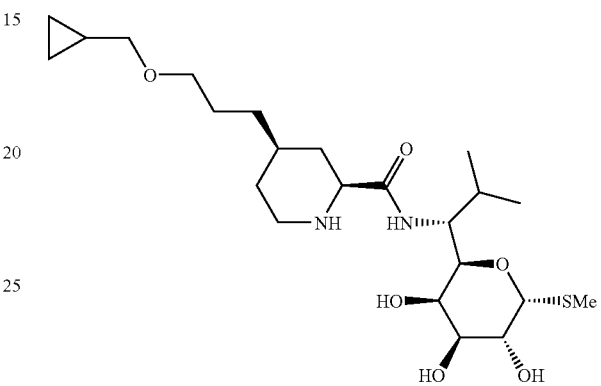

To a dry flask were added 13b ($R^1=R^2$=Me, $R^3$=H) made using method Q (200 mg, 0.42 mmol, 1 equiv), triphenylphosphine (69.7 mg, 0.27 mmol, 0.64 equiv), copper (I) iodide (50.6 mg, 0.27 mmol, 0.64 equiv), palladium acetate (29.8 mg, 0.13 mmol, 0.32 equiv) and triethylamine (2.4 mL). The mixture was deaerated with nitrogen, followed by addition of prop-2-ynyloxymethyl-cyclopropane (229 mg, 2.08 mmol, 5 equiv). The mixture was stirred at 50° C. overnight. The solvent was removed under vacuum to give a dark residue. The residue was purified by chromatography to give a 13c ($R^1=R^2$=Me, $R^3$=H, $R^{9'}$=3-Prop-2-ynyloxymethyl-cyclopropane) (113 mg, 59%). MS (ESPOS): 465.1 [M+H]$^+$.

1e;2qTo a mixture of 13c ($R^1=R^2$=Me, $R^3$=H, $R^{9'}$=3-Prop-2-ynyloxymethyl-cyclopropane) in MeOH (6 mL) and water (4 mL) were added platinum oxide (230 mg) and conc. HCl (19.3 μL, 0.232 mmol, 0.95 equiv). The mixture was purged and charged with hydrogen (65 psi) and shaken overnight. The platinum oxide was removed by filtration and the filtrate was evaporated. The residue was purified by chromatography to give a white solid, the title compound (20 mg, 17%).

$^1$H NMR (300 MHz, CD$_3$OD) δ 5.25 (d, J=5.7, 1), 4.21 (dd, J=3.6, 9.9, 1), 4.11–4.04 (m, 2), 3.87–3.78 (m, 2), 3.54–3.38 (m, 4), 3.08–2.98 (m, 1), 2.27–2.07 (m, 2), 2.11 (s, 3), 2.01–1.91 (m, 1), 1.80–1.25 (m, 9), 1.01–0.85 (m, 7), 0.56–0.47 (m, 2), 0.22–0.15 (m, 2); MS (ESPOS): 475.2 [M+H]$^+$.

Example 95

Preparation of 4-[3-(2-Fluoro-ethoxy)-propyl]-piperidine-2-carboxylic acid [2-methyl-1-(3,4,5-trihydroxy-6-methylsulfanyl-tetrahydro-pyran-2-yl)-propyl]-amide

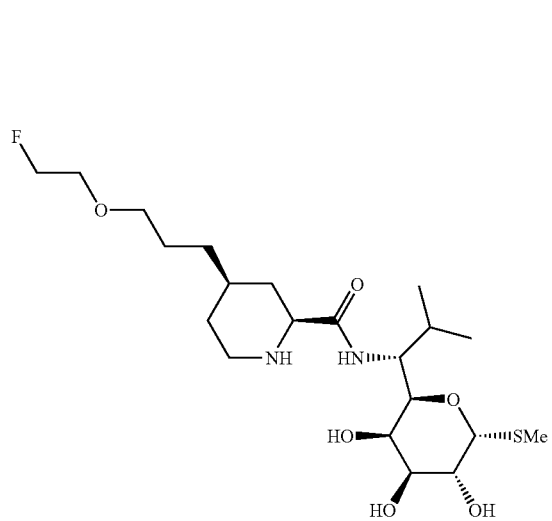

To a dry flask were added 13b ($R^1=R^2=Me$, $R^3=H$) made using method Q (230 mg, 0.48 mmol, 1 equiv), triphenylphosphine (80.1 mg, 0.31 mmol, 0.64 equiv), copper (I) iodide (58.2 mg, 0.31 mmol, 0.64 equiv), palladium acetate (34.2 mg, 0.15 mmol, 0.32 equiv) and triethylamine (2.7 mL). The mixture was deaerated with nitrogen, followed by addition of 3-(2-Fluoro-ethoxy)-propyne (244 mg, 2.39 mmol, 5 equiv). The mixture was stirred at 50° C. overnight. The solvent was removed under vacuum to give a dark residue. The residue was purified by chromatography to give 13c ($R^1=R^2=Me$, $R^3=H$, $R^{9'}=3$-(2-Fluoro-ethoxy)-propyne) (159 mg, 73%).

To a mixture of 13c ($R^1=R^2=Me$, $R^3=H$, $R^{9'}=3$-(2-Fluoro-ethoxy)-propyne) (159 mg, 73%). in MeOH (6 mL) and water (4 mL) were added platinum oxide (320 mg) and conc. HCl (27.7 µL, 0.33 mmol, 0.95 equiv). The mixture was purged and charged with hydrogen (65 psi) and shaken overnight. The platinum oxide was removed by filtration and the filtrate was evaporated. The residue was purified by chromatography to give a white solid, the title compound (25 mg, 15%).

$^1$H NMR (300 MHz, CD$_3$OD) δ 5.24 (d, J=5.7, 1), 4.60–4.56 (m, 1), 4.44–4.39 (m, 1), 4.20 (dd, J=3.3, 9.9, 1), 4.10–4.04 (m, 2), 3.81–3.75 (m, 2), 3.73–3.68 (m, 1), 3.63–3.58 (m, 1), 3.54–3.48 (m, 3), 3.43–3.34 (m, 1), 3.04–2.93 (m, 1), 2.23–2.12 (m, 2), 2.11 (s, 3), 1.98–1.88 (m, 1), 1.78–1.25 (m, 7), 0.95–0.87 (m, 6). MS (ESPOS): 467.2 [M+H]$^+$.

Example 96

Preparation of 4-[3-(3-Fluoro-propoxy)-propyl]-piperidine-2-carboxylic acid [2-methyl-1-(3,4,5-trihydroxy-6-methylsulfanyl-tetrahydro-pyran-2-yl)-propyl]-amide

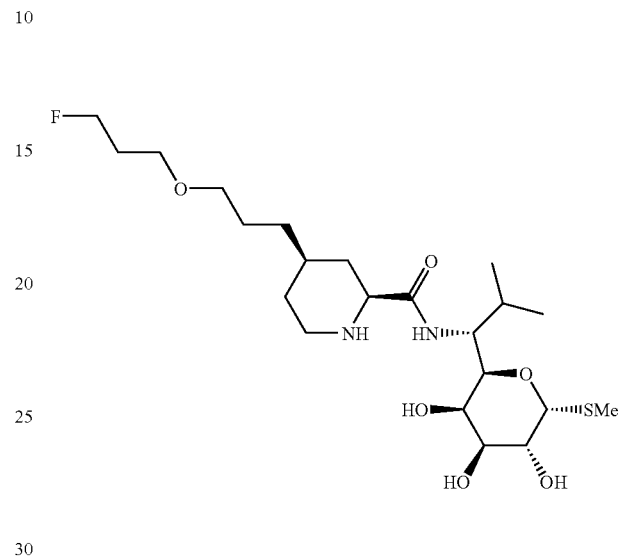

To a dry flask were added 13b ($R^1=R^2=Me$, $R^3=H$) made using method Q (230 mg, 0.48 mmol, 1 equiv), triphenylphosphine (80.1 mg, 0.31 mmol, 0.64 equiv), copper (I) iodide (58.2 mg, 0.31 mmol, 0.64 equiv), palladium acetate (34.2 mg, 0.15 mmol, 0.32 equiv) and triethylamine (2.7 mL). The mixture was deaerated with nitrogen, followed by addition of 3-(3-Fluoro-propoxy)-propyne (277 mg, 2.39 mmol, 5 equiv). The mixture was stirred at 50° C. overnight. The solvent was removed under vacuum to give a dark residue. The residue was purified by chromatography to give 13c ($R^1=R^2=Me$, $R^3=H$, $R^{9'}=3$-(3-Fluoro-propoxy)-propyne) (137 mg, 61%).

To a mixture of the 13c ($R^1=R^2=Me$, $R^3=H$, $R^{9'}=3$-(3-Fluoro-propoxy)-propyne) in MeOH (6 mL) and water (4 mL) were added platinum oxide (280 mg) and conc. HCl (23.1 µL, 0.28 mmol, 0.95 equiv). The mixture was purged and charged with hydrogen (65 psi) and shaken overnight. The platinum oxide was removed by filtration and the filtrate was evaporated. The residue was purified by chromatography to give a white solid, the title compound (23 mg, 16%).

$^1$H NMR (300 MHz, CD$_3$OD) δ 5.24 (d, J=5.7, 1), 4.57 (t, J=5.9, 1), 4.41 (t, J=6, 1), 4.20 (dd, J=3.2, 10.1, 1), 4.10–4.04 (m, 2), 3.81 (d, J=3, 1), 3.74–3.67 (m, 1), 3.55–3.42 (m, 5), 3.38–3.32 (m, 1), 2.98–2.87 (m, 1), 2.23–2.08 (m, 2), 2.11 (s, 3), 2.00–1.83 (m, 3), 1.72–1.57 (m, 2), 1.42–1.20 (m, 5), 0.97–0.87 (m, 6). MS (ESPOS): 481.2 [M+H]$^+$.

Example 97

Preparation of 4-(4-Methoxy-butyl)-piperidine-2-carboxylic acid [2-methyl-1-(3,4,5-trihydroxy-6-methylsulfanyl-tetrahydro-pyran-2-yl)-propyl]-amide

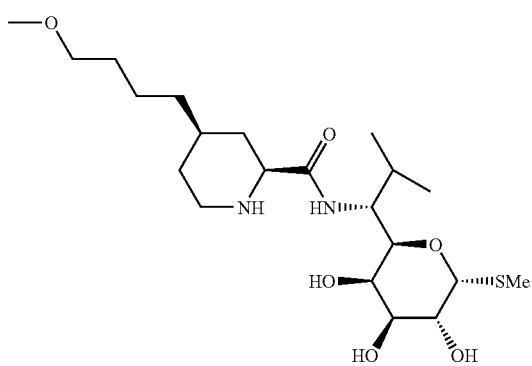

To a mixture of NaH (60%, 37.6 mg, 0.94 mmol, 1 equiv) in dry DMF (2 mL) at 0° C. was added a solution of 14c ($R^9$=4-methoxybutyl) prepared by method R (197 mg, 0.94 mmol, 1 equiv) in DMF (0.5 mL) dropwise. The mixture was stirred at 0° C. for 20 min, then was cooled to −78° C. To the mixture was added iodomethane (134 mg, 0.94 mmol, 1 equiv). The mixture was stirred at 0° C. for 2 hr, then at rt overnight. The reaction mixture was diluted with DCM, washed with brine, dried and concentrated. The residue was purified by preparative TLC to give 4-(4-Methoxy-butyl)-pyridine-2-carboxylic acid methyl ester (43 mg, 21%).

$^1$H NMR (300 MHz, CDCl$_3$) δ 8.61–8.58 (m, 1), 7.97–7.95 (m, 1), 7.29–7.26 (m, 1), 3.98 (s, 3), 3.37 (t, J=6, 2), 3.30 (s, 3), 2.70 (t, J=7.7, 2), 1.78–1.54 (m, 4).

To a mixture of 4-(4-Methoxy-butyl)-pyridine-2-carboxylic acid methyl ester ((107 mg, 0.48 mmol, 1 equiv) in THF (1.5 mL) and water (0.5 mL) was added lithium hydroxide monohydrate (30.2 mg, 0.72 mmol, 1.5 equiv). The mixture was stirred at rt for 4 h and diluted with methanol (20 mL). Then H$^+$ resin (0.4 g) was added and the mixture was shaken for 10 minutes. The resin was washed with methanol (1×), 1:1 acetonitrile/water (1×), and acetonitrile (1×). The product was eluted with 5% TEA in methanol (4×) and acetonitrile (1×). The combined organic solvents were evaporated and co-evaporated with toluene to give 4-(4-Methoxy-butyl)-pyridine-2-carboxylic acid (63.4 mg, 63%): $^1$H NMR (300 MHz, CD$_3$OD) δ 8.47–8.43 (m, 1), 7.98–7.94 (m, 1), 7.43–7.37 (m, 1), 3.41 (t, J=6.3, 2), 3.30 (s, 3), 2.75 (t, J=7.5, 2), 1.80–1.55 (m, 4).

To a solution of 4-(4-Methoxy-butyl)-pyridine-2-carboxylic acid (63.4 mg) in dry DMF (0.75 mL) at 0° C. were added a mixture of 7-Me MTL HCl salt 2b ($R^1$=Me, $R^2$=Me) (87.3 mg, 0.30 mmol, 1 equiv) and DIEA (78 mg, 0.61 mmol, 2 equiv) in DMF (0.75 mL), followed by the addition of HBTU (100 mg, 0.73 mmol, 1 equiv). The reaction mixture was stirred at rt for 3 h. The reaction mixture was evaporated under high vacuum to dryness. The residue was purified by chromatography to give a syrup (88 mg, 65%).

MS (ESPOS): 443.0 [M+H]$^+$; MS (ESNEG): 441.2 [M−H]$^−$.

To a mixture of the above syrup (88 mg, 0.20 mmol, 1 equiv) in MeOH (6 mL) and water (4 mL) were added conc. HCl (15.7 μL, 0.19 mmol, 0.95 equiv) and platinum oxide (180 mg). The mixture was purged and charged with hydrogen (65 psi) and shaken overnight. The platinum oxide was removed by filtration and the filtrate was evaporated to give a residue, which was purified by chromatography to provide the title compound (lower isomer, 20 mg, 22%) as a white solid.

$^1$H NMR (300 MHz, CD$_3$OD) δ 5.22 (d, J=5.7, 1), 4.15 (dd, J=3.2, 10.1, 1), 4.09–4.00 (m, 2), 3.78 (d, J=2.7, 1), 3.49 (dd, J=3.3, 10.5, 1), 3.38 (t, J=6.3, 2), 3.30 (s, 3), 3.26–3.22 (m, 1), 3.16–3.08 (m, 1), 2.66–2.55 (m, 1), 2.20–2.11 (m, 1), 2.09 (s, 3), 1.96–1.87 (m, 1), 1.73–1.64 (m, 1), 1.58–1.22 (m, 7), 1.11–0.97 (m, 2), 0.93–0.86 (m, 6); MS (ESPOS): 449.4 [M+H]$^+$; MS (ESNEG): 447.2 [M−H]$^−$.

Example 98

Preparation of 4-Propoxymethyl-piperidine-2-carboxylic acid [2-methyl-1-(3,4,5-trihydroxy-6-methylsulfanyl-tetrahydro-pyran-2-yl)-propyl]-amide

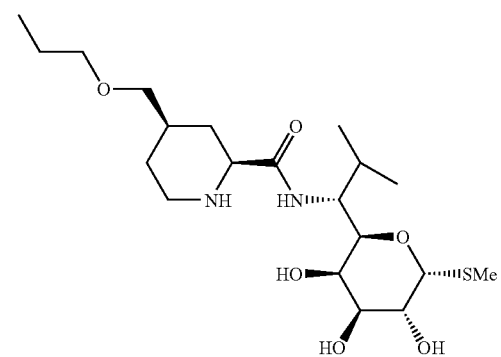

To (1-Oxy-pyridin-4-yl)-methanol (5g, 0.04 mol) in a solution of dichloromethane (10 mL) and pyridine (10 mL) was added acetic anhydride (12.2 mL, 0.12 mol) and the reaction mixture was stirred for 16 h at room temperature. The reaction mixture was then poured into water and extracted with dichloromethane (200 mL) and then washed with brine (100 mL). The crude product obtained (4.27 g, 64%) was taken without purification for the next reaction. To the crude product (4.27 g, 25.6 mmol) in DCM (25 mL) and trimethylsilyl cyanide (3.40 mL, 25.6 mmol), dimethylcarbamyl chloride (2.35 mL, 25.6 mmol) was added slowly and then the reaction mixture was stirred at room temperature over night. Aqueous potassium carbonate (100 mL, 10%) was added and stirred for 10 minutes. Extraction with ethyl acetate followed by removal of solvent resulted in crude product which was purified on silica gel column chromatography using 50% ethyl acetate in hexanes to obtain cyanopyridine 10a ($R^9$=acetoxymethylene) (2.37 g, 48%).

$^1$H NMR (300 MHz, CDCl$_3$) δ 8.68 (d, J=5.7 Hz, 1), 7.65 (s, 1), 7.45 (d, J=5.7 Hz, 1), 5.13 (s, 2), 2.16 (s, 3). MS (ESPOS): 199 [M+Na]$^+$.

To acetic acid 2-cyano-pyridin-4-ylmethyl ester 10a ($R^9$=acetoxymethylene) (2.37 g, 0.012 mol), aqueous hydrochloric acid (50 mL, 6N) was added and refluxed for 16 hr. Stripping off hydrochloric acid and water resulted in acid 10b ($R^9$=acetoxymethylene) (2.47 g, 100%).

$^1$H NMR (300 MHz, CD$_3$OD) δ 8.83 (d, J=5.7 Hz, 1), 8.56 (s, 1), 8.24 (d, J=5.7 Hz, 1), 4.92 (s, 2 MS (ESNEG): 152 [M−H]$^−$.

To the 10b ($R^9$=acetoxymethylene) (2.40 g, 0.012 mol) in methanol (25 mL), water (15 mL) and acetic acid (15 mL), platinum dioxide (1 g) was added and hydrogenated at 50 psi for 16 h. The catalyst was filtered and the solvent was removed to obtain the hydrogenated product (2.50 g, 100%) which was taken as such for the next reaction. To the crude product from previous reaction in dioxane (30 mL) and water (30 mL), sodium hydroxide (2.2 g, 0.05 mol) and di t-butyldicarbonate (12 g, 0.05 mol) was added and stirred at room temperature for 16 h. The reaction mixture was then extracted with ethyl acetate (100 mL) to remove any excess Boc-anhydride. The aqueous phase was then carefully acidified with dil. HCl (1N) and extracted with ethyl acetate. The crude product obtained on removal of solvent was purified on silica gel column chromatography using ethyl acetate to obtain the 4-hydroxymethyl-piperidine-1,2-dicarboxylic acid 1-tert-butyl ester (0.62 g, 20%).

$^1$H NMR (300 MHz, CD$_3$OD) δ 4.27 (d, J=6.3 Hz, 1), 3.37–3.65 (m, 4), 2.05 (m, 1), 1.70–1.84 (m, 4), 1.52 (s, 9). MS (ESNEG): 258 [M−H]$^-$.

To the 4-hydroxymethyl-piperidine-1,2-dicarboxylic acid 1-tert-butyl ester (100 mg, 0.39 mmol) in DMF (5 mL), sodium hydride (30 mg, 0.67 mmol) was added and stirred at 0° C. for 10 minutes. Propyl bromide (0.5 mL, 4.0 mmol) (0.5 mL, 0.35 mmol) was added and stirred at room temperature for 30 minutes and then at 50–60° C. for 2 h. DMF was removed, water (50 mL) was added and extracted with ethyl acetate (50 mL). The product obtained on removal of solvent was purified on column chromatography using 50% ethyl acetate in hexanes to provide 4-Butoxymethyl-piperidine-1,2-dicarboxylic acid 2-butyl ester 1-tert-butyl ester (100 mg, 75%).

$^1$H NMR (300 MHz, CDCl$_3$) δ 4.10 (q, J=6.6, 7.2 Hz, 4), 3.46–3.53 (m, 2), 3.25–3.36 (m, 2), 2.05 (m, 2), 1.44–1.75 (m, 6), 1.45 (s, 9), 0.88–0.98 (m, 6). MS (ESPOS): 366 [M+Na]$^+$.

To the 4-Butoxymethyl-piperidine-1,2-dicarboxylic acid 2-butyl ester 1-tert-butyl ester (100 mg, 0.29 mmol) in THF (5 mL), lithium hydroxide (122 mg, 2.90 mmol) in water (1 mL) was added and stirred at room temperature for 16 h. It was then poured into water and extracted with ethyl acetate and discarded. The water layer was acidified and then extracted with ethyl acetate (50 mL). Removal of solvent gave the acid which was taken as such for the next coupling reaction. To 4-Butoxymethyl-piperidine-1,2-dicarboxylic acid 1-tert-butyl ester (88 mg, 0.29 mmol) in DMF (3 mL), the amine 2b (R$^1$=Me, R$^2$=Me) (100 mg, 0.34 mmol), HBTU (132 mg, 0.34 mmol) and DIEA (0.1 mL, 0.58 mmol) was added and stirred at room temperature for 3 h. DMF was removed and product was purified on silica gel column chromatography using 50% ethyl acetate in hexanes provided the Boc protected lincosamide (R$^9$=4-Butoxymethyl) (77 mg, 49%).

$^1$H NMR (300 MHz, CD$_3$OD) δ 5.25 (m, 1), 4.47–4.64 (m, 2), 4.41 (t, J=6.0 Hz, 1), 4.26 (s, 1), 3.994.12 (m, 4), 3.85 (d, J=3.3 Hz, 1), 3.50–3.54 (m, 2), 3.31–3.36 (m, 2), 2.14–2.2.19 (m, 2), 1.81 (m, 3), 1.53 (m, 2), 1.45 (bs, 12), 0.88–0.98 (m, 9). MS (ESPOS): 535 [M+H]$^+$.

To the above Boc protected lincosamide (R$^9$=4-Butoxymethyl) (77 mg, 0.14 mmol), 30% TFA in DCE (30 mL), triethylsilane (1 mL) and water (1 mL) was added and stirred at room temperature for 1 hr. The residue obtained on removing the solvent was chromatographed using 20% methanol in DCM to obtain the title compound (10 mg, 16%) as a white solid.

$^1$H NMR (300 MHz, CD$_3$OD) δ 5.25 (d, J=5.7 Hz, 1), 4.05–4.19 (m, 3), 3.74–3.86 (m, 2), 3.50–3.54 (m, 2), 3.40–3.54 (m, 4), 2.14 (m, 2), 2.10 (s, 3), 2.00 (m, 1), 1.71–1.75 (m, 2), 1.54–1.61 (m, 2), 1.31 (m, 1), 0.89–0.94 (m, 9). MS (ESPOS): 435 [M+H]$^+$.

Example 99

Preparation of 4-(3-Fluoro-propoxymethyl)-piperidine-2-carboxylic acid [2-methyl-1-(3,4,5-trihydroxy-6-methylsulfanyl-tetrahydro-pyran-2-yl)-propyl]-amide

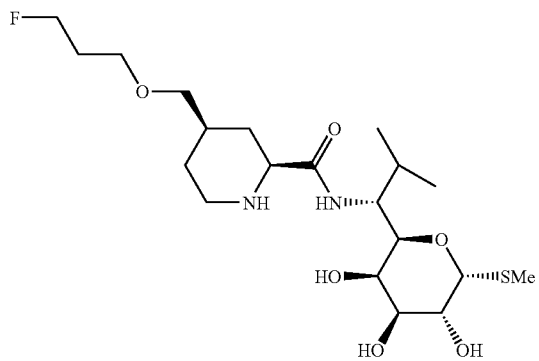

The title compound was prepared by the same reaction sequence described in example 98 starting from Boc protected 4-hydroxymethyl-piperidine-1,2-dicarboxylic acid 1-tert-butyl ester substituting the reagent 3-fluoropropyl bromide in the alkylation.

$^1$H NMR (300 MHz, CD$_3$OD) δ 5.22 (d, J=5.4 Hz, 1), 4.58 (q, J=3.9, 6.9 Hz, 1), 4.22 (q, J=5.1, 5.7 Hz, 1), 3.90–4.16 (m, 3), 3.82–3.86 (m, 1), 3.74 (d, J=2.1 Hz, 1), 3.47–3.59 (m, 3), 3.35–3.39 (m, 1), 3.04 (m, 2), 2.07 (s, 3), 1.85–1.98 (m, 4), 1.47–1.56 (m, 2), 1.02–1.12 (m, 2), 0.90–0.96 (m, 6). MS (ESPOS): 453 [M+H]$^+$.

Example 100

Preparation of 1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide

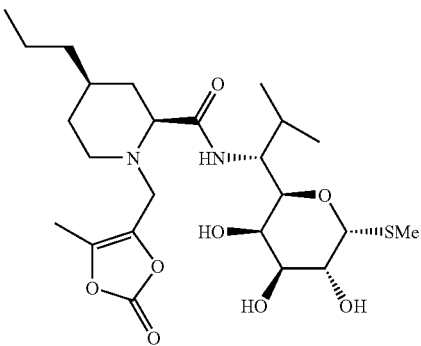

To the title compound from example 17 (50 mg, 0.123 mmol) in DMF (5 mL) at room temperature, sodium carbonate (25 mg, 0.246 mmol) and bromomethyl dioxalenone, prepared as described in J. Alexander, et. al. *J. Med. Chem*, 1996, 39, 480–486. (47 mg, 0.246 mmol) were added and stirred over night at room temperature. DMF was removed and the crude material was loaded into a silica gel column and eluted with a mixture of methanol (5%) and dichloromethane to obtain the title compound as a white solid (30 mg, 48%).

TLC: R$_f$=0.5 (EtOAc). MS (ESPOS): 517 [M+H]$^+$; $^1$H NMR (CD$_3$OD, 200 MHz): δ 5.22 (d, J=3.8 Hz, 1), 4.05–4.20 (m, 3), 3.86 (d, J=2 Hz, 1), 3.51–3.60 (m, 2), 2.88–3.01 (m, 2), 2.17 (m, 2), 2.13 (s, 3), 2.10 (s, 3), 1.88 (d,

J=6.2 Hz, 1), 1.70 (d, J=8.2 Hz, 1), 1.21–1.35 (m, 6), 0.90–0.96 (m, 9).

Example 101

Preparation of 2-[2-Methyl-1-(3,4,5-trihydroxy-6-methylsulfanyl-tetrahydro-pyran-2-yl)-propylcarbamoyl]-4-propyl-piperidine-1-carboxylic acid 5-methyl-2-oxo-[1,3]dioxol-4-ylmethyl ester

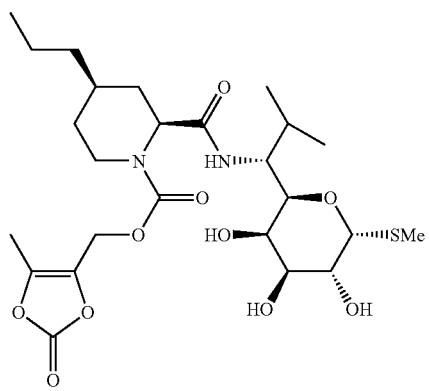

To the title compound from example 17 (50 mg, 0.123 mmol) in DMF (5 mL) at room temperature, potassium bicarbonate (20 mg, 0.30 mmol) and p-nitrophenyl dioxalenone, prepared as described in F. Sakamoto, et. al, *Chem. Pharm. Bull.* 1984, 32 (6), 2241–2348. (36 mg, 0.123 mmol) were added and stirred over night at room temperature. DMF was removed and the crude material was loaded into a silica gel column and eluted with a mixture of methanol (5%) and dichloromethane to obtain the title compound (30 mg, 44%) as a white solid.

TLC: Rf=0.5 (EtOAc). MS (ESPOS): 561 [M+H]$^+$; $^1$H NMR (CD$_3$OD, 200 MHz): δ 5.23 (d, J=3.8 Hz, 1), 4.92 (m, 2), 4.21–4.24 (m, 1), 4.07–4.13 (m, 3), 3.98 (m, 1), 3.57 (d, J=2.2 Hz, 1), 3.54 (d, J=2.2 Hz, 1), 2.16 (s, 3), 2.08 (s, 3), 1.95–1.97 (m, 2), 1.76–1.85 (m, 2), 1.60 (m, 1), 1.32 (m, 4), 0.88–0.98 (m, 9).

Example 102

Preparation of Hexadecanoic acid 4,5-dihydroxy-6-{2-methyl-1-[(4-propyl-piperidine-2-carbonyl)-amino]-propyl}-2-methylsulfanyl-tetrahydro-pyran-3-yl ester

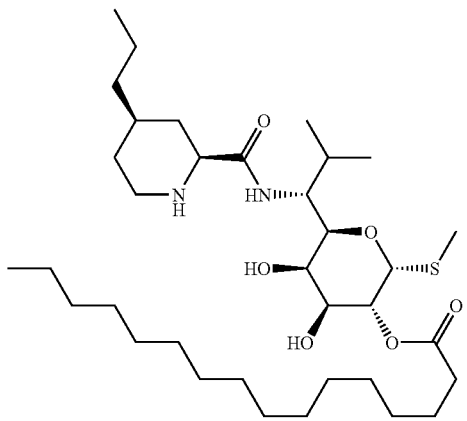

The title compound, 5 (wherein R$^1$=R$^2$=Me, R$^3$=H, R$^6$=H, R$^{9=4}$-cis-n-propyl, R$^{11}$=CO(CH$_2$)$_{14}$CH$_3$, m=2) may be prepared employing method V by treatment of alcohol 18b (wherein R$^1$=R$^2$=Me, R$^3$=H, R$^6$=Boc, R$^9$=4-cis-n-Pr, and m=2) with the acylating reagent palmitoyl chloride.

Example 103

Preparation of 1-(1-Methyl-3-oxo-but-1-enyl)-4-propyl-piperidine-2-carboxylic acid [2-methyl-1-(3,4,5-trihydroxy-6-methylsulfanyl-tetrahydro-pyran-2-yl)-propyl]-amide

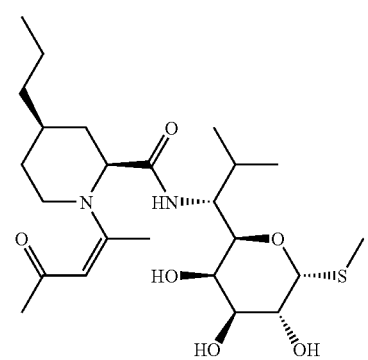

The title compound may be prepared employing the method described by Jensen et al, Journal of Medicinal Chemistry 1980, 23, by treatment of 1 (wherein R$^1$=R$^2$=Me, R$^3$=H, R$^6$=H, R$^9$=4-cis-n-propyl, and m=2) with acetylacetone.

Example 104

Preparation of 2-[2-Methyl-1-(3,4,5-trihydroxy-6-methylsulfanyl-tetrahydro-pyran-2-yl)-propylcarbamoyl]4-propyl-piperidine-1-carboxylic acid 1-acetoxy-ethyl ester

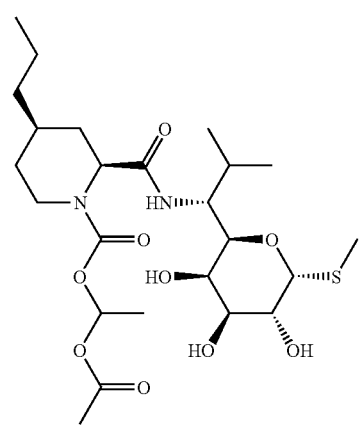

The title compound may be prepared employing the method described by Alexander et al, Journal of Medicinal Chemistry 1988, 31, 318–322, by treatment of 1 (wherein $R^1=R^2=$Me, $R^3=$H, $R^6=$H, $R^9=$4-cis-n-propyl, and m=2) with the acylating reagent Acetic acid 1-(4-nitro-phenoxycarbonyloxy)-ethyl ester.

Example 105

Preparation of 2-[2-Methyl-1-(3,4,5-trihydroxy-6-methylsulfanyl-tetrahydro-pyran-2-yl)-propylcarbamoyl]4-propyl-piperidine-1-carboxylic acid 2-amino-3-methyl-pentanoyloxymethyl ester

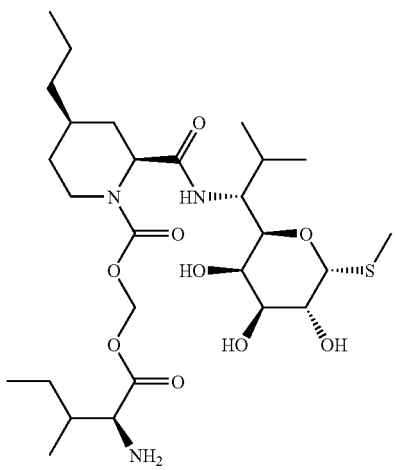

The title compound may be prepared employing the method described by Alexander et al, Journal of Medicinal Chemistry 1988, 31, 318–322, by treatment of 1 (wherein $R^1=R^2=$Me, $R^3=$H, $R^6=$H, $R^9=$4-cis-n-propyl, and m=2) with the appropriate acylating reagent (2-tert-butoxycarbonylamino-3-methyl-pentanoic acid 4-nitro-phenoxycarbonyloxymethyl ester), followed by TFA deprotection.

Example 106

Preparation of 2-[2-Methyl-1-(3,4,5-trihydroxy-6-methylsulfanyl-tetrahydro-pyran-2-yl)-propylcarbamoyl]4-propyl-piperidine-1-carboxylic acid piperidine-4-carbonyloxymethyl ester

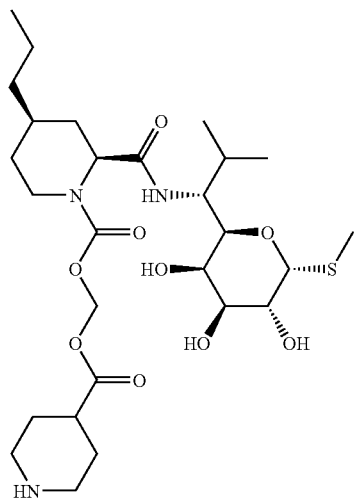

The title compound may be prepared employing the method described by Alexander et al, Journal of Medicinal Chemistry 1988, 31, 318–322, by treatment of 1 (wherein $R^1=R^2=$Me, $R^3=$H, $R^6=$H, $R^9=$4-cis-n-propyl, and m=2) with the appropriate acylating reagent (piperidine-1,4-dicarboxylic acid 1-tert-butyl ester 4-(4-nitro-phenoxycarbonyloxymethyl) ester), followed by TFA deprotection.

Example 107

Preparation of 1-(Propionylamino-methyl)-4-propyl-piperidine-2-carboxylic acid [2-methyl-1-(3,4,5-trihydroxy-6-methylsulfanyl-tetrahydro-pyran-2-yl)-propyl]-amide

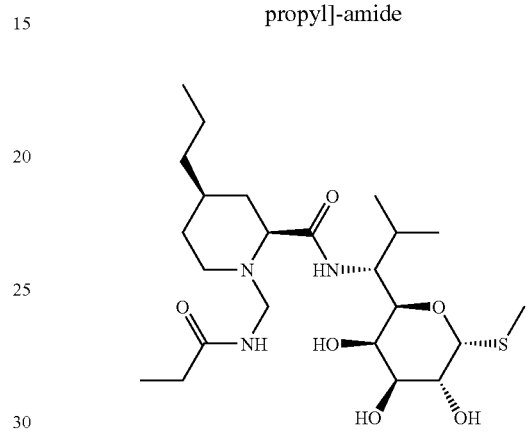

The title compound may be prepared from 1 (wherein $R^1=R^2=$Me, $R^3=$H, $R^6=$H, $R^9=$4-cis-n-propyl, and m=2) employing the method described by Bundgaard et al, Journal of Pharmaceutical Sciences, 1980, 69 (1), 44–46.

Example 108

Preparation of N-{2-[2-Methyl-1-(3,4,5-trihydroxy-6-methylsulfanyl-tetrahydro-pyran-2-yl)-propylcarbamoyl]-4-propyl-piperidin-1-ylmethyl}-nicotinamide

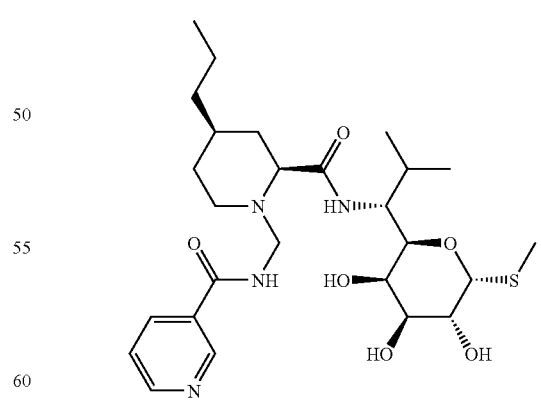

The title compound may be prepared from 1 (wherein $R^1=R^2=$Me, $R^3=$H, $R^6=$H, $R^9=$4-cis-n-propyl, and m=2) employing the method described by Bundgaard et al, Journal of Pharmaceutical Sciences, 1980, 69 (1), 44–46.

Example 109

Preparation of 1-(2-Amino-propionyl)-4-propyl-piperidine-2-carboxylic acid [2-methyl-1-(3,4,5-trihydroxy-6-methylsulfanyl-tetrahydro-pyran-2-yl)-propyl]-amide

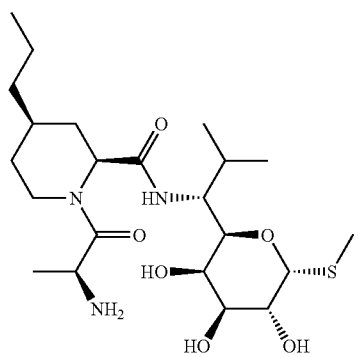

The title compound may be prepared employing the method described by Weiss et al, Antimicrobial Agents and Chemotherapy, 1999, 43 (3), 460–464, by treatment of 1 (wherein $R^1=R^2=Me$, $R^3=H$, $R^6=H$, $R^9=$4-cis-n-propyl, and m=2) with Boc-alanine and HATU in the presence of DIEA in an appropriate solvent followed by TFA deprotection.

Example 110

Preparation of 1-(2-Amino-3-phenyl-propionyl)-4-propyl-piperidine-2-carboxylic acid [2-methyl-1-(3,4,5-trihydroxy-6-methylsulfanyl-tetrahydro-pyran-2-yl)-propyl]-amide

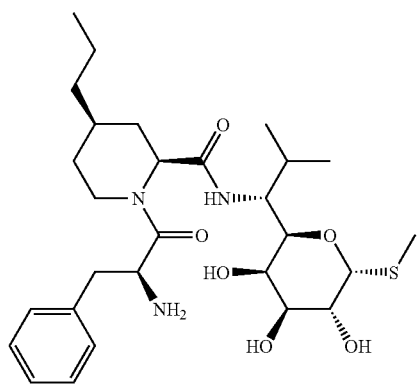

The title compound may be prepared employing the method described by Weiss et al, Antimicrobial Agents and Chemotherapy, 1999, 43 (3), 460–464, by treatment of 1 (wherein $R^1=R^2=Me$, $R^3=H$, $R^6=H$, $R^9=$4-cis-n-propyl, and m=2) with Boc-phenylalanine and HATU in the presence of DIEA in an appropriate solvent followed by TFA deprotection.

Example 111

Preparation of 1-(2-Amino-3-methyl-pentanoyl)-4-propyl-piperidine-2-carboxylic acid [2-methyl-1-(3,4,5-trihydroxy-6-methylsulfanyl-tetrahydro-pyran-2-yl)-propyl]-amide

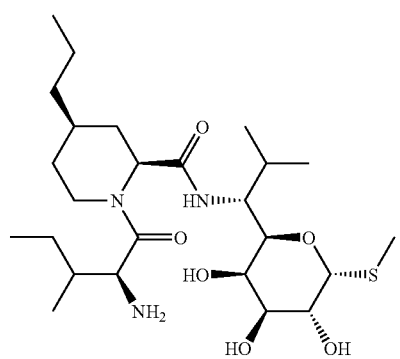

The title compound may be prepared employing the method described by Weiss et al, Antimicrobial Agents and Chemotherapy, 1999, 43 (3), 460–464, by treatment of 1 (wherein $R^1=R^2=Me$, $R^3=H$, $R^6=H$, $R^9=$4-cis-n-propyl, and m=2) with Boc-isoleucine and HATU in the presence of DIEA in an appropriate solvent followed by TFA deprotection.

Example 112

Preparation of 1-(2-Amino-3-methyl-butyryl)-4-propyl-piperidine-2-carboxylic acid [2-methyl-1-(3,4,5-trihydroxy-6-methylsulfanyl-tetrahydro-pyran-2-yl)-propyl]-amide

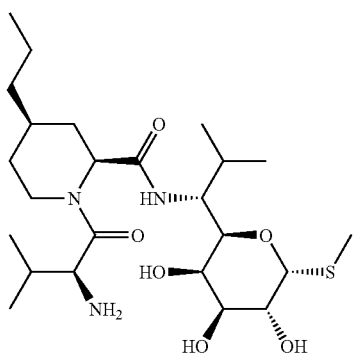

The title compound may be prepared employing the method described by Weiss et al, Antimicrobial Agents and Chemotherapy, 1999, 43 (3), 460–464, by treatment of 1 (wherein $R^1=R^2=Me$, $R^3=H$, $R^6=H$, $R^9=$4-cis-n-propyl, and m=2) with with Boc-valine and HATU in the presence of DIEA in an appropriate solvent followed by TFA deprotection.

Example 113

Preparation of 1-(1-Methyl-1,4-dihydro-pyridine-3-carbonyl)-4-propyl-piperidine-2-carboxylic acid [2-methyl-1-(3,4,5-trihydroxy-6-methylsulfanyl-tetrahydro-pyran-2-yl)-propyl]-amide

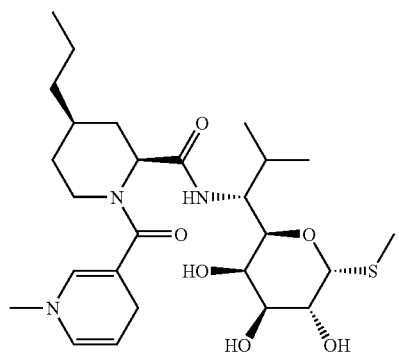

The title compound may be prepared from 1 (wherein R$^1$=R$^2$=Me, R$^3$=H, R$^6$=H, R$^9$=4-cis-n-propyl, and m=2) employing the method described by Shek et al, Journal of Medicinal Chemistry 1976, 19 (1), 108–112.

Example 114

Preparation of 2-[2-Methyl-1-(3,4,5-trihydroxy-6-methylsulfanyl-tetrahydro-pyran-2-yl)-propylcarbamoyl]4-propyl-piperidine-1-carboxylic acid 1-methyl-1,2,3,6-tetrahydro-pyridin-4-yl ester

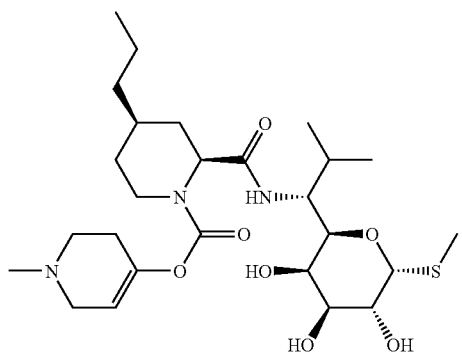

The title compound may be prepared from 1 (wherein R$^1$=R$^2$=Me, R$^3$=H, R$^6$=H, R$^9$=4-cis-n-propyl, and m=2) employing the method described by Flaherty et al, Journal of Medicinal Chemistry 1996, 39, 4756–4761.

Example 115

4-Cyclohexylmethyl-piperidine-2-carboxylic acid [2-methyl-1-(3,4,5-trihydroxy-6-methylsulfanyl-tetrahydro-pyran-2-yl)-propyl]-amide

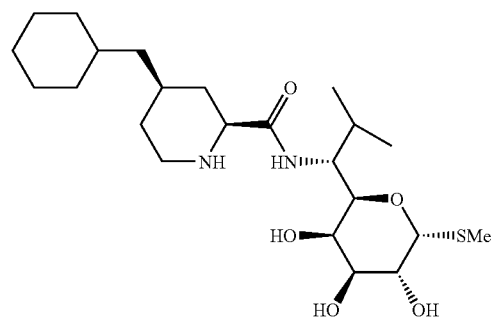

The intermediate 10b, (R$^9$=benzyl) was made by employing method P using 4-benzylpyridine as the starting material.

$^1$H NMR (300 MHz, CD$_3$OD) δ 8.78 (m, 1), 8.40 (s, 1), 8.03 (m, 1), 7.26–7.40 (m, 5), 4.39 (s, 2); MS (ESNEG): 212 [M−1]$^-$.

Lincosamine 2b (R$^1$=Me, R$^2$=Me) was coupled to 4-Benzylpyridine-2-carboxylic acid 10b (R$^9$=4-benzyl) as depicted in general coupling scheme 11 to provide intermediate 11b (R$^1$=Me, R$^2$=Me, R$^3$=H, R$^9$=benzyl, P$^1$=H), which was reduced by catalytic hydrogenation to the title compound.

$^1$H NMR (300 MHz, CD$_3$OD) δ 5.24 (d, J=5.4, 1), 4.03–4.19 (m, 4), 3.78 (m, 1), 3.48–3.52 (m, 2), 3.21–3.24 (m, 2), 2.77 (t, J=12.6, 1), 2.17 (m, 2), 2.15 (s, 3), 1.98–2.02 (m 1), 1.70–1.74 (m, 60), 1.12–1.37 (m, 8), 0.91 (d, J=6.9, 6); MS [ESPOS]: 459 [M+H]+.

Example 116

4-(2-Propyloxyethyl)-piperidine-2-carboxylic acid [2-methyl-1-(3,4,5-trihydroxy-6-methylsulfanyl-tetrahydro-pyran-2-yl)-propyl]-amide

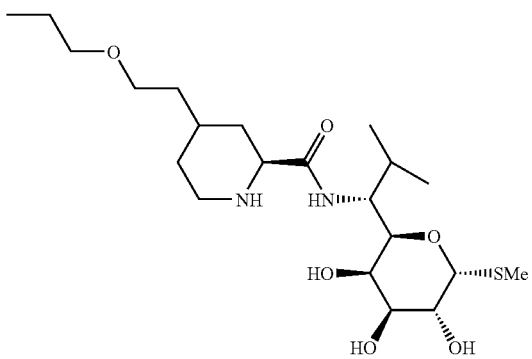

To a solution of 4-(2-hydroxyethyl)-pyridine (2.15 g, 17.48 mmol, 1 equiv) in glacial acetic acid (11.7 mL) was added 30% hydrogen peroxide (1.98 mL, 17.48 mmol, 1 equiv). The reaction mixture was refluxed overnight and concentrated. The residue was dissolved in DCM, and dried (MgSO4). Solvent was evaporated under vacuum and then again co-evaporated with toluene to give the N-oxide intermediate as a syrup.

A solution of the above syrup in DCM (17 mL) was added to trimethylsilyl cyanide (2.95 mL, 22.14, 1.27 equiv) at r.t. and then cooled to 0° C. To the mixture was added dropwise a solution of dimethylcarbamyl chloride in DCM (4.4 mL) over 10 min. The reaction mixture was stirred at r.t. overnight. A solution of 10% aqueous potassium carbonate (17.5 mL) was added dropwise and the mixture was stirred for 10 min. The organic layer was separated and the aqueous layer was extracted with DCM (2x). The combined organic layers were dried and concentrated. The residue was purified by chromatography to give the nitrile intermediate 10a ($R^9$=2-hydroxyethyl) (0.82 g, 25%) as a yellow oil.

$^1$H NMR (300 MHz, CDCl$_3$) δ 8.61 (d, J=5.1, 1), 7.56 (d, J=0.6, 1), 7.39–7.34 (m, 1), 4.31 (t, J=6.5, 2), 2.99(t, J=6.3, 2), 2.02 (s, 3).

A solution of above nitrile 10a ($R^9$=2-hydroxyethyl) (0.82 g, 4.32 mmol) in 6 N HCl (2 mL) was refluxed overnight. The reaction mixture was concentrated under vacuum. MeOH (18 mL) and water (18 mL) were added, followed by conc. aq. HCl (2.2 mL) and platinum oxide (450 mg). The mixture was purged and charged with hydrogen (1 atm) and stirred overnight. The platinum oxide was removed by filtration and the filtrate evaporated under vacuum to afford the intermediate pipecolic acid intermediate.

The above pipecolic acid intermediate was taken in 2N NaOH (5 mL) and t-butanol (5 mL), and di-t-butyl dicarbonate (1.33 g, 6.1 mmol) was added with stirring. The mixture was stirred at r.t. overnight. The solvent was removed under vacuum. The residue was diluted with water and organic layer washed with ether. The aqueous layer was acidified with 2N HCl to pH=2.0, and extracted with ethyl acetate (twice). The combined organic layers were dried (MgSO$_4$) and concentrated under vacuum. The crude N-Boc pipecolinic acid intermediate was purified by chromatography to give 4-(2-hydroxyethyl)-piperidine-1,2-carboxylic acid-1-tert-butyl ester (210 mg, 18%) as a clear syrup.

$^1$H NMR (300 MHz, CDCl$_3$) δ 4.45–4.38 (m, 1H), 3.64 (t, J=7.1, 2), 3.63–3.56 (m, 1), 3.34–3.24 (m, 1), 1.99–1.94 (m, 2), 1.85–1.65 (m, 2), 1.62–1.53 (m, 2), 1.48–1.43 (m, 1), 1.42 (s, 9).

Sodium hydride (60% in oil, 28.9 mg, 0.72 mmol, 2 equiv) was washed with hexane (2x), and dried under high vacuum. A solution of 4-(2-hydroxyethyl)-piperidine-1,2-carboxylic acid-1-tert-butyl ester (98.6 mg, 0.36, 1 equiv) in DMF (0.8 mL) was added to a mixture of the sodium hydride in DMF (0.7 mL) at 0° C. The mixture was stirred at 0° C. for 5 min, and then at r.t. for 20 min. 1-Bromopropane (0.33 mL, 3.6 mmol, 10 equiv) was added and the mixture stirred at r.t. for 3 h and then quenched with water. The mixture was diluted with ethyl acetate, washed with water (1x), brine (1x), dried and concentrated to give a clear oil, which was purified by chromatography to give the ether intermediate 4-(2-propyloxyethyl)-piperidine-1,2-carboxylic acid-1-tert-butyl ester-2-propyl ester (35.8 mg, 28%).

$^1$H NMR (300 MHz, CDCl$_3$) δ 4.36–4.29 (m, 1), 4.05 (t, J=6.8, 2), 3.65–3.53 (m, 1), 3.39 (t, J=6.5, 2), 3.32 (t, J=6.8, 2), 3.33–3.25 (m, 1), 2.03–1.92 (m, 1), 1.87–1.70 (m, 3), 1.68–1.48 (m, 6), 1.41 (s, 9), 1.41–1.34 (m, 1), 0.97–0.84 (m, 6); MS (ESPOS): 258.2 [M-Boc+H]$^+$.

To a solution of ether intermediate 4-(2-propyloxyethyl)-piperidine-1,2-carboxylic acid-1-tert-butyl ester-2-propyl ester (73 mg, 0.20 mmol, 1 equiv) in dioxane (1 mL) and water (0.8 mL) was added lithium hydroxide monohydrate (84 mg, 2 mmol, 10 equiv). The reaction mixture was stirred at r.t. overnight. The solvent was removed under vacuum. The residue was diluted with water, washed with ether. The aqueous layer was taken up in ethyl acetate, and partitioned with 10% citric acid. The organic layer was washed with water (1x), brine (1x), dried and concentrated to give the acid intermediate 4-(2-propyloxyethyl)-piperidine-1,2-carboxylic acid-1-tert-butyl ester (61.1 mg, 97%) as a syrup.

$^1$H NMR (300 MHz, CDCl$_3$) δ 4.37–4.30 (m, 1), 3.61–3.50 (m, 1), 3.42 (t, J=6.5, 2), 3.34 (t, J=6.8, 2), 3.42–3.35 (m, 1), 2.06–1.95 (m, 1), 1.88–1.70 (m, 3), 1.65–1.50 (m, 4), 1.43 (s, 9), 1.42–1.34 (m, 1), 0.88 (t, J=7.5, 3).

A mixture of lincosamine 2b hydrochloride ($R^1$=$R^2$=Me; 55.8 mg, 0.19 mmol, 1 equiv) and DIEA (50 mg, 0.39 mmol, 2 equiv) in DMF (1 mL), was added to above acid intermediate (61.1 mg, 0.19 mmol, 1 equiv), followed by the addition of HBTU (80 mg, 0.21 mmol, 1.1 equiv). The reaction mixture was stirred at r.t. for 3 h. The reaction mixture was evaporated under high vacuum to dryness. The residue was diluted with ethyl acetate, washed with 1:1 10% citric acid/brine (1x), sat. aqueous sodium bicarbonate (1x), brine (1x), dried and concentrated. The residue was purified by chromatography to give the N-Boc lincosamide intermediate (60 mg, 56%).

MS (ESPOS): 549.5[M+H]$^+$. MS (ESNEG): 547.2 [M-H]$^-$.

To a solution of above N-Boc intermediate in DCM (9 mL) with methyl sulfide (0.2 mL) were added trifluoroacetic acid (3 mL) and water (0.2 mL). The reaction mixture was stirred at r.t. for 1 h. The solvent was removed under vacuum and co-evaporated with toluene twice. The residue was purified by chromatography to provide the final product (lower Rf isomer, 12 mg, 25%) as a white solid.

$^1$H NMR (300 MHz, CD$_3$OD) δ 5.24 (d, J=5.7, 1), 4.20 (dd, J=3.3, 9.9, 1), 4.11–4.04 (m, 2), 3.83–3.76 (m, 2), 3.55–3.48 (m, 3), 3.45–3.37 (m, 1), 3.38 (t, J=6.6, 2), 3.07–2.94 (m, 1), 2.29–2.12 (m, 2), 2.11 (s, 3), 1.98–1.83 (m, 2), 1.65–1.51 (m, 4), 1.45–1.33 (m, 2), 0.96–0.86 (m, 9); MS (ESPOS): 449.4 [M+H]$^+$; MS (ESNEG): 447.2 [M-H]$^-$.

Example 117

4-Cyclopropylmethoxy-piperidine-2-carboxylic acid [2-methyl-1-(3,4,5-trihydroxy-6-methylsulfanyl-tetrahydro-pyran-2-yl)-propyl]-amide

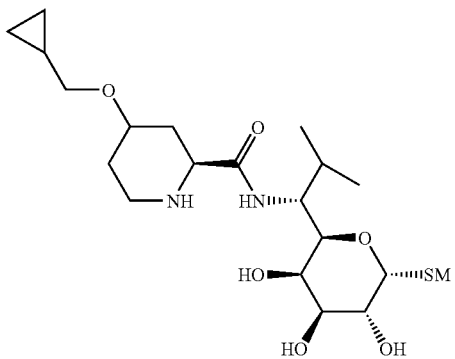

The title compound was made using the synthetic sequence found in method S starting from 4-hydroxypyridine-2-carboxylic acid, substituting cyclopropylmethylbromide as the alkylating agent.

Compound 15a ($R^{9'}$=cyclopropylmethyl): $^1$H NMR (300 MHz, CD$_3$OD) δ 8.41 (d, J=4.8, 1), 7.65 (d, J=2.4, 1), 7.20 (m, 1), 4.09 (d, J=6.9, 2), 1.32 (m, 1), 0.66 (m, 2), 0.43 (m, 2); MS (ESNEG): 192 [M−H]$^-$.

Compound 15b ($R^1$=Me, $R^2$=Me, $R^3$=H, $R^{9'}$=cyclopropylmethyl): $^1$H NMR (300 MHz, CD$_3$OD) δ 8.41 (d, J=5.7, 1), 7.61 (d, J=2.7, 1), 7.07 (dd, J=2.7, 5.7, 1), 5.27 (d, J=5.4, 1), 4.87 (m, 2), 4.12 (dd, J=3.0, 10.2, 1), 3.98 (d, J=6.9, 1), 3.84 (d, J=3.0, 1), 3.56 (dd, J=3.3, 9.6, 1), 3.33 (m, 1), 2.85 (m, 1), 2.25 (m, 1), 2.11 (s, 3), 1.29 (m, 1), 0.98 (t, J=5.7, 6), 0.66 (m, 2), 0.39 (m, 2); MS (ESPOS): 427 [M+H]$^+$.

Title compound (38 mg, 18%): $^1$H NMR (300 MHz, CD$_3$OD) δ 5.24 (d, J=5.4, 1), 4.88 (dd, J=6.3, 9.6, 1), 4.04 (m, 2), 4.21 (d, J=2.7, 1), 3.50 (m, 3), 3.33 (m, 2), 2.78 (m, 1), 2.30 (m, 1), 2.16 (m, 1), 2.10 (s, 3) 1.38 (m, 2), 1.02 (m, 9), 0.53 (m, 2), 0.22 (m, 2); MS (ESPOS): 433 [M+H]$^+$.

Example 118

4-Fluoro-4-butyl-piperidine-2-carboxylic acid [2-methyl-1-(3,4,5-trihydroxy-6-methylsulfanyl-tetrahydro-pyran-2-yl)-propyl]-amide

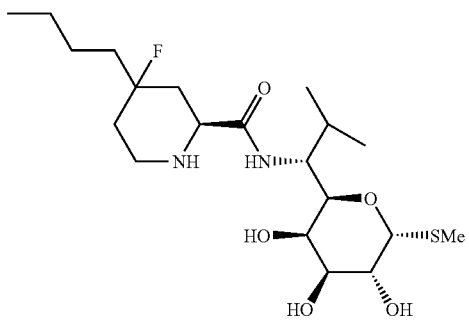

The title compound was made using the synthetic sequence found in method Y (general scheme 21) starting from 4-oxo-piperidine-1,2-dicarboxylic acid 1-tert-butyl ester 21a (m=2, P=H, P$_2$=Boc), substituting butyl lithium as the R$^9$ carbon nucleophile.

Lincosamine 2b ($R^1$=Me, $R^2$=Me) was coupled to carbamate 21d (P$_2$=Boc, m=2, $R^9$=n-butyl) as depicted in general coupling scheme 11 to provide intermediate 11a ($R^1$=Me, $R^2$=Me, $R^3$=H, $R^9$=butyl/fluoro, $P^1$=H, $P^2$=carboxylic acid-t-butyl ester, m=2) which was deprotected under acidic conditions to provide the title compound.

MS (ESPOS): 437 [M+H]$^+$.

Examples 119–122

Examples 119–124 are prepared in an analogous manner as in Example 118 (Method Y, scheme 21), substituting the appropriate R$^9$ carbon nucleophile.

Example 119

4-Fluoro-4-ethyl-piperidine-2-carboxylic acid [2-methyl-1-(3,4,5-trihydroxy-6-methylsulfanyl-tetrahydro-pyran-2-yl)-propyl]-amide

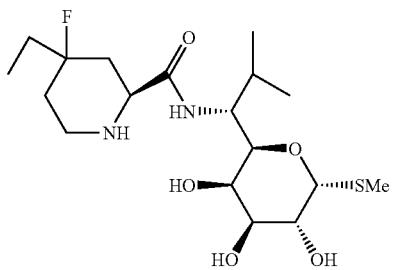

Example 120

4-Fluoro-4-(3-fluoropropyl)-piperidine-2-carboxylic acid [2-methyl-1-(3,4,5-trihydroxy-6-methylsulfanyl-tetrahydro-pyran-2-yl)-propyl]-amide

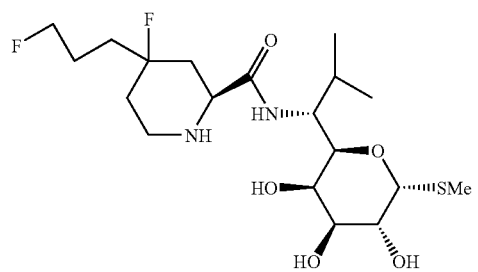

Example 121

4-Fluoro-4-(3,3-difluoropropyl)-piperidine-2-carboxylic acid [2-methyl-1-(3,4,5-trihydroxy-6-methylsulfanyl-tetrahydro-pyran-2-yl)-propyl]-amide

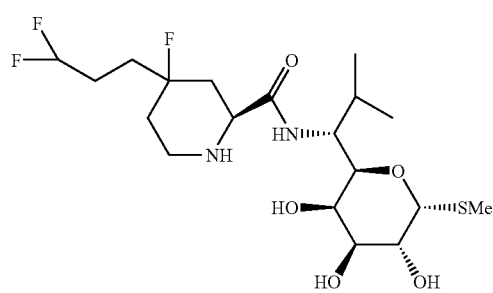

171

Example 122

4-Fluoro-4-(2,2-difluoroethoxymethyl)-piperidine-2-carboxylic acid [2-methyl-1-(3,4,5-trihydroxy-6-methylsulfanyl-tetrahydro-pyran-2-yl)-propyl]-amide

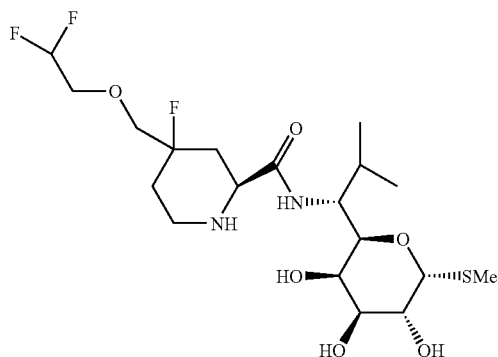

Example 123

4-Fluoro-4-(cyclopropylmethyl)-piperidine-2-carboxylic acid [2-methyl-1-(3,4,5-trihydroxy-6-methylsulfanyl-tetrahydro-pyran-2-yl)-propyl]-amide

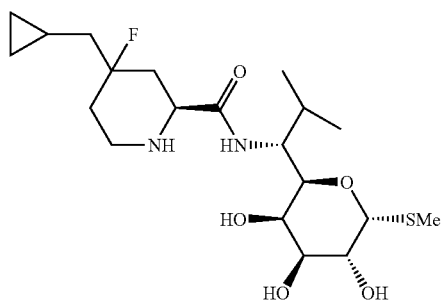

Example 124

4-Fluoro-4-(2-cyclopropyl-ethyl)-piperidine-2-carboxylic acid [2-methyl-1-(3,4,5-trihydroxy-6-methylsulfanyl-tetrahydro-pyran-2-yl)-propyl]-amide

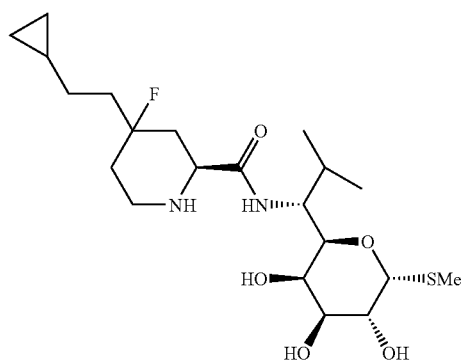

172

Example 125

4-Fluoro-4-cyclohexylmethyl-piperidine-2-carboxylic acid [2-methyl-1-(3,4,5-trihydroxy-6-methylsulfanyl-tetrahydro-pyran-2-yl)-propyl]-amide

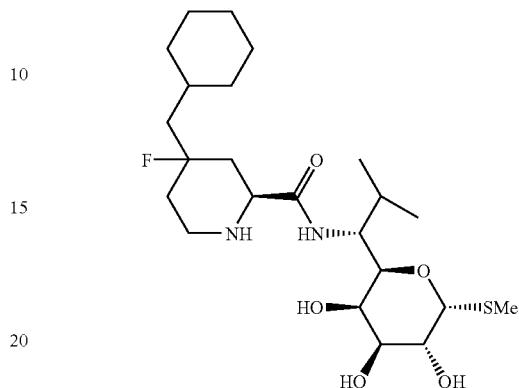

The following Examples may be used to test compounds of this invention.

Example A

Susceptibility Testing

Compounds were tested following the microdilution method of NCCLS (National Committee for Clinical Laboratory Standards. Methods for dilution antimicrobial susceptibility tests for bacteria that grow aerobically; Approved standard—fifth edition. NCCLS document M7-A5, NCCLS, Wayne, Pa. 2000; National Committee for Clinical Laboratory Standards. Methods for antimicrobial susceptibility testing of anaerobic bacteria; Approved standard—fifth edition. NCCLS document M11-A4, NCCLS, Wayne, Pa. 2001). Assays were performed in sterile plastic 96-well microtiter trays with round bottom wells (Greiner).

Compound Preparation

Stock solutions of test compounds and control antibiotics are prepared at 10 mg/mL in DMSO. Serial 2-fold dilutions of each drug are performed in a microtiter plate across each row using DMSO as solvent at 100-fold the desired final concentration. Wells in columns #1–11 contain drug and column #12 was kept as a growth control for the organism with no drug. Each well in the mother plate is diluted with sterile deionized water, mixed, and volumes of 10 µL distributed to each well in the resulting assay plates.

Preparation of Inoculum

Stock cultures were prepared using the Microbank™ method (Pro-Lab Diagnostics) and stored at −80° C. To propagate aerobic strains, one bead was removed from the frozen vial and aseptically streaked onto Trypticase Soy Agar (Difco), Chocolate Agar (Remel) or Blood Agar (Remel) which were incubated at 35° C. overnight. Anaerobes were cultivated in Brucella Agar (Remel) supplemented with hemin and vitamin K and incubated in anaerobiosis using an Anaerobic Jar (Mitsubishi) at 35° C. for 24 to 48 h. Standardized inocula were prepared using the direct colony suspension method according to NCCLS guidelines (National Committee for Clinical Laboratory Standards. Methods for dilution antimicrobial susceptibility tests for bacteria that grow aerobically; Approved standard—fifth edition. NCCLS document M7-A5, NCCLS, Wayne, Pa. 2000; National Committee for Clinical Laboratory Standards.

Methods for antimicrobial susceptibility testing of anaerobic bacteria; Approved standard—fifth edition. NCCLS document M11-A4, NCCLS, Wayne, Pa. 2001). Isolated colonies were selected from an 18–24 h agar plate and resuspended in 0.9% sterile saline to match a 0.5 McFarland turbidity standard. The suspension was used within 15 min. of preparation.

nylacetimidoyl-aminoacetamido)-3-(2-methyl-1,3,4-thiadiazol-5-ylthio methyl)ceph-3-em-4-carboxylic acid Antimicrob Agents Chemother. 3:40–48).

Compound Preparation

Compounds were dissolved in 2% Tween 80 for oral dosing or 0.9% NaCl solution for intravenous dosing. Com-

| | |
|---|---|
| Streptococcus pneumoniae VSPN1001 | Streptococcus pneumoniae ATCC 49619 |
| Streptococcus pneumoniae VSPN3026 | Streptococcus pneumoniae R6x |
| Streptococcus pneumoniae VSPN4054 | Streptococcus pneumoniae 488K |
| Streptococcus pneumoniae VSPN4021 | Streptococcus pneumoniae 9 |
| Staphylococcus aureus VSAU1017 | Staphylococcus aureus Smith |
| Staphylococcus aureus VSAU1003 | Staphylococcus aureus ATCC 25923 |
| Staphylococcus aureus VSAU4020 | Staphylococcus aureus125 |
| Staphylococcus aureus VSAU4048 | Staphylococcus aureus 85-EPI |
| Staphylococcus aureus VSAU4065 | Staphylococcus aureus VSAU4065 |
| Staphylococcus epidermidis VSEP1001 | Staphylococcus epidermidis ATCC 12228 |
| Enterococcus faecalis VEFL1003 | Enterococcus faecalis ATCC 51299 |
| Enterococcus faecium VEFA1005 | Enterococcus faecium BM4147.1 |
| Haemophilus infuenzae VHIN1003 | Haemophilus infuenzae ATCC 49766 |
| Haemophilus infuenzae VHIN1004 | Haemophilus infuenzae ATCC 31517 |
| Haemophilus infuenzae VHIN1005 acr | Haemophilus infuenzae LS-2 |
| Moraxella catarrhalis VMCA1001 | Moraxella catarrhalis ATCC 25238 |
| Escherichia coli VECO2096 | Escherichia coli MG1655 |
| Escherichia coli VECO2526 to1C | Escherichia coli MG1655 to1C |
| Bacteroides fragilis VBFR1001 | Bacteroides fragilis ATCC 25285 |
| Bacteroides thetaiotaomicron VBTH 1001 | Bacteroides thetaiotaomicron ATCC #29741 |
| Clostridium difficile VCDI1001 | Clostridium difficile ATCC 9689 |

Preparation of Assay Plates for MICs Preparation of Assay Plates for MICs

Media were prepared at 1.1× concentration. Mueller-Hinton Broth MHB (Difco) supplemented with Ca++ and Mg++ as recommended by NCCLS, MHB supplemented with 5% horse lysed blood, HTM Broth (Remel), or Brucella broth (Remel) supplemented with hemin and vitamin K. For each organism, the standardized suspension was diluted into appropriate growth medium in a sterile reservoir. After mixing, wells in the drug-containing assay plates were inoculated with a volume of 90 µl. Thus, for each MIC determination, each well contains a final volume of 100 µL with an inoculum size of approximately 5*105 cfu/mL and no more than 1% DMSO.

Interpretation of MIC

The completed microtiter plates were incubated 16–20 h at 35° C. in ambient air for aerobes, and at 35° C. for 46–48 h or in an anaerobe jar (Mitsubishi) for anaerobes. Optical density of each well was determined at 600 nm using a VersaMax Microplate reader (Molecular Devices, Sunnyvale, Calif.). The MIC was defined as the lowest drug concentration causing complete suppression of visible bacterial growth.

Example B

Efficacy in Murine *S. aureus* Septicemia

Efficacy studies were performed in an *S. aureus* murine septicemia model according to models published elsewhere (Goldstein, B. P., G. Candiani, T. M. Arain, G. Romano, I. Ciciliato, M. Berti, M. Abbondi, R. Scotti, M. Mainini, F. Ripamonti, and et al. 1995. Antimicrobial activity of MDL 63,246, a new semisynthetic glycopeptide antibiotic Antimicrob Agents Chemother. 39:1580–1588.; Misiek, M., T. A. Pursiano, F. Leitner, and K. E. Price 1973. Microbiological properties of a new cephalosporin, BL-S 339: 7-(phepounds were administered at 1 hour after bacterial inoculation. Vancomycin or ampicillin were used as controls.

Efficacy Model

Male or female ICR mice weighing 22±2 g from MDS Pharma Services were used for the evaluation. Food and water was given ad libitum. Groups of 6 mice weighing 22±g were used for the experiment. Mice were inoculated intraperitoneally with *Staphylococcus aureus* Smith at 4 104 CFU in 0.5 mL of Brain Heart Infusion Broth (Difco) containing 5% mucin (Sigma). Mortality was recorded once daily for 7 days following bacterial inoculation.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

Example C

In Vivo Animal Model

In vivo activity of various compounds of the subject invention was evaluated in a standard *Staphylococcus aureus* septicemia model (MDS Pharma Services, Bothell, Wash.).

Male ICR-derived mice (ICR is a strain of out-bred mice) provided by MDS Pharma Services animal breeding center were inoculated intraperitoneally with $LD_{90-100}$ of *Staphylococcus aureus* (Smith; ATCC19636) in 0.5 mL BHI broth containing 5% mucin (Sigma). Compounds were formulated in 2% Tween 80 (Sigma) and single doses were administered orally one hour after bacterial inoculation. Mortality was monitored daily for seven days.

In previous studies, the oral $ED_{50}$ (i.e., concentration that protected 50% of the mice) was determined to be 19.9 mg/kg for clindamycin, a commercially available lincosamide (Sigma). To screen the compounds of this invention that were tested, compounds were administered at 10 mg/kg to a group of eight ICR mice and the number of survivors at that concentration was compared to clindamycin. Results are presented in the table below.

| Compound Tested (Indicated by Example No.) | No. of surviving mice at 10 mg/kg |
| --- | --- |
| Clindamycin | 6 |
| 17 | 1 |
| 34 | 2 |
| 35 | 2 |
| 36 | 0 |
| 100 | 7 |
| 101 | 7 |

It is assumed that when compound from example 36 is tested at a higher dose, the number of surviving mice would increase.

What is claimed is:

1. A compound of formula (I):

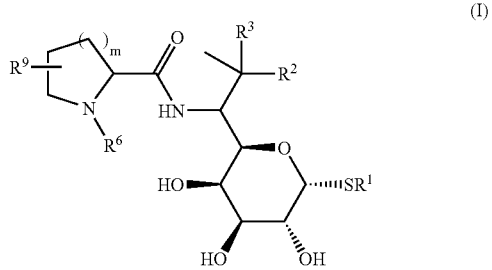

wherein:
R$^1$ is alkyl;
R$^2$ and R$^3$ are independently H, alkyl, hydroxy, fluoro, or cyanoalkyl or one of R$^2$ and R$^3$ is =NOR$^7$ and the other is absent, or one of R$^2$ and R$^3$ is =CH$_2$ and the other is absent, with the provisos that both R$^2$ and R$^3$ are not H; when one of R$^2$ and R$^3$ is fluoro, the other is not hydrogen or hydroxy; and when one of R$^2$ and R$^3$ is hydroxy, the other is not fluoro, hydrogen, or hydroxy;
R$^6$ is selected from the group consisting of H, alkyl, hydroxyalkyl, —C(O)O-alkylene-cycloalkyl, —C(O)O-alkylene-substituted cycloalkyl, —C(O)O-alkyl, —C(O)O-substituted alkyl, —C(O)O-aryl, —C(O)O-substituted aryl, —C(O)O-heteroaryl, —C(O)O-substituted heteroaryl, —[C(O)O]$_p$-alkylene-heterocycle, —[C(O)O]$_p$-alkylene-substituted heterocycle, wherein p is 0 or 1;
R$^7$ is H or alkyl;
R$^9$, which can be singly or multiply substituted in the ring on the same or different carbons, is independently selected from the group consisting of alkyl, substituted alkyl, alkoxy, substituted alkoxy, alkoxyalkoxy, cycloalkyl, substituted cycloalkyl, —OR$^d$, —NR$^e$R$^f$, halogen, phenyl, substituted phenyl, —(CH$_2$)$_n$—OH, —(CH$_2$)$_n$—NR$^4$R$^5$, -alkylene-R$^a$ where R$^a$ is selected from monofluorophenyl and monochlorophenyl, and branched chain isomers thereof, wherein n is an integer of from 1 to 8 inclusive and R$^4$ and R$^5$ are H or alkyl, wherein R$^d$ is selected from the group consisting of alkyl, haloalkyl, alkenyl, cycloalkyl, substituted cycloalkyl, aryl, substituted aryl, heteroaryl, and substituted heteroaryl, and wherein R$^e$ and R$^f$ are independently selected from the group consisting of H, alkyl, haloalkyl, alkenyl, cycloalkyl, substituted cycloalkyl, aryl, substituted aryl, heteroaryl, and substituted heteroaryl; and
m is 0, 1, 2 or 3;
or a prodrug, tautomer, or a pharmaceutically acceptable salt thereof;
with the proviso that the compound of formula I has a minimum inhibition concentration of 32 µg/mL or less against at least one of the organisms selected from the group consisting of *Streptococcus pneumoniae, Staphylococcus aureus, Staphylococcus epidermidis, Enterococcus faecalis, Enterococcus faccium, Haemophilus influenzae, Moraxella catarrhalis, Escherichia coil, Bacteroides fragilis, Bacteroides thetaiotaomicron*, and *Clostridium difficile*.

2. A compound of formula (II)

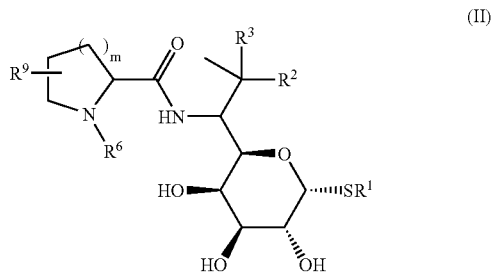

wherein:
R$^1$ is alkyl;
R$^2$ and R$^3$ are independently H, alkyl, or cyanoalkyl, with the proviso that both R$^2$ and R$^3$ are not H;
R$^6$ is H, alkyl, or hydroxyalkyl;
R$^9$, which can be singly or multiply substituted in the ring on the same or different carbons, is independently selected from the group consisting of alkyl, substituted alkyl, alkoxyalkoxy, cycloalkyl, substituted cycloalkyl, —OR$^d$, —NR$^e$R$^f$, halogen, phenyl, substituted phenyl, —(CH$_2$)$_n$—OH, —(CH$_2$)$_n$—NR$^4$R$^5$, -alkylene-R$^a$ where R$^a$ is selected from monofluorophenyl and monochlorophenyl, and branched chain isomers thereof, wherein n is an integer of from 1 to 8 inclusive and R$^4$ and R$^5$ are H or alkyl, wherein R$^d$ is selected from the group consisting of alkyl, haloalkyl, alkenyl, cycloalkyl, substituted cycloalkyl, aryl, substituted aryl, heteroaryl, and substituted heteroaryl, and wherein R$^e$ and R$^f$ are independently selected from the group consisting of H, alkyl, haloalkyl, alkenyl, cycloalkyl, substituted cycloalkyl, aryl, substituted aryl, heteroaryl, and substituted heteroaryl; and
m is 1 or 2;
or a prodrug or a pharmaceutically acceptable salt thereof;
with the proviso that the compound of formula II has a minimum inhibition concentration of 32 µg/mL or less against at least one of the organisms selected from the group consisting of *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron*, and *Clostridium difficile*.

3. A compound of formula (III):

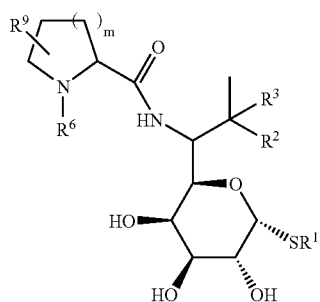

wherein:
$R^1$ is alkyl;
$R^2$ and $R^3$ are fluoro;
$R^6$ is H, alkyl, or hydroxyalkyl;
$R^9$, which can be singly or multiply substituted in the ring on the same or different carbons, is independently selected from the group consisting of alkyl, substituted alkyl, alkoxyalkoxy, cycloalkyl, substituted cycloalkyl, —$OR^d$, —$NR^eR^f$, halogen, phenyl, substituted phenyl, —$(CH_2)_n$—OH, —$(CH_2)_n$—$NR^4R^5$, -alkylene-$R^a$ where $R^a$ is selected from monofluorophenyl and monochlorophenyl, and branched chain isomers thereof, wherein n is an integer of from 1 to 8 inclusive and $R^4$ and $R^5$ are H or alkyl, wherein $R^d$ is selected from the group consisting of alkyl, haloalkyl, alkenyl, cycloalkyl, substituted cycloalkyl, aryl, substituted aryl, heteroaryl, and substituted heteroaryl, and wherein $R^e$ and $R^f$ are independently selected from the group consisting of H, alkyl, haloalkyl, alkenyl, cycloalkyl, substituted cycloalkyl, aryl, substituted aryl, heteroaryl, and substituted heteroaryl; and
m is 1 or 2;
or a prodrug or a pharmaceutically acceptable salt thereof, with the proviso that the compound of formula III has a minimum inhibition concentration of 32 µg/mL or less against at least one of the organisms selected from the group consisting of *Streptococcus pneumoniae*, *Staphylococcus aureus*, *Staphylococcus epidermidis*, *Enterococcus faecalis*, *Enterococcus faecium*, *Haemophilus influenzae*, *Moraxella catarrhalis*, *Escherichia coli*, *Bacteroides fragilis*, *Bacteroides thetaiotaomicron*, and *Clostridium difficile*.

4. A compound of formula (V):

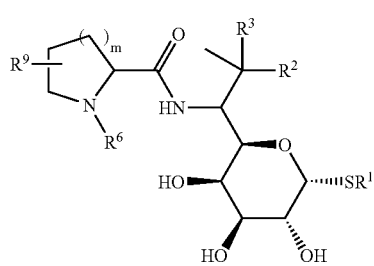

wherein:
$R^1$ is alkyl;
$R^2$ and $R^3$ are independently H, alkyl, hydroxy, fluoro, or cyanoalkyl or one of $R^2$ and $R^3$ is =$NOR^7$ and the other is absent, or one of $R^2$ and $R^3$ is =$CH_2$ and the other is absent, with the provisos that both $R^2$ and $R^3$ are not H; when one of $R^2$ and $R^3$ is fluoro, the other is not hydrogen or hydroxy; and when one of $R^2$ and $R^3$ is hydroxy, the other is not fluoro, hydrogen, or hydroxy;

$R^6$ is selected from the group consisting of —C(O)O-alkylene-cycloalkyl, —C(O)O-alkylene-substituted cycloalkyl, —C(O)O-alkyl, —C(O)O-substituted alkyl, —C(O)O-aryl, —C(O)O-substituted aryl, —C(O)O-heteroaryl, —C(O)O-substituted heteroaryl, —[C(O)O]$_p$-alkylene-heterocycle, —[C(O)O]$_p$-alkylene-substituted heterocycle, wherein p is 0 or 1 with the proviso that —C(O)O-substituted alkyl does not include the following:

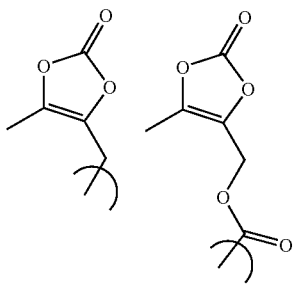

$R^7$ is H or alkyl;
$R^9$, which can be singly or multiply substituted in the ring on the same or different carbons, is independently selected from the group consisting of alkyl, substituted alkyl, alkoxyalkoxy, cycloalkyl, substituted cycloalkyl, alkoxyalkoxy, —$OR^d$, —$NR^eR^f$, halogen, phenyl, substituted phenyl, —$(CH_2)_n$—OH, —$(CH_2)_n$—$NR^4R^5$, -alkylene-$R^a$ where $R^a$ is selected from monofluorophenyl and monochlorophenyl, and branched chain isomers thereof, wherein n is an integer of from 1 to 8 inclusive and $R^4$ and $R^5$ are H or alkyl, wherein $R^d$ is selected from the group consisting of alkyl, haloalkyl, alkenyl, cycloalkyl, substituted cycloalkyl, aryl, substituted aryl, heteroaryl, and substituted heteroaryl, and wherein $R^e$ and $R^f$ are independently selected from the group consisting of H, alkyl, haloalkyl, alkenyl, cycloalkyl, substituted cycloalkyl, aryl, substituted aryl, heteroaryl, and substituted heteroaryl; and
m is 1 or 2;
or a prodrug, tautomer, or a pharmaceutically acceptable salt thereof,
with the proviso that the compound of formula V has a minimum inhibition concentration of 32 µg/mL or less against at least one of the organisms selected from the group consisting of *Streptococcus pneumoniae*, *Staphylococcus aureus*, *Staphylococcus epidermidis*, *Enterococcus faecalis*, *Enterococcus faccium*, *Haemophilus influenzae*, *Moraxella catarrhalis*, *Escherichia coli*, *Bacteroides fragilis*, *Bacteroides thetaiotaomicron*, and *Clostridium difficile*.

5. A compound of claim 1, wherein m is 1 or 2.

6. A compound of claim 1, wherein $R^1$ is methyl.

7. A compound of claim 1, wherein $R^6$ is H, alkyl, or hydroxyalkyl.

8. A compound of claim 1, wherein each $R^9$ is independently alkyl, substituted alkyl, alkoxy, substituted alkoxy, or cycloalkyl.

9. A compound selected from the group consisting of:

4-ethyl-piperidine-2-carboxylic acid [2-methyl-1-(3,4,5-trihydroxy-6-methylsulfanyl-tetrahydro-pyran-2-yl)-propyl]-amide;

1-methyl-4-propyl-pyrrolidine-2-carboxylic acid [2-methyl-1-(3,4,5-trihydroxy-6-methylsulfanyl-tetrahydro-pyran-2-yl)-propyl-amide;

1-methyl-4-propyl-pyrrolidine-2-carboxylic acid [3-cyano-2-methyl-1-(3,4,5-trihydroxy-6-methylsulfanyl-tetrahydro-pyran-2-yl)-propyl]-amide;

4-ethyl-piperidine-2-carboxylic acid [2-hydroxy-2-methyl-1-(3,4,5-trihydroxy-6-methylsulfanyl-tetrahydro-pyran-2-yl)-propyl]-amide;

1-methyl-4-propyl-pyrrolidine-2-carboxylic acid [2-hydroxyimino-1-(3,4,5-trihydroxy-6-methylsulfanyl-tetrahydro-pyran-2-yl)-propyl]-amide;

1-methyl-4-propyl-pyrrolidine-2-carboxylic acid [2-methoxyimino-1-(3,4,5-trihydroxy-6-methylsulfanyl-tetrahydro-pyran-2-yl)-propyl]-amide;

5-butyl-piperidine-2-carboxylic acid [2-methyl-1-(3,4,5-trihydroxy-6-methylsulfanyl-tetrahydro-pyran-2-yl)-propyl]-amide;

4-pentyl-pyrrolidine-2-carboxylic acid [2-methyl-1-(3,4,5-trihydroxy-6-methylsulfanyl-tetrahydro-pyran-2-yl)-propyl]-amide;

4-(3-methyl-butyl)-pyrrolidine-2-carboxylic acid [2-methyl-1-(3,4,5-trihydroxy-6-methylsulfanyl-tetrahydro-pyran-2-yl-propyl]-amide;

4-pentyl-pyrrolidine-2-carboxylic acid [2-methyl-1-(3,4,5-trihydroxy-6-methylsulfanyl-tetrahydro-pyran-2-yl)-propyl]-amide;

1-methyl-4-propyl-pyrrolidine-2-carboxylic acid [2,2-difluoro-1-(3,4,5-trihydroxy-6-methylsulfanyl-tetrahydro-pyran-2-yl)-propyl]-amide;

4-pentyl-pyrrolidine-2-carboxylic acid [2,2-difluoro-1-(3,4,5-trihydroxy-6-methylsulfanyl-tetrahydro-pyran-2-yl)-propyl]-amide;

4-[3-(4-fluoro-phenyl)-propyl]-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-propyl)-pyrrolidine-2-carboxylic acid [2-methyl-1-(3,4,5-trihydroxy-6-methylsulfanyl-tetrahydro-pyran-2-yl)-propyl]-amide;

4-[3-(4-chloro-phenyl)-propyl]-pyrrolidine-2-carboxylic acid [2-methyl-1-(3,4,5-trihydroxy-6-methylsulfanyl-tetrahydro-pyran-2-yl)-propyl]-amide;

4-(2,2-difluoro-pentyl)-pyrrolidine-2-carboxylic acid [2-methyl-1-(3,4,5-trihydroxy-6-methylsulfanyl-tetrahydro-pyran-2-yl)-propyl]-amide;

4-propyl-piperidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-hydroxy-propyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(3-hydroxy-propyl)-4-pentyl-pyrrolidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-(3-methyl-butyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-propyl)-1-(2-hydroxy-ethyl)-pyrrolidine-2-carboxylic acid [2-methyl-1-(3,4,5-trihydroxy-6-methylsulfanyl-tetrahydro-pyran-2-yl-propyl]-amide;

1-(2-hydroxy-ethyl)-4-pentyl-pyrrolidine-2-carboxylic acid [2,2-difluoro-1-(3,4,5-trihydroxy-6-methylsulfanyl-tetrahydro-pyran-2-yl)-propyl]-amide;

4-pentyl-piperidine-2-carboxylic acid [2-methyl-1-(3,4,5-trihydroxy-6-methylsulfanyl-tetrahydro-pyran-2-yl)-propyl]-amide;

4-Methoxy-piperidine-2-carboxylic acid [2-methyl-1-(3,4,5-trihydroxy-6-methylsulfanyl-tetrahydro-pyran-2-yl)-propyl]-amide;

4-(1-ethyl-propyl)-piperidine-2-carboxylic acid [2-methyl-1-(3,4,5-trihydroxy-6-methylsulfanyl-tetrahydro-pyran-2-yl)-propyl]-amide;

4-isopropyl-piperidine-2-carboxylic acid [2-methyl-1-(3,4,5-trihydroxy-6-methylsulfanyl-tetrahydro-pyran-2-yl)-propyl]-amide;

4-butyl-piperidine-2-carboxylic acid [2-methyl-1-(3,4,5-trihydroxy-6-methylsulfanyl-tetrahydro-pyran-2-yl)-propyl]-amide;

4-cyclohexyl-piperidine-2-carboxylic acid [2-methyl-1-(3,4,5-trihydroxy-6-methylsulfanyl-tetrahydro-pyran-2-yl)-propyl]-amide;

4-ethyl-1-(2-hydroxy-ethyl)-piperidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-pentyl-piperidine-2-carboxylic acid [2-methyl-1-(3,4,5-trihydroxy-6-methylsulfanyl-tetrahydro-pyran-2-yl)-propyl]-amide;

1-(2-hydroxy-ethyl)-4-propyl-piperidine-2-carboxylic acid [2-methyl-1-(3,4,5-trihydroxy-6-methylsulfanyl-tetrahydro-pyran-2-yl)-propyl]-amide;

4-(4,4-difluoro-pentyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-butyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-pentyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-pentyl)-1-(2-hydroxy-ethyl)-pyrrolidine-2-carboxylic acid [2-methyl-1-(3,4,5-trihydroxy-6-methylsulfanyl-tetrahydro-pyran-2-yl)-propyl]-amide;

4-(3,3-difluoro-propyl)-piperidine-2-carboxylic acid [2-methyl-1-(3,4,5-trihydroxy-6-methylsulfanyl-tetrahydro-pyran-2-yl)-propyl]-amide;

4-(4,4-difluoro-butyl)-piperidine-2-carboxylic acid [2-methyl-1-(3,4,5-trihydroxy-6-methylsulfanyl-tetrahydro-pyran-2-yl)-propyl]-amide 4-(5,5-difluoro-pentyl))-piperidine-2-carboxylic acid [2-methyl-1-(3,4,5-trihydroxy-6-methylsulfanyl-tetrahydro-pyran-2-yl)-propyl]-amide;

4-(5-fluoro-pentyl)-piperidine-2-carboxylic acid [2-methyl-1-(3,4,5-trihydroxy-6-methylsulfanyl-tetrahydro-pyran-2-yl)-propyl]-amide;

4-(4-fluoro-butyl)-piperidine-2-carboxylic acid [2-methyl-1-(3,4,5-trihydroxy-6-methylsulfanyl-tetrahydro-pyran-2-yl)-propyl]-amide;

4-(3-ethyl-3-hydroxy-pentyl)-piperidine-2-carboxylic acid [2-methyl-1-(3,4,5-trihydroxy-6-methylsulfanyl-tetrahydro-pyran-2-yl)-propyl]-amide;

4-butoxy-piperidine-2-carboxylic acid [2-methyl-1-(3,4,5-trihydroxy-6-methylsulfanyl-tetrahydro-pyran-2-yl)-propyl]-amide;

4-pentyloxy-piperidine-2-carboxylic acid [2-methyl-1-(3,4,5-trihydroxy-6-methylsulfanyl-tetrahydro-pyran-2-yl)-propyl]-amide;

4-(4-fluoro-butoxy)-piperidine-2-carboxylic acid [2-methyl-1-(3,4,5-trihydroxy-6-methylsulfanyl-tetrahydro-pyran-2-yl)-propyl]-amide;

4-butyl-pyrrolidine-2-carboxylic acid [2-methyl-1-(3,4,5-trihydroxy-6-methylsulfanyl-tetrahydro-pyran-2-yl)-allyl]-amide;

1,4-diethyl-piperidine-2-carboxylic acid (2-methyl-1-(3,4,5-trihydroxy-6-methylsulfanyl-tetrahydro-pyran-2-yl)-propyl]-amide;

4-(3-fluoro-propoxy)-piperidine-2-carboxylic acid [2-methyl-1-(3,4,5-trihydroxy-6-methylsulfanyl-tetrahydro-pyran-2-yl)-propyl]-amide;

4-(3,3,3-trifluoro-propoxy)-piperidine-2-carboxylic acid [2-methyl-1-(3,4,5-trihydroxy-6-methylsulfanyl-tetrahydro-pyran-2-yl)-propyl]-amide;

4-isobutyl-piperidine-2-carboxylic acid [2-methyl-1-(3,4,5-trihydroxy-6-methylsulfanyl-tetrahydro-pyran-2-yl)-propyl]-amide;

4-propyl-piperidine-2-carboxylic acid [2,2-difluoro-1-(3,4,5-trihydroxy-6-methylsulfanyl-tetrahydro-pyran-2-yl)-propyl]-amide;

4-fluoro-4-propyl-pyrrolidine-2-carboxylic acid [2-methyl-1-(3,4,5-trihydroxy-6-methylsulfanyl-tetrahydro-pyran-2-yl)-propyl]-amide;

4-butyl-4-fluoro-pyrrolidine-2-carboxylic acid [2-methyl-1-(3,4,5-trihydroxy-6-methylsulfanyl-tetrahydro-pyran-2-yl)-propyl]-amide;

4-(2-methoxyethoxy)-piperidine-2-carboxylic acid [2-methyl-1-(3,4,5-trihydroxy-6-methylsulfanyl-tetrahydro-pyran-2-yl)-propyl]-amide;

4-Butyl-pyrrolidine-2-carboxylic acid [2-methyl-1-(3,4,5-trihydroxy-6-methylsulfanyl-tetrahydro-pyran-2-yl)-propyl]-amide;

4-(4,4-Difluoro-pentyl)-piperidine-2-carboxylic acid [2-methyl-1-(3,4,5-trihydroxy-6-methylsulfanyl-tetrahydro-pyran-2-yl)-propyl]-amide;

4-(3-Fluoro-propyl)-piperidine-2-carboxylic acid [2-methyl-1-(3,4,5-trihydroxy-6-methylsulfanyl-tetrahydro-pyran-2-yl)-propyl]-amide;

4-Fluoro-4-propyl-piperidine-2-carboxylic acid [2-methyl-1-(3,4,5-trihydroxy-6-methylsulfanyl-tetrahydro-pyran-2-yl)-propyl]-amide;

4-(2-Fluoroethoxy)-piperidine-2-carboxylic acid [2-methyl-1-(3,4,5-trihydroxy-6-methylsulfanyl-tetrahydro-pyran-2-yl)-propyl]-amide;

4-(2-Cyclopropyl-ethyl)-piperidine-2-carboxylic acid [2-methyl-1-(3,4,5-trihydroxy-6-methylsulfanyl-tetrahydro-pyran-2-yl)-propyl]-amide;

4-Cyclopropylmethyl-piperidine-2-carboxylic acid [2-methyl-1-(3,4,5-trihydroxy-6-methylsulfanyl-tetrahydro-pyran-2-yl)-propyl]-amide;

4-(2-Cyclobutyl-ethyl)-piperidine-2-carboxylic acid [2-methyl-1-(3,4,5-trihydroxy-6-methylsulfanyl-tetrahydro-pyran-2-yl)-propyl]-amide;

4-Cyclobutylmethyl-piperidine-2-carboxylic acid [2-methyl-1-(3,4,5-trihydroxy-6-methylsulfanyl-tetrahydro-pyran-2-yl)-propyl]-amide;

3-Butyl-azetidine-2-carboxylic acid [2-methyl-1-(3,4,5-trihydroxy-6-methylsulfanyl-tetrahydro-pyran-2-yl)-propyl]-amide;

3-Cyclopropylmethyl-azetidine-2-carboxylic acid [2-methyl-1-(3,4,5-trihydroxy-6-methylsulfanyl-tetrahydro-pyran-2-yl)-propyl]-amide;

3-Propyl-azetidine-2-carboxylic acid [2-methyl-1-(3,4,5-trihydroxy-6-methylsulfanyl-tetrahydro-pyran-2-yl)-propyl]-amide;

3-Butyl-1-(2-hydroxy-ethyl)-azetidine-2-carboxylic acid [2-methyl-1-(3,4,5-trihydroxy-6-methylsulfanyl-tetrahydro-pyran-2-yl)-propyl]-amide;

3-Pentyl-azetidine-2-carboxylic acid [2-methyl-1-(3,4,5-trihydroxy-6-methylsulfanyl-tetrahydro-pyran-2-yl)-propyl]-amide;

3-(3-Methyl-butyl)-azetidine-2-carboxylic acid [2-methyl-1-(3,4,5-trihydroxy-6-methylsulfanyl-tetrahydro-pyran-2-yl)-propyl]-amide;

3-(3-Cyclobutyl-propyl)-azetidine-2-carboxylic acid [2-methyl-1-(3,4,5-trihydroxy-6-methylsulfanyl-tetrahydro-pyran-2-yl)-propyl]-amide;

3-(2-Cyclobutyl-ethyl)-azetidine-2-carboxylic acid [2-methyl-1-(3,4,5-trihydroxy-6- methylsulfanyl-tetrahydro-pyran-2-yl)-propyl]-amide;

3-(2-Cyclopropyl-ethyl)-azetidine-2-carboxylic acid [2-methyl-1-(3,4,5-trihydroxy-6-methylsulfanyl-tetrahydro-pyran-2-yl)-propyl]-amide;

3-(3-Cyclopropyl-propyl)-azetidine-2-carboxylic acid [2-methyl-1-(3,4,5-trihydroxy-6-methylsulfanyl-tetrahydro-pyran-2-yl)-propyl]-amide;

3-Butyl-1-methyl-azetidine-2-carboxylic acid [2-methyl-1-(3,4,5-trihydroxy-6-methylsulfanyl-tetrahydro-pyran-2-yl)-propyl]-amide;

4-Cyclopropylmethyl-pyrrolidine-2-carboxylic acid [2-methyl-1-(3,4,5-trihydroxy-6-methylsulfanyl-tetrahydro-pyran-2-yl)-propyl]-amide;

4-(2-Cyclobutyl-ethyl)-pyrrolidine-2-carboxylic acid [2-methyl-1-(3,4,5-trihydroxy-6-methylsulfanyl-tetrahydro-pyran-2-yl)-propyl]-amide;

4-(2-Cyclopropyl-ethyl)-pyrrolidine-2-carboxylic acid [2-methyl-1-(3,4,5-trihydroxy-6-methylsulfanyl-tetrahydro-pyran-2-yl)-propyl]-amide;

5-Propyl-azepane-2-carboxylic acid [2-methyl-1-(3,4,5-trihydroxy-6-methylsulfanyl-tetrahydro-pyran-2-yl)-propyl]-amide;

4-butyl-piperidine-2-carboxylic acid [2-methyl-1-(3,4,5-trihydroxy-6-methylsulfanyl-tetrahydro-pyran-2-yl)-propyl]-amide;

4-(3-Cyclopentyl-propyl)-piperidine-2-carboxylic acid [2-methyl-1-(3,4,5-trihydroxy-6-methylsulfanyl-tetrahydro-pyran-2-yl)-propyl]-amide;

4-(3-Methoxy-propyl)-piperidine-2-carboxylic acid [2-methyl-1-(3,4,5-trihydroxy-6-methylsulfanyl-tetrahydro-pyran-2-yl)-propyl]-amide;

4-(3-Ethoxy-propyl)-piperidine-2-carboxylic acid [2-methyl-1-(3,4,5-trihydroxy-6-methylsulfanyl-tetrahydro-pyran-2-yl)-propyl]-amide;

4-(3-Propoxy-propyl)-piperidine-2-carboxylic acid [2-methyl-1-(3,4,5-trihydroxy-6-methylsulfanyl-tetrahydro-pyran-2-yl)-propyl]-amide;

4-(3-Cyclopropylmethoxy-propyl)-piperidine-2-carboxylic acid [2-methyl-1-(3,4,5-trihydroxy-6-methylsulfanyl-tetrahydro-pyran-2-yl)-propyl]-amide;

4-[3-(2-Fluoro-ethoxy)-propyl]-piperidine-2-carboxylic acid [2-methyl-1-(3,4,5-trihydroxy-6-methylsulfanyl-tetrahydro-pyran-2-yl)-propyl]-amide;

4-[3-(3-Fluoro-propoxy)-propyl]-piperidine-2-carboxylic acid [2-methyl-1-(3,4,5-trihydroxy-6-methylsulfanyl-tetrahydro-pyran-2-yl)-propyl]-amide;

4-(4-Methoxy-butyl)-piperidine-2-carboxylic acid [2-methyl-1-(3,4,5-trihydroxy-6-methylsulfanyl-tetrahydro-pyran-2-yl)-propyl]-amide;

4-Propoxymethyl-piperidine-2-carboxylic acid [2-methyl-1-(3,4,5-trihydroxy-6-methylsulfanyl-tetrahydro-pyran-2-yl)-propyl]-amide;

4-(3-Fluoro-propoxymethyl)-piperidine-2-carboxylic acid [2-methyl-1-(3,4,5-trihydroxy-6-methylsulfanyl-tetrahydro-pyran-2-yl)-propyl]-amide;

4-Cyclohexylmethyl-piperidine-2-carboxylic acid [2-methyl-1-(3,4,5-trihydroxy-6-methylsulfanyl-tetrahydro-pyran-2-yl)-propyl]-amide;

4-(2-Propyloxyethyl)-piperidine-2-carboxylic acid [2-methyl-1-(3,4,5-trihydroxy-6-methylsulfanyl-tetrahydro-pyran-2-yl)-propyl]-amide;

4-Cyclopropylmethoxy-piperidine-2-carboxylic acid [2-methyl-1-(3,4,5-trihydroxy-6-methylsulfanyl-tetrahydro-pyran-2-yl)-propyl]-amide;

4-Fluoro-4-butyl-piperidine-2-carboxylic acid [2-methyl-1-(3,4,5-trihydroxy-6-methylsulfanyl-tetrahydro-pyran-2-yl)-propyl]-amide;

4-Fluoro-4-ethyl-piperidine-2-carboxylic acid [2-methyl-1-(3,4,5-trihydroxy-6-methylsulfanyl-tetrahydro-pyran-2-yl)-propyl]-amide;

4-Fluoro-4-(3-fluoropropyl)-piperidine-2-carboxylic acid [2-methyl-1-(3,4,5-trihydroxy-6-methylsulfanyl-tetrahydro-pyran-2-yl)-propyl]-amide;

4-Fluoro-4-(3,3-difluoropropyl)-piperidine-2-carboxylic acid [2-methyl-1-(3,4,5-trihydroxy-6-methylsulfanyl-tetrahydro-pyran-2-yl)-propyl]-amide;

4-Fluoro-4-(2,2-difluoroethoxymethyl)-piperidine-2-carboxylic acid [2-methyl-1-(3,4,5-trihydroxy-6-methylsulfanyl-tetrahydro-pyran-2-yl)-propyl]-amide;

and prodrugs, tautomers or pharmaceutically acceptable salts thereof.

10. A compound selected from the group consisting of:

2-[2-Methyl-1-(3,4,5-trihydroxy-6-methylsulfanyl-tetrahydro-pyran-2-yl)-propylcarbamoyl]-4-propyl-piperidine-1-carboxylic acid 9H-fluoren-9-ylmethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid ethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid phenyl ester;

Phosphoric acid mono-(4,5-dihydroxy-6-{2-methyl-1-[(4-propyl-piperidine-2-carbonyl)-amino]-propyl}-2-methylsulfanyl-tetrahydro-pyran-3-yl)ester;

Succinic acid mono-(4,5-dihydroxy-6-{2-methyl-1-[(4-propyl-piperidine-2-carbonyl)-amino]-propyl}-2-methylsulfanyl-tetrahydro-pyran-3-yl)ester;

N-(2-Morpholin-4-yl-ethyl)-succinamic acid 4,5-dihydroxy-6-{2-methyl-1-[(4-propyl-piperidine-2-carbonyl)-amino]-propyl}-2-methylsulfanyl-tetrahydro-pyran-3-yl ester;

Dimethylamino-acetic acid 4,5-dihydroxy-6-{2-methyl-1-[(4-propyl-piperidine-2-carbonyl)-amino]-propyl}-2-methylsulfanyl-tetrahydro-pyran-3-yl ester;

1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 5-methyl-2-oxo-[1,3]dioxol-4-ylmethyl ester;

Hexadecanoic acid 4,5-dihydroxy-6-{2-methyl-1-[(4-propyl-piperidine-2-carbonyl)-amino]-propyl}-2-methylsulfanyl-tetrahydro-pyran-3-yl ester;

1-(1-Methyl-3-oxo-but-1-enyl)-4-propyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 1-acetoxy-ethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid 2-amino-3-methyl-pentanoyloxymethyl ester;

2-[2-Methyl-1-(3,4,5-trihydroxy-6-methylsulfanyl-tetrahydro-pyran-2-yl)-propylcarbamoyl]-4-propyl-piperidine-1-carboxylic acid piperidine-4-carbonyloxymethyl ester;

1-(Propionylamino-methyl)-4-propyl-piperidine-2-carboxylic acid [2-methyl-1-(3,4,5-trihydroxy-6-methylsulfanyl-tetrahydro-pyran-2-yl)-propyl]-amide;

N-{2-[2-Methyl-1-(3,4,5-trihydroxy-6-methylsulfanyl-tetrahydro-pyran-2-yl)-propylcarbamoyl]-4-propyl-piperidin-1-ylmethyl}-nicotinamide;

1-(2-Amino-propionyl)-4-propyl-piperidine-2-carboxylic acid [2-methyl-1-(3,4,5-trihydroxy-6-methylsulfanyl-tetrahydro-pyran-2-yl)-propyl]-amide;

1-(2-Amino-3-phenyl-propionyl)-4-propyl-piperidine-2-carboxylic acid [2-methyl-1-(3,4,5-trihydroxy-6-methylsulfanyl-tetrahydro-pyran-2-yl)-propyl]-amide;

1-(2-Amino-3-methyl-pentanoyl)-4-propyl-piperidine-2-carboxylic acid [2-methyl-1-(3,4,5-trihydroxy-6-methylsulfanyl-tetrahydro-pyran-2-yl)-propyl]-amide;

1-(2-Amino-3-methyl-butyryl)-4-propyl-piperidine-2-carboxylic acid [2-methyl-1-(3,4,5-trihydroxy-6-methylsulfanyl-tetrahydro-pyran-2-yl)-propyl]-amide;

1-(1-Methyl-1,4-dihydro-pyridine-3-carbonyl)-4-propyl-piperidine-2-carboxylic acid [2-methyl-1-(3,4,5-trihydroxy-6-methylsulfanyl-tetrahydro-pyran-2-yl)-propyl]-amide;

2-[2-Methyl-1-(3,4,5-trihydroxy-6-methylsulfanyl-tetrahydro-pyran-2-yl)-propylcarbamoyl]-4-propyl-piperidine-1-carboxylic acid 1-methyl-1,2,3,6-tetrahydro-pyridin-4-yl ester;

and tautomers or pharmaceutically acceptable salts thereof.

11. A compound according to claim 9, wherein the compound is:

4-butyl-piperidine-2-carboxylic acid [2-methyl-1-(3,4,5-trihydroxy-6-methylsulfanyl-tetrahydro-pyran-2-yl)-propyl]-amide or a prodrug, tautomer, or a pharmaceutically acceptable salt thereof.

12. A compound according to claim 9, wherein the compound is:

4-Fluoro-4-propyl-piperidine-2-carboxylic acid [2-methyl-1-(3,4,5-trihydroxy-6-methylsulfanyl-tetrahydro-pyran-2-yl)-propyl]-amide or a prodrug, tautomer, or a pharmaceutically acceptable salt thereof.

13. A compound according to claim 9, wherein the compound is:

4-(2-Cyclopropyl-ethyl)-piperidine-2-carboxylic acid [2-methyl-1-(3,4,5-trihydroxy-6-methylsulfanyl-tetrahydro-pyran-2-yl)-propyl]-amide or a prodrug, tautomer, or a pharmaceutically acceptable salt thereof.

14. A compound according to claim 9, wherein the compound is:

4-Cyclopropylmethyl-piperidine-2-carboxylic acid [2-methyl-1-(3,4,5-trihydroxy-6-methylsulfanyl-tetrahydro-pyran-2-yl)-propyl]-amide or a prodrug, tautomer, or a pharmaceutically acceptable salt thereof.

15. A compound according to claim 9, wherein compound is:

5-Propyl-azepane-2-carboxylic acid [2-methyl-1-(3,4,5-trihydroxy-6-methylsulfanyl-tetrahydro-pyran-2-yl)- propyl]-amide or a prodrug, tautomer, or a pharmaceutically acceptable salt thereof.

16. A compound according to claim 10, wherein the compound is:
Phosphoric acid mono-(4,5-dihydroxy-6-{2-methyl-1-[(4-propyl-piperidine-2-carbonyl)-amino]-propyl}-2-methylsulfanyl-tetrahydro-pyran-3-yl)ester or a tautomer or a pharmaceutically acceptable salt thereof.

17. A compound according to claim 10, wherein the compound is:
1-(5-Methyl-2-oxo-[1,3]dioxol-4-ylmethyl)-4-propyl-piperidine-2-carboxylic acid [2-methyl-1-(3,4,5-trihydroxy-6-methylsulfanyl-tetrahydro-pyran-2-yl)-propyl]-amide or a tautomer or a pharmaceutically acceptable salt thereof.

18. A compound according to claim 10, wherein the compound is:
2-[2-Methyl-1-(3,4,5-trihydroxy-6-methylsulfanyl-tetrahydro-pyran-2-yl)-propylcarbamoyl]-4-propyl-piperidine-1-carboxylic acid 5-methyl-2-oxo-[1,3]dioxol-4-ylmethyl ester or a tautomer or a pharmaceutically acceptable salt thereof.

19. A pharmaceutical composition comprising a pharmaceutically acceptable carrier and a therapeutically effective amount of a compound of claim 1.

20. A method for the treatment of a bacterial infection in a mammal comprising administering to the mammal a therapeutically effective amount of a compound of claim 1.

21. The method according to claim 20, wherein the compound is administered to the mammal orally, parenterally, transdermally, topically, rectally, or intranasally in a pharmaceutical composition.

22. The method according to claim 20, wherein the compound is administered in an amount of from about 0.1 to about 100 mg/kg of body weight/day.

23. A compound of formula (IV):

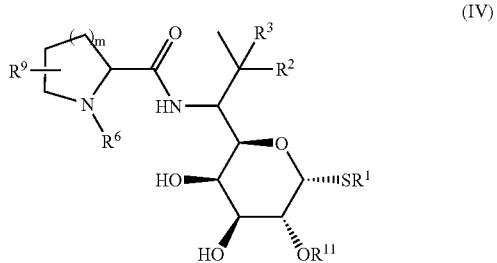

(IV)

$R^1$ is alkyl;
$R^2$ and $R^3$ are independently H, alkyl, hydroxy, fluoro, or cyanoalkyl or one of $R^2$ and $R^3$ is =NOR$^7$ and the other is absent, or one of $R^2$ and $R^3$ is =CH$_2$ and the other is absent, with the provisos that both $R^2$ and $R^3$ are not H; when one of $R^2$ and $R^3$ is fluoro, the other is not hydrogen or hydroxy; and when one of $R^2$ and $R^3$ is hydroxy, the other is not fluoro, hydrogen, or hydroxy;
$R^6$ is selected from the group consisting of hydrogen; 1-(acetyloxy)-ethyl-oxycarbonyl; 1-amino-2-methyl-butyl-carbonyl; 1-amino-2-methyl-butyl-carbonyl-oxy-methyl-oxycarbonyl; 1-amino-2-methyl-propyl-carbonyl; 1-amino-2-phenyl-ethyl-carbonyl; 1-amino-ethyl-carbonyl; 1-methyl-1,2,3,6 tetrahydro-pyridin-4-yl-oxycarbonyl; 1-methyl-1,4 dihydro-pyridin-3-yl-carbonyl; 1-methyl-3-oxo-but-1-enyl; 5-methyl-[1,3]dioxol-2-one-4-yl-methoxy-carbonyl; 5-methyl-[1,3]dioxol-2-one-4-yl-methyl; ethoxy-carbonyl; ethyl-carbonylamino-methyl; fluorenyl-methylene-oxy-carbonyl; phenoxy-carbonyl; piperidin-4-yl-carbonyl-oxy-methyl-oxycarbonyl; and pyridine-3-yl-carbonylamino -methyl;

$R^7$ is H or alkyl;

$R^9$, which can be singly or multiply substituted in the ring on the same or different carbons, is independently selected from the group consisting of alkyl, substituted alkyl, alkoxy, substituted alkoxy, alkoxyalkoxy, cycloalkyl, substituted cycloalkyl, —OR$^d$, —NR$^e$R$^f$, halogen, phenyl, substituted phenyl, —(CH$_2$)$_n$—OH, —(CH$_2$)$_n$—NR$^4$R$^5$, -alkylene-R$^a$ where R$^a$ is selected from monofluorophenyl and monochlorophenyl, and branched chain isomers thereof, wherein n is an integer of from 1 to 8 inclusive and $R^4$ and $R^5$ are H or alkyl, wherein R$^d$ is selected from the group consisting of alkyl, haloalkyl, alkenyl, cycloalkyl, substituted cycloalkyl, aryl, substituted aryl, heteroaryl, and substituted heteroaryl, and wherein R$^e$ and R$^f$ are independently selected from the group consisting of H, alkyl, haloalkyl, alkenyl, cycloalkyl, substituted cycloalkyl, aryl, substituted aryl, heteroaryl, and substituted heteroaryl;

$R^{11}$ is selected from the group consisting of hydrogen; 2-(N-(2-morpholin-4-yl-ethyl)-amino-carbonyl)-ethyl-carbonyl; —C(O)CH$_2$CH$_2$COOH; N,N-dimethyl-amino-methyl-carbonyl; pentadecyl-carbonyloxy; and —PO$_3$H$_2$;

m is 0, 1, 2 or 3;

or a prodrug, tautomer, or a pharmaceutically acceptable salt thereof, with the proviso that the compound of formula IV has a minimum inhibition concentration of 32 μg/mL or less against at least one of the organisms selected from the group consisting of *Streptococcus pneumoniae, Staphylococcus aureus, Staphylococcus epidermidis, Enterococcus faecalis, Enterococcus faecium, Haemophilus influenzae, Moraxella catarrhalis, Escherichia coli, Bacteroides fragilis, Bacteroides thetaiotaomicron,* and *Clostridium difficile.*

24. A compound of the structure:

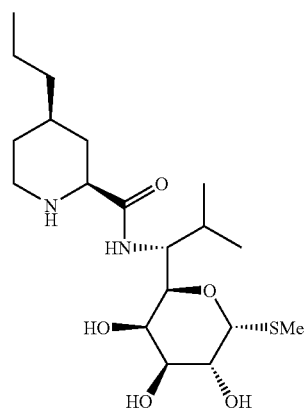

or a prodrug, tautomer, or a pharmaceutically acceptable salt thereof.

25. A pharmaceutical composition comprising a pharmaceutically acceptable carrier and a therapeutically effective amount of a compound of claim 24.

26. A method for the treatment of a bacterial infection in a mammal comprising administering to the mammal a therapeutically effective amount of a compound of claim 24.

27. The method according to claim 26, wherein the compound is administered to the mammal orally, parenterally, transdermally, topically, rectally, or intranasally in a pharmaceutical composition.

28. The method according to claim 26, wherein the compound is administered in an amount of from about 0.1 to about 100 mg/kg of body weight/day.

29. A compound of the formula:

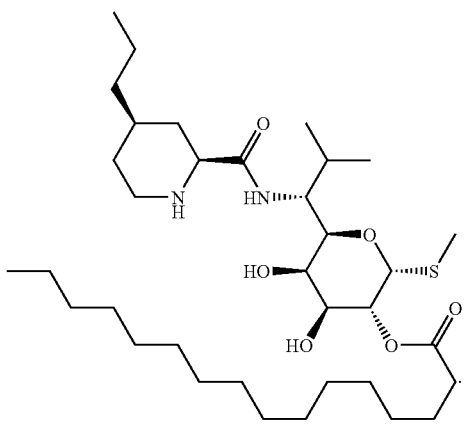

* * * * *